US007008768B1

(12) United States Patent
Fornace, Jr. et al.

(10) Patent No.: US 7,008,768 B1
(45) Date of Patent: Mar. 7, 2006

(54) METHOD FOR DETECTING RADIATION EXPOSURE

(75) Inventors: Albert J. Fornace, Jr., Bethesda, MD (US); Sally A. Amundson, New York, NY (US); Jeffrey M. Trent, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/913,171

(22) PCT Filed: Feb. 25, 2000

(86) PCT No.: PCT/US00/04897

§ 371 (c)(1),
(2), (4) Date: Aug. 8, 2001

(87) PCT Pub. No.: WO00/50643

PCT Pub. Date: Aug. 31, 2000

Related U.S. Application Data

(60) Provisional application No. 60/121,756, filed on Feb. 26, 1999.

(51) Int. Cl.
*C12Q 1/68* (2006.01)
*C12P 19/34* (2006.01)
*C07H 21/04* (2006.01)

(52) U.S. Cl. ..................... 435/6; 435/91.1; 435/91.2; 536/23.1

(58) Field of Classification Search .................. 435/6, 435/91.1, 91.2; 536/24.3, 24.33
See application file for complete search history.

(56) References Cited

U.S. PATENT DOCUMENTS

| | | | |
|---|---|---|---|
| 5,563,060 A | 10/1996 | Hozier | |
| 5,691,157 A | 11/1997 | Gong et al. | |
| 5,707,807 A | 1/1998 | Kato | |
| 5,744,305 A | 4/1998 | Fodor et al. | |
| 5,770,722 A | 6/1998 | Lockhart et al. | |
| 5,830,645 A | 11/1998 | Pinkel et al. | |
| 5,843,655 A | 12/1998 | McGall | |
| 5,866,330 A | 2/1999 | Kinzler et al. | |
| 5,877,215 A * | 3/1999 | McClay et al. | 514/573 |
| 5,910,309 A * | 6/1999 | Ullrich | 424/198.1 |
| 5,965,352 A * | 10/1999 | Stoughton et al. | 435/4 |
| 5,998,136 A * | 12/1999 | Kamb | 435/6 |

FOREIGN PATENT DOCUMENTS

| | | |
|---|---|---|
| WO | WO 97/30179 | 8/1997 |
| WO | WO 98/18961 | 5/1998 |
| WO | WO 98/56954 | 12/1998 |
| WO | WO 99/55913 | 11/1999 |

OTHER PUBLICATIONS

Amundson et al., "Identification of Gamma-Ray Responsive Genes by cDNA Array Hybridization," *Proceedings of the American Association for Cancer Research Annual Meeting* 39:454 (1998).
Amundson et al., "Induction of Stress Genes by Low Doses of Gamma Rays," *Radiat, Res.* 152:225-231 (1999).
Amundson et al., "Fluorescent cDNA Microarray Hybridization Reveals Complexity and Heterogeneity of Cellular Genotoxic Stress Responses," *Oncogene* 18:3666-3672 (1999).
Carulli et al., "High Throughput Analysis of Differential Gene Expression," *J. Cell. Biochem.Suppl.* 30/31:286-296 (1998).
Derisi et al., "Use of a cDNA Microarray to Analyse Gene Expression Patterns in Human Cancer," *Nature Genetics* 14:457-460 (1996).
Fiscella et al., "Wip1. A Novel Human Protein Phosphatase that is Induced in Response to Ionizing Radiation in a p53-Dependent Manner," *Proc. Natl. Acad. Sci. USA* 94: 6048-6053 (1997).
Fornace et al., "The Complexity of Radiation Stress Responses: Analysis by Informatics and Functional Genomics Approaches," *Gene Expr.* 7:387-400 (1999).
Goltry et al., "Induction of Serum Amyloid A Inflammatory Response Genes in Irradiated Bone Marrow Cells," *Radiat. Res.* 149:570-578 (1998).
Higuchi et al., "Search for Genes Involved in UV-Resistance in Human Cells by mRNA Differential Display: Increased Transcriptional Expression of Nucleophosmin and T-Plastin Genes in Association with the Resistance," *Biochem. Biophys. Res. Comm.* 248:597-602 (1998).

(Continued)

*Primary Examiner*—Kenneth R. Horlick
*Assistant Examiner*—Young J. Kim
(74) *Attorney, Agent, or Firm*—Klarquist Sparkman LLP

(57) ABSTRACT

A method is disclosed for detecting exposure of organisms to biologically significant or hazardous amounts of ionizing radiation. The method uses nucleic acid microarray hybridization to evaluate biological effects, such as patterns of expression of genes after radiation exposure. Numerous genes are provided which have been found to be responsive to radiation exposure in a variety of cell lines. These genes are incorporated into probe sets, which are exposed to a labeled nucleic acid composition from a test cell, such as cDNA reverse transcribed from mRNA in the test cell, which specifically hybridizes to members of the probe set when the cell has been exposed to a biologically significant amount of ionizing radiation. Whether the nucleic acid composition hybridizes to the nucleic acid molecules representing genes that are differentially expressed is determined. The invention also includes methods for determining a dose response relationship between radiation exposure and differential expression of one or more genes, for example to determine a probable radiation dose in cells that have actually or potentially been exposed to the ionizing radiation. The invention also includes probe sets and microarrays used in this method.

58 Claims, 11 Drawing Sheets

OTHER PUBLICATIONS

Iordanov et al., "Ultraviolet Radiation Triggers the Ribotoxic Stress Response in Mammalian Cells," *J. Biol. Chem.* 273:15794-15803 (1998).

Monks et al., "Feasibility of High-Flux Anticancer Drug Screen Using a Diverse Panel of Cultured Human Tumor Cell Lines," *J. Natl. Cancer Inst.* 83:757-766 (1991).

Myers et al., "A Protein Expression Database for the Molecular Pharmacology of Cancer," *Electrophoresis* 18:647-653 (1997).

Prasad et al., "Activation of Nuclear Factor kB in Human Lymphoblastoid Cells by Low Dose Ionizing Radiation," *Radiation Res.* 138:367-372 (1994).

Schena et al., "Quantitative Monitoring of Gene Expression Patterns with a Complementary DNA Microarray," *Science* 270:467-470 (1995).

Schena et al., "Parallel Human Genome Analysis: Microarray-Based Expression Monitoring of 1000 Genes," *Proc. Natl. Acad. Sci. USA* 93:10614-10619 (1996).

Weinstein et al., "An Information-Intensive Approach to the Molecular Pharmacology of Cancer," *Science* 275:343-349 (1997).

Zhang et al., "Differential Display of mRNA," *Mol. Biotech.* 10:155-165 (1998).

* cited by examiner

FIG. 5A

| | | RCH1 | BCL3 | FRA1 | REL-B | ATF3 | IAP-1 | PC-1 | MBP-1 | SSAT | MDM2 | CIP1/WAF | BAX |
|---|---|---|---|---|---|---|---|---|---|---|---|---|---|
| p53 wild type | ML-1 | 0.4 | 5.6 | 6.9 | 57.0 | 9.2 | 2.1 | 19.5 | 3.7 | 3.4 | 12.0 | 31.0 | 9.5 |
| | Molt4 | 0.5 | 1.1 | 1.4 | 9.5 | 13.7 | 1.2 | 10.0 | 1.1 | 1.0 | 4.5 | 31.0 | 5.8 |
| | SR | 0.5 | 0.9 | 1.7 | 5.6 | 6.1 | 2.9 | 3.1 | 2.0 | 1.2 | 8.9 | 8.7 | 1.2 |
| | A549 | 0.6 | 1.1 | 1.1 | 1.4 | 1.6 | 1.2 | 1.8 | 0.8 | 1.1 | 4.8 | 22.4 | 1.9 |
| | MCF7 | 0.4 | 1.8 | 9.5 | 4.4 | 1.7 | 0.6 | 0.6 | 1.1 | 1.2 | 2.5 | 7.5 | 2.9 |
| | RKO | 0.7 | 2.2 | 0.7 | 3.4 | 5.3 | 3.0 | 3.5 | 1.7 | 1.4 | 4.0 | 4.0 | 1.7 |
| p53 mutant | CCRF-CEM | 0.5 | 3.8 | 1.0 | 13.4 | 10.7 | 1.3 | 11.9 | 1.7 | 0.7 | 1.0 | 1.8 | 0.9 |
| | HL60 | 0.5 | 6.2 | 1.9 | 8.3 | 3.2 | 1.0 | 5.2 | 1.6 | 2.2 | 1.0 | 2.0 | 0.5 |
| | K562 | 0.7 | 1.4 | 1.2 | 1.6 | 0.9 | 1.0 | 4.7 | 1.3 | 1.0 | 1.2 | 1.4 | 1.0 |
| | H1299 | 0.7 | 0.7 | 0.7 | 2.1 | 1.0 | 1.0 | 1.0 | 1.1 | 0.9 | 1.0 | 1.3 | 1.1 |
| | RKO-E6 | 0.2 | 3.1 | 0.5 | 7.2 | 1.4 | 3.8 | 4.6 | 1.4 | 2.2 | 1.6 | 1.5 | 1.3 |
| | T47D | 0.7 | 1.8 | 0 | 4.8 | 1.5 | 1.9 | 1.9 | 1.1 | 1.4 | 0.8 | 4.0 | 0.7 |

FIG. 5B

|  |  | RCH1 | BCL3 | FRA1 | REL-B | ATF3 | IAP-1 | PC-1 | MBP-1 | SSAT | MDM2 | CIP1/WA | BAX |
|---|---|---|---|---|---|---|---|---|---|---|---|---|---|
| p53 wild type | ML-1 MMS | 0.7 | 0.8 | 0.8 | 1.8 | 7.3 | 0.7 | 1.4 | 0.9 | 1.5 | 9.2 | 11.3 | 2.1 |
|  | Molt4 MMS | 1.4 | 1.0 | 3.7 | 0.5 | 32.0 | 1.3 | 1.3 | 0.6 | 1.2 | 1.1 | 12.6 | 0.9 |
|  | SR MMS | 1.2 | 0.4 | 1.1 | 1.6 | 10.3 | 1.2 | 1.0 | 0.8 | 0.9 | 3.2 | 6.3 | 0.5 |
|  | A549 MMS | 0.6 | 1.1 | 1.1 | 1.4 | 4.4 | 0.6 | 1.8 | 0.5 | 1.1 | 4.8 | 7.5 | 1.9 |
|  | UV | 0.8 | 0.6 | 1.5 | 0.6 | 22.0 | 0.8 | 1.3 | 0.6 | 1.4 | 0.5 | 5.7 | 1.4 |
|  | MCF7 MMS | 1.0 | 0.6 | 4.8 | 1.0 | 39.0 | 0.5 | 1.2 | 0.9 | 0.9 | 2.8 | 9.8 | 1.6 |
|  | UV | 0.9 | 1.5 | 24.7 | 1.0 | 3.9 | 1.4 | 1.3 | 1.0 | 0.9 | 2.3 | 5.0 | 1.0 |
|  | RKO MMS | 0.8 | 1.2 | 0.7 | 1.5 | 4.6 | 1.1 | 0.7 | 1.4 | 1.2 | 0.5 | 3.7 | 0.7 |
|  | UV | 0.8 | 1.7 | 0.9 | 0.8 |  | 1.1 | 1.1 | 1.4 | 1.4 | 1.4 | 2.7 | 1.0 |
| p53 mutant | CCRF-CEM MMS | 0.8 | 0.8 | 1.2 | 0.5 | 26.0 | 0.9 | 0.8 | 1.1 | 0.8 | 1.2 | 0.7 | 1.2 |
|  | HL60 MMS | 0.9 | 1.1 | 3.7 | 1.3 | 9.4 | 1.2 | 1.7 | 0.9 | 0.6 | 3.6 | 5.9 | 0.7 |
|  | K562 MMS | 1.0 | 1.7 | 1.2 | 0.8 | 37.0 | 0.9 | 0.8 | 1.3 | 1.3 | 1.2 | 1.8 | 0.9 |
|  | H1299 MMS | 0.9 | 0.7 | 0.6 | 1.0 | 21.0 | 0.5 | 1.9 | 0.9 | 0.7 | 0.6 | 6.3 | 0.9 |
|  | UV | 0.6 | 0.6 | 0.5 | 1.2 | 3.8 | 0.5 | 3.8 | 0.7 | 0.8 | 0.9 | 2.2 | 1.5 |
|  | RKO/E6 MMS | 0.3 | 1.3 | 1.1 | 0.8 | 42.0 | 1.1 | 0.6 | 1.3 | 0.9 | 0.9 | 2.3 | 0.7 |
|  | UV | 0.2 | 1.0 | 0.7 | 0.7 | 2.8 | 0.5 | 0.8 | 0.7 | 0.9 | 0.5 | 2.8 | 0.7 |
|  | T47D MMS | 0.8 | 0.8 | 0 | 1.6 | 38.0 | 1.5 | 0.9 | 0.8 | 0.9 | 0.7 | 3.9 | 0.6 |
|  | UV | 1.1 | 1.3 | 0 | 1.9 | 3.5 | 1.5 | 3.3 | 0.5 | 1.2 | 0.9 | 2.7 | 0.8 |

SEQUENCE LISTING

<160> NUMBER OF SEQ ID NOS: 28

<210> SEQ ID NO 1
<211> LENGTH: 495
<212> TYPE: DNA
<213> ORGANISM: Homo sapiens

<400> SEQUENCE: 1

```
atggcgacga aggccgtgtg cgtgctgaag ggcgacggcc cagtgcaggg catcatcaat      60
ttcgagcaga aggaaagtaa tggaccagtg aaggtgtggg gaagcattaa aggactgact     120
gaaggcctgc atggattcca tgttcatgag tttggagata atacagcagg ctgtaccagt     180
gcaggtcctc actttaatcc tctatccaga aaacacggtg ggccaaagga tgaagagagg     240
catgttggag acttgggcaa tgtgactgct gacaaagatg gtgtggccga tgtgtctatt     300
gaagattctg tgatctcact ctcaggagac cattgcatca ttggccgcac actggtggtc     360
catgaaaaag cagatgactt gggcaaaggt ggaaatgaag aaagtacaaa gacaggaaac     420
gctggaagtc gtttggcttg tggtgtaatt gggatcgccc aataaacatt cccttggatg     480
tagtctgagg cccct                                                      495
```

<210> SEQ ID NO 2
<211> LENGTH: 4035
<212> TYPE: DNA
<213> ORGANISM: Homo sapiens

<400> SEQUENCE: 2

```
tcccctggac ccgccgcaga gccagtgcag aatacagaaa ctgcagccat gaccacgcac      60
gtcaccctgg aagatgccct gtccaacgtg gacctgcttg aagagcttcc cctcccgac      120 cagcagccat gcatcgagcc tccaccttcc tccatcatgt accaggctaa ctttgacaca     180
aactttgagg acaggaatgc atttgtcacg ggcattgcaa ggtacattga gcaggctaca     240
gtccactcca gcatgaatga gatgctggag aaggacatg agtatgcggt catgctgtac     300
acctggcgca gctgttcccg ggccattccc caggtgaaat gcaacgagca gcccaaccga     360
gtagagatct atgagaagac agtagaggtg ctggagccgg aggtcaccaa gctcatgaag     420
ttcatgtatt ttcagcgcaa ggccatcgag cggttctgca gcgaggtgaa gcggctgtgc     480
catgccgagc gcaggaagga ctttgtctct gaggcctacc tcctgaccct tggcaagttc     540
atcaacatgt ttgctgtcct ggatgagcta aagaacatga agtgcagcgt caagaatgac     600
cactctgcct acaagagggc agcacagttc ctgcggaaga tggcagatcc ccagtctatc     660
caggagtcgc agaacctttc catgttcctg gccaaccaca caggatcac ccagtgtctc     720 caccagcaac ttgaagtgat cccaggctat gaggagctgc tggctgacat tgtcaacatc     780
tgtgtggatt actacgagaa caagatgtac ctgactccca gtgagaaaca tatgctcctc     840
aaggtgatgg gctttggcct ctacctaatg gatggaaatg tcagtaacat ttacaaactg     900
gatgccaaga agagaattaa tcttagcaaa attgataaat tctttaagca gctgcaggtg     960
gtgccccttt tcggcgacat gcagatagag ctggccagat acattaagac cagtgctcac    1020
```

-continued

```
tatgaagaga acaagtccaa gtggacgtgc acccagagca gcatcagccc ccagtacaat    1080
atctgcgagc agatggttca gatccgggat gaccacatcc gcttcatctc cgagctcgct    1140
cgctacagca acagtgaggt ggtgacgggc tcagggctgg acagccagaa gtcagacgag    1200
gagtatcgcg agctcttcga cctagccctg cggggtctgc agcttctatc caagtggagc    1260
gcccacgtca tggaggtgta ctcttggaag ctggttcatc ccacagacaa gttctgcaac    1320
aaggactgtc ctggcaccgc ggaggaatat gagagagcca cacgctacaa ttacaccagt    1380
gaggaaaaat ttgccttcgt tgaggtgatc gccatgatca aaggcctgca ggtgctcatg    1440
ggcaggatgg agagcgtctt caaccaggcc atcaggaaca ccatctacgc ggcattgcag    1500
gacttcgccc aggtgacgct gcgtgagccc ctgcggcagg cggtacggaa gaagaagaat    1560
gtcctcatca gcgtcctaca ggcaattcga aagaccatct gtgactggga gggagggcga    1620
gagcccccta atgacccatg cttgagaggg gagaaggacc ccaaaggtgg atttgatatc    1680
aaggtgcccc ggcgtgctgt ggggccatcc agcacacagc tgtacatggt gcggaccatg    1740
cttgaatcac tcattgcaga caaaagcggc tccaagaaga ccctgaggag cagcctggat    1800
ggacccattg tcctcgccat agaggacttt cacaaacagt ccttcttctt cacacatctg    1860
ctcaacatca gtgaagccct gcagcagtgt tgtgacctct cccagctctg gttccgagaa    1920
ttcttcctgg agttaaccat gggccgacga atccagttcc ccatcgagat gtccatgccc    1980
tggattctaa cggaccatat cctggaaacc aaagaacctt ccatgatgga gtatgtcctc    2040
tacccctctg gatctgtacaa cgacagcgcc tactatgctc tgaccaagtt taaaaagcag    2100
ttcctgtacg atgagataga agctgaggtg aacctgtgtt ttgatcagtt tgtctacaag    2160
ctggcagacc agatctttgc ttactacaaa gccatggctg gcagtgtcct gttggataaa    2220
cgttttcgag ctgagtgtaa gaattatggc gtcatcattc cgtatccacc gtccaatcgc    2280
tatgaaacac tgctgaagca gagacacgtc cagctgttgg gtagatcaat tgacttgaac    2340
agactcatta cccagcgcat ctctgccgcc atgtataaat ccttggacca agctatcagc    2400
cgctttgaga gtgaggacct gacctccatt gtggagctgg agtggctgct ggagattaac    2460
cggctcacgc atcggctgct ctgtaagcat atgacgctgg acagcttcga tgccatgttc    2520
cgagaggcca atcacaatgt gtccgccccc tatggccgta tcaccctgca tgtcttctgg    2580
gaactgaact ttgactttct ccccaactac tgctacaatg ggtccactaa ccgttttgtg    2640
cggactgcca ttcctttcac ccaagaacca aacgagaca aacctgccaa cgtccagcct    2700
tattacctct atggatccaa gcctctcaac attgcctaca gccacatcta cagctcctac    2760
aggaatttcg tggggccacc tcatttcaag actatctgca gactcctggg ttatcagggc    2820
atcgctgtgg tcatggagga actgctaaag attgtgaaga gcttgctcca aggaaccatt    2880
ctccagtatg tgaaaacact gatagaggtg atgcccaaga tatgccgctt gccccgacat    2940
gagtatggct ccccagggat cctggagttc ttccaccacc agctgaagga catcattgag    3000
tacgcagagc tcaaaacaga cgtgttccag agcctgaggg aagtgggcaa tgccatcctc    3060
ttctgcctcc tcatagagca agctctgtct caggaggagg tctgcgattt gctccatgcc    3120
gcacccttcc aaaacatctt gcctagagtc tacatcaaag aggggagcg cctggaggtc    3180
cggatgaaac gtctggaagc caagtatgcc ccgtccacc tggtccctct gatcgagcgg    3240
ctggggaccc ctcagcaaat cgccattgct cgcgagggtg acctcctgac caaggagcgg    3300
ctgtgctgtg gcctgccat gttcgaggtc atcctgaccc gcattcggag ctacctgcag    3360
gaccccatct ggcggggccc accgcccacc aatggcgtca tgcacgtcga tgagtgtgtg    3420
```

```
gagttccacc ggctgtggag cgccatgcag ttcgtgtact gcatccctgt gggaaccaac    3480
gagttcacag ctgagcagtg tttcggcgat ggcttgaact gggctggttg ctccatcatt    3540
gtcctgctgg gccagcagcg tcgctttgac ctgttcgact tctgttacca cctgctaaaa    3600
gtgcagaggc aggacgggaa ggatgaaatc attaagaatg tgcccctgaa gaagatggcc    3660
gaccggatca ggaagtatca gatcttgaac aatgaggttt ttgccatcct gaacaaatac    3720
atgaagtccg tggagacaga cagttccact gtggagcatg tgcgctgctt ccagccaccc    3780
atccaccagt ccttggccac cacttgctaa gcagaagatc ctgcagaccc ttatctggag    3840
gaggaagaga agcaggagag agaaagccac agccagcctg ccataggatc caactggaca    3900
acgtgtggga tggacctgga aacaagcacc tccccaaaca catcaccact ccctagggcg    3960
gggcctgtgc atgctctccc atgacatctc catgctggtt tctccatagc ataaatgaaa    4020
aaaaaaaaaa aaaaa                                                     4035
```

<210> SEQ ID NO 3
<211> LENGTH: 2392
<212> TYPE: DNA
<213> ORGANISM: Homo sapiens

<400> SEQUENCE: 3

```
agcggggcag cggctgcgcc ctgcgccggg gcggagccgg gggcgggccg gcggccggca      60
ggcgggggct ggggcccgag gccgggagtg cctgagcgcc ggcggcgacg acggcagcgg     120
cggcccagcg ggctcggtgg ttgggtccgc ggcggctcgg ggtccgcccg cgggctgcgg     180
tgcgagcggg cggcccggct ccctcctcc cccgcccgcc gccgccgctg tgattgggtg      240
gaagatggcg ctggccggat ggaaatccta atgcacagtct ccaaattcgc ctccatctgt   300
accatgggcg ccaatgcttc ggcattagag aaagagattg gtccagaaca gtttccggtc    360
aatgagcact atttttggatt agtcaatttt gggaatacct gctactgcaa ttcagttctt    420
caagcacttt attttttgtcg tccatttcgg gaaaaagttc ttgcgtataa gagtcaacct    480
aggaaaaagg agagccttct tacatgctta gcagatctct tccatagcat agccactcag    540
aagaaaaagg ttggagtaat accccctaag aagttcatca caagattacg gaaagaaaat    600 gagcttttttg acaactacat gcaacaagat gcccatgaat tcttaaatta cctactaaat    660
acaattgctg atattttaca agaagagaga agcaggaaa aacaaaatgg tcgtttacct    720
aatggtaata ttgataatga aaataataac agcacaccag acccaacgtg ggttgatgag    780
atttttcagg gaacattaac taatgaaacc agatgtctta cttgtgaaac tataagcagc    840
aaagatgaag attttttaga cctttctgtt gacgtggaac aaaatacatc aattactcac    900
tgcttaaggg gtttcagcaa cacagaaact ctgtgcagtg aatacaagta ttactgtgaa    960
gagtgtcgca gcaaacagga agcacacaaa cggatgaaag ttaaaaaact gcccatgatt   1020
ctagctctac acctgaagag atttaaatat atggatcaac ttcatcgata tacaaaactc   1080
tcttaccggg tagtttttcc tttagaactt cgtctgttta acacttcagg tgatgccacc   1140
aatccagaca gaatgtacga ccttgttgct gttgtggttc actgtggaag tggtcccaat   1200
cgaggccatt atattgcaat agttaagagt catgattttt ggttgttgtt tgatgacgac   1260
attgtagaaa aaatagatgc acaagctatt gaagaattct acgggttgac atcagatatc   1320
tcaaagaact ctgagtctgg ttacatcctt ttctatcagt ctcgggactg agagggaacc   1380
gtgatgaaga gacactttct gcctcatttc ttctctggtt attttggaaa ggatcaagca   1440
```

```
ctgatttttc aagaaaagag aaatgcagga agctcagggg gcagtagcac actttgcaca   1500
cgataaagca aagacgatgg attgacaagc ccttccgatc atggtagttg atttatttgc   1560
tcaggtatca tgctgtctgt acagttccat acaacaagga ggtgaaatca gagataccag   1620
ctcctctttt aaaacagcct tccagtcatt ggcacgcatt ttctctttat taattgcacc   1680
aataatgctt tgaattcctt gggggtgcag tagaaagaat cggaatctgt gccgtattga   1740
taaggagatg atgttgaaca cactgcataa atttgcctgg ttcagtatgt atagaagcat   1800
attcagtggt cttttcaaga gtaaaccaga atacttttg ggcccaacac ttgcagttgc   1860
cttcctgatg taaaaactaa catgctagat aatccagtgt cgggaagaca agatgttttt   1920
gcttctctga agaagcttat aataatatac agtatatgta tatgtaggga gcaattggtc   1980
aaaagtggct ttttgtttcc ccaaggggaa agactggctt tgtaattata attttttcct   2040
tatttatttt acttaaaact ggtagagtct aagtattata tgaagtgccc atgattctgt   2100
cagtaaattt gaacatattt ttattagtta atgtcagttt aagttgtcct tttgtttgtt   2160 tctatttta aggtgaattt taatttctat ctgaaatcag ttaagatacc ttgagaaaaa   2220
ctgcagtgag aggagataaa tatccttttt caggaggaac tgatatctct ggctaaatat   2280 ttgtccttt attatggttt ctaaatcagt tattttcttc agctttaatt tcataaaatt   2340
aaaaaactat tttaaaaaaa aaaaaaaaaa aaaaaaaaa aaaaaaaaaa aa             2392

<210> SEQ ID NO 4
<211> LENGTH: 2207
<212> TYPE: DNA
<213> ORGANISM: Homo sapiens

<400> SEQUENCE: 4 cccttcctg tggggttcat tggggcatcc cctttctgct gcaggaacct ctcatcagac     60
cgcctgaggg aagcggcgcc cggagacccg ccccggcccg gtccacattc tccccaggaa    120
gccggactct atggggcggg accctggggg agcctgagcc gagcccggag ccagccccga    180
acccctgaac ctccagccag gggcgccccg ggagcagcca gccgtgggc gagccgcccg    240 cccgccgagc agccatgagc gagacggtca tctgttccag ccgggccact gtgatgcttt    300
atgatgatgg caacaagcga tggctccctg ctggcacggg tccccaggcc ttcagccgcg    360
tccagatcta ccacaacccc acggccaatt cctttcgcgt cgtgggccgg aagatgcagc    420
ccgaccagca ggtggtcatc aactgtgcca tcgtccgggg tgtcaagtat aaccaggcca    480
cccccaactt ccatcagtgg cgcgacgctc gccaggtctg gggcctcaac ttcggcagca    540
aggaggatgc ggcccagttt gccgccggca tggccagtgc cctagaggcg ttggaaggag    600
gtgggccccc tccacccca gcacttccca cctggtcggt cccgaacggc ccctccccgg    660
aggaggtgga gcagcagaaa aggcagcagc ccggcccgtc ggagcacata gagcgccggg    720
tctccaatgc aggaggccca cctgctcccc ccgctggggg tccacccca ccaccaggac    780 ctccccctcc tccaggtccc ccccacccc caggtttgcc cccttcgggg gtcccagctg    840
cagcgcacgg agcaggggga ggaccacccc ctgcaccccc tctcccggca gcacagggcc    900
ctggtggtgg gggagctggg gccccaggcc tggccgcagc tattgctgga gccaaactca    960
ggaaagtcag caagcaggag gaggcctcag ggggcccac agcccccaaa gctgagagtg   1020
gtcgaagcgg aggtggggga ctcatggaag atgaacgc catgctggcc cggagaagga   1080
aagccacgca agttggggag aaaacccca aggatgaatc tgccaatcag gaggagccag   1140
aggccagagt cccggcccag agtgaatctg tgcggagacc ctgggagaag aacagcacaa   1200
```

-continued

```
ccttgccaag gatgaagtcg tcttcttcgg tgaccacttc cgagacccaa ccctgcacgc      1260
ccagctccag tgattactcg gacctacaga gggtgaaaca ggagcttctg aagaggtga       1320 agaaggaatt gcagaaagtg aaagaggaaa tcattgaagc cttcgtccag gagctgagga      1380
agcggggttc tccctgacca cagggaccca gaagacccgc ttctcctttc cgcacacccg      1440
gcctgtcacc ctgctttccc tgcctctact tgacttggaa ttggctgaag acacaggaat     1500
gcatcgttcc cactccccat cccacttgga aaactccaag ggggtgtggc ttccctgctc     1560
acacccacac tggctgctga ttggctgggg aggcccccgc ccttttctcc ctttggtcct     1620
tcccctctgc catccccttg ggccggtcc  ctctgctggg gatgcaccaa tgaacccac      1680 aggaaggggg aaggaaggag ggaatttcac attcccttgt tctagattca ctttaacgct     1740
taatgccttc aaagttttgg ttttttttaag aaaaaaaaat atatatatat ttgggtttg     1800 ggggaaaagg gaaattttt tttctctttg gttttgataa aatgggatgt gggagttttt     1860
aaatgctata gccctgggct tgccccatt  ggggcagcta tttaagggga ggggatgtct    1920
caccgggctg ggggtgagat atccccccac cccagggact cccctttccct ctggctcctt   1980 cccctttct atgaggaaat aagatgctgt aacttttgg aacctcagtt ttttgatttt      2040
ttatttgggt aggttttggg gtccaggcca tttttttttac cccttggagg aaataagatg    2100
agggagaaag gagaagggga ggaaacttct cccctcccac cttcaccttt agcttcttga     2160
aaatgggccc ctgcagaata aatctgccag tttttataaa aaaaaa                    2207

<210> SEQ ID NO 5
<211> LENGTH: 2189
<212> TYPE: DNA
<213> ORGANISM: Homo sapiens

<400> SEQUENCE: 5
gcagagggag cgagcgggcg gccggctagg gtggaagagc cgggcgagca gagctgcgct      60
gcgggcgtcc tggaaggga  gatccggagc gaatagggg cttcgcctct ggcccagccc     120
tcccgctgat cccccagcca gcggtccgca acccttgccg catccacgaa actttgccca    180
tagcagcggg cgggcacttt gcactggaac ttacaacacc cgagcaagga cgcgactctc    240
ccgacgcggg gaggctattc tgcccatttg gggacacttc cccgccgctg ccaggacccg    300
cttctctgaa aggctctcct tgcagctgct tagacgctgg atttttttcg ggtagtggaa    360
aaccagcagc ctcccgcgac gatgcccctc aacgttagct tcaccaacag gaactatgac    420
ctcgactacg actcggtgca gccgtatttc tactgcgacg aggaggagaa cttctaccag    480
cagcagcagc agagcgagct gcagcccccg gcgcccagcg aggatatctg gaagaaattc    540
gagctgctgc ccaccccgcc cctgtcccct agccgccgct ccgggctctg ctcgccctcc    600
tacgttgcgg tcacaccctt ctcccttcgg ggagacaacg acggcggtgg cgggagcttc    660
tccacggccg accagctgga gatggtgacc gagctgctgg aggagacat  ggtgaaccag    720 agtttcatct gcgacccgga cgacgagacc ttcatcaaaa acatcatcat ccaggactgt    780
atgtggagcg gcttctcggc cgccgccaag ctcgtctcag agaagctggc ctcctaccag    840
gctgcgcgca aagacagcgg cagcccgaac cccgcccgcg ccacagcgt  ctgctccacc    900 tccagcttgt acctgcagga tctgagcgcc gccgcctcag agtgcatcga ccctcggtg    960 gtcttcccct accctctcaa cgacagcagc tcgcccaagt cctgcgcctc gcaagactcc   1020
agcgccttct ctccgtcctc ggattctctg ctctcctcga cggagtcctc cccgcagggc   1080
```

```
agccccgagc ccctggtgct ccatgaggag acaccgccca ccaccagcag cgactctgag    1140
gaggaacaag aagatgagga agaaatcgat gttgtttctg tggaaaagag gcaggctcct    1200
ggcaaaaggt cagagtctgg atcaccttct gctggaggcc acagcaaacc tcctcacagc    1260
ccactggtcc tcaagaggtg ccacgtctcc acacatcagc acaactacgc agcgcctccc    1320
tccactcgga aggactatcc tgctgccaag agggtcaagt tggacagtgt cagagtcctg    1380
agacagatca gcaacaaccg aaaatgcacc agccccaggt cctcggacac cgaggagaat    1440
gtcaagaggc aaacacacaa cgtcttggag cgccagagga ggaacgagct aaaacggagc    1500
ttttttgccc tgcgtgacca gatcccggag ttggaaaaca atgaaaaggc ccccaaggta    1560
gttatcctta aaaagccac agcatacatc ctgtccgtcc aagcagagga gcaaaagctc    1620
atttctgaag aggacttgtt gcggaaacga cgagaacagt tgaaacacaa acttgaacag    1680
ctacggaact cttgtgcgta aggaaaagta aggaaaacga ttccttctaa cagaaatgtc    1740
ctgagcaatc acctatgaac ttgtttcaaa tgcatgatca aatgcaacct cacaaccttg    1800
gctgagtctt gagactgaaa gatttagcca taatgtaaac tgcctcaaat tggactttgg    1860
gcataaaaga acttttttat gcttaccatc ttttttttt ctttaacaga tttgtattta    1920
agaattgttt ttaaaaaatt ttaagattta cacaatgttt ctctgtaaat attgccatta    1980
aatgtaaata actttaataa aacgtttata gcagttacac agaatttcaa tcctagtata    2040
tagtacctag tattataggt actataaacc ctaattttt ttatttaagt acattttgct    2100
ttttaaagtt gattttttc tattgttttt agaaaaaata aaataactgg caaatatatc    2160
attgagccaa aaaaaaaaa aaaaaaaa                                        2189

<210> SEQ ID NO 6
<211> LENGTH: 3658
<212> TYPE: DNA
<213> ORGANISM: Homo sapiens

<400> SEQUENCE: 6
gcccagacaa gcaacatggc tcggaaacgc gcggccggcg gggagccgcg gggacgcgaa      60
ctgcgcagcc agaaatccaa ggccaagagc aaggcccggc gtgaggagga ggaggaggat     120
gcctttgaag atgagaaacc cccaaagaag agccttctct ccaaagtttc acaaggaaag     180
aggaaaagag gctgcagtca tcctggggt tcagcagatg gtccagcaaa aaagaaagtg     240
gccaaggtga ctgttaaatc tgaaaacctc aaggttataa aggatgaagc cctcagcgat     300
ggggatgacc tcagggactt tccaagtgac ctcaagaagg cacaccatct gaagagaggg     360
gctaccatga atgaagacag caatgaagaa gaggaagaaa gtgaaaatga ttgggaagag     420
gttgaagaac ttagtgagcc tgtgctgggt gacgtgagag aaagtacagc cttctctcga     480
tctcttctgc ctgtgaagcc agtggagata gagattgaaa cgccagagca ggcgaagaca     540
agagaaagaa gtgaaaagat aaaactggag tttgagacat atcttcggag ggcgatgaaa     600
cgtttcaata aggggtcca tgaggacaca cacaaggttc accttctctg cctgctagca     660
aatggcttct atcgaaataa catctgcagc cagccagatc tgcatgctat ggcctgtcc     720 atcatcccag cccgcttac cagagtgctg cctcgagatg tggacaccta ctacctctca     780
aacctggtga agtggttcat tggaacattt acagttaatg cagaacttc agccagtgaa     840 caagataacc tgcagactac attggaaagg agatttgcta tttactctgc tcgagatgat     900
gaggaattgg tccatatatt cttactgatt ctccgggctc tgcagctctt gacccggctg     960
gtattgtctc tacagccaat tcctctgaag tcagcaacag caaagggaaa gaaaccttcc    1020
```

-continued

```
aaggaaagat tgactgcgga tccaggaggc tcctcagaaa cttccagcca agttctagaa    1080
aaccacacca aaccaaagac cagcaaagga accaaacaag aggaaacctt tgctaagggc    1140
acctgcaggc caagtgccaa agggaagagg aacaagggag gcagaaagaa acggagcaag    1200
ccctcctcca gcgaggaaga tgagggccca ggagacaagc aggagaaggc aacccagcga    1260
cgtccgcatg gccgggagcg gcgggtggcc tccagggtgt cttataaaga ggagagtggg    1320
agtgatgagg ctggcagcgg ctctgatttt gagctctcca gtggagaagc ctctgatccc    1380
tctgatgagg attccgaacc tggccctcca agcagagga aagccccgc tcctcagagg      1440
acaaaggctg ggtccaagag tgcctccagg acccatcgtg ggagccatcg taaggaccca    1500
agcttgccag cggcatcctc aagctcttca agcagtaaaa gaggcaagaa aatgtgcagc    1560
gatggtgaga aggcagaaaa agaagcata gctggtatag accagtggct agaggtgttc     1620
tgtgagcagg aggaaaagtg ggtatgtgta gactgtgtgc acggtgtggt gggccagcct    1680
ctgacctgtt acaagtacgc caccaagccc atgacctatg tggtgggcat tgacagtgac    1740
ggctgggtcc gagatgtcac acagaggtac gacccagtct ggatgacagt gacccgcaag    1800
tgccgggttg atgctgagtg gtgggccgag accttgagac cataccagag cccatttatg    1860
gacagggaga agaaagaaga cttggagttt caggcaaaac acatggacca gcctttgccc    1920
actgccattg gcttatataa gaaccaccct ctgtatgccc tgaagcggca tctcctgaaa    1980
tatgaggcca tctatcccga gacagctgcc atccttgggt attgtcgtgg agaagcggtc    2040
tactccaggg attgtgtgca cactctgcat tccagagaca cgtggctgaa gaaagcaaga    2100
gtggtgaggc ttggagaagt accctacaag atggtgaaag gcttttctaa ccgtgctcgg    2160
aaagcccgac ttgctgagcc ccagctgcgg gaagaaaatg acctgggcct gtttggctac    2220
tgcagacag aggagtatca gcccccagtg gccgtggacg ggaaggtgcc ccggaacgag     2280
tttgggaatg tgtacctctt cctgcccagc atgatgccta ttggctgtgt ccagctgaac    2340
ctgcccaatc tacaccgcgt ggcccgcaag ctggacatcg actgtgtcca ggccatcact    2400
ggctttgatt ccatggcgg ctactcccat cccgtgactg atggatacat cgtctgcgag     2460
gaattcaaag acgtgctcct gactgcctgg gaaaatgagc aggcagtcat tgaaaggaag    2520
gagaaggaga aaaaggagaa gcgggctcta gggaactgga agttgctggc caaaggtctg    2580
ctcatcaggg agaggctgaa gcgtcgctac gggcccaaga gtgaggcagc agctccccac    2640
acagatgcag gaggtggact ctcttctgat gaagaggagg ggaccagctc tcaagcagaa    2700
gcggccagga tactggctgc ctcctggcct caaaaccgag aagatgaaga aaagcagaag    2760
ctgaagggtg ggcccaagaa gaccaaaagg gaaaagaaag cagcagcttc ccacctgttc    2820
ccatttgaga gctgtgagc tgagcgccca ctagagggc acccaccagt tgctgctgcc      2880
ccactacagg ccccacacct gccctgggca tgcccagccc tggtggtgg gggcttctct     2940
gctgagaagg caaactgagg cagcatgcac ggaggcgggg tcagggaga cgaggccaag     3000
ctgaggaggt gctgcaggtc ccgtctggct ccagcccttg tcagattcac ccagggtgaa    3060
gccttcaaag cttttgcta ccaaagccca ctcacccttt gagctacaga acactttgct     3120
aggagatact cttctgcctc ctagacctgt tctttccatc tttagaaaca tcagttttg     3180
tatggaagcc accgggagat ttctggatgg tggtgcatcc gtgaatgcgc tgatcgtttc    3240
ttccagttag agtcttcatc tgtccgacaa gttcactcgc ctcggttgcg gacctaggac    3300
catttctctg caggccactt accttcccct gagtcaggct tactaatgct gccctcactg    3360
```

-continued

```
cctctttgca gtaggggaga gagcagagaa gtacaggtca tctgctggga tctagttttc    3420
caagtaacat tttgtggtga cagaagccta aaaaaagcta aaatcaggaa agaaaaggaa    3480
aaatacgaat tgaaaattaa ggaaatgtta gtaaaataga tcagtgttaa actagattgt    3540
attcattact agataaaatg tataaagctc tctgtactaa ggagaaatga cttttataac    3600
attttgagaa aataataaag catttatcta aaaaaaaaaa aaaaaaaaaa aaaaaaa       3658
```

<210> SEQ ID NO 7
<211> LENGTH: 1704
<212> TYPE: DNA
<213> ORGANISM: Homo sapiens

<400> SEQUENCE: 7

```
ggcacgaggt accccttcac acggaggacg cgatggctcc caagaaacgc ccagaaaccc      60
agaagacctc cgagattgta ttacgcccca ggaacaagag gagcaggagt cccctggagc     120
tggagcccga ggccaagaag ctctgtgcga agggctccgg tcctagcaga agatgtgact     180
cagactgcct ctgggtgggg ctggctggcc cacagatcct gccaccatgc cgcagcatcg     240
tcaggacccc ccaccagcat aagctgggca gagcttcctg gccatctgtc agcaggggc     300 tccagcagtc cttttgcac actctggatt cttaccggat attacaaaag gctgccccct     360
ttgacaggag ggctacatcc ttggcgtggc acccaactca ccccagcacc gtggctgtgg    420
gttccaaagg gggagatatc atgctctgga attttggcat caaggacaaa cccaccttca    480
tcaaagggat tggagctgga gggagcatca ctgggctgaa gtttaaccct ctcaatacca    540
accagtttta cgcctcctca atggagggaa caactaggct gcaagacttt aaaggcaaca    600
ttctacgagt ttttgccagc tcagacacca tcaacatctg gttttgtagc ctggatgtgt    660
ctgctagtag ccgaatggtg gtcacaggag acaacgtggg gaacgtgatc ctgctgaaca    720
tggacggcaa agagctttgg aatctcagaa tgcacaaaaa gaaagtgacg catgtggccc    780
tgaacccatg ctgtgattgg ttcctggcca cagcctccgt agatcaaaca gtgaaaattt    840
gggacctgcg ccaggttaga gggaaagcca gcttcctcta ctcgctgccg cacaggcatc    900
ctgtcaacgc agcttgtttc agtcccgatg gagcccggct cctgaccacg gaccagaaga    960
gcgagatccg agtttactct gcttcccagt gggactgccc cctgggcctg atcccgcacc    1020
ctcaccgtca cttccagcac ctcacaccta tcaaggcagc ctggcatcct cgctacaacc    1080
tcattgttgt gggccgatac ccagatccta atttcaaaag ttgtacccct tatgaattga    1140
ggacgatcga cgtgttcgat ggaaactcag gaagatgat gtgtcagctc tatgacccag    1200
aatcttctgg catcagttcg cttaatgaat tcaatcccat ggggacacg ctggcctctg    1260 caatgggtta ccacattctc atctggagcc aggaggaagc caggacacgg aagtgagaga    1320
cactaaagaa ggtgtgggcc agacaaggcc ttggagccca cacatgggat caagtcctgc    1380
aagcagaggt ggcgatttgt taagggcca aaagtatcca aggttagggt tggagcaggg    1440
gtgctgggac ctgggcact gtgggactgg gacactttta tgttaatgct ctggacttgc    1500
ctccagagac tgctccagag ttggtgacac agctgtccca agggccctc tgtatctagc    1560 ctggaaccaa ggttatcttg gaactaaatg acttttctcc tctcagtggg tggtagcaga    1620
gggatcaagc agttatttga tttgtgctca cttttgatat ggccaataaa accataccga    1680
ctgaaaaaaa aaaaaaaaaa aaaa                                           1704
```

<210> SEQ ID NO 8
<211> LENGTH: 1578

<212> TYPE: DNA
<213> ORGANISM: Homo sapiens

<400> SEQUENCE: 8

| | | | | | |
|---|---|---|---|---|---|
| gatcagggcc | gagttgtctc | ggcggcgctg | ccgaggcctc | cacccaggac | agtccccctc | 60 |
| cccgggcctc | tctcctcttg | cctacgagtc | ccctctcctc | gtaggcctct | cggatctgat | 120 |
| atcgtggggt | gaggtgagca | ggcccgggga | gggtggttac | cgctgaggag | ctgcagtctc | 180 |
| tgtcaagatg | atagaggtac | tgacaacaac | tgactctcag | aaactgctac | accagctgaa | 240 |
| tgccctgttg | aacaggagt | ctagatgtca | gccaaaggtc | tgtggtttga | gactaattga | 300 |
| gtctgcacac | gataatggcc | tcagaatgac | tgcaagacta | agggactttg | aagtaaaaga | 360 |
| tcttcttagt | ctaactcagt | tctttggctt | tgacacagag | acatttttct | tagctgtgaa | 420 |
| tttactggac | agattcctgt | ctaaaatgaa | ggtacagccc | aagcaccttg | ggtgtgttgg | 480 |
| actgagctgc | ttttatttgg | ctgtaaaatc | aatagaagag | gaaaggaatg | tcccattggc | 540 |
| aactgacttg | atccgaataa | gtcaatatag | gtttacggtt | tcagacttga | tgagaatgga | 600 |
| aaagattgta | ttggagaagg | tgtgttggaa | agtcaaagct | actactgcct | ttcaatttct | 660 |
| gcaactgtat | tattcactcc | ttcaagagaa | cttgccactt | gaaggagaa | atagcattaa | 720 |
| ttttgaaaga | ctagaagctc | aactgaaggc | atgtcattgc | aggatcatat | tttctaaagc | 780 |
| aaagccttct | gtgttggcat | tgtctatcat | tgcattagag | atccaagcac | agaagtgtgt | 840 |
| agagttaaca | aaggaatag | aatgtcttca | gaaacattcc | aagataaatg | gcagagatct | 900 |
| gaccttctgg | caagagcttg | tatccaaatg | tttaactgaa | tattcatcaa | ataagtgttc | 960 |
| caaaccaaat | gttcagaagt | tgaaatggat | tgtttctggg | cgtactgcac | ggcaattgaa | 1020 |
| gcatagctac | tacagaataa | ctcaccttcc | aacaattcct | gaaatggtcc | cttaactgga | 1080 |
| ttattacagc | accaaaaaac | ttctctgaag | cctttctcca | caaccttgtt | ctatggattc | 1140 |
| cataatgtta | caatggattt | aagctatgaa | gcctcaaaac | atcacgagat | aagcatgatg | 1200 |
| gtctcagact | tgggaaaact | gcctaatatt | atgctgtagt | ggaattatgt | ttatgatttg | 1260 |
| aattcatctg | tgaaggcatt | caaatcaaag | ctaaaagcct | aaatgtgaaa | tgctaatgac | 1320 |
| aagcctgaga | aggtaaacta | tgaatcttca | tttctatcat | tgatctaact | ttagatattg | 1380 |
| gatcaatata | tttaggtggt | attgaaaatg | ctattggagg | agtcacacta | atactatcaa | 1440 |
| ctatcagtct | tcccacagct | tcaatcactg | tcattattct | aatcctactc | ctacttaaat | 1500 |
| tttaagttat | gaggtttatg | tcgaaagcaa | catttcacaa | atgtacttt | aaggcataat | 1560 |
| aagggttaac | attctagg | | | | | 1578 |

<210> SEQ ID NO 9
<211> LENGTH: 1776
<212> TYPE: DNA
<213> ORGANISM: Homo sapiens

<400> SEQUENCE: 9

| | | | | | |
|---|---|---|---|---|---|
| tttcatttcc | tcactgacta | taaaagaata | gagaaggaag | ggcttcagtg | accggctgcc | 60 |
| tggctgactt | acagcagtca | gactctgaca | ggatcatggc | tatgatggag | gtccaggggg | 120 |
| gacccagcct | gggacagacc | tgcgtgctga | tcgtgatctt | cacagtgctc | ctgcagtctc | 180 |
| tctgtgtggc | tgtaacttac | gtgtacttta | ccaacgagct | gaagcagatg | caggacaagt | 240 |
| actccaaaag | tggcattgct | tgtttcttaa | agaagatga | cagttattgg | gaccccaatg | 300 |
| acgaagagag | tatgaacagc | ccctgctggc | aagtcaagtg | gcaactccgt | cagctcgtta | 360 |

```
gaaagatgat tttgagaacc tctgaggaaa ccatttctac agttcaagaa aagcaacaaa      420
atatttctcc cctagtgaga gaaagaggtc ctcagagagt agcagctcac ataactggga      480
ccagaggaag aagcaacaca ttgtcttctc caaactccaa gaatgaaaag gctctgggcc      540
gcaaaataaa ctcctgggaa tcatcaagga gtgggcattc attcctgagc aacttgcact      600
tgaggaatgg tgaactggtc atccatgaaa aagggtttta ctacatctat tcccaaacat      660
actttcgatt tcaggaggaa ataaaagaaa cacaaagaa cgacaaacaa atggtccaat       720
atatttacaa atacacaagt tatcctgacc ctatattgtt gatgaaaagt gctagaaata      780
gttgttggtc taaagatgca gaatatggac tctattccat ctatcaaggg ggaatatttg      840
agcttaagga aaatgacaga attttttgttt ctgtaacaaa tgagcacttg atagacatgg     900
accatgaagc cagttttttc ggggcctttt tagttggcta actgacctgg aaagaaaaag      960
caataacctc aaagtgacta ttcagttttc aggatgatac actatgaaga tgtttcaaaa     1020
aatctgacca aaacaaacaa acagaaaaca gaaaacaaaa aaacctctat gcaatctgag     1080
tagagcagcc acaaccaaaa aattctacaa cacacactgt tctgaaagtg actcacttat     1140
cccaagagaa tgaaattgct gaaagatctt tcaggactct acctcatatc agtttgctag     1200
cagaaatcta gaagactgtc agcttccaaa cattaatgca atggttaaca tcttctgtct     1260
ttataatcta ctccttgtaa agactgtaga agaaagagca caatccatc tctcaagtag      1320 tgtatcacag tagtagcctc caggtttcct taagggacaa catccttaag tcaaaagaga     1380
gaagaggcac cactaaaaga tcgcagtttg cctggtgcag tggctcacac ctgtaatccc     1440
aacattttgg gaacccaagg tgggtagatc acgagatcaa gagatcaaga ccatagtgac     1500
caacatagtg aaaccccatc tctactgaaa gtacaaaaat tagctgggtg tgttggcaca     1560
tgcctgtagt cccagctact tgagaggctg aggcaagaga attgtttgaa cccgggaggc     1620
agaggttgca gtgtggtgag atcatgccac tacactccag cctggcgaca gagcgagact     1680
tggtttcaaa aaaaaaaaaa aaaaaaactt cagtaagtac gtgttatttt tttcaataaa     1740
attctattac agtatgtcaa aaaaaaaaaa aaaaaa                                1776

<210> SEQ ID NO 10
<211> LENGTH: 1172
<212> TYPE: DNA
<213> ORGANISM: Homo sapiens

<400> SEQUENCE: 10
gagacattcc tcaattgctt agacatattc tgagcctaca gcagaggaac ctccagtctc       60
agcaccatga atcaaactgc gattctgatt tgctgcctta tctttctgac tctaagtggc      120
attcaaggag tacctctctc tagaaccgta cgctgtacct gcatcagcat tagtaatcaa      180
cctgttaatc caaggtcttt agaaaaactt gaattattc ctgcaagcca attttgtcca       240
cgtgttgaga tcattgctac aatgaaaaag aagggtgaga agagatgtct gaatccagaa      300
tcgaaggcca tcaagaattt actgaaagca gttagcaagg aaatgtctaa aagatctcct      360
taaaaccaga ggggagcaaa atcgatgcag tgcttccaag gatggaccac acagaggctg      420
cctctcccat cacttcccta catggagtat atgtcaagcc ataattgttc ttagtttgca      480
gttacactaa aaggtgacca atgatggtca ccaaatcagc tgctactact cctgtaggaa      540
ggttaatgtt catcatccta agctattcag taataactct accctggcac tataatgtaa      600
gctctactga ggtgctatgt tcttagtgga tgttctgacc ctgcttcaaa tatttccctc      660
acctttccca tcttccaagg gtactaagga atctttctgc tttgggtttt atcagaattc      720
```

```
tcagaatctc aaataactaa aaggtatgca atcaaatctg cttttaaag aatgctcttt      780 acttcatgga cttccactgc catcctccca aggggcccaa attctttcag tggctaccta      840
catacaattc caaacacata caggaaggta gaaatatctg aaaatgtatg tgtaagtatt      900
cttatttaat gaaagactgt acaaagtata agtcttagat gtatatattt cctatattgt      960
tttcagtgta catggaataa catgtaatta agtactatgt atcaatgagt aacaggaaaa     1020
ttttaaaaat acagatagat atatgctctg catgttacat aagataaatg tgctgaatgg     1080
ttttcaaata aaaatgaggt actctcctgg aaatattaag aaagactatc taaatgttga     1140
aagatcaaaa ggttaataaa gtaattataa ct                                    1172

<210> SEQ ID NO 11
<211> LENGTH: 3302
<212> TYPE: DNA
<213> ORGANISM: Homo sapiens

<400> SEQUENCE: 11
ttgtttgatt actgtggctt ttctttacct acaacccaag cctgacgtcc ctcggtttta       60
aatagcaggg agagggaat caatgtttga ttcaggtgtt tcgaagacca cgccacaggc      120
gatgagcaga actcttcatg ttgaaacggt tctgctacag tactagattg ctctcaggcg      180
atttggggtt gatacaggca agccggtgca aaactggaat actggatatg aagtgaaatg      240
tataaaagac ataaatgtca caaaatagtt tgatcacaag tgttgatttt cctggtgagt      300
tggggctgcg tgtttccatg ttttctgaag gttcacataa acatgcagcc tgccaattct      360
ctgtacattt ttttttttca atgagtggta tttcggtttt cacgtttagt tgtaagacag      420
aaattggaga cttatatgta gctggagtgg atgacttctt tcttttgggg gaagaatgag      480
agatgcacat tcgttagta aattgtgaac aacttgaaac aaacccaaat ccaattttga      540
atttaagaag tagagttaaa atgaaaggta gccattcaaa tactatgcct tgctgccttc      600
acttattaag ttaggatttt cttcctttta gcccttagg gatacagtag tttaaaagag      660
cagtagccac atatgaaagg atcagattta gcttagaggg aattccttag accagccctg      720
ctgttaagac ttgacattca atattgtttg atcacattcc aaaatatagc ttagctaatg      780
gcaacatttg taaacatata aattgcaaaa gaagctttct tgtgtacata cattttaaa      840 agcttgaaat tgatgtgaac ttttaaaaac acgtaggatc tgtattacat tctacatctc      900
aaaacaaatt taattaaagt gaatatcatt ccagtatata caatatgcct aagacccaga      960
attggcacat tgatttacta gttgaaaata taacagtatt caccaaactt caatgtatac     1020 ttttttggaga gaatgaaatt acagtatttc ttaatttact gtaatgtcat ctttgtaatt     1080
atgaactaac aattcaatga gaggagactt ggctgattaa attaatgctg gtcctacaca     1140
ttatatctaa aggatcttcg tatatgacta ctatcctctt ggattatttt aacagttaaa     1200
atatacaaag tggcccatta aaaacagagt tgacttttca ccattgctgt ttttctggtg     1260
agacatgtgg aaaggaagga caggtggact tttcaactaa ctagctctct gattttaat     1320 aagataccctc agttcttttg gcctcagttt acttatctgt acaaagggta agtcatatgc     1380
ttaatcacta agatctgtta gatactgcag ttaagattct ttatcagcaa attactgaac     1440
tctagtgtta acatagctag aggtggaaaa gggagcaaga ccaggtgttg ggatgaataa     1500
ttaactaatc gagataacat cagttttcac cataggaaca agtaccatgg ttgctcttaa     1560
agtaagagat gtttcctatt ttatgtaatt ttactaaggg atagtgtttt cttttgtcac     1620
```

```
tgacttaaat gtacctggat gtttctcagc catttggcta agatcgaaca caagtaatac    1680
ctgggccttt tatatctaat ctaatgtaga ccagcctgtt aaaagagaaa gacaattggt    1740
taaactgctg atgtgttgct ttgtcttctc aaaagcttgt tctataatac aatatgtaaa    1800
aagttgttac agtgtagtaa ccgtagataa tcccttttatg atttgtacct aatggcgaag    1860
accttttatt ttctgaaaat aacgtgtttg ttttcattac cgacattaga agccaatatt    1920
tattaatcta tttctcatcc tgacatttca gtcagactct taaaataatc ttgctgtgtt    1980
ttgatttaat gtgcttatca acttataata ttgaattaat gttaatagtg tcattttagg    2040
tgaactagac ttcattgaag gaggtgggag cctttatggag agagagtata tgattatctc    2100
tatttgtatt taattaccat ttcatctaac cattcagaac atatttcaag aataatttta    2160
attcaagttg tagataaaac ttactatacc attttcattt tgacgctttc caagaatgag    2220
atacacggta ttttaaagac aaagattgat cttacatgtt actattaaaa aaaacacgat    2280
aattttgttc tacattttata cttttaattt ttctgtggat aataagaaat gccaagagtc    2340
gattgtgtcc atgctggcaa gtggcctaat aaattgtcct tttatttggt ggtcctcaga    2400
gtggcagtta acatcttgct attctgcctt gtggacttga ggtggaaagg ttcatggaat    2460
tatatccttg cttttggatg tgcaaactga ggctcagaga gtttaagaca catagtcact    2520
ttcaccaatt aaatgatgaa gctgccatgt aaacgtattt catcacactc ccgagacctt    2580
cttctccagt agtgttttca agcttttga gcatgcagac actaccatca aaaaattatg    2640
tagagacata cttgagagtt acagtttaaa gaaaaaacaa ggtgtaatta tttggttatt    2700
agtagcattt acatatgctt gaaaacttct gctatatata cagtaagatt aatttattct    2760
aacaatgatc ttgataatcc ccctgattcc cagactcctt ggaatagctc cacagctatc    2820
agtggttctg ccacaggttc agagccttcc cagtactgcc ttcttatttg agaggtgtgc    2880
taagagctat aaagcagagg cttcaattgt acacagtttg gaagtttagg caaaagtcat    2940
ttcttcccta tattttgtca tgcttatctc ctgtctcttt ctgttttaca gattagcaat    3000
aaactcctta aaacccaaag gtttgggctt ctgttccttt cacttgcagt cagacatgga    3060
gttagtggta gaagaaacag aagggtaac ctgcatggtg acagctactg aggggatgga    3120
taggaaagca ggctgagtcc ccggggccag tggttaccaa agccaaggag agagcaaggg    3180
gagcccagtg ggcctggcca tggactgctc tggaattccg agtgtgaact ttcagccaag    3240
aaggtagtgt gaaatatta ctgtgaggtt ttaaaagtac acaaataaca attgtttttt    3300
gt                                                                  3302
```

<210> SEQ ID NO 12
<211> LENGTH: 2943
<212> TYPE: DNA
<213> ORGANISM: Homo sapiens

<400> SEQUENCE: 12

```
tgagagaccg tgttgcaatg ttccgttcag cttggtgtca atggcctgtg tccacctggc      60
ttccaagata gaagaggccc caagacgcat acgggacgtc atcaatgtgt ttcaccgcct     120
tcgacagctg agagacaaaa agaagcccgt gcctctacta ctggatcaag attatgttaa     180
tttaaagaac caaattataa aggcggaaag acgagttctc aaagagttgg gtttctgcgt     240
ccatgtgaag catcctcata agataatcgt tatgtacctt caggtgttag agtgtgagcg     300
taaccaacac ctggtccaga cctcatgggt agccctgag ggtaagtgac taagacttct     360
cctctgctgt ccaagcgctt tggtgcaggg acagcggcat cttcagccaa tccagtgcag     420
```

-continued

| | |
|---|---|
| gctctccacc gaaggctggc tctagactgg ttggcagcgg ctctgatgag cccgagaaga | 480 |
| ggcctgactc cttgggtgcg gagtctccct ccgcacgatg ctcccacgcg tccaacttgc | 540 |
| acccaagcgg gctttggtcc ctcttccaag tggactcctt caaggaagct gcagctcggt | 600 |
| cagcagagaa ggggcctgcc gccagcgccc tggaggaaga ggaagaggaa cccaagagga | 660 |
| tggcttgtct cccagcagcc acaccggctt tgtgctcagc cagttcattt gagtttgcat | 720 |
| gtttctctgc actatggatt tgagcattt agatttcttt aatcaaaagc gttttagtga | 780 |
| ctccagtaga cattttcttt ctgaggcatc gtgctttgca tgagagcagg ccaaggttga | 840 |
| ggggaaaagt aaagttaaag tcggttctct ttcatagcaa cacgtattgt ctgacattca | 900 |
| gccagctttt ttttttttct aataatttct gtgcctttct gtcctgtatt tactgtattt | 960 |
| agaaaaagca gctagaatat ttctccatta actcttgaga ttcacaggac tgtctagctc | 1020 |
| tgagtcctag caatagactc cttagaggag tagtacgttt atctagattt tctctagata | 1080 |
| atgcaggcgg aagacctggg ttcccgggtg gggcattgca gttcttcctg tgtttggctt | 1140 |
| ccaggaatta catgaacgac agccttcgca ccgacgtctt cgtgcggttc cagccagaga | 1200 |
| gcatcgcctg tgcctgcatt tatcttgctg cccggacgct ggagatccct ttgcccaatc | 1260 |
| gtccccattg gtttcttttg tttggagcaa ctgaagaaga aattcaggaa atctgcttaa | 1320 |
| agatcttgca gctttatgct cggaaaaagg ttgatctcac acacctggag ggtgaagtgg | 1380 |
| aaaaagaaa gcacgctatc gaagagcaag gcccaagccc ggggcctgtt gcctgggggc | 1440 |
| acacaggtgc tggatggtac ctcggggttc tcccatgtca gtggtctcaa tgtattgact | 1500 |
| ttgtgatcgc cctcctcggc gctatctggg atcactgcaa gctccgccta ccagattctg | 1560 |
| gtgattcttg tgcctcagcc tcccaagtag ctgggattgc aggcgcccac caccacgctc | 1620 |
| agagtctcgc tgtgttgcca gtggaatccc ccaagaagg taagggagc aagccttccc | 1680 |
| cactgtctgt gaagaacacc aagaggaggc tggagggcgc caagaaagcc aaggcggaca | 1740 |
| gccccgtgaa cggcttgcca aaggggcgag agagtcggag tcggagccgg agccgtgagc | 1800 |
| agagctactc gaggtcccca tcccgatcag cgtctcctaa gaggaggaaa agtgacagcg | 1860 |
| gctccacatc tggtgggtcc aagtcgcaga gccgctcccg gagcaggagt gactccccac | 1920 |
| cgagacaggc ccccgcagc gctccctaca aaggctctga gattcgggc tcccggaagt | 1980 |
| ccaaggactg caagtacccc cagaagccac acaagtctcg gagccggagt tcttcccgtt | 2040 |
| ctcgaagcag gtcacgggag cggcggata atccgggaaa atacaagaag aaaagtcatt | 2100 |
| actacagaga tcagcgacga gagcgctcga ggtcgtatga acgcacaggc cgtcgctatg | 2160 |
| agcgggacca ccctgggcac agcaggcatc ggaggtgagg cggggttgca gtgactggtg | 2220 |
| gccgcaagcc cttccctggg gagtacctga tggctgccct ttgaccccg gtggctgccc | 2280 |
| tttgaccccc gggtgtgctc tcagcgcaag tggtcctaga acaggattct ttttggaaat | 2340 |
| gtctgtcgac tggaccttgg tggatttgga aatggaactg agggaccggt gacacgtgct | 2400 |
| tcagaccggt ctgggtgcg gcgcacacct gggcccgtgc agggctcagc tcggcagcag | 2460 |
| ctctgagggc agctcaatga aaaagtgaat gcacacgccc ttgttggcgt ggcctggcat | 2520 |
| ggcctggtgc tatcggcagc cgctctccac tcccgactg atactcaatt acgtgaagcc | 2580 |
| aagaaagatg atttttagaa cctttgccta tattaggttg tacttatgta catattttgc | 2640 |
| agtgttttcac aggagaaagt ggccttaact gccccttatt ctctctccac gttgtaaata | 2700 |
| aacatgtgtt taatacaagt taaagctatg tatgaaaact cagaacttga atcccgtcag | 2760 |

```
cttaaaacttt gtgtagggaa tcctgacttt taaaatgtga gggtatttgg atctgtgttg      2820
aaagtcgtat attttatct gtgcggtgct gagtgcaggc caccagctcc taaatagagg       2880
ttccctatat gcgcgtatga catggtgaat aaacacaact ctctccacca aaaaaaaaa       2940 aaa                                                                    2943
```

<210> SEQ ID NO 13
<211> LENGTH: 397
<212> TYPE: DNA
<213> ORGANISM: Homo sapiens
<220> FEATURE:
<221> NAME/KEY: misc_feature
<222> LOCATION: (1)..(397)
<223> OTHER INFORMATION: n is a, c, t, or g.

<400> SEQUENCE: 13

```
aattaatata nnnntgaaac aatttggtaa tgcagactgg gacaatgtca ctatacccac      60
tgaggtaact gagacatgag agctttccaa cccaaggtca gaaatcactg aaacagctta    120
tgaaaccctc actattttag tgttttaaat tcagaatgct gtattttct cttgggcaac     180 agataacctt cattttgac gtaaatgata atggtggctt cacatggccc agggcaaact    240
tcaaaacaaa actgtaggga ccacatttt ctaacctgga aaataagtca tataagggt     300 ccaaataagg gtaaaatttg ggaatttaat tattcctggg gggaaaatat tgtgggggta    360
tccctggtat cctngggccc ggtaatcccg ggtttta                              397
```

<210> SEQ ID NO 14
<211> LENGTH: 323
<212> TYPE: DNA
<213> ORGANISM: Homo sapiens
<220> FEATURE:
<221> NAME/KEY: misc_feature
<222> LOCATION: (1)..(323)
<223> OTHER INFORMATION: n is a, c, t, or g.

<400> SEQUENCE: 14

```
gagtttaata ggccagacag aagggagaag gcagaaggaa gaagctcccc cgtacagaga    60
cagagggagg gaggctccaa agccaagaga agggatcccc aagtgcggtg gacaccagcc   120
aggtatatat gcagaggctg gagaaggtgg tnttcgattt gcatagggct ccggggattg    180
ggttgactag gcgcatcatt cacatagctc atgaaaaagc tggctcttcc accctgggnc    240
ttttaatatg caaatacatg ggcgccatga tgttctacgc tcgtcgggat tccnggggac    300
atgtaggggc aagggcaaga agg                                           323
```

<210> SEQ ID NO 15
<211> LENGTH: 497
<212> TYPE: DNA
<213> ORGANISM: Homo sapiens
<220> FEATURE:
<221> NAME/KEY: misc_feature
<222> LOCATION: (1)..(497)
<223> OTHER INFORMATION: n is a, c, t, or g.

<400> SEQUENCE: 15

```
gtgggcagaa gaaagtcata atttctgaag ataacaaatg cagcacagaa gtggaatagg    60
gccatgaata cctgaaaaca ctaacgttct tttttcctgt ggatttatgc atggagggct   120
tcgtataatg acttggtact accactgcta ttaggaacca ttggaattct gtgataattt    180
tggattgctt tttaattcac caagactact gtggatgatg tcagccacat tatggtgtga    240
gccctaaatt taaggtcaat atcatgtgct accttcatat ctggtgatac tagtattacc    300
```

```
tcaaatggtc tgagtacaaa tccccttcc cactctgctc ttttgtataa tgtgtcctag      360
cctaactacc ctttaaatca agaggactaa gcagagttnc ccgtttatta tttatttgta    420
ggcaagtttn gaatttcatt nctacacaca gagtttattt caaacaagcc gttacagctg    480
ggtgtgggtg tcgcaca                                                   497

<210> SEQ ID NO 16
<211> LENGTH: 317
<212> TYPE: DNA
<213> ORGANISM: Homo sapiens

<400> SEQUENCE: 16
ttaataggaa agtaaagagc actttcccca aacagcaaga acaaaatcgc tttctcttaa     60
cacattgatt tatttcattt gctaagcaca ggaaccatga aatgcttcat cccattagca    120
cattaaatat gtgcagaagt aaaattacag ctgaacagca ccttgtactt tgtactcatg    180
gtgtgtacat ttcagtaggc taggaggaaa aaacgaactg tagaaagata attttatggg    240
aattaaatta cctgttttgt attgctctga agctgtgcat gtaggctgtg ggatttcaga    300
gggacttgaa ctgttgc                                                   317

<210> SEQ ID NO 17
<211> LENGTH: 2596
<212> TYPE: DNA
<213> ORGANISM: Homo sapiens

<400> SEQUENCE: 17
ggcacgaggc cgggctcgcc gcgccgcgcc cgcgcgtcct tagcggggcc accgagcgat      60
gcccgccggg cgcccgcgaa agtttgtcgg ctcctgctga agggcagcgg cgcccccgca    120 ccccgtgcc ccgctccggc caggagcctt cacgtaaatg ggtccagtca tgcctcccag    180
taagaagcca gaaagctcag gaattagtgt ctccagtgga ctgagtcagt gttacggggg    240
cagcggtttc tccaaggccc ttcaggaaga cgatgacctc gacttttctc tgcctgacat    300
ccgattagaa gaggggccca tggaagatga agagctgacc aacctgaact ggctgcacga    360
gagcaagaac ttgctgaaga gctttgggga gtcggtcctc aggagtgtca gccccgtcca    420
ggacctggac gatgacaccc ccccatcccc tgcccactct gacatgccct acgatgccag    480
gcagaacccc aactgcaaac ccctactc cttcagctgc ctcatatta tggccatcga     540 ggactctcca accaagcgcc tgccagtgaa ggatatctac aactggatct ggaacatttt    600
tccgtatttt gcaaatgcac ctactgggtg aaaaactca gtgagacaca atttatcatt    660
gaataagtgt tttaagaaag tggacaaaga gaggagtcag agtattggga aagggtcgtt    720
gtggtgcata gacccagagt atagacaaaa tctaattcag gctttgaaaa agacacctta    780
tcacccacac ccacacgtgt tcaatacacc tcccacctgt cctcaggcat atcaaagcac    840
atcaggtcca cccatctggc cgggcagtac cttcttcaag agaaatggag cccttctcca    900
agttcctcca ggagtgatcc aaaatggagc gcggtcctg agccgagggc tgtttcctgg    960
cgtgcggccg ctgccaatca ctcccattgg ggtgacagcg gccatgagga atggcatcac   1020
cagctgccgg atgcggactg agagtgagcc atcttgtggc tccccagtgg tcagcggaga   1080
ccccaaggag gatcacaact acagcagtgc caagtcctcc aacgcccgga gcacctcgcc   1140
caccagcgac tccatctcct cctcctcctc ctcagccgac gaccactatg agtttgccac   1200
caaggggagc caggagggca gcgagggcag cgaggggagc ttccggagcc acgagagccc   1260
```

```
cagcgacacg gaagaggacg acaggaagca cagccagaag gagcccaagg attctctggg    1320
ggacagcggg tacgcatccc agcacaagaa gcgccagcac ttcgccaagg ccaggaaggt    1380
ccccagcgac acactgcccc tcaaaaagag acgcaccgaa aagcccccg agagcgatga    1440 tgaggagatg aaagaagcgg cagggtccct cctgcactta gcaggatcc ggtcctgttt    1500 gaataacatc accaatcgga cggcaaaggg cagaaagag caaaaggaaa ccacaaaaaa    1560
ttaaaaacaa gtcactgatt tgttttgaac ttacgaccat ttggtttcag catgtcagga    1620
gatttctaat gatttgtggc aatatcagca attttttttc tttttcttg tttttggttt    1680 ggttttcttt cttttctttt ccttttattt tgttttaatt tgcccctct tctttgtttt    1740 ggacccttaa gaattttatt tttaaaggag attgaagcca tagaactcat attgacactc    1800
agctgtttta caaaagcttt tcattatctg aagacaaaac cgaaaagcc aaaattacca    1860 ttgcttcctc cagcttgtca gaaacctgtg gctgaatccg cagggatgtc aacgtcaata    1920
tcacaggaac acacattcgg cacctagaag gcacgtgggc aaagtaatca tcgttcaggc    1980 ccaacccta ggtttaaaaa gtcaggttgt ccatcccatt gggttcactg agtgaaggca    2040
cataaagcaa ttgaggagga ggaggaaccc ctcgtccccc taggagcaga cccaagcttg    2100
tggcaccagg catctgatgg tgccaggaaa gccactggaa ttgtcacacg gcgagcacag    2160
agggccggcc accagtcctc gatgcttctg aaccctgaag cccgatgaca tcttacgagg    2220
tggacgttgg actgttcatg cgcatcgggt gtcagtgact catggagaag aaatggggta    2280 aattttagt gatgttgcta atcattgaat tctgttctct attaaattaa gaaaatgttc    2340
caaaagccat aagcctgaag attggccctg tgcacgcacg cacacacaca cacacaca    2400 cacacacaca cacacaca cgaaggagag agagagaaaa ctgatgggga aaacaagctg    2460
tgtcttctta actgcccaag tgaaaagcaa ccaagtccag gaaattacaa tagctgttaa    2520
ggaaaggaaa taatggtaca gatcttttc tgtctatcaa aactatttga tccaagtgaa    2580
aaaaaaaaaa aaaaaa                                                      2596
```

<210> SEQ ID NO 18
<211> LENGTH: 2919
<212> TYPE: DNA
<213> ORGANISM: Homo sapiens

<400> SEQUENCE: 18

```
catccttgga tgatgaagga gatactcaaa acatagattc atggtttgag gagaaggcca     60
atttggagaa taagttactg gggaagaatg gaactggagg gcttttcag ggcaaaactc     120 ctttgagaaa ggctaatctt cagcaagcta ttgtcacacc tttgaaacca gttgacaaca     180
cttactacaa agaggcagaa aaagaaaatc ttgtggaaca atccattccg tcaaatgctt     240
gttcttccct ggaagttgag gcagccatat caagaaaaac tccagcccag cctcagagaa     300
gatctcttag gctttctgct cagaaggatt tggaacagaa agaaaagcat catgtaaaaa     360
tgaaagccaa gagatgtgcc actcctgtaa tcatcgatga aattctaccc tctaagaaaa     420
tgaaagtttc taacaacaaa aagaagccag aggaagaagg cagtgctcat caagatactg     480
ctgaaaagaa tgcatcttcc ccagagaaag ccaagggtag acatactgtg ccttgtatgc     540
cacctgcaaa gcagaagttt ctaaaaagta ctgaggagca agagctggag aagagtatga     600
aaatgcagca agaggtggtg gagatgcgga aaagaatga agaattcaag aaacttgctc     660
tggctggaat agggcaacct gtgaagaaat cagtgagcca ggtcaccaaa tcagttgact     720
tccacttccg cacagatgag cgaatcaaac aacatcctaa gaaccaggag gaatataagg     780
```

-continued

```
aagtgaactt tacatctgaa ctacgaaagc atccttcatc tcctgcccga gtgactaagg      840
gatgtaccat tgttaagcct ttcaacctgt cccaaggaaa gaaagaaaca tttgatgaaa      900
cagtttctac atatgtgccc cttgcacagc aagttgaaga cttccataaa cgaacccta       960 acagatatca tttgaggagc aagaaggatg atattaacct gttaccctcc aaatcttctg     1020
tgaccaagat ttgcagagac ccacagactc ctgtactgca aaccaaacac cgtgcacggg     1080
ctgtgacctg caaaagtaca gcagagctgg aggctgagga gctcgagaaa ttgcaacaat     1140
acaaattcaa agcacgtgaa cttgatccca gaatacttga aggtgggccc atcttgccca     1200
agaaaccacc tgtgaaacca cccaccgagc ctattggctt tgatttggaa attgagaaaa     1260
gaatccagga gcgagaatca aagaagaaaa cagaggatga acactttgaa tttcattcca     1320
gaccttgccc tactaagatt ttggaagatg ttgtgggtgt tcctgaaaag aaggtacttc     1380
caatcaccgt ccccaagtca ccagccttg cattgaagaa cagaattcga atgcccacca     1440
aagaagatga ggaagaggac gaaccggtag tgataaaagc tcaacctgtg ccacattatg     1500
gggtgccttt taagcccaa atcccagagg caagaactgt ggaaatatgc cctttctcct     1560
ttgattctcg agacaaagaa cgtcagttac agaaggagaa gaaaataaaa gaactgcaga     1620
aaggggaggt gcccaagttc aaggcacttc ccttgcctca ttttgacacc attaacctgc     1680
cagagaagaa ggtaaagaat gtgacccaga ttgaaccttt ctgcttggag actgacagga     1740
gaggtgctct gaaggcacag acttggaagc accagctgga agaagaactg agacagcaga     1800
aagaagcagc ttgtttcaag gctcgtccaa acaccgtcat ctctcaggag ccctttgttc     1860
ccaagaaaga gaagaaatca gttgctgagg gcctttctgg ttctctagtt caggaacctt     1920
ttcagctggc tactgagaag agagccaaag agcggcagga gctggagaag agaatggctg     1980
aggtagaagc ccagaaagcc cagcagttgg aggaggccag actacaggag gaagagcaga     2040 aaaagagga gctggccagg ctacggagag aactggtgca taaggcaaat ccaatacgca     2100
agtaccaggg tctggagata aagtcaagtg accagcctct gactgtgcct gtatctccca     2160
aattctccac tcgattccac tgctaaactc agctgtgagc tgcggatacc gcccggcaat     2220
gggacctgct cttaacctca aacctaggac cgtcttgctt tgtcattggg catggagaga     2280
acccatttct ccagactttt acctacccgt gcctgagaaa gcatacttga caactgtgga     2340
ctccagtttt gttgagaatt gttttcttac attactaagg ctaataatga gatgtaactc     2400
atgaatgtct cgattagact ccatgtagtt acttccttta aaccatcagc cggcctttta     2460
tatgggtctt cactctgact agaatttagt ctctgtgtca gcacagtgta atctctattg     2520
ctattgcccc ttacgactct caccctctcc ccacttttt taaaaatttt aaccagaaaa     2580
taaagatagt taaatcctaa gatagagatt aagtcatggt ttaaatgagg aacaatcagt     2640
aaatcagatt ctgtcctctt ctctgcatac cgtgaattta tagttaagga tcccttgct      2700 gtgagggtag aaaacctcac caactgcacc agtgaggaag aagactgcgt ggattcatgg     2760
ggagcctcac agcagccacg cagcaggctc tgggtgggc tgccgttaag gcacgttctt      2820
tccttactgg tgctgataac aacagggaac cgtgcagtgt gcattttaag acctggcctg     2880
gaataaatac gttttgtctt tccctcaaaa aaaaaaaaa                            2919
```

<210> SEQ ID NO 19
<211> LENGTH: 3526
<212> TYPE: DNA
<213> ORGANISM: Homo sapiens -continued

```
<400> SEQUENCE: 19
ccacgcgtcc ggacaggctt aagcatggcc aagaagcttg agagaagaaa aatttcagaa      60
aaattgtctc aatttgacta gaatatcaat gaaccaggaa aactgaagca ccttccctaa     120
agaaaacttg ggtatacaat tactccacag acagagctga gggtttttta cccaaatcag     180
tcactggatt ttgctgcctg atacgtgaat cttcttggaa tttttctcat gtggatctaa     240
ggggaatgct ttattatggc tgctgttgtc aacagaacg acctagtatt tgaatttgct      300
agtaacgtca tggaggatga acgacagctt ggtgatccag ctattttttcc tgccgtaatt    360 gtggaacatg ttcctggtgc tgatattctc aatagttatg ccggtctagc ctgtgtggaa     420
gagcccaatg acatgattac tgagagttca ctggatgttg ctgaagaaga aatcatagac     480
gatgatgatg atgacatcac ccttacagtt gaagcttctt gtcatgacgg ggatgaaaca     540
attgaaacta ttgaggctgc tgaggcactc ctcaatatgg attcccctgg ccctatgctg     600
gatgaaaaac gaataaataa taatatattt agttcacctg aagatgacat ggttgttgcc     660
ccagtcaccc atgtgtccgt cacattagat gggattcctg aagtgatgga acacagcag      720 gtgcaagaaa aatatgcaga ctcaccggga gcctcatcac cagaacagcc taagaggaaa     780
aaaggaagaa aaactaaacc accacgacca gattccccag ccactacgcc aaatatatct     840
gtgaagaaga aaacaaaga tggaaaggga acacaatttt atctttggga gtttttactg      900
gcactgctcc aggacaaggc tacttgtcct aaatacatca agtggaccca gcgagagaaa     960 ggcatttttta aattggtgga ttctaaagca gtgtccaggt tgtgggggaa gcacaaaaac    1020
aaacctgata tgaattatga gaccatggga agagcactca ggtactatta ccaaaggggt    1080
attctggcaa aagtggaagg tcagcgcttg tgtatcagt ttaaagaaat gccaaaagat     1140
cttatatata taaatgatga ggatccaagt tccagcatag agtcttcaga tccatcacta    1200
tcttcatcag ccacttcaaa taggaatcaa accagccggt cgagagtatc ttcaagtcca    1260
ggggtaaaag gaggagccac tacagttcta aaaccaggga attctaaagc tgcaaaaccc    1320
aaagatcctg tggaagttgc acaaccatca gaagttttga ggacagtgca gcccacgcag    1380
tctccatatc ctacccagct cttccggact gttcatgtag tacagccagt acaggctgtc    1440
ccagagggag aagcagctag aaccagtacc atgcaggatg aaacattaaa ttcttccgtt    1500
cagagtatta ggactataca ggctccaacc caagttccag tggttgtgtc tcctaggaat    1560
cagcagttgc atacagtaac actccaaaca gtgccactca caacagttat agccagcaca    1620
gatccatcag caggtactgg atctcagaag tttatttttac aagccattcc atcatcacag    1680
cccatgacag tactgaaaga aaatgtcatg ctgcagtcac aaaaggcggg ctctcctcct    1740
tcaattgtct gggccctgc ccaggttcag caggtcctta ctagcaatgt tcagaccatt     1800
tgcaatggaa ccgtcagtgt ggcttcctct ccatccttca gtgctactgc acctgtggtg    1860
accttttctc ctcgcagttc acagctggtt gctcacccac ctggcactgt aatcacttca    1920
gttatcaaaa ctcaagaaac aaaaactctt acacaggaag tagagaaaaa ggaatctgaa    1980
gatcatttga aagagaacac tgagaaaacg gagcagcagc cacagcctta tgtgatggta    2040
gtgtccagtt ccaatggatt tacttctcag gtagctatga acaaaacga actgctggaa     2100 cccaactctt tttagttaat ataccaaagc ttatgaataa ttgtttgtta attgaacatt    2160
ttcaattata tgcagactga ctgattctaa gataaattct aaggaggttt ctaatttgt     2220 aattgttaaa aatagagtta attttgactt tgttagatga gggaggaaaa ctcaactgtt    2280
tctctttgtt atctaaatgt ttcagaattc aatcgtgaag gaacaggcat tttacactat    2340
```

```
gaagacattc ttttgagatt tttatttcag ttgctatatc ataagcattt ttaaagtttc    2400
ttttctaatt ttacattgta ttagattttc tgattctttt gtaaatacag aacttaaata    2460
gaaggcaaca ggaaatttat ataggaacta ttttcattcc acttgtgtaa gttaagtctt    2520
gactctttca aatgcaaaaa acctatttta tgctttgtta aaattatggt gtcacttaga    2580
ttgactttag ttgactgcac tatataatat agaactatga atatgtagaa taacatgaaa    2640
aattggaggt gctggtggta tggctgaccc tgtttcagaa gcaggatagt ataaaagcat    2700
cagcctaaga atggcactcc cactaactag ctatgtaatc ttgacctctt tgggctttag    2760
ttcctctcat aaaaggaaga gatgtattgg attagactag attatcacca ctttctcttc    2820
tagttctaat ttttttaatt ctaataccta tattttcaag ttatgtcaat taaatcatta    2880
tcaggttatt tcctaatgta agaatagcta aaatgttgca gagaaataag tgacccaaca    2940
aaatttattc atctgttatg ggtaagatct gccataaatt cttcctaaat aatttgttta    3000
ctaactcttt aggccactgt gctttgcggt ccattagtaa acttgtgttg ctaagtgcta    3060
aacagaatac tgctattttg agagagtcaa gactctttct taagggccaa gaaagcaact    3120
tgagccttgg gctaatctgg ctgagtagtc agttataaaa gcataattgc tttatatttt    3180
ggatcatttt ttactggggg cggacttggg ggggttgca tacaaagata acatatatat    3240
ccaactttct gaaatgaaat gttttttagat tactttttca actgtaaata atgtacattt    3300
aatgtcacaa gaaaaaatg tcttctgcaa attttctagt ataacagaaa ttttttgtaga    3360 tgaaaaaaat cattatgttt agaggtctaa tgctatgttt tcatattaca gagtgaattt    3420
gtatttaaac aaaaatttaa attttggaat cctctaaaca tttttgtatc tttaattggt    3480
ttattattaa ataaatcata taaaaattct caaaaaaaaa aaaaa    3526

<210> SEQ ID NO 20
<211> LENGTH: 5441
<212> TYPE: DNA
<213> ORGANISM: Homo sapiens

<400> SEQUENCE: 20
ccacgcgtcc gcggacgcgt gggccgggag accctgacat atgcccaggc ccagcggatt      60
gtcgaggtag acattgatgg acgcctgcat cgtatcagca tctatgaccc actcaaaatc     120
attactgaag atgagctaac tgcccaggat atcaccgaat gcaatagtaa caaggaaaac     180
agtgaacagc tcagttccc tggcaagtcc aagaaaccct catccaaggg caaaagaag     240 gaatcctgct ccaagcatgc atctggtact tccttccacc tcccacagcc cagcttccgt     300
atggtggact caggcatcca gccagaagca ccccgctgc tgctgccta ctaccgctac     360 attgagaagc cacctgaaga cctggatgca gaggtagagt atgacatgga tgaggaggac     420
cttgcctggc tggacatggt gaatgaaaaa cggcgagtag atgggcacag tttggtgtct     480
gcagatacct ttgagctgct ggtagaccgg cttgagaaag agtcatactt ggagagtcgc     540
agcagtgggg cccaacagtc actcatcgat gaagacgctt tctgctgtgt gtgcctggat     600
gatgaatgtc acaatagcaa tgttattctc ttctgtgaca tctgcaacct ggctgtacac     660
caggagtgct atggcgtccc atacatccct gagggccagt ggctatgccg ctgctgcctg     720
cagtctccct cccggcctgt ggattgcatc ctttgcccca ataagggtgg cgccttcaaa     780
cagaccagtg atgggcactg ggcccatgtg gtgtgtgcca tctggatccc tgaagtctgc     840
tttgctaaca ccgtgttctt ggaacctatt gagggcattg acaatatccc gcctgcccgc     900
```

```
tggaaactaa cctgctatat ctgcaagcag aaagggctag gtgcagccat ccagtgccat      960
aaggtgaact gctacacagc attccatgtg acatgtgcac agcgggctgg gctcttcatg     1020
aagattgagc ccatgcgcga aaccagcctc aatggcacca tctttacagt gcgcaagact     1080
gcctactgtg aggcccactc gccaccaggt gcggccactg ctaggaggaa gggcgactcc     1140
cctagaagca tcagtgagac tggcgatgag aagggctga aggagggtga tggagaggag      1200
gaagaagagg aagaggtgga ggaagaagag caggaagctc aaggcggggt gagtggctcc     1260
ctcaagggag tgcccaagaa aagcaagatg agtttgaagc agaagatcaa gaaggagcca     1320
gaggaagcag gccaagacac accctccact ctccccatgc ttgctgtccc acagataccc     1380
tcttacaggt tgaacaagat ctgtagtggt ctctcctttc agaggaaaaa ccagtttatg     1440
cagcggcttc acaattattg gctgttgaag cggcaggcac ggaatggtgt ccctcttatc     1500
cggcgcttgc actcccatct gcagtcccaa agaaacgctg agcagcgaga gcaggatgag     1560
aagacaagtg cagtgaagga ggagctgaag tattggcaga agctccggca tgacttggag     1620
cgggcgcggc tgctgattga gctgattcgg aagagagaga agctcaaacg agagcaggtc     1680
aaagtccagc aggctgccat ggagctggag ctgatgccat tcaatgttct gttgaggaca     1740
acactggacc tgctgcagga gaaggatcct gcacacatct tcgcagaacc agtcaacttg     1800
agtgaggttt tatatgttta ggttccagat tacctggaat tcatatccaa gccaatggat     1860
ttttctacta tgaggcggaa gctggagtcc cacctgtacc gcaccttgga ggagtttgag     1920
gaggacttta accttatagt taccaactgc atgaagtata atgctaaaga cacaatttc      1980 caccgagcag ctgtccgcct gcgggacctg ggaggggcca tcctacggca cgcccggcgg     2040
caggcagaga acatcggcta tgaccccgag agggggcactc acctgcccga gtcacccaaa    2100
ttggaagact tttaccgctt ctcctgggaa gacgtggaca acatcctcat cccagagaac     2160
cgggcccatt tgtccccaga ggtgcagctg aaggagctgc tggagaaact ggacctggtg     2220
agcgccatgc ggtccagtgg ggcccgcacc cgtcgtgtcc gcctgctacg ccgggagatc     2280
aatgcccttc ggcagaagct ggcacagcca ccaccaccac agccaccatc actcaacaag     2340
acagtatcca atggggagct gccagcaggg ccccagggg atgcagctgt gctggagcag      2400
gccttgcagg aggagccaga agacgatggg gacagagatg actccaaaact gcctcctccg     2460 ccaaccctgg agcccactgg gcctgcacct tccttgtctg agcaagaatc ccccccggag      2520
ccccctactc tgaaacccat taatgatagc aaacctccaa gcaggttcct aaagcccaga      2580
aaggtggaag aagatgagct cttggaaaaa tcaccactgc agctagggaa tgagcctttg      2640
caacgcttgc tcagtgacaa tggcatcaac agactatccc tcatggcccc tgacaccccg     2700
gccggtaccc cacttagtgg tgtgggtcgc cgcacatcag tcctcttcaa gaaggccaag     2760
aatggggtta agctacagag aagcccagac agggtcctgg agaatggcga ggaccatggt     2820
gtggcaggct ctcctgcctc tccagccagc atcgaggaag agcgccactc ccggaagcgg     2880
ccaaggagca ggagctgtag tgagagcgaa ggggagaggt cccccagca ggaggaagag       2940 acaggcatga ccaacggctt tggaaaacac accgaaagcg ggtctgactc tgaatgtagt     3000
ttgggtctca gtggtggact ggcatttgaa gcttgcaggc agtggcttcc aagggacaaa     3060
gtcctgccct gggtgtggaa agacaccgtg gacaagctca gatgctggaa ggccgcaag      3120 accagcatcc gcaagtcagt gcaggtggcc tatgaccgtg cgatgatcca cctgagcaga     3180
gtccgggggc cccactcctt cgtcacttcc agctacctgt aagggcaggg ctgggcctgc     3240
atccgcttgc cctgcctcca tcccgcaggg cacagagaag cctcttctgc ccctgccaga     3300
```

-continued

```
tgtatggccg gcagcttccc cctctcatgg taggccaggg actgggcttt ctccccacta      3360
agggcaaggc cccagttttg accaatcgca tggttctcct ggcaggcctg ctctgtgcca      3420
aaaactccca cccaaggtcc ctcaggggat atttcactga agaaccagtt agaagtagaa      3480
acagctgtgg ggcttgggcc cagcttagga gattgcccag atggcaagag gtcctgggct      3540
ccttcttgag gggctgcctg gcccgctcca tcctactccc actaactaca cctcagggcg      3600
ggtgaggttc cgacactgat cccagagatg ccgtggatac gccagggtcc caggggggaat     3660
ctccccaagc tcacactctc tcccgcttat cgcctattct cacacctctt ctcggtccca      3720
tcttctgcac ccattgccca gtcttgcttt ctctttccca tattccttttt cttttctct      3780
tgtgccaaac tgacagaaac cgtcaccaca ctggtctttt tctttaatgt ctcattcccc      3840
ttgaggccag ctgctatgcc aggtggtgtc tctgccaggc tcctcaggcc cagacagagg      3900
ccagcccaca acctatgacc ccctccccca ggacaccacc tcccacccac agaccttccc      3960
tttagctgtt gacacaactt cccagctctg caagtgtgcc ccctggatca aggcgggtcc      4020
cctcttgttt ttttctttgc tgccacgagg tggtccaagc cttcaggtg ggctcctatc       4080
aggctgggtg tgcgagtgtc catctgtcca catggatgtc gagggtggtt tgtgtggagc      4140
tgtgctcgtc agctgggtct gccctcttcc ccctttctc cttcttctct cctcatggac       4200
tttttctgca attgcagtct taagcttcac tctccaccac ctggatggca tggcgcctgc      4260
caccaaacat cttcctggcc tgcgctctgc cctgccctgc ctagcctctg ctactcccac      4320
ttcccaactc cagggaatgc attactttta tttcaaaccc tctgcctcct tccttctttc      4380
tcttcaaccc cctcccccacc ttcaccttct caaaaatgga aggaaaaaaa aactgtgaat    4440
ggggaatgct gactgacaaa ccaacacaac tttcagaggc ttcagtgtct gttctctgga     4500
catttctttt cacctcctga gcaccaaagt cgcagggcca gttgcaggcc gctgattgcc     4560
atgttgattt ttaacctgat attcttttta attgttttaa attttcata ggggagtttt     4620
ggacaaaaca gtcactgggg agatcactgc catttttaca cacttgactt tttaaaaata     4680
caaccaacca accaccacaa cttccttatac atttgggaca tgagccagag tttaaaaggg   4740
aaccaacaaa acactataac ttaaaaggat ggggttttgg attttgtata ataataaaaa     4800
caatacagca tatggctagg gaaggacatg gtgtatataa ttgtaaaata ctgttctaaa    4860
ttattcaggc ctatagtttc cattactgga gtcctccatt gtgtggccac acagtgtcgt    4920
tgatttaaag gagccagtgc ttcccctctc cccaggtagt tggtcagctg tggactctgt     4980
gacctttgtc taaacctgtg ttgtaagatc ttgggacttc ctctctttct atgtctatct    5040
cttcccccca acactttctc ttcttagtct ctctctttat ttttcaatct ctgaatattt    5100
tagtctctct ctgagtctca ttttttaaaa tgctcttta gaacgggaaa cggctcagat     5160
cctgctgtgg cacggggcct atgtgtctct gtcgcgtctg ctgtgaagca catgatgctc    5220
tatttattgt agagagtgac tttatttgct ttctagaatt gtttataaca gatggtataa    5280
gagaggtaat aaacagagaa aaatctatgc ttgtaaagaa tacaaaagtt aattttacct    5340
actataatat gactgtctga aacttatttt ctctctgaga aataaatgtt ctaatgggca    5400
gtaaaaaaaa aaaaaaaaaa aaaaaaaaaa aaaaaaaaa a                          5441
```

<210> SEQ ID NO 21
<211> LENGTH: 1868
<212> TYPE: DNA
<213> ORGANISM: Homo sapiens

<400> SEQUENCE: 21

```
ccatttaaag aagatgctcg gccttaaagg aaatggcggt gcggttctgt ccatggccct      60
tccttttcag ccagagcaga gagattcaga ggatttattg aagaatttta attcagagtg     120
tgatacacac tgtggccttg atactgcacg acaagaatat ttgggtaact cattaagaca     180
ggaatcagac ttgaaaaaat ccacctcgtc agataattca agctctcatc atggtgaaaa     240
taaacaaaat ctgactgttg atccctgtga cattttgggt ggagttgata atcagcaaag     300
actgctacac attgtctggc ctcacaggtg ggagcatgat aaagatccag aaagcttttt     360
taaggtatta atgcatctta aagacttagg actcaatttc cacgtgtctg tacttggaga     420
aaccttcaca gatgtcccag atattttttc agaggccaaa aaggcattgg gatcttctgt     480
cttacactgg ggctacttac ccagcaaaga tgactacttc caagtactgt gcatggctga     540
tgttgtcatc tcaacagcta agcatgaatt ctttggagtg gcaatgttgg aagctgtgta     600
ctgtgggtgt tacccacttt gtcctaaaga tttggtttat cccgaaatat ttccagctga     660
atatctgtat tctacacctg aacagctttc aaaaaggctc cagaatttct gcaagagacc     720
agatattata agaaaacatc tctataaggg tgaaatcgct ccgttttctt gggcagccct     780
acatggtaaa ttcaggtctc tgcttacaac agagcctagg aagatttgt gacagatggg     840
gctaagtcac aaacttgcag cctaaggcag aatctgaaga actttccaga gtgtgcccat     900
atttacctga tcagagagaa aagaaaatct gcagaggaag ctgagcctgg ctgcttgtca     960
tagctgacac agagccatct gccacaaacc tgtggcggct tcagatctcc aatccctgcc    1020
accaccccaa ctcaaattaa atacagattc ctagagacgt tatgatggtt acacatgtcc    1080
tcggcatcac atgtaggaga ctgttcaaaa aaaatatgtg gcctgttgta taaccgcact    1140
catgtatccc atatgtggtg ccacattgaa tttccggttg aatccgtttt tatcctttgt    1200
actggatgac atggtgcctg aattcttttct tttcgccgac acgatggcag ccaaactgca    1260
gcttcaaacg ctcacacttg gctgggtttc tacctaggtt gccaggttat catcggagcc    1320
ttcttgtgtc ctcaaagggc cacgaggcct gaaaggagga tcagaatgct ttgggattaa    1380
ttgggcagcc atcgcagaat tgtttgtggg caaagggctg ctttagcact tttcttttag    1440
caaattaatg actctcaggc acaggggggtt ttaagtgaag gtattaataa gaggtctggc    1500
aggtattccc atgattcaca gagttacatt tgcatttaat taatcttaaa gttgcaagat    1560
aaacagctgt aattcggaca acatgacaa acacagtgaa gccaactatc ccataaaatg    1620
aacactgaca tacttgtttt aattttttc ccagcgtaaa aatagaaaaa tcaaaatact    1680
cctaacaaaa ccagtgattt tgatagaaat atttctccaa tatacttgca tccacctaca    1740
aatataacct tttcaagata aatcgcttat gatttcaata gtcaaactgc tgtgtttgtt    1800
gatgtaaaga tgttttgaat ggctagatgg taaaataaat tcttaataaa gtacccactg    1860
caattttt                                                            1868
```

<210> SEQ ID NO 22
<211> LENGTH: 1322
<212> TYPE: DNA
<213> ORGANISM: Homo sapiens

<400> SEQUENCE: 22

```
taaaaatatc ctatcagtcc tttctaagaa gcctgaattg accaaaaaac atccccacca      60
ccactttata aagttgattc tgctttatcc tgcagtattg tttagccatc ttctgctctt     120
ggtaaggttg acatagtata tgtcaattta aaaaataaaa gtctgctttg taaatagtaa     180
```

-continued

```
ttttacccag tggtgcatgt ttgagcaaac aaaaatgatg atttaagcac actacttatt      240
gcatcaaata tgtaccacag taagtatagt ttgcaagctt tcaacaggta atatgatgta      300
attggttcca ttatagtttg aagctgtcac tgctgcatgt ttatcttgcc tatgctgctg      360
tatcttattc cttccactgt tcagaagtct aatatgggaa gccatatatc agtggtaaag      420
tgaagcaaat tgttctacca agacctcatt cttcatgtca ttaagcaata ggttgcagca      480
aacaaggaag agcttcttgc tttttattct tccaaccttta attgaacact caatgatgaa      540
aagcccgact gtacaaacat gttgcaagct gcttaaatct gtttaaaata tatggttaga      600
gttttctaag aaaatataaa tactgtaaaa agttcatttt attttatttt tcagccttt       660 gtacgtaaaa tgagaaatta aaagtatctt caggtggatg tcacagtcac tattgttagt      720
ttctgttcct agcactttta aattgaagca cttcacaaaa taagaagcaa ggactaggat      780
gcagtgtagg tttctgcttt tttattagta ctgtaaactt gcacacattt caatgtgaaa      840
caaatctcaa actgagttca atgtttattt gctttcaata gtaatgcctt atcattgaaa      900
gaggcttaaa gaaaaaaaaa atcagctgat actcttggca ttgcttgaat ccaatgtttc      960
cacctagtct ttttattcag taatcatcag tcttttccaa tgtttgttta cacagataga     1020
tcttattgac ccatatggca ctagaactgt atcagatata atatgggatc ccagcttttt     1080
ttcctctccc acaaaaccag gtagtgaagt tatattacca gttacagcaa atactttgt      1140 gtttcacaag caacaataaa tgtagattct ttatactgaa gctattgact tgtagtgtgt     1200
tggtgaaatg catgcaggaa aatgctgtta ccataaagaa cggtaaacca cattacaatc     1260
aagccaaaag aataaaggtt tcgcttttgt ttttgtattt aagaaaaaaa aaaaaaaaa      1320 aa                                                                    1322
```

<210> SEQ ID NO 23
<211> LENGTH: 2608
<212> TYPE: DNA
<213> ORGANISM: Homo sapiens

<400> SEQUENCE: 23

```
ccgatgaccc ttctcctgtc ccgcatcccg agctgagctt ggctgaaagc ctgtggactt       60
ccaaaccacc acctctcttc catgaaggag caccttatcc tccccctttg tttatcaggg      120
acacatataa ccaatcaata cctcagccac ctcctcggaa aattaagcga cccaaacgaa      180
aaatgtacag ggaagaaccc acttcaataa tgaatgctat taaactacga cccaggcaag      240
ttctgtgtga taaatgtaaa aacagtgttg ttgctgaaaa aaaggaaatt agaaaaggta      300
gtagtgcaac tgactcttct aaatatgaag ataaaaaacg gagaaatgaa agtgtaacta      360
ctgtgaacaa aaaactgaaa actgaccata agtggatgg gaaaaaccaa aatgaaagcc      420
agaaaagaaa tgctgtggtt aaggtttcaa atattgctca cagcagaggc agagtagtaa      480
aagtttctgc tcaggcaaat acatcaaaag ctcagttaag tactaaaaaa gttctccaga      540
gtaagaacat ggatcatgcg aaagctcggg aagtgttaaa aattgccaaa gaaaaggcac      600
aaaagaagca aaatgaaacc tctacttcca aaaatgcaca ttcaaaagtc catttcacac      660
gtcgatatca gaatcctagc tcaggttccc ttccacccg ggttcgttta aaaccacaga      720
ggtacaggaa tgagaaaaat gactcttctc tgaagacagg acttgagaaa atgcggagtg      780
gcaagatggc acccaagccc cagtctcgct gcacctctac ccgctcagca ggtgaggccc      840
cttcagaaaa tcagagtccc tcaaaaggcc ctgaagaggc cagcagtgag gttcaggaca      900
```

-continued

```
caaatgaagt gcatgtgcct ggtgatcagg atgaaccaca gacattgggc aaaaagggca    960
gcaaaaacaa tatctctgtt tatatgaccc taaatcaaaa gaaatctgac tcttccagtg   1020
cttcagtgtg tagcattgat agcacagatg atttgaaatc ttccaactct gagtgtagtt   1080
cttctgaaag ctttgatttt cctccaggca gtatgcatgc accttccacc tcctccactt   1140
cctcctcttc aaaggaagag aaaaagctca gtaattcctt gaaatgaaa gtcttttcca    1200 aaaacgtctc taaatgcgtc acaccagatg gcaggaccat atgtgtaggg gacattgttt   1260
gggccaagat atatggcttc ccttggtggc cagcccgtat tcttactata actgtgagcc   1320
ggaaagataa cggccttta gtccgacagg aggcccgtat ttcatggttt gggtctccaa    1380
caacatcttt ccttgctctt tcacaactct cccccttttt agaaaacttc cagtcacgct   1440
ttaataagaa gagaaagggc ctgtatcgca aggctatcac agaggcagct aaggctgcca   1500
agcagctgac ccccgaagtg cgggctttgt tgacacagtt tgaaacgtga acatgggcag   1560
taaggtaggg aagaccattg gaagtcacca cagattttct agtctagtta ggaataattt   1620
ctacaaaata gcgtggccag attggagaga gaagttgcac tcagttggct ggcttttaa    1680 tacttacctt atagccattt ttagactgag agcttaaact gaacatataa tcaaattttg   1740
tgttaaggaa gtgagatttt agcagtattt ttcagttttg aagttcgaaa ccatcccaag   1800
gcataggagc catagcctca actgaaattg aattttgta gggactgtta attgccattt    1860
gtacctaata ctgtatatat acatatatat acgtgtgtgt gtatatatat atatatatat   1920
atatatatat atatatccgt gtatgtatat atacacacat atatatgtat atacacacat   1980
atatatatat gaaatacagc ctgtcactgt gtgacacaga ttgcatattt gggattgcaa   2040
taagggcttg gtgagctggg ggaatagtgg atatttaatg actacttgtt ttttaaataa   2100
tgaacactta gcctttctat gcgcataatg gtgtaaaagt tagatggtta ggtgtttgac   2160
aaacagatgg ttgcaattca gttacagact ggggaaatag cccagtgttt gggattaaaa   2220
ctgtcaagac tggataggtg ttagtcatca ctgtctttcg tccagtgggg atttaataaa   2280
tactttcaag cttctggttt gggagtttag ataggtttga ttttggattt gtaaatagtg   2340
attgctaaat ttggtcagat ttctcctgac tggctgttcc taaattctta ggatatgtcc   2400
cagtaaaatt atactttgtg aattaattgt catatgtgta attgttgcat tttggatgta   2460
cctaatttga taattaaaac aaaataattt ccgtttaagg tatctgtttg caggtcagaa   2520
aatgagaaaa tgtaattgtg taatgctctg aaatgtaaaa aaaaaaaaaa aaaccaaaaa   2580
aaagctgtaa ataaaatcaa ctaaatcc                                     2608
```

```
<210> SEQ ID NO 24
<211> LENGTH: 1567
<212> TYPE: DNA
<213> ORGANISM: Homo sapiens

<400> SEQUENCE: 24
```

```
gggtgaggag gaagaggagg aggaagagga ggaagaggat gacctgagtg agctgccacc     60
gctggaggac atgggacaac ccccggcgga ggaggctgag cagcctgggg ccctggcccg    120
agagttcctt gctgccatgg agcccgagcc cgccccagcc ccggcccag aagagtggct     180 ggacattctg ggaacgggc tgttgaggaa gaagacgctg gtcccagggc cgccaggttc    240
gagccgcccg gtcaagggcc aggtggtcac cgtacatctg cagacgtcgc tggagaatgg   300
cacacgggtg caggaggagc cggagctggt gttcactctg ggtgactgtg acgtcatcca   360 ggcctggat ctcagtgtcc cactcatgga cgtgggggag acggccatgg tcactgctga    420
```

-continued

| | | |
|---|---|---|
| ctccaagtac tgctacggcc cccaaggcag caggagccca tacatccccc cgcacgcggc | 480 |
| cctgtgcctg gaggtgaccc tgaagacggc tgtggacggg cctgacctgg agatgctcac | 540 |
| ggggcaggag cgcgtggccc tggccaaccg gaagcgggag tgcggcaacg cccactacca | 600 |
| gcggcggac ttcgtcctgg ccgccaactc ctacgacctc gccatcaagg ctatcacctc | 660 |
| cagcgccaaa gtggacatga cgttcgagga ggaggcacag ctcctgcagt tgaaggtgaa | 720 |
| gtgtctgaac aacctggcgg cctcgcagct gaagctcgac cactaccgcg cagccctgcg | 780 |
| ctcctgcagc cttgtgctgg agcaccagcc agacaacatc aaggctctct ccgcaagggg | 840 |
| caaggtgctg gcccagcagg gggagtacag tgaggccatc cccatcctga gggcagccct | 900 |
| gaagctggaa ccttccaaca gacgatcca cgcagagctc tcaaagctgg tgaagaagca | 960 |
| tgcggcgcag cggagcacgg agaccgcctt gtaccggaaa atgctgggca accccagccg | 1020 |
| gctgcctgct aagtgccctg caagggtgc ctggtccatc ccatggaagt ggctgtttgg | 1080 |
| ggcgactgct gttgccttgg ggggtgtggc actctctgtg gtcatcgctg ccaggaactg | 1140 |
| accacctagg tggctgccac cccctctgca caccatggac cctgcctgc gctccccaac | 1200 |
| tcccccaggc tccctgtcca ctgccctccc tggtctggcc ccctcctccg ggttagggga | 1260 |
| gcaaggattg ggggtcgtgc agcccagcca gcaggaggga ctgaggccct ctaggaggaa | 1320 |
| agcccagagg gaggggccc tcattccttc agacccagtt ttcccccacc ctccttaccc | 1380 |
| cgctgggcta ggtctccgcc agggctggcc tcagtttctc ctcaacaggc ctggggcag | 1440 |
| ccccttcccct gcctagtccc cgcctgagtg ccagcccccc accccgcctg ccgcccctg | 1500 |
| tccaggttcc ctccccgcca cagtgaaata agcatccca ccctgcaaaa aaaaaaaaa | 1560 |
| aaaaaaa | 1567 |

<210> SEQ ID NO 25
<211> LENGTH: 2815
<212> TYPE: DNA
<213> ORGANISM: Homo sapiens

<400> SEQUENCE: 25

| | | |
|---|---|---|
| gaattcggca cgagctcttc tcccctgatt caagactcct ctgctttgga ctgaagcact | 60 |
| gcaggagttt gtgaccaaga acttcaagag tcaagacaga aggaagccaa gggagcagtg | 120 |
| caatggattt ctcagtaaag gtagacatag agaaggaggt gacctgcccc atctgcctgg | 180 |
| agctcctgac agaacctctg agcctagatt gtggccacag cttctgccaa gcctgcatca | 240 |
| ctgcaaagat caaggagtca gtgatcatct caagagggga aagcagctgt cctgtgtgtc | 300 |
| agaccagatt ccagcctggg aacctccgac ctaatcggca tctggccaac atagttgaga | 360 |
| gagtcaaaga ggtcaagatg agcccacagg aggggcagaa gagagatgtc tgtgagcacc | 420 |
| atggaaaaaa actccagatc ttctgtaagg aggatgaaaa agtcatttgc tgggtttgtg | 480 |
| aactgtctca ggaacaccaa ggtcaccaaa cattccgcat aaacgaggtg gtcaaggaat | 540 |
| gtcaggaaaa gctgcaggta gccctgcaga ggctgataaa ggaggatcaa gaggctgaga | 600 |
| agctggaaga tgacatcaga caagagagaa ccgcctggaa gatcgagaga cagaagattc | 660 |
| tgaaagggtt caatgaaatg agagtcatct tggacaatga ggagcagaga gagctgcaaa | 720 |
| agctggagga aggtgaggtg aatgtgctgg acaacctggc agcagctaca gaccagctgg | 780 |
| tccagcagag gcaggatgcc agcacgctca tctcagatct ccagcggagg ttgacgggat | 840 |
| cgtcagtaga gatgctgcag gatgtgattg acgtcatgaa aaggagtgaa agctggacat | 900 |

-continued

```
tgaagaagcc aaaatctgtt tccaagaaac taaagagtgt attccgagta ccagatctga      960
gtgggatgct gcaagttctt aaagagctga cagatgtcca gtactactgg gtggacgtga     1020
tgctgaatcc aggcagtgcc acttcgaatg ttgctatttc tgtggatcag agacaagtga     1080
aaactgtacg cacctgcaca tttaagaatt caaatccatg tgattttttct gcttttggtg    1140 tcttcggctg ccaatatttc tcttcgggga aatattactg ggaagtagat gtgtctggaa     1200
agattgcctg gatcctgggc gtacacagta aaataagtag tctgaataaa aggaagagct     1260
ctgggtttgc ttttgatcca agtgtaaatt attcaaaagt ttactccaga tatagacctc     1320
aatatggcta ctgggttata ggattacaga atacatgtga atataatgct tttgaggact     1380
cctcctcttc tgatcccaag gttttgactc tctttatggc tgtgctccct gtcgtattgg     1440
ggttttccta gactatgagg caggcattgt ctcattttttc aatgtcacaa accacggagc    1500
actcatctac aagttctctg gatgtcgctt ttctcgacct gcttatccgt atttcaatcc     1560
ttggaactgc ctagtcccca tgactgtgtg cccaccgagc tcctgagtgt tctcattcct     1620
ttacccactt ctgcatagta gcccttgtgc tgagactcag attctgcacc tgagttcatc     1680
tctactgaga ccatctcttc cttttctttcc ccttcttttta cttagaatgt ctttgtattc    1740
atttgctagg gcttccatag caaagcatca tagattgctg atttaaactg taattgtatt     1800
gccgtactgt gggctggaaa tcccaaatct agattccagc agagttggtt ctttctgagg     1860
tctgcaagga agggctctgt tccatgcctc tctccttggc ttgtagaagg catcttgtcc     1920
ctatgactct tcacattgtc tttatgtaca tctctgtgcc caagttttcc cttttttatta    1980 agacaccagt catactggct cagggcccac cgctaatgcc ttaatgaaat catttttaaca    2040 ttatattctc tacaaagacc ttatttccaa ataagataat atttggaggt attgggaata     2100
aaatttgagg aaggcacgat ttcactcata acaatcttac cctttcttgc aagagatgct     2160
tgtacattat tttcctaata ccttggtttc actagtagta aacattatta tttttttttat    2220 atttgcaaag gaaacatatc taatccttcc tatagaaaga acagtattgc tgtaattcct     2280
tttcttttct tcctcatttc ctctgcccct taaaagattg aagaaagaga aacttgtcaa     2340
ctcatatcca cgttatctag caaaagtcat aagaatctat cactaagtaa tgtatccttc     2400
agaatgtgtt ggtttaccag tgacaccca tattcatcac aaaattaaag caagaagtcc      2460 atagtaatttt atttgctaat agtggatttt taatgctcag agtttctgag gtcaaatttt    2520
atcttttcac ttacaagctc tatgatctta ataatttac ttaatgtatt ttggtgtatt      2580
ttcctcaaat taatattggt gttcaagact atatctaatt cctctgatca ctttgagaaa    2640
caaactttta ttaaatgtaa ggcactttttc tatgaatttt aaatataaaa ataaatattg    2700
ttctgattat tactgaaaag atgtcagcca tttcaatgtc ttgggaaaca attttttgtt     2760
tttgttctgt tttcttttttg cttcaataaa acaatagctg gctctaaaaa aaaaa         2815
```

```
<210> SEQ ID NO 26
<211> LENGTH: 1699
<212> TYPE: DNA
<213> ORGANISM: Homo sapiens

<400> SEQUENCE: 26
```

```
ggcacgaggg gcgccaccgc ggaggacagg ggcagctggc gggcagcggg tgaggggtg       60 gcggggacgc gagtggcggc gcgggggccc cggacaaggg tccgcagagc tgcagccttc     120
gagggccagc cctctccgag tccggggctg ggtcccacca gtgacaaggc ggcagccccg    180
cgcacaccaa agagaaggcg gctgtggcgg cagcggcagc cccagccatg ctgtgttatg    240
```

-continued

```
tgacgaggcc ggacgcggtg ctgatggagg tggaggtgga ggcgaaagcc aacggcgagg      300
actgcctcaa ccaggtgtgc aggcgactgg gaatcataga agttgactat tttggactgc      360
agtttacggg tagcaaaggt gaaagtttat ggctaaacct gagaaaccgg atctcccagc      420
agatggatgg gctagcccct tacaggctta aacttagagt caagttcttc gtggagcctc      480
atctcatctt acaggagcag actaggcata tcttttctt gcacatcaag gaggccctct       540
tggcaggcca cctcttgtgt tccccagagc aggcagtgga actcagtgcc ctcctggccc      600
agaccaagtt tggagactac aaccagaaca ctgccaagta taactatgag gagctctgtg      660
ccaaggagct ctcctctgcc accttgaaca gcattgttgc aaaacataag gagttggagg      720
ggaccagcca ggcttcagct gaataccaag ttttgcagat tgtgtcggca atggaaaact      780
atggcataga atggcattct gtgcgggata gcgaagggca gaaactgctc attgggggttg     840
gacctgaagg aatctcaatt tgtaaagatg actttagccc aattaatagg atagcttatc      900
ctgtggtgca gatggccacc cagtcaggaa agaatgtata tttgacggtc accaaggaat      960
ctgggaacag catcgtgctc ttgtttaaaa tgatcagcac cagggcggcc agcgggctct     1020
accgagcgat aacagagacg cacgcattct acaggtgtga cacagtgacc agcgccgtga     1080
tgatgcagta tagccgtgac ttgaagggcc acttggcatc tctgtttctg aatgaaaaca     1140
ttaaccttgg caagaaatat gtctttgata ttaaaagaac atcaaaggag gtgtatgacc     1200
atgccaggag ggctctgtac aatgctggcg ttgtggacct cgtttcaaga aacaaccaga     1260
gcccttcaca ctcgcctctg aagtcctcag aaagcagcat gaactgcagc agctgcgagg     1320
gcctcagctg ccagcagacc cgggtgctgc aggagaagct acgcaagctg aaggaagcca     1380
tgctgtgcat ggtgtgctgc gaggaggaga tcaactccac cttctgtccc tgtggccaca     1440
ctgtgtgctg tgagagctgc gccgcccagc tacagtcatg tcccgtctgc aggtcgcgtg     1500
tggagcatgt ccagcacgtc tatctgccaa cgcacaccga tcttctcaat ctgactgtaa     1560
tctaatctgt tgtgcttttg ttggacttgg catgtttcca tgaactgcac tattataaac     1620
tattaaaatg atagattgtg gagaaagtaa ttattccaac acccatctgc catgcgatgt     1680
taaaaaaaaa aaaaaaaaa                                                  1699
```

<210> SEQ ID NO 27
<211> LENGTH: 1976
<212> TYPE: DNA
<213> ORGANISM: Homo sapiens

<400> SEQUENCE: 27

```
gccacacggt ctttgagctg agtcgaggtg gacccttga acgcagtcgc cctacagccg       60
ctgattcccc ccgcatcgcc tcccgtggaa gcccaggccc gcttcgcagc tttctcccctt    120
tgtctcataa ccatgtccac caacgagaat gctaatacac cagctgcccg tcttcacaga     180
ttcaagaaca agggaaaaga cagtacagaa atgaggcgtc gcagaataga ggtcaatgtg     240
gagctgagga aagctaagaa ggatgaccag atgctgaaga ggagaaatgt aagctcattt     300
cctgatgatg ctacttctcc gctgcaggaa aaccgcaaca accagggcac tgtaaattgg     360
tctgttgatg acattgtcaa aggcataaat agcagcaatg tggaaaatca gctccaagct     420
actcaagctg ccaggaaact actttccaga gaaaaacagc cccccataga caacataatc     480
cgggctggtt tgattccgaa atttgtgtcc ttcttgggca gaactgattg tagtcccatt     540
cagtttgaat ctgcttgggc actcactaac attgcttctg ggacatcaga acaaaccaag     600
```

-continued

| | |
|---|---|
| gctgtggtag atggaggtgc catcccagca ttcatttctc tgttggcatc tccccatgct | 660 |
| cacatcagtg aacaagctgt ctgggctcta ggaaacattg caggtgatgg ctcagtgttc | 720 |
| cgagacttgg ttattaagta cggtgcagtt gacccactgt tggctctcct tgcagttcct | 780 |
| gatatgtcat ctttagcatg tggctactta cgtaatctta cctggacact ttctaatctt | 840 |
| tgccgcaaca agaatcctgc accccgata gatgctgttg agcagattct tcctacctta | 900 |
| gttcggctcc tgcatcatga tgatccagaa gtgttagcag atacctgctg ggctatttcc | 960 |
| taccttactg atggtccaaa tgaacgaatt ggcatggtgg tgaaaacagg agttgtgccc | 1020 |
| caacttgtga agcttctagg agcttctgaa ttgccaattg tgactcctgc cctaagagcc | 1080 |
| atagggaata ttgtcactgg tacagatgaa cagactcagg ttgtgattga tgcaggagca | 1140 |
| ctcgccgtct ttcccagcct gctcaccaac cccaaaacta acattcagaa ggaagctacg | 1200 |
| tggacaatgt caaacatcac agccggccgc caggaccaga tacagcaagt tgtgaatcat | 1260 |
| ggattagtcc cattccttgt cagtgttctc tctaaggcag attttaagac acaaaaggaa | 1320 |
| gctgtgtggg ccgtgaccaa ctataccagt ggtggaacag ttgaacagat tgtgtacctt | 1380 |
| gttcactgtg gcataataga accgttgatg aacctcttaa ctgcaaaaga taccaagatt | 1440 |
| attctggtta tcctggatgc catttcaaat atctttcagg ctgctgagaa actaggtgaa | 1500 |
| actgagaaac ttagtataat gattgaagaa tgtggaggct tagacaaaat tgaagctcta | 1560 |
| caaaaccatg aaaatgagtc tgtgtataag gcttcgttaa gcttaattga gaagtatttc | 1620 |
| tctgtagagg aagaggaaga tcaaaacgtt gtaccagaaa ctacctctga aggctacact | 1680 |
| ttccaagttc aggatggggc tcctgggacc tttaacttttt agatcatgta gctgagacat | 1740 |
| aaatttgttg tgtactacgt ttggtattttt gtcttattgt ttctctacta agaactcttt | 1800 |
| cttaaatgtg gtttgttact gtagcacttt ttacactgaa actatacttg aacagttcca | 1860 |
| actgtacata catactgtat gaagcttgtc ctctgactag gtttctaatt tctatgtgga | 1920 |
| atttcctatc ttgcagcatc ctgtaaataa acattcaagt ccacccttaa aaaaaa | 1976 |

<210> SEQ ID NO 28
<211> LENGTH: 2371
<212> TYPE: DNA
<213> ORGANISM: Homo sapiens

<400> SEQUENCE: 28

| | |
|---|---|
| gacggggtgg ggggtggggg gaccccggtt gtgcagtttg atattgaggg agcccccacc | 60 |
| tactcgctgg ggctgcgtaa tctgtacgct tccaaactga agcgaaggcg tcggagact | 120 |
| aggcctcaga gaaccatggc tactgccaag ggaatcgcca taggcatcga cctgggcacc | 180 |
| acctactcct gtgtggggt gttccagcac ggcaaggtgg agatcatcgc caacgaccag | 240 |
| ggcaaccgca ccaccccag ctacgtggcc ttcacagaca ccgagcggct cattggggat | 300 |
| gcggccaaga accaggtagc aatgaatccc cagaacactt tttttgatgc taaacgtctg | 360 |
| atcggcagga aatttaatga tcctgttgta caagcagata tgaaactttg gccttttcaa | 420 |
| gtgattaatg aaggaggcaa gcccaaagtc cttgtgtcct acaaaggga gaataaagct | 480 |
| ttctaccctg aggaaatctc ttcgatggta ttgactaagt tgaaggagac tgctgaggcc | 540 |
| tttttgggcc accctgtcac caatgcagtg attaccgtgc cagcctattt caatgactct | 600 |
| caacgtcagg ctactaagga tgcaggtgtg attgctggac ttaatgtgct aagaatcatc | 660 |
| aatgagccca cggctgctgc cattgcctat ggtttagata aggaggtca aggagaacga | 720 |
| catgtcctga tttttgatct gggtggaggc acatttgatg tgtcaattct gaccatagat | 780 |

-continued

```
gatgggattt ttgaggtaaa ggccactgct ggggacactc acctgggtgg ggaggacttt      840
gacaacaggc ttgtgagcca cttcgtggag gagttcaaga ggaaacacaa aaaggacatc      900
agccagaaca agcgagccgt gaggcggctg cgcaccgcct gcgagagggc caagaggacc      960
ctgtcgtcca gcacccaggc caacctagaa attgattcac tttatgaagg cattgacttc     1020
tatacatcca tcaccagagc tcgatttgaa gagttgtgtg cagacctgtt tagggtacc      1080
ctggagcctg tagaaaaagc gcttcgggat gccaagatgg ataaggctaa aatccatgac     1140
attgttttag tagggggctc cacccgcatc cccaaggtgc agcggctgct tcaggactac     1200
ttcaatggac gtgatctcaa caagagcatc aaccctgatg aggccgtagc atatggggct     1260
gcggtacaag cagccatcct gatggggggac aagtctgaga aggtacagga cctgctgctg    1320
ctggacgtgg ctcccctgtc cctggggctg gagacggctg ggggcgtgat gactgccctg    1380
ataaagcgca actccaccat ccccaccaag cagacacaga ttttcaccac ctactctgac    1440
aaccaacccg gggtgctgat ccaggtgtat gagggcgaga gggccatgac aaaggacaac    1500
aacctgctgg ggcggtttga cctgactgga atccctccag cacccagggg agttcctcag    1560
atcgaggtga cgtttgacat tgatgccaat ggtattctca atgtcacagc catggacaag    1620
agcaccggca aggtgaacaa gatcaccatc accaatgaca agggccgcct gagcaaggag    1680
gagattgagc gcatggttct ggatgctgag aaatataaag ctgaagatga ggtccagagg    1740
gagaaaattg ctgcaaagaa tgccttagaa tcctatgctt ttaacatgaa gagtgttgtg    1800
agtgatgaag gtttgaaggg caagattagt gagtctgata aaaataaaat attggataaa    1860
tgcaacgagc tcctttcgtg gctggaggtc aatcaactgg cagagaaaga tgagtttgat    1920
cataagagaa aggaattgga gcagatgtgt aaccctatca tcacaaaact ctaccaagga    1980
ggatgcactg ggcctgcctg cggaacaggg tatatgcctg gaaggcctgc cacaggcccc    2040
acaattgaag aagtagatta attcttttta gaactgaagc atcctaggat gcctctacat    2100
gtatttcatt cccctcatct tcaaacatca ttattattct tgaccagacc tgaatctaag    2160
ttaccatccc ttggaaattc tggagaagga gtctcatgca ccacctatca cactccctca    2220
catcctgttt ctgactttgg aatggactca ggaaaactag gcccctcttt aaaccgtgtg    2280
atgtatttga atgtctgtta tttccagcca ccctaacatt cttcttcctg tgtggatgct    2340
tatttgtcaa tcagtaaatt tgttcgtaaa g                                   2371
```

METHOD FOR DETECTING RADIATION EXPOSURE

This application is a U.S. national stage § 371 application of PCT/US00/04897 filed Feb. 25, 2000, which was published in English under PCT Article 21(2), which claims the benefit of U.S. provisional application No. 60/121,756 filed Feb. 26, 1999.

FIELD

The present invention concerns gene expression, and is related to the detection of differential gene expression following exposure of cells to ionizing radiation.

BACKGROUND

Ionizing radiation has many medical, industrial and military uses. Although ionizing radiation can be used in the therapy of diseases such as cancer, exposure to biologically significant levels of such radiation can also cause genotoxic stress. Similarly, many industrial processes (such as the production of nuclear power) and military uses (such as nuclear weapons) can expose individuals to hazardous levels of ionizing radiation. Such radiation can elicit a variety of cellular responses, ranging from cell-cycle arrest to mutation, malignant transformation, or cell death. Many of the responses (such as genotoxicity) are often subtle, and exposed persons may be unaware or unsure if they have been exposed. Moreover, it may require years to evince an untoward effect (such as the development of a malignancy) caused by the exposure.

Many of the assumptions about low dose effects have been based on extrapolations from effects measured at high doses. Transcriptional responses to doses of ionizing radiation with relatively little effect on cell survival have not been as well investigated, although small variations in expression levels of several isolated genes have been detected. A dose of 50 cGy reportedly reduced expression of β- and γ-actin (Woloschak and Chang-Liu, *Int. J. Radial. Biol.* 59:1173–83, 1991) and induced RB-1 and H4 histone (Woloschak and Chang-Liu, *Cancer Lett.* 97:169–75, 1995) in Syrian Hamster Embryo cells, while a decrease in c-myc and increase in c-jun was detected in these cells following a dose as low as 6 cGy (Woloschak and Chang-Liu, *Cancer Lett.* 97:169–75, 1995). In a transformed human lymphoblast cell line, activation of NF-κB has been reported with as little as 10 cGy of radiation (Prasad et al., *Radial. Res.* 138:367–72, 1994), along with induction of c-FOS, c-JUN, c-MYC and c-Ha-RAS in the 25–200 cGy range (Prasad et al., *Radial. Res.* 143:263–72, 1995). The induction by 25 cGy of PBP74, a member of the heat shock 70 gene family, has also been reported in two human cancer cell lines (Sadekova et al., *Int. J. Radial. Biol.* 72:653–60, 1997).

SUMMARY

It would be advantageous to have a method for detecting exposure of organisms to biologically significant or hazardous amounts of ionizing radiation. Although small variations in expression levels of several isolated genes in cell lines have been detected at lower doses, none of these studies have demonstrated a dose-response relationship for gene induction at low radiation doses, and overall qualitative and/or quantitative patterns of differential expression have not been investigated. The present invention uses nucleic acid microarray hybridization to evaluate biological effects, such as patterns of expression of genes after radiation exposure. Using these methods, numerous genes have been found which are responsive to radiation exposure in a variety of cell lines, and microarrays have been constructed which are capable of detecting biological responses (such as patterns of expression) to radiation exposure with great sensitivity and specificity.

The present invention includes a method of identifying cells that have been exposed to radiation induced biological stress. The method further includes providing a probe set that includes nucleic acid molecules representing genes that are differentially expressed in cells that have been exposed to a biologically significant amount of ionizing radiation. The probe set is exposed to a labeled nucleic acid composition from a test cell which specifically hybridizes to members of the probe set when the cell has been exposed to a biologically significant amount of ionizing radiation. Whether the nucleic acid composition hybridizes to the nucleic acid molecules representing genes that are differentially expressed is determined.

The probe set may be nucleic acid molecules (such as cDNAs or oligonucleotides) bound in an array to a surface, wherein the nucleotides specifically hybridize to sequences in the nucleic acid composition from the test cell. In one example, the nucleic acid composition includes cDNA reverse transcribed from mRNA in the test cell, and labeled with a fluorophore that detects hybridization of the cDNA to the probe set. In another example, the method also includes exposing the probe set to a labeled nucleic acid composition from a control cell which has not been exposed to a biologically significant amount of ionizing radiation. Genes which are expressed in the absence of radiation exposure will therefore produce mRNA from which labeled cDNA is made that specifically hybridizes to some members of the probe set. The nucleic acids from the test cell and control cell can be labeled with different signals (such as red and green colors) to indicate differential (either increased or decreased) expression of genes in the test cell as compared to the control cell.

The probe set may include probes that specifically hybridize to the labeled nucleic acid composition from specimens obtained more than four hours after exposure to the biologically significant amount of ionizing radiation, and/or less than 24 hours after exposure. In another embodiment of the invention, the probe set includes probes that specifically hybridize to the labeled nucleic acid composition from specimens obtained more than 24 or 48 hours after exposure to the biologically significant amount of ionizing radiation. Probes which detect such late effect exposures may be used to screen for radiation exposure when such screening is not done until one or two days following potential radiation exposure, when a subject is examined in a medical or laboratory facility.

In yet other embodiments of the invention, the probe set includes probes that specifically hybridize to the labeled nucleic acid composition from specimens which have been exposed to less than about 25 cGy of ionizing radiation. The probe set may also include genes that are differentially expressed by at least 1.5-fold or 2-fold following exposure to a biologically significant amount of ionizing radiation. The probe set may include at least 10%, 30% 40%, 50%, 75%, 80%, 90%, 95%, or 99% of the probes identified in Tables 9, 10, 11, 12, 13 or 14 or the entire probe set shown in any of those Tables. The probe set may also include at least 10 or 20 of the probes identified in Tables 9, 10, 11, 12, 13 or 14. Examples of probes that represent such late effects include those listed in Tables 9–12. In another embodiment, the probe set includes nucleic acid sequences that are selected for having differential expression following exposure to a biologically significant amount of ionizing radiation. The probe set may be at least 50%, 75%, 80%, 90%, 95%, 99%, or consist essentially of nucleic acid sequences that are differentially expressed following exposure to a biologically significant amount of ionizing radiation. In yet another embodiment, the probe set includes nucleic acid sequences that are selected for having a differential expression of at least 1.5- or 2-fold following exposure to a biologically significant amount of ionizing radiation.

In yet other embodiments of the method, a plurality of nucleic acid probe elements are bound to a surface, for example in an array, wherein the nucleic acid represents a gene product (including a protein or a nucleic acid such as RNA) that is differentially expressed by a cell following radiation induced biological stress. The plurality of probe elements are contacted with a plurality of gene products from a test cell, under conditions that allow the gene products (such as the nucleic acid sequences) to specifically hybridize to one of more of the probe elements, and provide a signal which indicates differential expression of one or more genes in a test cell has been exposed to biologically significant levels of ionizing radiation, and detecting the presence or absence of the signal. The probe elements may be selected from a set of nucleic acids that specifically hybridize to nucleic acids obtained from cells exposed to ionizing radiation. For example, the target elements are nucleic acid sequences that are differentially expressed by a cell more than 4, 24 or even 48 hours after exposure to the ionizing radiation. The probe elements may also include, or be limited to, nucleic acid sequences that are differentially expressed by at least 1.5-fold or 2-fold following exposure to a biologically significant amount of ionizing radiation.

The target elements may be one or more of the clones listed in Tables 9, 10, 11, 12, 13, or 14, for example Image ID clones 39993, 47475, 109123, 120362, 136114, 195365, 202549, 209340, 221846, 232837, 241412, 244227, 251516, 260619, 280386, 297442, 308588, 549146, 753418, 841278, 51699, 417226 and 28116. The probe nucleic acids may be DNA, such as cDNA, and cDNA obtained from mRNA expressed by the test cell. When the probe is reverse transcribed from cellular RNA, it may average about 1000–2000 nucleotides in length, but may in some instances be as long as 10,000 nucleotides. The probe nucleic acids of the probe set may be about as short as 8 or 10 nucleotides in length, but may also be as long as about 1000 to 1,000,000 nucleotides in length.

The method can also include contacting the probe elements with a plurality of control nucleic acids obtained from mRNA (for example by reverse transcription) of a control cell that has not been exposed to biologically significant levels of ionizing radiation and determining whether the nucleic acids from mRNA of the control cells hybridize differentially to the probe elements than the nucleic acid composition from the test cell. The test nucleic acid sequences are labeled with a first label that detects hybridization of the test nucleic acid sequences to the probe sequences, and the control nucleic acid sequences are labeled with a second label that detects hybridization of the control nucleic acid sequences to the probe sequences. The first and second labels interact to indicate whether expression of a nucleic acid sequence in the test cell has increased or decreased, relative to a baseline level. The first and second labels may be fluorophores of different colors. The nucleic acids from the control cells may, for example, be labeled with a green fluorophore, and the nucleic acids from the test cells may be labeled with a red fluorophore. Hence target elements for which differential gene expression does not occur will appear yellow, while underexpressed (decreased) gene expression will be indicated by green and overexpression (increased expression) by red.

The test cells may be animal cells, such as human cells, for example human peripheral blood cells, for example peripheral blood mononuclear cells, such as lymphocytes. In addition, the cells may be microbial or plant cells, such as microbes or cells from plants in the vicinity of a suspected environmental exposure to ionizing radiation.

In view of the set of stress response genes which have been identified, and may be identified using the present methods, the invention also includes methods of making microarrays for identifying cells that have actually or potentially been exposed to a biologically significant amount of ionizing radiation, by identifying genes that are differentially expressed by a cell following exposure to biologically significant amounts of ionizing radiation. A probe set is then provided, each element of the set including a nucleic acid sequence from a gene that is identified as differentially expressed by a cell following radiation induced biological stress. The target nucleic acid sequence is capable of hybridizing to a nucleic acid sequence which is differentially expressed by the cell following exposure to the biologically significant amount of ionizing radiation. In other embodiments, the genes that are differentially expressed by a cell are identified by exposing the cell to a biologically significant amount of ionizing radiation, obtaining mRNA expressed by the cell, reverse transcribing the mRNA into cDNA, labeling the cDNA, and hybridizing the labeled cDNA to a probe set that represents potential genes that may be differentially expressed and identifying members of the probe set that hybridize with the labeled cDNA. Any high throughput genomic analysis may be used to analyze the differential expression of the stress response genes, as may more standard molecular biology techniques such as dot-blot hybridization. The genes may include p53 regulated genes.

In another embodiment, the method further includes determining a dose response relationship between radiation exposure and differential expression of one or more genes, for example to determine a probable radiation dose in cells that have actually or potentially been exposed to the ionizing radiation. In yet another embodiment, identifying genes that are differentially expressed, for making a microarray, includes identifying genes that are differentially expressed in a cell type that is to be obtained from a subject for testing. The microarray may be used to measure a biological response to potential radiation exposure in the subject, for example in a cell type. The invention also includes microarrays which are made by this method.

The cell type may be peripheral blood cells, for example peripheral blood mononuclear cells, such as lymphocytes. In addition, the cell type may be any microbial or plant cell.

The invention also includes a method of diagnosing biologically significant radiation exposure in a subject, by obtaining a biological specimen from the subject, synthesizing cDNA from mRNA expressed in one or more cells of the biological specimen, and labeling the mRNA with a detectable label. The labeled mRNA is exposed to a probe set which represents genes that are differentially expressed in the biological specimen following exposure to the radiation. A determination is then made whether the labeled mRNA selectively hybridizes to one or more probes of the probe set that are associated with the radiation exposure, or hybridizes in a pattern that is associated with radiation exposure. Particular patterns of hybridization can also be associated with specified exposure doses, or time periods following exposure. The probe set may be one or more of the probes listed in any of Tables 9, 10, 11, 12, 13 or 14, or a probe set that includes at least 10%, 30% 40%, 50%, 75%, 80%, 90%, 95%, or 99% of the probes listed in any of Tables 9, 10, 11, 12, 13 or 14. In another embodiment, the method detects patterns of differential expression associated with biologically significant radiation exposure.

The invention also includes use of the microarrays of the present invention for measuring a biological response to in a subject, by obtaining a biological sample from the subject, synthesizing cDNA from mRNA expressed in one or more cells of the biological sample, labeling the mRNA with a detectable label, and exposing the labeled mRNA to a probe set which represents genes that are differentially expressed in the biological sample following radiation exposure, and determining if the labeled mRNA selectively hybridizes to one or more probes of the probe set that are associated with radiation exposure. The subject may be undergoing radiotherapy (or a candidate for radiotherapy) for the treatment of cancer, and the microarray can used to monitor or predict the subject's biological response to the radiotherapy.

Also included in the invention are the probe sets that provide information about exposure to biologically significant doses of ionizing radiation, for example probe sets including the DNA probe sets shown in any of Tables 9, 10, 11, 12, 13 or 14, or subsets of the probe sets of Tables 13 or Table 14. Such subsets may include sets having at least 10%, 30% 40%, 50%, 75%, 80%, 90%, 95%, or 99% of the probes sets shown in any of Tables 9, 10, 11, 12, 13 or 14.

BRIEF DESCRIPTION OF THE FIGURES

FIGS. 5A and 5B are schematic diagrams illustrating increased or decreased expression of transcripts identified on a microarray. The expression was measured in a panel of human cancer cell lines listed along the left margin, where the cell lines are shown divided into p53 wild type cells and p53 mutant cells. Numbers shown in the diagram measure relative induction for each gene over levels in untreated controls four hours after treatment with a 20 Gy dose of (A) ionizing radiation or (B) following treatment with 100 μg/ml methyl methanesulfonate (MMS) or 14 J/m$^2$ ultraviolet (UV) radiation. A zero indicates no detectable expression in either control or treated cells. The results are coded: red (vertical lines) for >2-fold induction, green (horizontal lines) for >2-fold reduction, and yellow (horizontal and vertical lines) for <2-fold change from untreated control.

SEQUENCE LISTING

Figure 1:
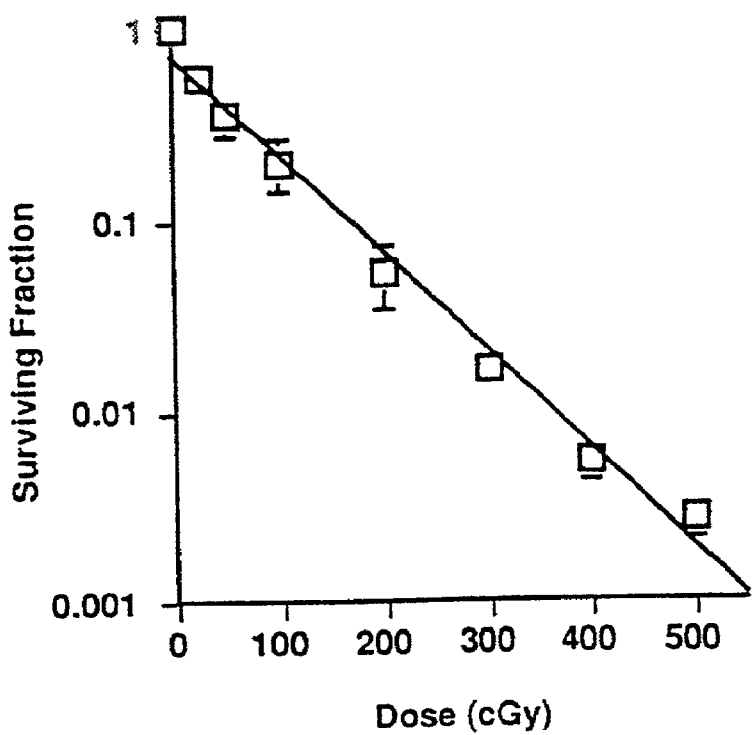
FIG. 1 is a graph showing the clonal survival of ML-1 cells exposed to $^{137}$Cs γ-rays. Points are the average of five independent experiments, and error bars are standard errors. Linear regression of the data was used to fit the curve shown.

SEQ ID NO: 1 is the nucleic acid sequence of Image ID Number 39993.
SEQ ID NO: 2 is the nucleic acid sequence of Image ID Number 47475.
SEQ ID NO: 3 is the nucleic acid sequence of Image ID Number 260619.
SEQ ID NO: 4 is the nucleic acid sequence of Image ID Number 753418.
SEQ ID NO: 5 is the nucleic acid sequence of Image ID Number 51699.
SEQ ID NO: 6 is the nucleic acid sequence of Image ID Number 701112.
SEQ ID NO: 7 is the nucleic acid sequence of Image ID Number 753447.
SEQ ID NO: 8 is the nucleic acid sequence of Image ID Number 547058.
SEQ ID NO: 9 is the nucleic acid sequence of Image ID Number 203132.
SEQ ID NO: 10 is the nucleic acid sequence of Image ID Number 1493160.
SEQ ID NO: 11 is the nucleic acid sequence of Image ID Number 109123.
SEQ ID NO: 12 is the nucleic acid sequence of Image ID Number 120362.
SEQ ID NO: 13 is the nucleic acid sequence of Image ID Number 136114.
SEQ ID NO: 14 is the nucleic acid sequence of Image ID Number 195365.
SEQ ID NO: 15 is the nucleic acid sequence of Image ID Number 202549.
SEQ ID NO: 16 is the nucleic acid sequence of Image ID Number 209340.
SEQ ID NO: 17 is the nucleic acid sequence of Image ID Number 221846.
SEQ ID NO: 18 is the nucleic acid sequence of Image ID Number 232837.
SEQ ID NO: 19 is the nucleic acid sequence of Image ID Number 241412.
SEQ ID NO: 20 is the nucleic acid sequence of Image ID Number 244227.
SEQ ID NO: 21 is the nucleic acid sequence of Image ID Number 251516.
SEQ ID NO: 22 is the nucleic acid sequence of Image ID Number 280386.
SEQ ID NO: 23 is the nucleic acid sequence of Image ID Number 297442.
SEQ ID NO: 24 is the nucleic acid sequence of Image ID Number 308588.
SEQ ID NO: 25 is the nucleic acid sequence of Image ID Number 549146.
SEQ ID NO: 26 is the nucleic acid sequence of Image ID Number 841278.
SEQ ID NO: 27 is the nucleic acid sequence of Image ID Number 28116.
SEQ ID NO: 28 is the nucleic acid sequence of Image ID Number 50615.

DETAILED DESCRIPTION OF SEVERAL EMBODIMENTS

Abbreviations and Definitions

The following definitions and methods are provided to better define the present invention and to guide those of ordinary skill in the art in the practice of the present invention. It must be noted that as used herein and in the appended claims, the singular forms "a" or "an" or "the" include plural referents unless the context clearly dictates otherwise. Thus, for example, reference to "a protein" includes a plurality of such proteins and reference to "the array" includes reference to one or more arrays and equivalents thereof known to those skilled in the art, and so forth.

Unless defined otherwise, all technical and scientific terms used herein have the same meaning as commonly understood to one of ordinary skill in the art to which this invention belongs. Although methods and materials similar or equivalent to those described herein can be used in the practice or testing of the present invention, suitable methods and materials are described below. The materials, methods, and examples are illustrative only and are not intended to be limiting.

MMS: methanesulfonate
RT: room temperature
Animal Cells: Cells obtained from multicellular vertebrate organisms, a category which includes, for example: mammals, primates, rodents, veterinary subjects, and birds. The cells can be obtained from any source, for example peripheral blood, urine, saliva, tissue biopsy, surgical specimen, amniocentesis samples and autopsy material. From these cells, genomic DNA, cDNA, mRNA, RNA, or protein can be isolated.

Biologically significant radiation exposure: An amount of radiation exposure sufficient to cause differential expression of stress genes in cells after they are exposed to the radiation.

Biological Specimen/Sample: One or more cells obtained from an animal or plant.

Cancer: malignant neoplasm that has undergone characteristic anaplasia with loss of differentiation, increased rate of growth, invasion of surrounding tissue, and is capable of metastasis.

cDNA (complementary DNA): A piece of DNA lacking internal, non-coding segments (introns) and regulatory sequences which determine transcription. cDNA may be synthesized in the laboratory by reverse transcription from messenger RNA extracted from cells.

Control Cells: Cells which have not been exposed to biologically significant levels of ionizing radiation.

DNA: Deoxyribonucleic acid. DNA is a long chain polymer which comprises the genetic material of most living organisms (some viruses have genes comprising ribonucleic acid, RNA). The repeating units in DNA polymers are four different nucleotides, each of which comprises one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

DNA chip: A DNA array in which multiple DNA molecules (such as cDNAs) of known DNA sequences are arrayed on a substrate, usually in a microarray, so that the DNA molecules can hybridize with nucleic acids (such as cDNA or RNA) from a specimen of interest. DNA chips are further described in Ramsay (*Nature Biotech.* 16:40–44, 1998).

Differential expression of a gene: This refers to either an increased or decreased expression of a gene, or any other change from the normal expression of a gene.

EST (Expressed Sequence Tag): This refers to a partial DNA or cDNA sequence, typically of between 1000 and 2000 sequential nucleotides, obtained from a genomic or cDNA library, prepared from a selected cell, cell type, tissue or tissue type, organ or organism, which corresponds to an mRNA of a gene found in that library. An EST is generally a DNA molecule sequenced from and shorter than the cDNA from which it is obtained.

Fluorophore: A chemical compound, which when excited by exposure to a particular wavelength of light, emits light (i.e., fluoresces), for example at a different wavelength. Fluorophores can be described in terms of their emission profile, or "color." Green fluorophores, for example Cy-3, FITC, and Oregon Green, are characterized by their emission at wavelengths generally in the range of 515–540 λ. Red fluorophores, for example Texas Red, Cy-5 and tetramethylrhodamine, are characterized by their emission at wavelengths generally in the range of 590–690 λ.

Examples of fluorophores that may be used in the present invention are provided in U.S. Pat. No. 5,866,366 to Nazarenko et al.: 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5''-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron .RTM. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other suitable fluorophores include GFP, Lissamine™, diethylaminocoumarin, fluorescein chlorotriazinyl, naphthofluorescein, 4,7-dichlororhodamine and xanthene and derivatives thereof. Other fluorophores known to those skilled in the art may also be used.

Gene expression microarrays: Microscopic arrays of cDNAs printed on a substrate, which serve as a high density hybridization target for mRNA probes, for example as described in Schena (*BioEssays* 18:427–431, 1996).

Genomic target sequence: A sequence of nucleotides located in a particular region in the human genome that corresponds to one or more specific loci.

High throughput genomics: This refers to application of genomic or genetic data or analysis techniques that use microarrays or other genomic technologies to rapidly identify large numbers of genes or proteins, or distinguish their structure, expression or function from normal or abnormal cells or tissues.

Human Cells: Cells obtained from *Homo sapiens*. The cells can be obtained from any source, for example peripheral blood, urine, saliva, tissue biopsy, surgical specimen, amniocentesis samples and autopsy material. From these cells, genomic DNA, cDNA, mRNA, RNA, or protein can be isolated.

Ionizing radiation (IR): An amount of radiation sufficient to separate orbiting electrons from an atomic nucleus. Ionizing radiation includes photons and accelerated particles. Photons (also called gamma rays) are given off in many types of nuclear decay. Ionizing rays (x-rays) occur when an electron is stopped in a dense material. Accelerated particles include protons from solar radiation, heavy nuclei in cosmic rays, and beta and alpha particles given up in nuclear decay.

Isolated: An "isolated" biological component (such as a nucleic acid, peptide, protein, or organelle) has been substantially separated, produced apart from, or purified away from other biological components in the cell of the organism in which the component naturally occurs, i.e., other chromosomal and extrachromosomal DNA and RNA, organelles, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Label: Detectable marker or reporter molecules, which can be attached to nucleic acids, for example probes. Typical labels include fluorophores, radioactive isotopes, ligands, chemiluminescent agents, and enzymes. Methods for labeling and guidance in the choice of labels appropriate for various purposes are discussed, e.g., in Sambrook et al., in *Molecular Cloning: A Laboratory Manual*, Cold Spring Harbor Laboratory Press (1989) and Ausubel et al., in

*Current Protocols in Molecular Biology*, Greene Publishing Associates and Wiley-Intersciences (1987).

Malignant: cells which have the properties of anaplasia, invasion and metastasis.

Messenger RNA (mRNA): RNA that is translated into protein. cDNA can be reverse transcribed from mRNA using standard molecular biology methods.

Microarray: An array that is miniaturized so as to require microscopic examination for visual evaluation.

Microbes: Any microorganism. Includes for example, viruses and members of the Monera, Protista or Fungi Kingdoms, for example bacteria and parasites.

Neoplasm: abnormal growth of cells

Normal cells: Non-tumor, non-malignant cells.

Nucleic acid array: An arrangement of nucleic acids (such as DNA or RNA) in assigned locations on a matrix, such as that found in cDNA or CGH arrays.

Nucleic acid: A deoxyribonucleotide or ribonucleotide polymer in either single or double stranded form, including known analogs of natural nucleotides.

Nucleic acid molecules representing genes: Any nucleic acid, for example DNA, cDNA or RNA, of any length suitable for use as a probe that is informative about the genes.

Oligonucleotide: A linear single-stranded polynucleotide sequence ranging in length from 2 to about 1,000,000 bases, for example a polynucleotide (such as DNA or RNA) which is at least 6 nucleotides, for example at least 15, 50, 100, 200, 1,000, 10,000 or even 1,000,000 nucleotides long. Oligonucleotides are often synthetic but can also be produced from naturally occurring polynucleotides.

Plant Cells: Cells obtained from any member of the Plantae Kingdom, a category which includes, for example, trees, flowering and non flowering plants, grasses, and *Arabidopsis*. The cells can be obtained from any part of the plant, for example roots, leaves, stems, or any flower part. From these cells, nucleic acid or protein can be isolated.

Probes and primers: A probe is an oligonucleotide or isolated nucleic acid capable of binding to a target nucleic acid of complementary sequence through one or more types of chemical bonds, usually through complementary base pairing with hydrogen bond formation. Oligonucleotide probes are often 10–50 or 15–30 bases long, and can be as long as about 1,000,000 bases. An oligonucleotide probe may include natural (A, T, C, G) or modified bases (7-deazaguanosine, inosine, etc.). In addition, the bases in an oligonucleotide probe may be joined by a linkage other than a phosphodiester bond, so long as it does not interfere with hybridization. Thus, oligonucleotide probes may be peptide nucleic acids in which the constituent bases are joined by peptide bonds rather than phosphodiester linkages.

Detectable label or reporter molecules can be attached to probes. Typical labels include fluorophores, radioactive isotopes, ligands, chemiluminescent agents, and enzymes. Methods for labeling and guidance in the choice of labels appropriate for various purposes are discussed, e.g., in Sambrook et al., in *Molecular Cloning: A Laboratory Manual*, Cold Spring Harbor Laboratory Press (1989) and Ausubel et al., in *Current Protocols in Molecular Biology*, Greene Publishing Associates and Wiley-Intersciences (1987).

Primers are short nucleic acids, such as DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (*Molecular Cloning: A Laboratory Manual*, Cold Spring Harbor Laboratory Press, 1989), Ausubel et al., in *Current Protocols in Molecular Biology*, Greene Publishing Associates and Wiley-Intersciences (1987), and Innis et al., *PCR Protocols, A Guide to Methods and Applications*, 1990, Innis et al. (eds.), 21–27, Academic Press, Inc.; San Diego, Calif. PCR primer pairs can be derived from a known sequence, for example, by using computer programs intended for that purpose such as Primer (Version 0.5,© 1991, Whitehead Institute for Biomedical Research, Cambridge, Mass.). One of skill in the art will appreciate that the specificity of a particular probe or primer increases with its length. Thus, for example, a primer comprising 20 consecutive nucleotides of a cDNA or gene will anneal to a target sequence contained within a cDNA or genomic DNA library with a higher specificity than a corresponding primer of only 15 nucleotides. Thus, in order to obtain greater specificity, probes and primers may be selected that comprise 20, 25, 30, 35, 40, 50 or more consecutive nucleotides of a cDNA or gene sequence.

Thus isolated nucleic acid molecules that comprise specified lengths of a nucleic acid sequence can be used in the present invention. Such molecules may comprise at least 20, 40, 50, 100, 1000, 10,000, or even 1,000,000 or more consecutive nucleotides of a nucleic acid sequence and may be obtained from any region of a nucleic acid sequence.

Probe Element: A nucleic acid sequence from a gene which is represented in a probe set. For example, the gene may be differentially expressed by a cell following radiation induced biological stress. In addition, the gene may be unaffected in its expression following radiation induced biological stress, for example control genes.

Probe set: A population of two or more probes which represent genes that are differentially expressed in cells that have been exposed to a biologically significant amount of ionizing radiation. The probe set may be nucleic acids, for example RNA, cDNAs, and/or oligonucleotides that specifically hybridize to complementary sequences in a nucleic acid composition, for example from test cells which may have been exposed to ionizing radiation. For example, the probe set may contain any of the probes shown in Tables 4 or 5. In addition, the probe set can be bound in an array to a surface.

Purified: the term purified does not require absolute purity; rather, it is intended as a relative term. Thus, for example, a purified protein preparation is one in which the protein is more pure than the protein in its natural environment within a cell. In one embodiment, a preparation of a protein is purified such that the protein represents at least 50% of the total protein content of the preparation.

Radiation dose: Defined in terms of energy deposition. The basic unit is the gray (Gy), equal to 1 joule per kilogram.

Radiation induced biological stress: The induction of differential expression of stress genes in cells after they are exposed to radiation. Examples include, but are not limited to: CIP1/WAF1, GADD45, MDM2, BCL2, FOS, JUN, REL-B, ATF3, BAX.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of nucleic acid or amino acid sequences will possess a relatively high degree of sequence identity when aligned using standard methods. This homology will be more significant when the orthologous proteins or nucleic acids are derived from species which are more closely related (e.g., human and chimpanzee sequences), compared to species more distantly related (e.g., human and C. elegans sequences). Typically, orthologs are at least 50% identical at the nucleotide level and at least 50% identical at the amino acid level when comparing human orthologous sequences.

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237–44, 1988; Higgins & Sharp, CABIOS 5:151–3, 1989; Corpet et al., Nuc. Acids Res. 16:10881–90, 1988; Huang et al. Computer Appls. in the Biosciences 8, 155–65, 1992; and Pearson et al., Meth. Mol. Bio. 24:307–31, 1994. Altschul et al, J. Mol. Biol. 215:403–10, 1990, presents a detailed consideration of sequence alignment methods and homology calculations.

The NCBI Basic Local Alignment Search Tool (BLAST) (Altschul et al. J. Mol. Biol. 215:403–10, 1990) is available from several sources, including the National Center for Biotechnology Information (NCBI, Bethesda, Md.) and on the Internet, for use in connection with the sequence analysis programs blastp, blastn, blastx, tblastn and tblastx. A description of how to determine sequence identity using this program is available at the NCBI website.

Homologs are typically characterized by possession of at least 60%, 70%, 75%, 80%, 90%, 95% or at least 98% sequence identity counted over the full length alignment with a sequence using the NCBI Blast 2.0, gapped blastp set to default parameters. Queries searched with the blastn program are filtered with DUST (Hancock, and Armstrong, 1994, Comput. Appl. Biosci. 10:67–70). Other programs use SEG.

One of ordinary skill in the art will appreciate that these sequence identity ranges are provided for guidance only; it is entirely possible that strongly significant homologs could be obtained that fall outside of the ranges provided. The present invention provides not only the peptide homologs described above, but also nucleic acid molecules that encode such homologs.

One indication that two nucleic acid sequences are substantially identical is that the polypeptide which the first nucleic acid encodes is immunologically cross reactive with the polypeptide encoded by the second nucleic acid.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that all encode substantially the same protein.

An alternative indication that two nucleic acid molecules are closely related is that the two molecules hybridize to each other under stringent conditions, as described under "specific hybridization."

Specific hybridization: Specific hybridization refers to the binding, duplexing, or hybridizing of a molecule only or substantially only to a particular nucleotide sequence when that sequence is present in a complex mixture (e.g. total cellular DNA or RNA). Specific hybridization may also occur under conditions of varying stringency.

Hybridization conditions resulting in particular degrees of stringency will vary depending upon the nature of the hybridization method of choice and the composition and length of the hybridizing DNA used. Generally, the temperature of hybridization and the ionic strength (especially the Na$^+$ concentration) of the hybridization buffer will determine the stringency of hybridization. Calculations regarding hybridization conditions required for attaining particular degrees of stringency are discussed by Sambrook et al. (In: Molecular Cloning: A Laboratory Manual, Cold Spring Harbor, N.Y., 1989 ch. 9 and 11). By way of illustration only, a hybridization experiment may be performed by hybridization of a DNA molecule to a target DNA molecule which has been electrophoresed in an agarose gel and transferred to a nitrocellulose membrane by Southern blotting (Southern, J. Mol. Biol. 98:503, 1975), a technique well known in the art and described in Sambrook et al. (Molecular Cloning: A Laboratory Manual, Cold Spring Harbor, N.Y., 1989).

Hybridization with a target probe labeled with [$^{32}$P]-dCTP is generally carried out in a solution of high ionic strength such as 6×SSC at a temperature that is 20–25° C. below the melting temperature, $T_m$, described below. For such Southern hybridization experiments where the target DNA molecule on the Southern blot contains 10 ng of DNA or more, hybridization is typically carried out for 6–8 hours using 1–2 ng/ml radiolabeled probe (of specific activity equal to 10$^9$ CPM/μg or greater). Following hybridization, the nitrocellulose filter is washed to remove background hybridization. The washing conditions should be as stringent as possible to remove background hybridization but to retain a specific hybridization signal.

The term $T_m$ represents the temperature (under defined ionic strength, pH and nucleic acid concentration) at which 50% of the probes complementary to the target sequence hybridize to the target sequence at equilibrium. Because the target sequences are generally present in excess, at $T_m$ 50% of the probes are occupied at equilibrium. The $T_m$ of such a hybrid molecule may be estimated from the following equation (Bolton and McCarthy, Proc. Natl. Acad. Sci. USA 48:1390, 1962): $T_m$=81.5° C.−16.6(log$_{10}$[Na$^+$])+0.41(% G+C)−0.63(% formamide)−(600/l); where l=the length of the hybrid in base pairs.

This equation is valid for concentrations of Na$^+$ in the range of 0.01 M to 0.4 M, and it is less accurate for calculations of $T_m$ in solutions of higher [Na$^+$]. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al. (Molecular Cloning: A Laboratory Manual, Cold Spring Harbor, N.Y., 1989).

Thus, by way of example, for a 150 base pair DNA probe derived from a cDNA (with a hypothetical % GC=45%), a calculation of hybridization conditions required to give particular stringencies may be made as follows: For this example, it is assumed that the filter will be washed in 0.3×SSC solution following hybridization, thereby: [Na$^+$] =0.045 M; % GC=45%; Formamide concentration=0; l=150 base pairs; $T_m$=81.5−16.6(log$_{10}$[Na$^+$])+(0.41×45)− (600/150); and so $T_m$=74.4° C.

The $T_m$ of double-stranded DNA decreases by 1–1.5° C. with every 1% decrease in homology (Bonner et al., J. Mol. Biol. 81:123, 1973). Therefore, for this given example, washing the filter in 0.3×SSC at 59.4–64.4° C. will produce a stringency of hybridization equivalent to 90%; that is, DNA molecules with more than 10% sequence variation relative to the target cDNA will not hybridize. Alternatively, washing the hybridized filter in 0.3×SSC at a temperature of 65.4–68.4° C. will yield a hybridization stringency of 94%; that is, DNA molecules with more than 6% sequence variation relative to the target cDNA molecule will not hybridize. The above example is given entirely by way of theoretical illustration. One skilled in the art will appreciate that other hybridization techniques may be utilized and that variations in experimental conditions will necessitate alternative calculations for stringency.

In the present invention, stringent conditions may be defined as those under which DNA molecules with more than 25%, 15%, 10%, 6% or 2% sequence variation (also termed "mismatch") will not hybridize. Stringent conditions are sequence dependent and are different in different circumstances. Longer sequences hybridize specifically at higher temperatures. Generally, stringent conditions are selected to be about 5° C. lower than the thermal melting point $T_m$ for the specific sequence at a defined ionic strength and pH. An example of stringent conditions is a salt concentration of at least about 0.01 to 1.0 M Na ion concentration (or other salts) at pH 7.0 to 8.3 and a temperature of at least about 30° C. for short probes (e.g. 10 to 50 nucleotides). Stringent conditions can also be achieved with the addition of destabilizing agents such as formamide. For example, conditions of 5×SSPE (750 mM NaCl, 50 mM Na Phosphate, 5 mM EDTA, pH 7.4) and a temperature of 25–30° C. are suitable for allele-specific probe hybridizations.

A perfectly matched probe has a sequence perfectly complementary to a particular target sequence. The test probe is typically perfectly complementary to a portion (subsequence) of the target sequence. The term "mismatch probe" refers to probes whose sequence is deliberately selected not to be perfectly complementary to a particular target sequence.

Transcription levels can be quantitated absolutely or relatively. Absolute quantitation can be accomplished by inclusion of known concentrations of one or more target nucleic acids (for example control nucleic acids such as Bio B or with a known amount the target nucleic acids themselves) and referencing the hybridization intensity of unknowns with the known target nucleic acids (for example by generation of a standard curve).

Subject: Living multicellular vertebrate organisms, a category which includes, both human and veterinary subjects for example, mammals, birds and primates.

Test Cell: A cell which has been or may have been exposed to biologically significant levels of ionizing radiation. Using the method of the present invention, whether a test cell has been exposed to biologically significant levels of ionizing radiation can be determined. Test cells can be from any origin, including for example plant and animal cells. In particular examples, the test cells are peripheral blood cells.

Tumor: a neoplasm

Additional definitions of terms commonly used in molecular genetics can be found in Benjamin Lewin, *Genes V* published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

EXAMPLE 1

Apoptosis of ML Cells after Irradiation

This example describes experiments in which the percent of cells undergoing apoptosis following different levels of irradiation was calculated.

ML-1 cells, a human myeloid leukemia cell line, were grown in RPMI 1640 medium supplemented with 10% heat-inactivated (56° C. for 45 minutes) fetal calf serum and 100 U/ml penicillin and 100 µg/ml streptomycin in a humidified, 5% $CO_2$ atmosphere in a 37° incubator. Cells were irradiated at approximately 5.1 cGy/minute to total doses between 2 and 2000 cGy using a Mark 1-68 $^{137}$Cs source (J.L. Shepherd and Associates, Inc., San Fernando, Calif.) with lead attenuators in place. The dosimetry of the source was confirmed by exposing TLD monitors (Landauer Inc., Glenwood, Ill.) in the same configuration used for cellular irradiations to the range of doses used. Even at the lowest doses, the calculated absorbed dose (Landauer special dosimetry services) varied by less than 3% from the dose expected. Due to the nature of sparsely ionizing radiation such as γ-rays, it is highly unlikely that cells in the irradiated population will remain unexposed at even the lowest doses used.

To determine if cells underwent apoptosis following irradiation, the cells were irradiated and then incubated for 1, 2, or 3 days. The cells were subsequently fixed in methanol, and stained with DAPI solution (50 ng/ml final concentration). An Olympus fluorescent microscope was used to score nuclei exhibiting characteristic morphological features of apoptosis, and results were expressed as the number of apoptotic nuclei over the total number of nuclei counted. Flow cytometry was used to measure the effects of irradiation on the cell cycle. In this method, cells were fixed in 70% ethanol 0, 8, 10, 12 and 24 hours after irradiation, treated with RNase (100 ug/ml) at 37° C., then stained with propidium iodide. Samples were analyzed using a Becton-Dickenson FacScan and cell cycle distributions were fitted using the Cell Quest data analysis program.

ML-1 cells irradiated with $^{137}$Cs γ-rays showed a survival response similar to that of other human cell lines of myeloid or lymphoid lineage (FIG. 1), which are typically more radiosensitive than cell lines derived from other tissue types. The survival curve had no apparent shoulder and predicted a $D_0$ of approximately 73 cGy. The changes in plating efficiency induced by doses of 2, 5, and 10 cGy were so low as not to be measurably different from fluctuations in the colony formation assay (p>0.1). In four independent experiments, the mean plating efficiency of untreated controls was 0.129+/−0.069 while the mean plating efficiency for all doses combined (2, 5 and 10 cGy) was 0.127+/−0.058.

Figure 2:
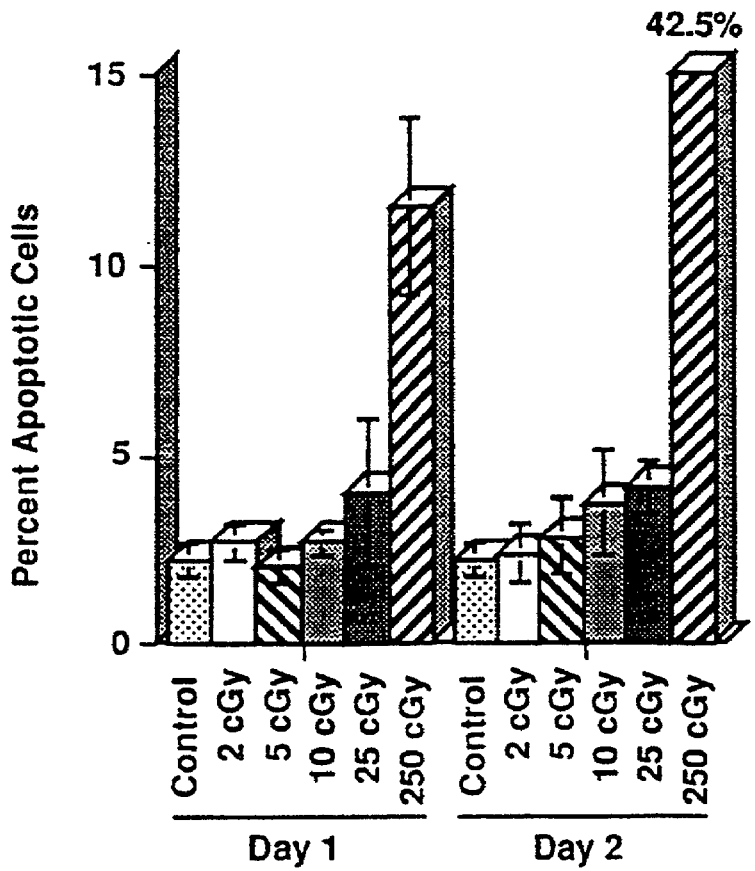
FIG. 2 is a bar graph showing the percent of apoptotic cells one or two days after radiation treatment. Results are the average of 3–4 independent experiments in which at least 250 cells were scored for each point. Error bars are standard errors.

Although previous studies demonstrated that high doses of ionizing radiation efficiently induce rapid apoptosis in ML-1 cells (Zhan et al. *Oncogene* 9:3743–51, 1994), at lower, relatively non-toxic doses (cells irradiated with 25 cGy or less), very little apoptosis was measurable. A more sensitive method for detecting apoptotic cells was achieved by scoring morphology of DAPI stained cells. As shown in FIG. 2, two days after irradiation, a trend of increasing apoptosis with increasing dose emerged between 2 and 25 cGy, although due to experimental fluctuations, this increase was only significant at the p<0.01 level (paired t-test) following the 25 cGy dose. In contrast, cultures treated with 250 cGy showed over 40% morphologically apoptotic cells two days after irradiation. No further increases in apoptotic fraction were observed at times later than two days following treatment for any of the doses tested.

Figure 3A:
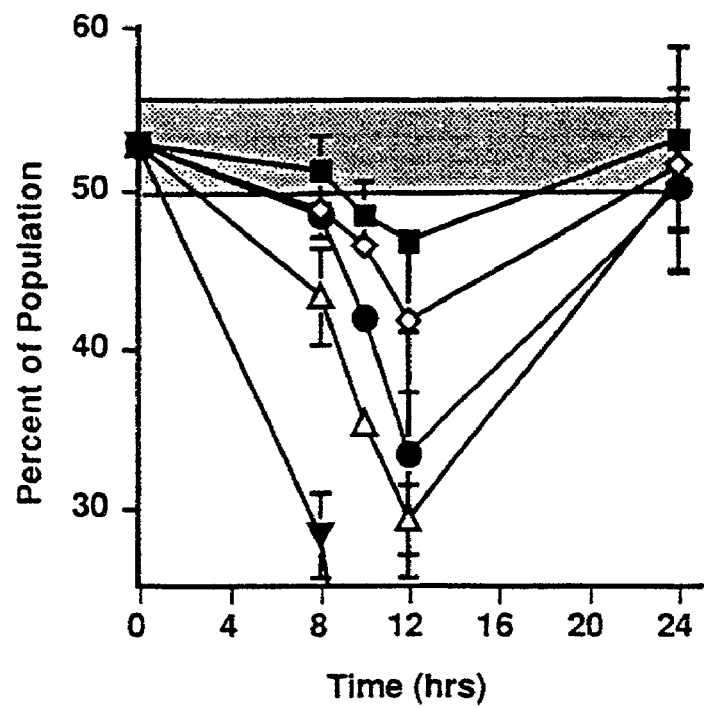
FIG. 3A is a graph showing the fraction of S-phase cells in the population at various times after irradiation of exponentially growing ML-1 cells with 2 cGy (■), 5 cGy (◇), 10 cGy (●), 25 cGy (Δ), or 250 cGy (▼) of $^{137}$Cs γ-rays. Points are the mean of three independent experiments, and error bars are standard deviations. The points for the 12 and 24 hour timepoints have been offset slightly to make the error bars more distinguishable. The shaded area represents the range of S-phase fractions in untreated control populations and is the mean plus and minus the standard deviation of the control measurements at all timepoints.
Figure 3B:
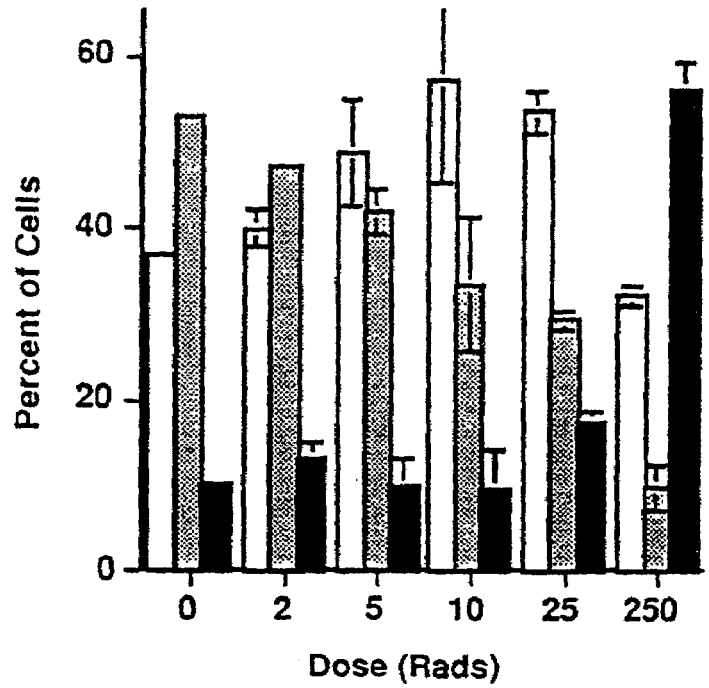
FIG. 3 B is a bar graph showing the cell cycle distribution at the time of maximum perturbation (12 hours) for the low dose treatments. For each dose, the percent of cells in G1 is represented by the open bar, cells in S by the grey bar, and cells in G2 by the black bar. The values shown are the mean of three independent experiments, and error bars are standard deviations. Where error bars are not visible the standard deviation was 0.76. An asterisk indicates a point not significantly different from the control at or below the $p<0.005$ level.

In contrast to their effect on apoptosis, doses below 25 cGy significantly and reproducibly perturbed cell cycle progression in a dose-dependent manner (FIGS. 3A and 3B). Even the lowest dose tested, 2 cGy, caused a transient reduction of the S-phase fraction. This effect was only significant at 12 hours after irradiation with 2 cGy, while increased doses resulted in larger and more rapid decreases in the S-phase fraction of the population (FIGS. 3A and 3B). By 24 hours post-irradiation, the populations treated with doses of 25 cGy or below had all recovered their normal cell cycle distributions, while cells treated with the higher dose of 250 cGy still showed a profoundly arrested profile with very few (6.6+/−1.9 percent) S-phase cells.

These results demonstrate that low-levels of non-toxic irradiation can be effectively administered, and that even at these low doses, progression of the cell cycle is perturbed.

EXAMPLE 2

Construction of cDNA Microarrays

This example describes experiments conducted to identify genes which are differentially expressed in cells exposed to radiation, such as low level radiation, which were used to construct cDNA microarrays. Before a probe set can be constructed which identifies differential expression of genes in radiation exposed cells, probes are selected for the set. This selection can be achieved by using cDNA arrays having a general sampling of ESTs, for example from human, mouse, or plant genes. The array of ESTs can be exposed to nucleic acid compositions from test cells that have been exposed to a dose of ionizing radiation sufficient to induce differential expression of stress genes in the test cells. The nucleic acids can then be labeled (for example by reverse transcription from cellular mRNA to labeled cDNA), and exposed to the array. Specific hybridization to an EST in the array, or differential hybridization by a cDNA from a cell that has been irradiated, identifies a potential probe for the probe set. Subsequent confirmation of differential expression can be achieved by northen blot analysis, or other techniques.

The microarray used in this example included a general sampling of human genes (622 ESTs) plus another set of genes (616 ESTs) which were chosen on the basis of their roles in cancer or lymphoid biology. The genes represented in the 1.2K array are shown in Table 1. The sequences are identified in Table 1 by Image Consortium Clone number (hereinafter "Image No."). This number can be searched on the ATCC Image Consortium Clones database at the ATCC (Manassas, Va.) website, with links to the ATCC accession number of clones from which the sequences can be obtained, and links to Genbank sequence listings which correspond to the Image Number. The array was constructed with ESTs informative for the exposure of interest, namely radiation exposure. A panel of housekeeping genes and other internal controls was also included on the array. The selection of this panel has been described (DeRisi et al., *Nat. Genet.* 14:457–460, 1996).

TABLE 1

Image ID Numbers of Genes Present in the 1.2K array.

21420; 22036; 29054; 33941; 34327; 38805; 42894; 43110; 47359; 471252; 486375; 80549; 161023; 51363; 310406; 470470; 485963;

TABLE 1-continued

Image ID Numbers of Genes Present in the 1.2K array.

298371; 62186; 41959; 25081; 25725; 32198; 36593; 36844; 40765; 44527; 44710; 49888; 51528; 51740; 31116; 253773; 266486; 364278; 51825; 193913; 363805; 344482; 360201; 21477; 22040; 29204; 34011; 34357; 38829; 42906; 43129; 47384; 471494; 486233; 81221; 162584; 51439; 310490; 470685; 486161; 298371; 80549; 135118; 25154; 25764; 32304; 36676; 36904; 40831; 44537; 44721; 49897; 51540; 51785; 32790; 253869; 267246; 364982; 52193; 196543; 364110; 344769; 361401; 21468; 22230; 29234; 34005; 34349; 38840; 42910; 43194; 47386; 471715; 486086; 82991; 162772; 51746; 310390; 470730; 486074; 299626; 110589; 136769; 25169; 25880; 32319; 36681; 36916; 40874; 44563; 44722; 49898; 51555; 51814; 32983; 257766; 267682; 364752; 52564; 199381; 364975; 345527; 361815; 21531; 22260; 29435; 34141; 34355; 38859; 42927; 43229; 47463; 472067; 486785; 82850; 48398; 51854; 310428; 470691; 486716; 300051; 113941; 154763; 25400; 26052; 32409; 36700; 36922; 40886; 44584; 45188; 49926; 51621; 51940; 33368; 258589; 268652; 364716; 178169; 200209; 366539; 347573; 366981; 21652; 28573; 29438; 34217; 38567; 38876; 42993; 47229; 47475; 484993; 62186; 84730; 49164; 307741; 322000; 471217; 296021; 301363; 121147; 25485; 31852; 32407; 36717; 40493; 40911; 44605; 49751; 49967; 51666; 27944; 34005; 260052; 362009; 365147; 178508; 361692; 366509; 347685; 21656; 28595; 29627; 34247; 38573; 38966; 43021; 47306; 47493; 485690; 77577; 85906; 49950; 309615; 322604; 471620; 296642; 303109; 129268; 25495; 31855; 32438; 36775; 40562; 40959; 44666; 49777; 49980; 51685; 28573; 35326; 261518; 362332; 365647; 182633; 361692; 366942; 357357; 22012; 28776; 29629; 34255; 38647; 38983; 43060; 47343; 47499; 486012; 79742; 86017; 50576; 309477; 323162; 471822; 297589; 306170; 26503; 25517; 31988; 32427; 36796; 40670; 40991; 44689; 49788; 50038; 51687; 28774; 35516; 262575; 362926; 366420; 183661; 362702; 375620; 358677; 21810; 28985; 29640; 34304; 38770; 39086; 43092; 47333; 47631; 486335; 80239; 23464; 50503; 310141; 323001; 471918; 298187; 307471; 26599; 25584; 32141; 32531; 36790; 40764; 41094; 44699; 49849; 50032; 51699; 30781; 36074; 264606; 363799; 366576; 191007; 363539; 375635; 358538; 22285; 22589; 30543; 34396; 34671; 39173; 43231; 43563; 47833; 486560; 488373; 110589; 52489; 193736; 323776; 486510; 489217; 321246; 162479; 231292; 26082; 26483; 32649; 36927; 37230; 41439; 45222; 45643; 50232; 51961; 52587; 43129; 268727; 279482; 375922; 205905; 236420; 377275; 375635; 417127; 22293; 22611; 30573; 34537; 34761; 39195; 43338; 43601; 47874; 486844; 488801; 110503; 52162; 190711; 324698; 487130; 489194; 321308; 50576; 247869; 26087; 26531; 32644; 36950; 37231; 41452; 45233; 45658; 50234; 52019; 52629; 131828; 270148; 279954; 376362; 209655; 239287; 377181; 375724; 418320; 22379; 22798; 30578; 34555; 34860; 39205; 43241; 43622; 47884; 487417; 488989; 112035; 52681; 200378; 324655; 487097; 510130; 322148; 52681; 252185; 26129; 26541; 32658; 36983; 37234; 41511; 45291; 45794; 50271; 52222; 52650; 132420; 270980; 281029; 376285; 213502; 241489; 377441; 375843; 428248; 22445; 22790; 30588; 34606; 34945; 39270; 43409; 43631; 48077; 487264; 489419; 114116; 179711; 201797; 324815; 487777; 510258; 322452; 190107; 256323; 26128; 26572; 32682; 36975; 37269; 41559; 45376; 45851; 50308; 52342; 52652; 133122; 271478; 281778; 376737; 219735; 242134; 415206; 376294; 470792; 22493; 29799; 30592; 34637; 39093; 39285; 43504; 47648; 48085; 487386; 108284; 114648; 180447; 323028; 325182; 487965; 308392; 323181; 192694; 26147; 32609; 32684; 37040; 41208; 41773; 45421; 50117; 50322; 52338; 36215; 135381; 271416; 366647; 376649; 231089; 376110; 415060; 376218; 22545; 30012; 30622; 34647; 39148; 39380; 43541; 47679; 48097; 487878; 108837; 115277; 183950; 323390; 327396; 488891; 320514; 323648; 193901; 26184; 32615; 32717; 37118; 41199; 41796; 45564; 50106; 50359; 52415; 36844; 137531; 271662; 366824; 380403; 231292; 376303; 415636; 376507; 22568; 30149; 30619; 34662; 39159; 39391; 43549; 47727; 48234; 488103; 110022; 115408; 187987; 323555; 328692; 489042; 320903; 324700; 209310; 26286; 32626; 32707; 37145; 41356; 41792; 45568; 50171; 50363; 52489; 39920; 137575; 272110; 366904; 415102; 231497; 376781; 415679; 380738; 22589; 30272; 30664; 34660; 39169; 39542; 43550; 47838; 48406; 488596; 109957; 115336; 192694; 323500; 340644; 489327; 321242; 328330; 222502; 26366; 32636; 32750; 37196; 41392; 41813; 45604; 50203; 50503; 52530; 41565; 138460; 278409; 375724; 415731; 232714; 376725; 416184; 381219; 23014; 23731; 30885; 34974; 35609; 39827; 43711; 44105; 48677; 489395; 510245; 121849; 201673; 221690; 343166; 510467; 112500; 343465; 257458; 282065; 26585; 27473; 32898; 37347; 37508; 42059; 45840; 46329; 50603; 52681; 53084; 140358; 283116; 293274; 417403; 243143; 262691; 427923; 471218; 488658; 23019; 23804; 30970; 35110; 35623; 39861; 43719; 44159; 48717; 509710; 512458; 123586; 203132; 221619; 343871; 512391; 120466; 343311; 260288; 286197; 26593; 27511; 33008; 37366; 37513; 42088; 45941; 46339; 50666; 52753; 53107; 140827; 284031;

TABLE 1-continued

Image ID Numbers of Genes Present in the 1.2K array.

293934; 417592; 253545; 264576; 427943; 471631; 488904; 23073; 23831; 30966; 35284; 35615; 39876; 43826; 44173; 48713; 509731; 512472; 123953; 203017; 223176; 344109; 198205; 124086; 343646; 264200; 288650; 26659; 27549; 33045; 37380; 37622; 42096; 46019; 46354; 50816; 52773; 53128; 143751; 284459; 295208; 417689; 254428; 264554; 427943; 471889; 509710; 23132; 23866; 30981; 35297; 35665; 39884; 43858; 44180; 48762; 509820; 512385; 124554; 204301; 230976; 345600; 322029; 26992; 345645; 271416; 290117; 26789; 27624; 33183; 37435; 37679; 42130; 46042; 46419; 50888; 52896; 53155; 144944; 288797; 298314; 418111; 254187; 268412; 427750; 485192; 509682; 23185; 30691; 31061; 35313; 39686; 39903; 43885; 48452; 48803; 510101; 116906; 125187; 204681; 340734; 345928; 60298; 328467; 345722; 272110; 26801; 32774; 33176; 37433; 41857; 42214; 46171; 50555; 50941; 52931; 138604; 144693; 289606; 417226; 418138; 258747; 417136; 427686; 486199; 23332; 30730; 31116; 35320; 39728; 39965; 43960; 48458; 49161; 510151; 116713; 125676; 205633; 341130; 346534; 72869; 340947; 346587; 279727; 26922; 32790; 33267; 37451; 41918; 42284; 46213; 50561; 50999; 53024; 138917; 145503; 291057; 417124; 427857; 258790; 417218; 428404; 486410; 23346; 30802; 31131; 35483; 39781; 39993; 44014; 48503; 49243; 510405; 116781; 126379; 209310; 340922; 357309; 73515; 341763; 346396; 280465; 27230; 32822; 33274; 37477; 42020; 42295; 46302; 50576; 51018; 53068; 139073; 145932; 291503; 417322; 428248; 259241; 418105; 428231; 487982; 23692; 30852; 31143; 35559; 39796; 40008; 44050; 48629; 49255; 510595; 120157; 126542; 213597; 340878; 357239; 23173; 342256; 346305; 280735; 27052; 32875; 33415; 37485; 42058; 42349; 46303; 50609; 51209; 53071; 138998; 147075; 291736; 417357; 429142; 259291; 418436; 429135; 488092; 24110; 24652; 31210; 35850; 36232; 40151; 44178; 44367; 49403; 512276; 26503; 231302; 244355; 358467; 36809; 43504; 357374; 291943; 309924; 27681; 28116; 33632; 37721; 38397; 42576; 46427; 47038; 51318; 53164; 53322; 153355; 299198; 306013; 430027; 271198; 290493; 469543; 509588; 203184; 24145; 24886; 31238; 35865; 36291; 40205; 44193; 44414; 49509; 512294; 26474; 233194; 248032; 358168; 146307; 47559; 358848; 293032; 320538; 27715; 28245; 33643; 37760; 38393; 42615; 46449; 47110; 51332; 53173; 53358; 154015; 299539; 306134; 469256; 280376; 290871; 470602; 509882; 241412; 24269; 24899; 31242; 35933; 36393; 40276; 44218; 44477; 49584; 512244; 26167; 234198; 248613; 359171; 151767; 49576; 359119; 295093; 322000; 27794; 28309; 33690; 37796; 38471; 42648; 46548; 47125; 51373; 53184; 154472; 300973; 307293; 469724; 280768; 290724; 470493; 510381; 248258; 24392; 24927; 31355; 36007; 36560; 40304; 44255; 44495; 49608; 512429; 26871; 234357; 249348; 359051; 152762; 51686; 359077; 298314; 327111; 27815; 28410; 33692; 37797; 38500; 42677; 46574; 47202; 51418; 53185; 154441; 301723; 307342; 470185; 284546; 295389; 470635; 124927; 296476; 24588; 31155; 31454; 36060; 40026; 40360; 44266; 49277; 49665; 127089; 26811; 236338; 357435; 359412; 154420; 347032; 359466; 300071; 27818; 33438; 33794; 37892; 42352; 42700; 46711; 51219; 51432; 53238; 147744; 154536; 302394; 429057; 470196; 284669; 429539; 470610; 125555; 24609; 31154; 31456; 36109; 40117; 40450; 44302; 49318; 49666; 128100; 26599; 236422; 357442; 359769; 154420; 347751; 359465; 300960; 27848; 33477; 33803; 37904; 42363; 42777; 46777; 51241; 51454; 53227; 149910; 155717; 302157; 429368; 470251; 286249; 429861; 470817; 126519; 24638; 31169; 31687; 36191; 40110; 40440; 44307; 49322; 49691; 127821; 26599; 238577; 357909; 360531; 158970; 356890; 359793; 304947; 27927; 33525; 33831; 37962; 42380; 42844; 46920; 51302; 51461; 53292; 153025; 156103; 302490; 429926; 470062; 288733; 469272; 471096; 194384; 24642; 31164; 31863; 36202; 40111; 40442; 44311; 49383; 49725; 129632; 27899; 243159; 357807; 361381; 158970; 356964; 361728; 305455; 28089; 33620; 33943; 37964; 42532; 42888; 46936; 51293; 51504; 53316; 152844; 159833; 305455; 429976; 470621; 289428; 469731; 471174; 195889

The human myeloid leukemia cell line ML-1 is available from the National Cancer Institute's Anti-Neoplastic Drug Screen Panel (NCI-ADS). The members of this panel are listed in Table 2, and are described in many publications, including Monks et al. (*J. Nat. Cancer Institut.* 83:757–66, 1991), and on the NCI Web page. ML-1 was selected as the test cell in which radiation induced differential expression of genes would be measured. A characteristic of this cell that made it particularly useful for this purpose was that it contains endogenous wild-type p53, which is a cellular stress response mediator following exposure to ionizing radiation. ML-1 contains physiologic levels of p53, rather than the unnatural and often highly overexpressed levels often seen in artificially engineered systems. Moreover, ML-1 is a myeloid cell line, which is prone to undergo rapid apoptosis following genotoxic stress. This characteristic results in the induction of genes specifically associated with rapid apoptosis, such as BAX, MCLI, GADD34 and BCL-X (Zhan et al., *Oncogene* 9:3743–51, 1994 and *Oncogene* 14:1031–9, 1997). In addition to ML-1 cells, other cells that can be used to assess the induction of differential expression of genes in radiation exposed cells include other lymphoid cell lines, such as those with wild-type levels of p53, such as Molt4, WMN, TK6 or SR, which may induce genes not found to be regulated in ML-1. Cell lines derived from blood cells (such as these lines) are selected to provide responses more characteristic of peripheral blood responses than would cell lines from other sites, such as colon or breast cell lines (for example RKO or MCF7, respectively). Gene induction can also be measured directly in ex vivo irradiated human peripheral blood cells, as a particularly relevant model system, for methods in which peripheral blood specimens are analyzed to clinically screen for biologically significant radiation exposure (see EXAMPLE 9).

TABLE 2

The National Cancer Institute's Anti-Neoplastic Drug Screen Panel*

| Tissue Origin | Cell Line Names |
|---|---|
| Breast Cancer | BT-549; HS 578T; MCF7; MDA-MB-231; MDA-MB435; MDA-N; NCI-ADR; T-47D; NCI/ADR-RES; MAXF 401; MDA-MB-468; SK-BR-3 |
| CNS Cancer | SF-268; SF-295; SF-539; SNB-19; SNB-75; U251; SNB-78; TE671; XF 498 |
| Colon Cancer | COLO205; HCC-2998; HCT116; HCT15; HT29; KM12; RKO; SW-620; DLD-1; KM20L2 |
| Non Small Cell Lung Cancer | A549; EKVX; HOP-62; HOP-92; NCI-H226; NCI-H23; NCI-H322M; NCI-H460; NCI-H522; HOP-18; HOP-19; LXFL 529 |
| Small Cell Lung Cancer | DMS 114; DMS 273; SHP-77 |
| Leukemia | CCRF-CEM; HL60; K562; MOLT4; RPMI-8226; SR; P388 P388/ADR |
| Melanoma | LOX-IVMI; M14; MALME-3M; SK-MEL-2; SK-MEL-28; SK-MEL-5; UACC-257; UACC-62; RPMI-7951; M19-MEL |
| Ovarian Cancer | IGROV-1; OVCAR-3; OVCAR-4; OVCAR-5; OVCAR-8; SK-OV-3 |
| Prostate Cancer | DU-145; PC-3 |
| Renal Cancer | 786-O; A498; ACHN; CAKI-1; RXF 393; SN12C; TK-10; UO-31; RXF-631; SN12K1 |

*Cells are available either from ATCC (Manassas, VA) or from the Frederick cancer research facility in Frederick, MD.

ML-1 cells were grown and irradiated at approximately 3.1 Gy/minute to total doses of 0.25, 2 or 20 Gy using a Mark 1-68 $^{137}$Cs source, as described in EXAMPLE 1. EST targets identified in Table 1 were prepared by PCR amplification and arrayed on poly-L-lysine coated glass slides by high speed robotic printing as previously described (DeRisi et al., *Nat. Genet.* 14:457–460, 1996).

A complex cDNA probe was prepared from whole-cell RNA by a single round of reverse transcription using SuperscriptII (Gibco-BRL, Grand Island, N.Y.) for two hours at 42° C. according to the manufacturer's instructions in the presence of fluorescent dNTP (Cy3 dUTP or Cy5 dUTP, Amersham Pharmacia Biotech, Piscataway, N.J.). Probes were hybridized to the slides for 16 hours in 3×SSC (8.77 g/L NaCl, 4.4 g sodium citrate at pH 7.4) at 65° C. in the presence of blockers (8 µg Poly d A; 4 µg yeast tRNA; and 10 μg human Cot 1 per 10 μl hybridization). Hybridized slides were washed at room temperature (RT) in 0.5×SSC, 0.01% SDS, then in 0.06×SSC. The two fluorescent intensities (Cy3 and Cy5) were scanned separately using a laser confocal microscope, and the DeArray program was then used to identify target sites by image segmentation, calibrate relative ratios, and to develop confidence intervals for testing the significance of the ratios obtained (Chen et al., *J. Biomed. Optics* 2:364–374, 1997).

Local background was calculated for each target location. A normalization factor was estimated from a set of 88 internal control targets (De Risi et al., *Nat. Genet,* 14:457–60, 1996) with a theoretical ratio of 1.0, and the confidence interval for the array was estimated from the variance of these 88 control ratios from the expected value of 1.0. The ratios for all the targets on the array were then calibrated using the normalization factor, and ratios outside the 99% confidence interval (less than 0.54 or greater than 2.37) were determined to be significantly changed by the radiation treatment.

Figure 4:
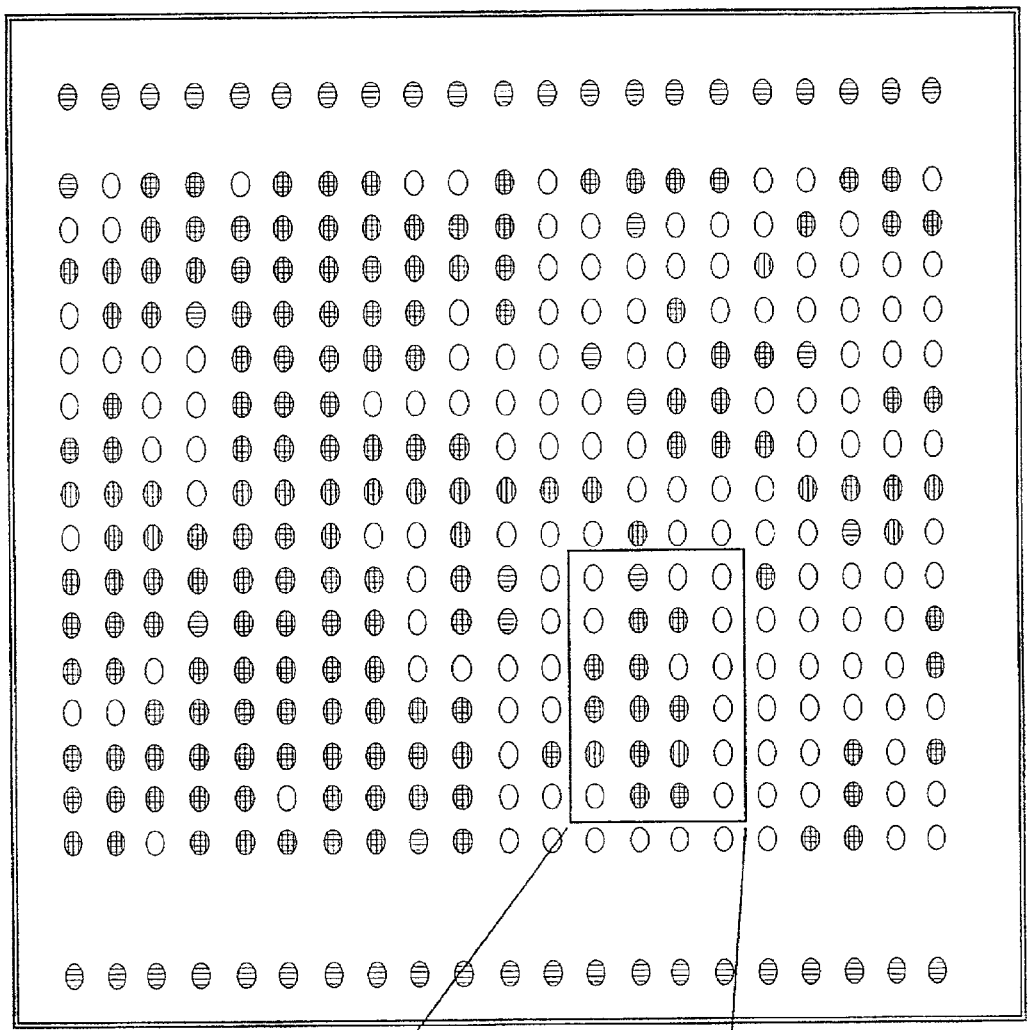
FIG. 4 is a schematic drawing of a quadrant of a microarray hybridized to RNA from untreated ML-1 cells (labeled with a green fluorophore, represented as circles containing horizontal lines) and ML-1 cells four hours after treatment with 20 Gy$^{137}$ (labeled with a red fluorophore, represented as circles containing vertical lines). Targets appearing as yellow spots (represented as circles containing horizontal and vertical lines) have equal representation of both fluorophores and indicate no change in expression by the irradiation. Red spots (circles containing vertical lines) are targets associated with increased expression following irradiation, and green spots (circles containing horizontal lines) are associated with decreased expression. Blank circles represent areas where no hybridization occurred. A horizontal row of green dots (circles containing horizontal lines) at the top and bottom of the schematic microarray represent DNA labeled prior to printing on the array, and serve as orientation markers for a computerized scanner.
Figure 4:
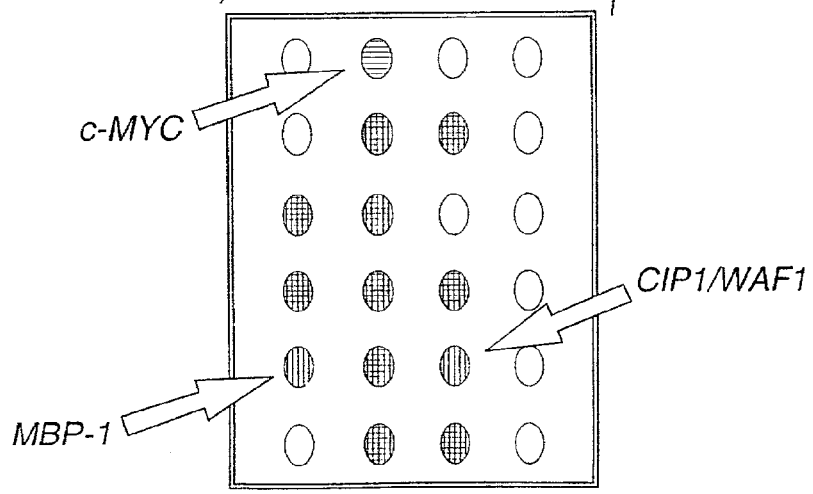

In the hybridized microarray, induced transcripts hybridized with more of the probe from the IR-treated sample (labeled with a red fluorophore), resulting in red spots, such as that observed at the CIP1/WAF1 target. A transcript down-regulated by IR, such as c-MYC, instead produced a green spot. Intermediate induction ratios result in a gradation of color, such as MBP-1. A schematic drawing showing the hybridized microarray is shown in FIG. 4, in which red spots are shown with vertical lines, green spots with horizontal lines; and yellow spots (which have an equal representation of read an green label) are represented with both horizontal and vertical lines. One skilled in the art will appreciate that the color of the labels used is not critical, so long as the emission wavelength of the different fluorophores used can be resolved, and can be used to measure differential expression. Other fluorophores or labels can be used to practice the method of the present invention.

Transcripts significantly changed by radiation treatment are shown in Table 3 which also gives the mean intensities of hybridization to the unirradiated control on the microarray. This measure correlates with transcript abundance (Schena et al., *Science* 270:467–70, 1995; Schena et al., *Proc. Natl. Acad. Sci. USA* 93:10614–9, 1996), and demonstrates identification of IR modulated genes over three orders of magnitude of basal expression. Many of the stress regulated transcripts identified in Table 3 are known to be expressed at very low levels in ML-1 cells, consistent with their relative hybridization intensities on the array. For example, GADD45 and CIP1/WAF1 represent approximately $1/10^5$ transcripts in unirradiated cells.

TABLE 3

Stress gene responses in γ-irradiated human myeloid cells

| Transcript | Image ID | Microarray[a] | Mean Green Intensity[b] |
| --- | --- | --- | --- |
| CIP1/WAF1 | 268652 | 42.0[c] | 1121 |
| ATF3 | 428248 | 11.3[c] | 784 |
| FAS | 151767 | 9.5 | 1352 |
| IAP-1 | 129632 | 9.3[d] | 132 |
| RELB | 52681 | 7.2[d] | 1027 |
| cyclin I | 512391 | 6.9 | 974 |
| RAB | 52530 | 6.4 | 1688 |
| GADD45 | 310141 | 5.8[d] | 2230 |
| FRA1 | 110503 | 4.8[c] | 672 |
| IL-8 | 328692 | 4.8 | 5307 |
| CSF-1 | 124554 | 4.7 | 356 |

TABLE 3-continued

Stress gene responses in γ-irradiated human myeloid cells

| Transcript | Image ID | Microarray[a] | Mean Green Intensity[b] |
| --- | --- | --- | --- |
| BCL3 | 236422 | 4.6[c] | 584 |
| MIP1α | 153355 | 4.3 | 475 |
| c-FOS | 26474 | 4.2 | 1314 |
| JUN-B | 309477 | 4.2 | 1892 |
| PC-1 | 52753 | 3.4[c] | 343 |
| CDC5 | 280376 | 3.4 | 1259 |
| MRC OX-2 | 51363 | 3.4[d] | 290 |
| ERR1 | 470602 | 3.2 | 490 |
| MDM2 | 147075 | 3.2[d] | 328 |
| Immunoglobulin J chain | 161023 | 3.1 | 331 |
| OX40 ligand | 35326 | 3.1 | 310 |
| DNA ligase III | 470062 | 3.0 | 636 |
| cytochrome p450 4A | 120466 | 3.0 | 218 |
| MEK1 | 486074 | 2.9 | 1885 |
| TPK receptor UFO | 112500 | 2.8 | 285 |
| Retinoic acid gamma-1 | 471252 | 2.8 | 288 |
| HPTP alpha | 487130 | 2.8 | 282 |
| MBP-1 | 291503 | 2.8[c] | 206 |
| SSAT | 41452 | 2.7[c] | 4160 |
| BAK | [e] | 2.7[c] | 341 |
| MBP-2 | 23464 | 2.5 | 462 |
| iL-TMP | 243143 | 2.5[d] | 383 |
| MIP1beta | 205633 | 2.5 | 352 |
| N-RAS | 284031 | 2.5 | 341 |
| nucleotide binding protein mRNA | 21420 | 2.5 | 394 |
| CAP-R | 48677 | 2.4 | 577 |
| BCL-XL | [e] | 2.3[c] | 313 |
| ch-TOG | 43060 | 0.53 | 9209 |
| ERK | 487417 | 0.51 | 9323 |
| CDC2 | 346534 | 0.47 | 19501 |
| SATB1 | 233194 | 0.46[c] | 30364 |
| SPI-B | 295093 | 0.45 | 3747 |
| ERF-1 | 48085 | 0.44 | 6935 |
| MADP2 homolog | 26541 | 0.43 | 20543 |
| neuron-specific protein gene | 28089 | 0.38 | 8098 |
| TOPO II | 248032 | 0.34[c] | 37173 |
| CDK RS2 | 359119 | 0.27 | 13935 |
| RCH-1 | 28116 | 0.23[c] | 24932 |
| c-MYC | 51699 | 0.12[c] | 17913 |

[a]Ratios of relative induction by γ-rays compared to basal levels in ML-1 cells. See also http://rex.nci.nih.gov/RESEARCH/basic/lbc/fornace.htm.
[b]Fluorescence intensity of untreated control on the microarray.
[c]Microarray measurement confirmed by quantitative dot blot hybridization where expression varied by less than 2-fold.
[d]Quantitation varied by more than 2-fold.
[e]Inserts for BAK (Chittenden et al., Nature 374:733–6, 1995) and BCL-XL (Boise et al., Cell 74:597–608, 1993) from clones other than Image Consortium ESTs.

a. Ratios of relative induction by γ-rays compared to basal levels in ML-1 cells.

b. Fluorescence intensity of untreated control on the microarray.

c. Microarray measurement confirmed by quantitative dot blot hybridization where expression varied by less than 2-fold.

d. Quantitation varied by more than 2-fold.

e. Inserts for BAK (Chittenden et al., *Nature* 374:733–6, 1995) and BCL-XL (Boise et al., *Cell* 74:597–608, 1993) from clones other than Image Consortium ESTs.

A subset of the IR-responsive genes indicated by the microarray with a range of relative ratios were chosen for further study. This subset of probes included the following: Image ID clones 268652, 428248, 129632, 52681, 52530, 310141, 110503, 236422, 153355, 52753, 51363, 147075, 291503, 41452, 243143, 233194, 248032, 28116, 51699.

Probes were obtained from the same plasmids used as targets on the array, and γ-ray induction of these genes was confirmed in independent experiments by northern blot hybridization. Estimates of induction or repression as measured by the microarray were compared to quantitative hybridization with single labeled probes. As indicated in Table 3, estimated expression varied by less than 2-fold for many transcripts. However, all tested sequences that were identified on the microarray as induced showed an appreciable (>2-fold) induction by the quantitative hybridization approach, with the exception of MRC-OX, which showed only 1.5-fold induction. In the case of genes showing less than 2.4-fold induction by the microarray, useful data may still be obtainable. For example, MCL-1 showed 1.9-fold induction by the microarray and 2.5-fold induction by quantitative hybridization.

The time course of induction for nine of these genes was examined in ML-1 cells. The response over time of Rag cohort 1 (RCH1) (Cuomo et al., *Proc. Natl. Acad. Sci. USA* 91:6156–60, 1994), a newly recognized IR-down-regulated gene, was very similar to the response of TOPOII. Both repressed genes showed a similar rapid decrease of mRNA levels following irradiation, and remain maximally repressed 24 hours after treatment. The levels of most of the newly-identified IR-induced genes rose rapidly following treatment, peaked by four hours, and declined again to near the original levels by 24 hours after treatment, following the pattern of rapid response typical of many stress-induced immediate-early genes (Fornace, *Ann. Rev. Genet.* 26:507–26, 1992; Smith and Fornace, *Mutation Res.* 340: 109–24, 1996). By analogy, the genes described here appear to have roles in acute cellular responses to damage and may share some regulatory mechanisms with previously characterized IR-response genes.

Induction of nine of the newly-identified stress-response genes was next measured in a panel of human cancer cell lines to determine the scope of their IR-response, and to monitor for induction by exposure to two DNA-base-damaging agents, the alkylating agent methyl methanesulfonate (MMS) and ultraviolet (UV) radiation. The full list of cell lines from this panel is shown in Table 2.

The cell lines used in this comparison included six cell lines of myeloid-lymphoid lineage [ML-1 (myeloid), Molt4 (lymphoid), SR (lymphoid), CCRF-CEM (lymphoid), HL60 (myeloid) and K562 (myeloid)], two lung cancer lines (A549 and H1299), two breast carcinoma lines (MCF7 and T47D), and the colon cancer line RKO, along with its derivative transfected with E6 (RKO/E6) (Zhan et al., *Mol. Cell. Biol.* 13:4242–50, 1993). Relative induction of particular genes was measured four hours after treatment with a 20 Gy dose of ionizing radiation (FIG. 5A) or 100 μg/ml MMS or 14 J/m$^2$ UV radiation (FIG. 5B) as measured by quantitative dot-blot hybridization (Hollander and Fornace, *Biotechniques* 9:174–9, 1990), using the same conditions as described above. Differential expression of genes in tumor cells following radiation exposure can be used as a measure of therapeutic radiosensitivity, or to help study expression patterns that can be the subject of other therapeutic (e.g. drug) interventions.

A summary of the results of these induction experiments is shown in FIGS. 5A and 5B, in which induced genes are indicated by vertical lines, reduced expression is indicated by horizontal lines, and a combination of horizontal and vertical lines indicate substantially unchanged expression. Induction levels of the three p53-regulated genes MDM2, CIP1/WAF1 and BAX were also measured for comparison. CIP1/WAF1 is regulated by both p53-dependent and independent mechanisms, while BAX induction by IR appears to require p53 plus an "apoptosis-proficiency" factor frequently present in cells that undergo rapid apoptosis after IR. These three genes were more responsive in the p53 wildtype (wt) lines, with little or no IR-responsiveness in the p53 deficient lines. As reported previously, strong BAX induction was only seen in myeloid-lymphoid lines with weaker induction in MCF-7 cells. In the case of the SR leukemia line, constitutive BAX expression was approximately an order of magnitude greater than in the other lines, and appreciable induction was not seen. In contrast to these previously described genes, the ionizing radiation response of the newly characterized genes shows far more heterogeneity among different cell lines (FIG. 5A). Hence the present method can be used to select genes that are expressed in certain cells types (such as myeloid or other blood cells) that will be sampled in subjects who have been or have potentially been exposed to ionizing radiation.

While all of the newly-identified genes respond to IR in at least one cell line in addition to ML-1, two of the cell lines, K562 and A549, did not show γ-ray regulation of any of the newly-defined IR-responsive genes, and only ATF3 was induced by any stress agent tested in these two lines (FIG. 5B). Interestingly, K562 was the least responsive of any of the cell lines, and was the only line derived from a patient with chronic myelogenous leukemia. Of the nine genes screened, five: SSAT, c-Myc promoter binding protein (MBP-1, or PRDII-BF1), cellular inhibitor of apoptosis 1 (c-IAP1), RELB and BCL3 were primarily induced by IR in the 12 cell lines examined. Fos-related antigen-1 (FRA-1), RCH1, and prohormone convertase1 (PC1) or neuroendocrine convertase1 (NEC1), all showed regulation by the base-damaging agents MMS or UV radiation in some cell lines (FIG. 5B). The most wide ranging response was seen for activating transcription factor 3 (ATF3), which was induced by both MMS and UV radiation in all cell lines tested. With such a strong and pervasive response, ATF3 was selected as playing an important role in generalized genotoxic stress responses. Such a strong and pervasive response is a factor that can be used in selecting a probe for the arrays of the present invention.

This example illustrates that a single cell type may provide a less optimal model for cellular response to genotoxic stress, such as IR. However, using the techniques in this example, genes can be chosen which are often or usually induced in response to a genotoxic stress, such as radiation exposure. Such identified genes can be incorporated into a probe set of a microarray.

In addition, particular cells to be sampled (such as peripheral blood lymphocytes, see EXAMPLE 9) can be studied to determine the genes that are differentially expressed in those cells in response to irradiation. Those genes identified as being differentially expressed in response to irradiation can be incorporated into a probe set of a microarray, which would be specific for the particular cell type to be tested. For example, a microarray can be developed which contains probes which are differentially expressed in a specific type of cell (for example peripheral blood mononuclear cells such as lymphocytes) in response to irradiation. Such a microarray can then be used to determine/monitor radiation exposure in that cell type.

The large number of probes in the probe set also overcomes the problem of using induction in a single cell line as evidence of radiation exposure induction. Hence a review of the results shown in FIGS. 5A and 5B illustrates that MDM2 and CIP1/WAF1 are suitable for incorporation into a probe set for detecting radiation induced stress in p53 wild type cells, because their expression is substantially induced in all or many of the cell lines tested. REL-B is also shown to be generally informative in both p53 mutants and wild type cells.

EXAMPLE 3

Dose Response Curves

This example describes methods used to generate a dose response curve which can be used to determine the time period during which a gene is differentially expressed following exposure to ionizing radiation. Such information is useful in determining which probes to incorporate into the probe set, particularly if the probe set is prepared for analysis of potential biological damage at a given time period after a known or suspected exposure. The genes studied in this example, CIP1/WAF1, GADD45, MDM2, ATF3 and BAX, were chosen since they were shown in the previous example to be differentially regulated in response to irradiation.

ML-1 cells were grown and exposed to various doses of radiation at approximately 5.1 cGy/min, to total doses of 2–50 cGy using the Mark 1-68 $^{137}$Cs source as described in EXAMPLE 1. Gene induction was measured by incubating the irradiated cells at 37° C. for a predetermined number of hours (such as 1–4, or 24–48 hours following irradiation) followed by RNA extraction using a modified guanidine thiocyanate method (as detailed in Chomczynski and Sacchi, *Anal. Biochem.* 162:156–9, 1987). Gene expression was measured by quantitative dot-blot hybridization. Serial dilutions of RNA were immobilized on nylon membranes, hybridized with cDNA probes at 55° C. in a buffer containing 50% formamide (Hybrisol I, Oncor, Intergen, Purchase, N.Y.), and washed under standard conditions. Hybridization is quantitated on a phosphorimager (Molecular Dynamics, Piscataway, N.J.), and relative signal levels, normalized to the polyA content of each sample, determined using the RNA-Think program. The values for relative RNA levels are directly proportional to RNA abundance, and differences of 1.5-fold or more can reliably be measured.

Figure 6A:
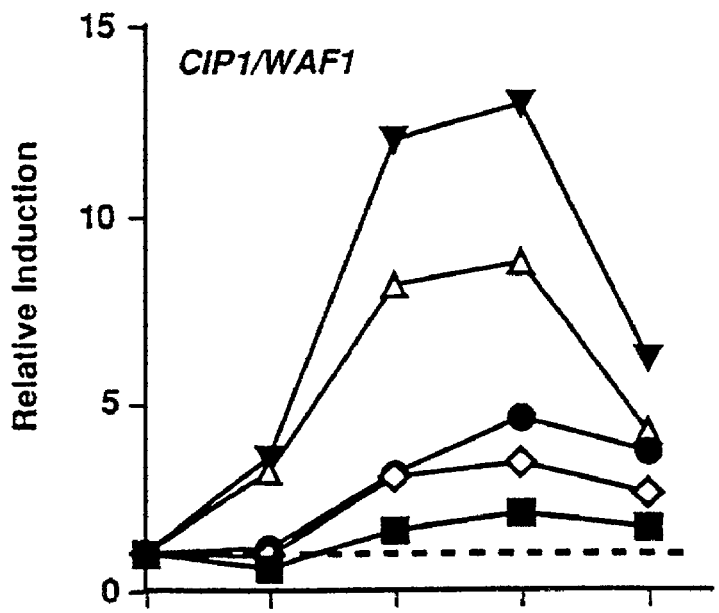
FIGS. 6A and 6B are graphical representations showing the time-course of induction of the (A) C1P1/WAF1 and (B) GADD45 genes following irradiation by 2 cGy (■), 5 cGy (◇), 10 cGy (●), 25 cGy (Δ), or 50 cGy (▼) of γ-rays. Data is shown from a representative experiment. The dashed line indicates the basal level in untreated controls.
Figure 6B:
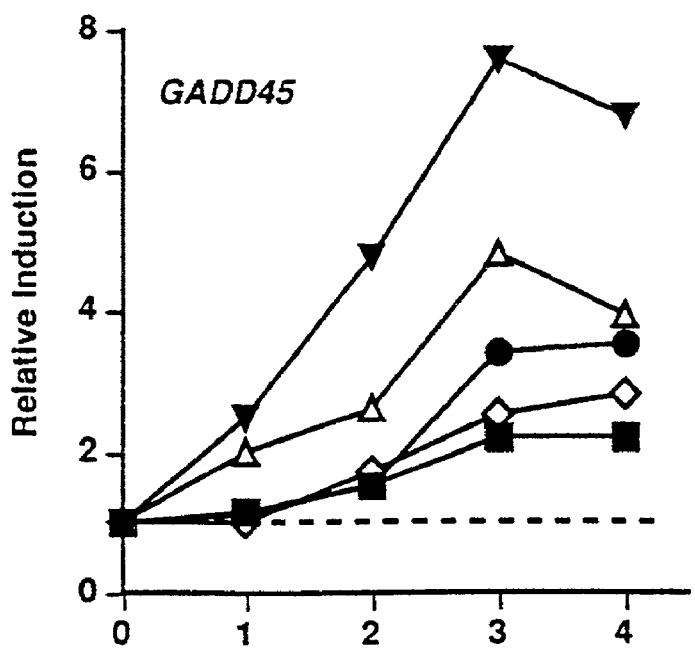

Following treatment with 20 Gy γ-rays, the CIP1/WAF1, GADD45, MDM2, ATF3 and BAX genes reached maximal induction four hours after irradiation, then declined rapidly until they reached basal levels by 24 hours. The induction of CIP1/WAF1 (FIG. 6A) and GADD45 (FIG. 6B) by lower doses of γ-rays was more rapid than the induction seen with supra-lethal doses, reaching maximum levels two to three hours post-irradiation, and in most cases beginning to decline after four hours.

Figure 7A:
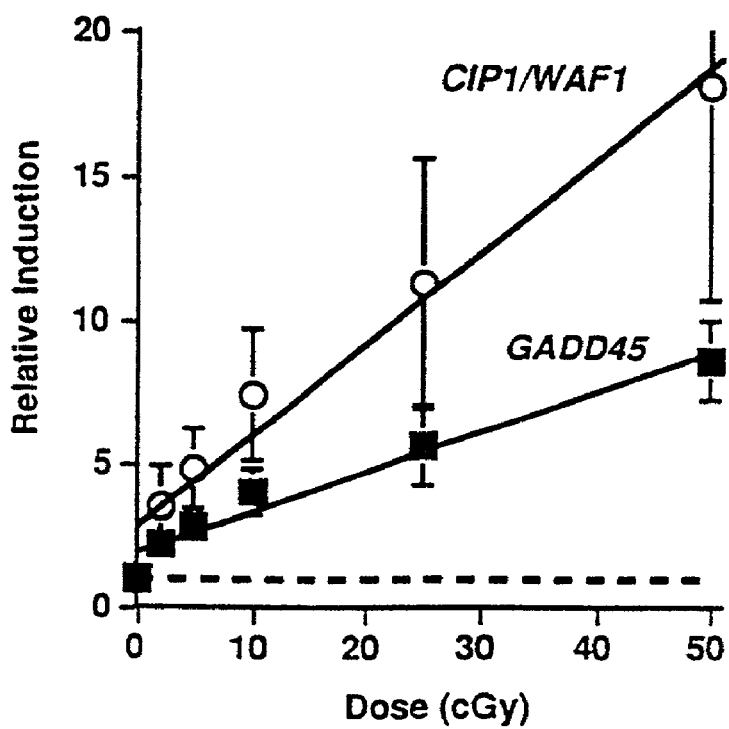
FIGS. 7A and 7B are graphical representations showing the maximal induction of (A) CIP1/WAF1 (○), GADD45 (■) and (B) MDM2 (■), ATF3 (○), and BAX (♦) by low doses of γ-rays. Points are the average of 4 independent experiments, and error bars are standard errors. The dashed line indicates the basal level in untreated controls, solid lines were fit by linear regression through the data.
Figure 7B:
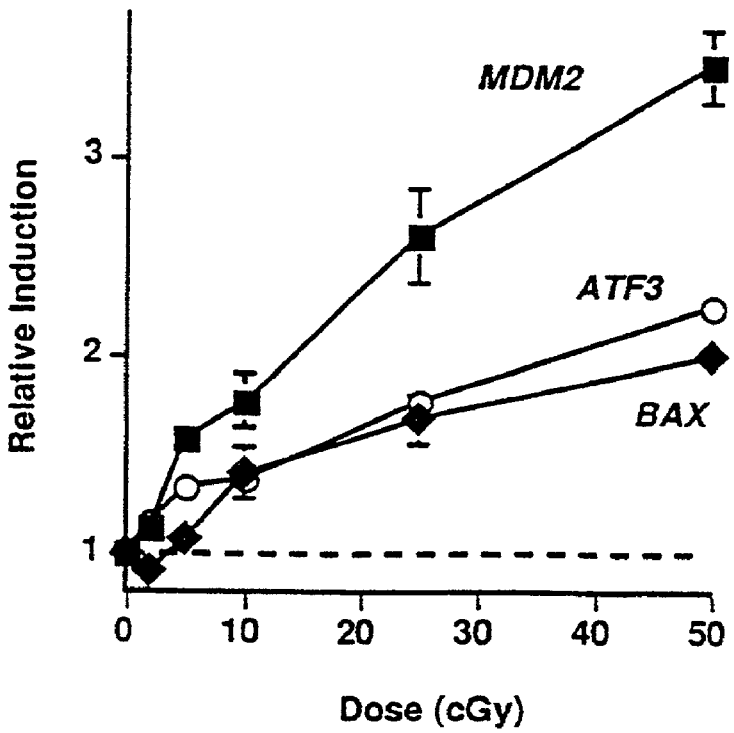

Relative induction of expression can be correlated to dosage, as shown in FIGS. 7A, 7B and 8 for several different genes. The maximal induction of CIP1/WAF1 and GADD45 was approximately linear between 2 and 50 cGy, and showed no indication of a threshold for gene induction (FIG. 7A). Significant induction over basal control levels was observed for both genes at all doses. A more gradual dose-dependent response was observed for the other genes tested (FIG. 7B). MDM2, BAX, and ATF3 were induced between two and three hours following low doses of IR, but 50 cGy only resulted in a 2–3 fold increase in the expression of these genes over control levels (FIG. 7B). The lower inducibility of these genes by low doses of radiation was consistent with their induction by high doses, which was considerably less than that of CIP1/WAF1 and GADD45 (Table 3). The maximal induction appeared linear between 5 and 50 cGy for MDM2, and between 10 and 50 cGy for the other genes. Below these doses, induction fell off sharply, dropping below the limit of accurate quantitation by this technique, previously shown to be approximately 1.5-fold.

Figure 8A:
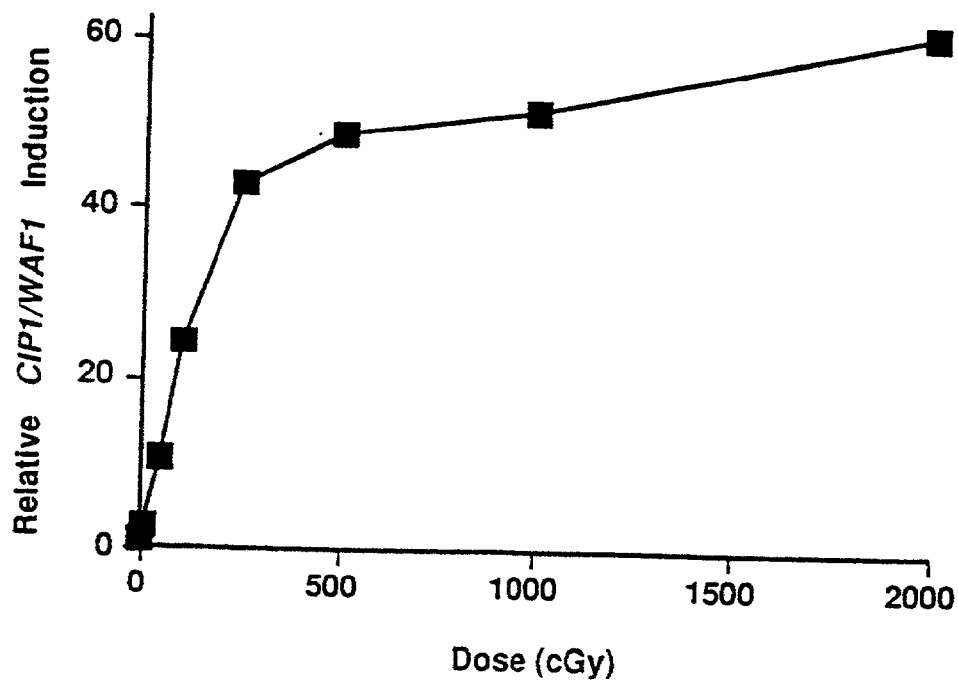
FIG. 8A is a graphical representation showing the dose response of maximal induction of CIP1/WAF1 across a broader range of doses. Data is shown from a representative experiment.

A broader dose range was next tested for the induction of CIP1/WAF1 to determine the point at which the induction response begins to saturate. Induction continued to increase in a dose-dependent manner up to approximately 250 cGy (FIG. 8A). Beyond this point, the dose-dependent increase in relative induction leveled off sharply, although a trend of increased induction appeared to continue up to 20 Gy, the highest dose tested.

The extrapolation of data gathered at high doses to predict effects at low doses can present difficulties. In particular, it cannot necessarily be assumed that the dose-response relationship observed at high doses applies to the entire dose spectrum. For example, very low doses of ionizing radiation may be more toxic per cGy than higher doses. Therefore, extrapolation from survival at high doses may not predict the low-dose hypersensitivity revealed by the more accurate methods. This response may reflect an induction of radio-resistance, perhaps through inducible DNA repair, which requires a certain threshold dose to be triggered in some cell lines. Understanding the mechanistic basis for such induced resistance could have broad implications in areas from risk assessment to cancer treatment.

Low-dose hypersensitivity and induced radio-resistance may be related to the adaptive response to ionizing radiation, another potentially important physiological effect of low dose exposures. Exposure to a "priming" or "adapting" dose, usually in the range of 1–25 cGy, reduces the effects of a subsequent higher "challenge" dose (Stecca and Gerber, *Biochem. Pharmacol.* 55:941–51, 1998).

The phenomena of low-dose hypersensitivity and radio-adaptation raise the question of the requirement for a minimum threshold dose to induce a transcriptional response. The threshold effect is a factor to be considered for modeling low dose effects from results gathered at high doses, as the existence of a threshold implies that a dose can be identified below which exposure carries no risk of response (at least for the endpoint under consideration). The experiments showing low dose hypersensitivity have been interpreted to indicate a threshold, usually in the neighborhood of 25–30 cGy, which is required to activate inducible repair. Doses below this threshold are proportionately more toxic than doses which trigger the putative repair system. Radio-adaptive protection against cytogenetic aberrations or cell killing, however, has been shown to occur following doses as low as 1–2 cGy, indicating a much lower or even absent threshold for induction of this effect, and perhaps a distinct mechanism of action for the two phenomena.

While the genes studied in this example have not been implicated in induced repair, changes in mRNA levels in response to radiation in the dose range relevant to these phenomena have been observed. The data reveal no indication of a threshold for the induction of the genes studied. CIP1/WAF1 and GADD45 were significantly induced by as little as 2 cGy with a linear dose-response through 50 cGy (FIG. 7A). For MDM2, ATF3 and BAX, however, the possibility of a threshold for induction could not be distinguished from the noise of the assay (FIG. 7B). An additional complication to the interpretation of this data is that it is currently unknown if a threshold exists for biological significance of relative gene expression levels. It is likely that no generalized answer to this question will apply to all genes in all cell lines or cell types.

Figure 8B:
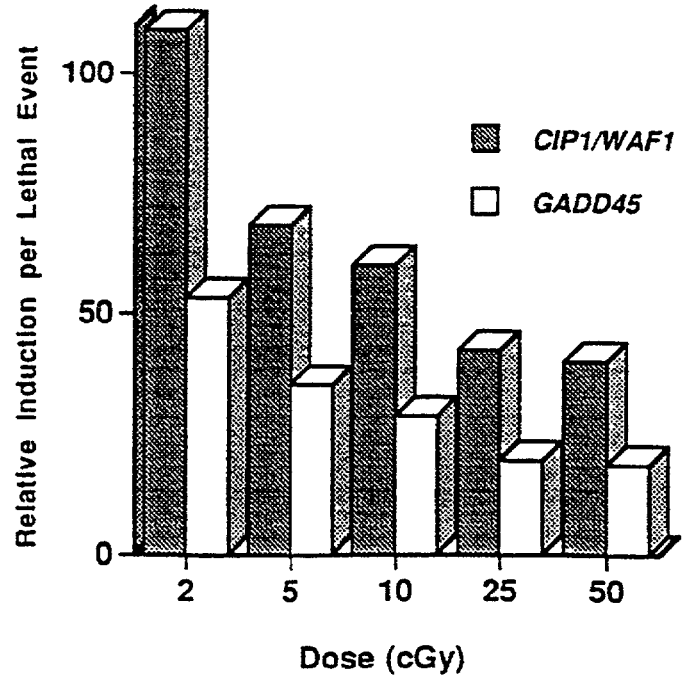
FIG. 8B is a bar graph showing the relative induction of CIP1/WAF1 and GADD45 which would be required per lethal event if the gene induction measured at low doses occurred only in lethally damaged cells. If only lethally damaged cells contributed to the observed gene induction, the induction per lethal event would be expected to be a constant for all doses. As this is not the case, it suggests surviving cells do contribute significantly to gene induction.

Although no evidence of a minimum threshold for induction of CIP1/WAF1 was observed, there was an upper limit to the linear increase in induction, as the induction by 50 cGy was about half that previously observed by 20 Gy (FIG. 7A). In experiments covering a wider range of doses from 10 cGy to 20 Gy, a saturation of induction of approximately 250 cGy was observed (FIG. 8A). At this dose, less than 5% of the cells retain mitotic viability. The coincidence of saturation for gene induction with nearly complete cell killing raises the issue of whether surviving cells contribute to the transcriptional response following even low doses of ionizing radiation, or if gene induction occurs only in lethally damaged cells. To address this question, the relative induction per lethally damaged cell which would be required to produce the inductions observed in the treated population as a whole, if the measured gene induction were due entirely to the response of lethally damaged, reproductively dead cells was calculated (FIG. 8B). For the doses where surviving fractions could not be measured directly, they were predicted from the survival curve (FIG. 1). In this model, each cell responding to 2 cGy would have to produce a relative induction of CIP1/WAF1 greater than 100-fold over the basal level to result in the observed induction of approximately 3.5-fold across the whole population. This relative induction per responding cell would then have to decrease with increasing dose through 50 cGy. Furthermore, as the proportion of the population suffering lethal damage increased further, the induction per responding cell would level out, then begin to increase again at doses above 5 Gy. A similar relationship was also calculated for the dose-response of GADD45 induction (FIG. 8B). If the measured gene induction were due entirely to the response of lethally damaged cells, the relative induction per lethal event would be expected to remain constant with changing dose and surviving fraction, so the relative induction of cell killing in an irradiated population would not appear to account for the observed increases in mRNA levels.

The contribution of cells which survive the treatment to the gene inductions measured at low doses would also be consistent with the disturbances in cell cycle progression observed at all doses tested. Even with 2 cGy, there was a transient decrease of S-phase cells in the population. This decrease corresponded to a larger proportion of the population than the predicted non-surviving fraction. A transient G1 delay following a consistent trend in both dose-response and temporal kinetics was observed (FIG. 3B). While the lowest dose used, 2 cGy, resulted in a brief accumulation of cells in GI, accumulation of cells in G2 appeared to require a higher dose. CIP1/WAF1, the transcript most strongly induced by low doses of γ-rays, is a major mediator of G1 arrest (Di Leonardo et al. *Genes Dev.* 8:2540–51, 1994; Waldman et al. *Cancer Res.* 55:5187–90, 1995). Thus, the observed G1 delay is consistent with this CIP1/WAF1 induction. A complete understanding of low-dose effects should not come solely from high dose experiments, but instead may require further careful studies in the low dose range.

Measurable differential gene expression effects were observed at relatively low, biologically relevant doses, such as 2 cGy. In radiotherapy the standard daily dose is about 2 Gy. Therefore, the results of these experiments indicate that the expression of many genes is altered at this dose. The probe sets of the present invention is capable of measuring exposure to relatively low doses of ionizing radiation (for example less than 2 Gy or 1 Gy) that may be considered non-toxic because of the absence of acute effects, but which may have short term effects that induce differential gene expression, and may have long term effects (such as carcinogenesis).

This example illustrates that probe sets that measure not only the fact of exposure to radiation, but also a probable dose of exposure to ionizing radiation, can be created by identifying genes that are differentially expressed at certain radiation doses. For example, probe sets can be designed which contain genes which are only differentially expressed at higher doses of irradiation (for example 20 Gy), or genes which are differentially expressed at lower doses of irradiation (for example 1–50 cGy). Furthermore, the methods for generating dose response curves described in this example can be used to select probes for the probe set, based on the probable time after radiation exposure occurred. Curves that show sustained or maximal expression 12, 24 or 48 hours after irradiation would identify probes that are useful for evaluation of genotoxic stress from exposure to ionizing radiation at times when clinical evaluations are likely to occur. In addition, patterns of probe set hybridization can also be associated with specified times following probable irradiation. After identifying the genes of interest, they can be incorporated into a probe set of a microarray.

EXAMPLE 4 p53-Associated Components of IR-Induction

Figure 9A:
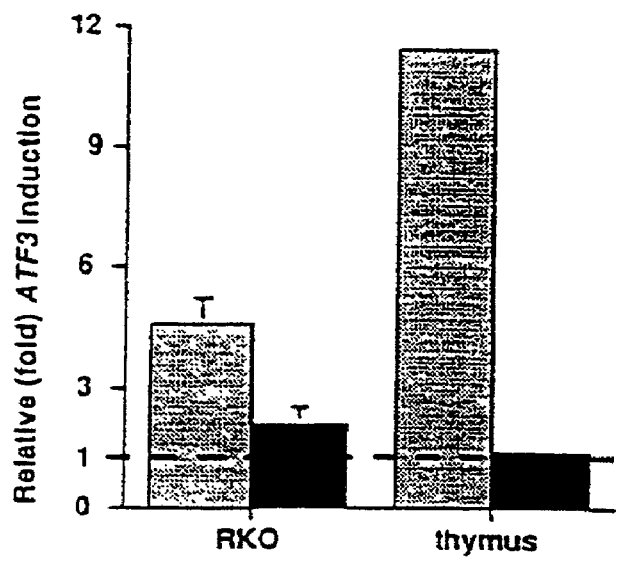
FIGS. 9A and 9B are bar graphs showing the induction of (A) ATF3 in p53 wild-type RKO cells (light bar), RKO/E6 cells (dark bar) and the thymus of p53 wild-type mouse (light bar), or p53−/− (dark bar); and (B) FRA-1 in p53 wild-type MCF7 cells (light bar), or in MCF7/E6 cells (dark bar) and in the thymus of p53 wild-type mouse (light bar), or p53−/− mouse (dark bar). The results shown for the RKO cell lines are the average of 4 independent experiments, and error bars are standard errors of the means. The results for the MCF7 cell lines are the average of 3 independent experiments.

This example demonstrates how to determine if the IR-induction of FRA-1 and ATF3 involve a p53 regulatory component. FRA-1 was induced by IR in some of the wt p53 lines, but was not induced in any of the p53 mutant lines studied (FIGS. 5A and 5B). In addition, the 5-fold IR-induction of ATF3 in RKO was attenuated in the RKO/E6 cell line, although some IR-induction was observed among the other p53 mutant cell lines. FIG. 9A shows the IR-induction of ATF3 in the p53 wild-type human carcinoma cell line RKO and in RKO/E6, in which p53 function has been abrogated by an E6 expression vector. RKO/E6 lacks appreciable functional p53. The disruption by E6 of ATF3 induction by IR supports a role for p53 in its induction.

To further examine the extent of dependence of ATF3 IR-induction on p53 status, in vivo induction was examined in wild-type and p53−/− (knockout) mice (Donehower et al., *Nature* 356:215–21, 1992) using 5 Gy whole-body γ-irradiation. While ATF3 was well induced by two hours after irradiation in the thymus of wild-type mice, there was no significant induction in the p53−/− mouse (FIG. 9A). ATF3 levels remained elevated at four and eight hours after irradiation in the thymus of wild-type mice, without any induction in the p53−/− mice. A similar trend was observed in the liver, where ATF3 was induced about 4-fold in the wild-type mouse, but showed no induction in the p53 knockout.

ATF3 is a member of the activating transcription factor/cAMP response element binding protein (ATF/CREB) family which homodimerizes to repress transcription from promoters with ATF sites. An alternatively spliced form of the ATF3 transcript, which lacks DNA binding activity, is also expressed in cells, but this form promotes transcription (Chen et al., *J. Biol. Chem.* 269:15819–26, 1994). The sizes of ATF3 transcripts hybridizing on the northern blot demonstrated that the smaller alternatively spliced form was the major transcript expressed in untreated ML-1 cells, whereas the IR-induced transcript was predominantly of the full length form.

The induction of ATF3 by the DNA-damaging agents MMS and UV radiation in all 12 cell lines examined (FIG. 5) extends the range of stress responses in which ATF3 is involved. Its wide-ranging responsiveness is similar to CIP1/WAF1 and GADD45, which are stress inducible by both p53-dependent and independent mechanisms, and highlights the complexity of ATF3 regulation.

Figure 9B:
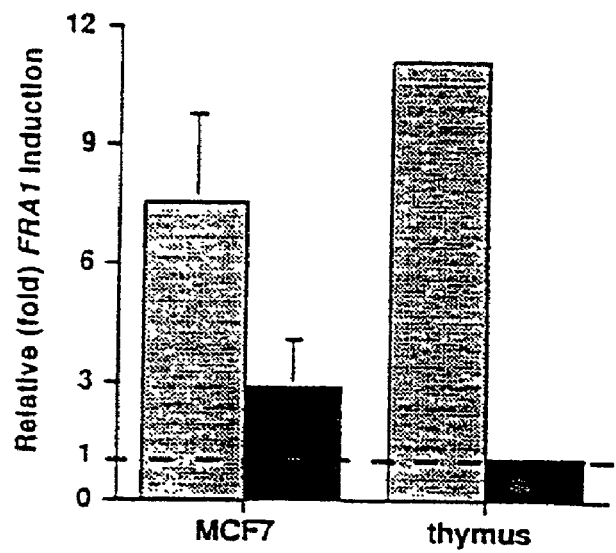

Although FRA-1 was not IR-inducible in RKO cells, a similar comparison was possible using the MCF7 and MCF7/E6 cell lines. The human breast carcinoma cell line MCF7 has wild-type p53, while MCF7/E6 has lacked appreciable wild-type p53 function. The reduced IR-induction of FRA-1 in MCF7/E6 compared to MCF7 supports a role for p53 in the IR-induction of this gene (FIG. 9B). Furthermore, whole-body γ-irradiation of wild-type mice resulted in FRA-1 induction in the thymus, but no induction occurred in the thymus of the p53−/− (FIG. 9B). Such results can be used to select certain probes (for example FRA-1) for detection of whole-body radiation. FRA-1 is an immediate early gene induced by serum stimulation, the product of which shares several regions of amino acid homology with Fos. It is also down-regulated by UVB and upregulated by UVA. Because of its homology to Fos, and the involvement of p53 in its IR-induction, FRA-1 the use of the present assay can be taken to demonstrate a link between p53 and AP1 function and the MAPK pathway.

MBP-1 represented another potentially p53 regulated gene, showing a pattern similar to that seen for BAX or BCL-X, in that it was induced only in p53-wild-type cell lines of lymphoid or myeloid lineage. The induction of the murine homolog of MBP-1 in the tissues of wild-type and p53−/− mice was observed to have marginal to absent expression in liver and thymus, but strong expression in spleen. Treatment with ionizing radiation resulted in a 2-fold induction of this gene in the spleens of both p53 wild-type and p53−/− mice, suggesting that this gene does not require p53 function for its induction, but that its expression and induction are both limited to a subset of cell types. This would be consistent with a role for MBP-1 in tissue specific p53-independent stress responses.

The finding that only two of nine of these genes examined in this cell line panel showed a recognizable p53 component to their regulation belies the recent focus of stress-gene studies primarily on p53-regulated genes. In light of the loss of functional p53 in the majority of tumors, the non-p53-dependent stress response genes appears to also be an important consideration in cancer treatment.

An advantage o the present invention is its ability to examine both p53-regulated and non-p53 regulated genes, or other combinations of gene types (for example genes which are recognized oncogenes or genes which are not recognized oncogenes). Quantitative functional genomics approaches, such as cDNA microarray hybridization, can also be used in combination with the radiation sensor array to unravel the inter-relationships of the molecular response pathways involved. Although radioactive-probe hybridization to nylon filter arrays provides a useful method to screen for potential genes of interest which differ in expression levels between two samples, differential screening has its own limitations (Fargnoli et al., *Anal Biochem* 187:364–73, 1990) some of which are avoided by the use of probes labeled with different fluorochromes co-hybridized to the same microarray. Other methods for identification of differentially expressed mRNAs, such as differential display, subtractive library hybridization and serial analysis of gene expression (SAGE) (Velculescu et al., *Science* 270:484–7, 1995), can be biased toward detection of highly-expressed and/or strongly-induced transcripts.

With the microarray approach of the present invention, quantitative results over a wide dynamic range were obtained for many genes. The application and further refinement of quantitative fluorescent cDNA microarray hybridization have the potential to advance our understanding of the fields of stress gene response and radiation biology, and to extend this technology beyond simple pair-wise comparisons to applications such as tumor typing, pharmacological screening, biomonitoring, and rapid carcinogen screening.

This example combined with the results from EXAMPLE 2 illustrate that probe sets that measure differential expression in response to a biologically significant amount of radiation for specific tumors can be generated. Such probe sets can be used to monitor a subject who is undergoing radiotherapy for the treatment of a tumor. For example, probe sets can be designed which contain genes from a specific type of tumor, which are differentially expressed in response to irradiation of the tumor cells. This probe set would then be used to monitor a subject's response to the radiotherapy. Further details are provided in EXAMPLE 10. As an extension of this probe set, the present method can be used in "tumor profiling," wherein gene expression profiles are used to predict the most effective treatment for each individual subject. In this method, cells would be isolated from the tumor in a subject, and the differential expression of the genes in that tumor in response to irradiation measured as described in the examples herein. A pattern of differential expression found to be associated with a particular therapeutic response to radiation therapy can then be used as a factor when considering whether to include radiation therapy in the treatment of the tumor. For example, a pattern of differential expression associated with a good response to radiation therapy could be used to indicate that radiation therapy should be instituted.

EXAMPLE 5

New Radiation Responsive Sequences

Using the ML-1 cancer cell line and the cDNA microarray hybridization technology described in this specification, 30 sequences from ML-1 were identified that were not previously known to be radiation-responsive. These sequences are Image ID Nos. 428248, 129632, 52681, 52530, 110503, 236422, 153355, 52753, 51363, 161023, 35326, 487130, 291503, 41452, 23464, 243143, 205633, 21420, 48677, 43060, 233194, 295093, 48085, 26541, 28089, 359119, 28116, 80549, 485963, 24927. Arrays can be made that incorporate these sequences, or probe fragments thereof, along with controls and/or other sequences that are already known to be informative about radiation exposure, and/or dosage of radiation exposure.

EXAMPLE 6

Late Induced Genes

This example describes detection of differential gene expression in irradiated ML-1 cells using different microarrays. Although the specific example discloses expression in ML-1 cells, this method can be used to detect differential gene expression in any cell type.

ML-1 cells were grown and irradiated as described in EXAMPLE 1. Labeled cDNA subsequently prepared from the irradiated cells was exposed to various arrays as described in EXAMPLE 2. cDNA microarray hybridization studies were performed with the 1.2K chip described in EXAMPLE 2 which contained 1,200 probes in a probe set (Table 1), a 5K chip which contained 5,000 probes in a probe set, and a 7K chip which contained 7,000 probes in a probe set. The 5K and 7K chips contained representative verified expressed ESTs from the human genome, and were designed to permit as much as possible of the human genome to be screened using irradiated ML-1 cells. The arrays used represent the largest sequence verified clone sets available to print at the time of the experiments. As more clones become available, they are added to new prints to be screened. The 1.2K array was a smaller set of ESTs designed for the same purpose (EXAMPLE 2).

Table 4 shows the clones used to make the 1.2K array along with data showing the relative expression detected at each position of the array. The clones used to make the 5K array are identified in Table 5 and for the 7K array in Table 6. Although these particular arrays were used in these experiments, other arrays may be used. For example, as additional arrays become available that include even more ESTs, additional biomarkers of radiation exposure can be found and added to the probe sets disclosed in Tables 9–13. Moreover, the 1.2K, 5K, and 7K arrays can also be used with different cells (such as human peripheral lymphocytes) to screen for other markers that would be even more informative when testing those cells.

TABLE 4

Results from the 1.2K microarray.

| Image ID or clone name | array ratio* |
| --- | --- |
| Waf1 | 42.02 |
| 268652 | 18.76 |
| 428248 | 14.53 |
| 428248 | 11.32 |
| 151767 | 9.48 |
| 129632 | 9.29 |
| 52681 | 7.17 |
| 512391 | 6.92 |
| 52530 | 6.37 |
| 110503 | 4.83 |
| 328692 | 4.82 |
| 124554 | 4.73 |
| 236422 | 4.64 |
| 153355 | 4.32 |
| 26474 | 4.20 |
| 309477 | 4.17 |
| 52681 | 4.03 |
| 52753 | 3.40 |
| 280376 | 3.39 |
| 51363 | 3.38 |
| 470602 | 3.23 |
| 147075 | 3.17 |
| 161023 | 3.13 |
| 35326 | 3.12 |
| HIV F2 | 3.10 |
| 470062 | 3.03 |
| 120466 | 3.02 |
| CoT1 | 3.01 |
| 486074 | 2.93 |
| 112500 | 2.83 |
| 471252 | 2.81 |
| 487130 | 2.77 |
| 291503 | 2.76 |
| Mdm2 | 2.72 |
| 41452 | 2.65 |
| 52681 | 2.64 |
| Bak | 2.57 |
| 23464 | 2.53 |
| 243143 | 2.51 |

TABLE 4-continued

Results from the 1.2K microarray.

| Image ID or clone name | array ratio* |
| --- | --- |
| 205633 | 2.51 |
| 284031 | 2.49 |
| 21420 | 2.47 |
| 48677 | 2.41 |
| 485963 | 2.34 |
| 162772 | 2.32 |
| Hu placental | 2.32 |
| 51439 | 2.30 |
| 126379 | 2.29 |
| 253545 | 2.27 |
| 80549 | 2.26 |
| Bcl-xl | 2.26 |
| 156103 | 2.25 |
| 489395 | 2.24 |
| 24927 | 2.23 |
| 27899 | 2.19 |
| 427923 | 2.17 |
| 286249 | 2.15 |
| 53164 | 2.14 |
| 470685 | 2.10 |
| 47679 | 2.09 |
| 116906 | 2.08 |
| HIV F8 | 2.07 |
| 21531 | 2.04 |
| 280768 | 2.04 |
| 178508 | 2.03 |
| 512472 | 2.03 |
| 121849 | 2.02 |
| 42906 | 2.01 |
| 52650 | 2.01 |
| 145503 | 2.01 |
| 110022 | 1.98 |
| 343311 | 1.98 |
| 149910 | 1.98 |
| 137531 | 1.97 |
| mouse c-kit | 1.97 |
| 231292 | 1.94 |
| mouse EDNRB | 1.94 |
| 290871 | 1.92 |
| 52193 | 1.91 |
| 26871 | 1.91 |
| 152844 | 1.91 |
| 23173 | 1.90 |
| 49164 | 1.89 |
| 512385 | 1.89 |
| 289606 | 1.89 |
| 108837 | 1.88 |
| 283116 | 1.86 |
| 361381 | 1.86 |
| 51746 | 1.85 |
| 187987 | 1.85 |
| 132420 | 1.84 |
| 299198 | 1.84 |
| 154420 | 1.84 |
| 33941 | 1.83 |
| 376218 | 1.83 |
| 140358 | 1.83 |
| 116781 | 1.83 |
| 154420 | 1.83 |
| 359769 | 1.82 |
| 471494 | 1.81 |
| 486844 | 1.81 |
| 486716 | 1.80 |
| 308392 | 1.79 |
| empty | 1.79 |
| HIV F4 | 1.79 |
| 47229 | 1.78 |
| 39920 | 1.78 |
| 486785 | 1.77 |
| 203132 | 1.77 |
| 200209 | 1.76 |
| 123586 | 1.76 |
| 60298 | 1.76 |
| 296642 | 1.75 |

TABLE 4-continued

Results from the 1.2K microarray.

| Image ID or clone name | array ratio* |
|---|---|
| 146307 | 1.74 |
| 429539 | 1.74 |
| 260288 | 1.73 |
| 73515 | 1.72 |
| 53173 | 1.72 |
| HIV F12 | 1.72 |
| 322604 | 1.71 |
| 125187 | 1.71 |
| 417357 | 1.71 |
| 77577 | 1.70 |
| 279954 | 1.70 |
| 417403 | 1.70 |
| 428231 | 1.69 |
| 120157 | 1.69 |
| 321242 | 1.68 |
| 264576 | 1.68 |
| 486199 | 1.68 |
| 158970 | 1.68 |
| 153025 | 1.68 |
| 41959 | 1.67 |
| 72869 | 1.67 |
| empty | 1.67 |
| HIV F5 | 1.66 |
| 53184 | 1.66 |
| 327111 | 1.66 |
| 307342 | 1.66 |
| 155717 | 1.66 |
| Alk | 1.65 |
| 135118 | 1.65 |
| 183661 | 1.65 |
| 34974 | 1.65 |
| 52162 | 1.64 |
| 22790 | 1.64 |
| mouse c-met | 1.64 |
| 154472 | 1.64 |
| 22036 | 1.63 |
| 35516 | 1.63 |
| 362702 | 1.63 |
| 417592 | 1.63 |
| 46427 | 1.63 |
| 360531 | 1.63 |
| 359793 | 1.63 |
| 298371 | 1.61 |
| 486161 | 1.61 |
| 310141 | 1.61 |
| 22589 | 1.61 |
| 418111 | 1.61 |
| 139073 | 1.61 |
| 31687 | 1.61 |
| 289428 | 1.61 |
| 366539 | 1.60 |
| 512276 | 1.60 |
| 127821 | 1.60 |
| mouse EDN3 | 1.59 |
| 377275 | 1.59 |
| 109957 | 1.59 |
| 147744 | 1.59 |
| 258589 | 1.58 |
| 29627 | 1.58 |
| 53358 | 1.58 |
| 306134 | 1.58 |
| 295389 | 1.58 |
| 21656 | 1.57 |
| 127089 | 1.57 |
| 30966 | 1.56 |
| mouse pmel17 | 1.56 |
| 470730 | 1.55 |
| 471822 | 1.55 |
| 43231 | 1.55 |
| HIV F9 | 1.54 |
| 35665 | 1.54 |
| 154015 | 1.54 |
| 158970 | 1.54 |
| 363805 | 1.53 |
| 36676 | 1.53 |
| 47306 | 1.53 |
| 28774 | 1.53 |
| 209655 | 1.53 |
| 488103 | 1.53 |
| 50603 | 1.53 |
| 469543 | 1.53 |
| 143751 | 1.52 |
| 284546 | 1.52 |
| 51825 | 1.51 |
| 22012 | 1.51 |
| 509731 | 1.51 |
| 144693 | 1.51 |
| 138917 | 1.51 |
| 126542 | 1.51 |
| 38573 | 1.50 |
| 36927 | 1.50 |
| 236420 | 1.50 |
| 488801 | 1.50 |
| 137575 | 1.50 |
| 86017 | 1.49 |
| 31061 | 1.49 |
| 303109 | 1.48 |
| 22589 | 1.48 |
| 35865 | 1.48 |
| 359466 | 1.48 |
| 238577 | 1.48 |
| 302490 | 1.48 |
| 40442 | 1.48 |
| 36593 | 1.47 |
| 344482 | 1.47 |
| 471715 | 1.47 |
| 288650 | 1.47 |
| 470251 | 1.47 |
| 364110 | 1.46 |
| 154763 | 1.46 |
| 36809 | 1.46 |
| 36904 | 1.45 |
| 37797 | 1.45 |
| 298371 | 1.44 |
| 253869 | 1.44 |
| 21468 | 1.44 |
| 50503 | 1.44 |
| 270980 | 1.44 |
| 345928 | 1.44 |
| 35559 | 1.44 |
| mouse pdgfra | 1.43 |
| 366420 | 1.43 |
| 205905 | 1.43 |
| 37347 | 1.43 |
| 288797 | 1.43 |
| 50941 | 1.43 |
| 37513 | 1.42 |
| 33415 | 1.42 |
| 221619 | 1.41 |
| 429976 | 1.41 |
| 136769 | 1.40 |
| 44180 | 1.40 |
| 254187 | 1.40 |
| 362009 | 1.39 |
| 30981 | 1.39 |
| 272110 | 1.39 |
| 51332 | 1.39 |
| 49725 | 1.39 |
| 472067 | 1.38 |
| 49967 | 1.38 |
| 36074 | 1.38 |
| 34396 | 1.38 |
| 418138 | 1.38 |
| 49509 | 1.38 |
| 154441 | 1.38 |
| 357807 | 1.38 |
| 281029 | 1.37 |
| syn cDNA 33 | 1.37 |

TABLE 4-continued

Results from the 1.2K microarray.

| Image ID or clone name | array ratio* |
|---|---|
| 48803 | 1.37 |
| 46171 | 1.37 |
| 53155 | 1.36 |
| 429142 | 1.36 |
| 26811 | 1.36 |
| syn cDNA 33 | 1.36 |
| 32427 | 1.35 |
| 47874 | 1.35 |
| 270148 | 1.35 |
| 489419 | 1.35 |
| 266486 | 1.34 |
| 48398 | 1.34 |
| 34247 | 1.34 |
| 31855 | 1.34 |
| lambda | 1.34 |
| 162479 | 1.34 |
| 41439 | 1.34 |
| 193901 | 1.34 |
| 376303 | 1.34 |
| 254428 | 1.34 |
| 299539 | 1.34 |
| 510381 | 1.34 |
| 25880 | 1.33 |
| 364752 | 1.33 |
| 178169 | 1.33 |
| 25495 | 1.33 |
| 510258 | 1.33 |
| 39285 | 1.33 |
| 204301 | 1.33 |
| 26992 | 1.33 |
| 268412 | 1.33 |
| 26801 | 1.33 |
| 358168 | 1.33 |
| 44495 | 1.33 |
| 40117 | 1.33 |
| 182633 | 1.32 |
| mouse ece1 | 1.32 |
| 264554 | 1.32 |
| 31210 | 1.32 |
| 49576 | 1.32 |
| 300973 | 1.32 |
| 44307 | 1.32 |
| 288733 | 1.32 |
| 323001 | 1.31 |
| 22379 | 1.31 |
| 487264 | 1.31 |
| 346396 | 1.31 |
| 44193 | 1.31 |
| 51293 | 1.31 |
| 82991 | 1.30 |
| 34217 | 1.30 |
| 27944 | 1.30 |
| 40562 | 1.30 |
| 363539 | 1.30 |
| 50503 | 1.30 |
| 264200 | 1.30 |
| 50816 | 1.30 |
| 417689 | 1.30 |
| 258790 | 1.30 |
| 417218 | 1.30 |
| 124927 | 1.30 |
| lambda | 1.29 |
| 35284 | 1.29 |
| 203017 | 1.29 |
| 213597 | 1.29 |
| 38393 | 1.29 |
| 509882 | 1.29 |
| 154536 | 1.29 |
| 128100 | 1.29 |
| 296021 | 1.28 |
| 52587 | 1.28 |
| 35609 | 1.28 |
| 359412 | 1.28 |
| 159833 | 1.28 |
| 33368 | 1.27 |
| 376781 | 1.27 |
| 512294 | 1.27 |
| 234198 | 1.27 |
| empty | 1.27 |
| 49666 | 1.27 |
| 162584 | 1.26 |
| 365147 | 1.26 |
| 268727 | 1.26 |
| 183950 | 1.26 |
| 489042 | 1.26 |
| 44722 | 1.25 |
| 486510 | 1.25 |
| 179711 | 1.25 |
| 41208 | 1.25 |
| 320903 | 1.25 |
| 23866 | 1.25 |
| 53024 | 1.25 |
| 47359 | 1.24 |
| 191007 | 1.24 |
| 48097 | 1.24 |
| 344109 | 1.24 |
| 198205 | 1.24 |
| 46019 | 1.24 |
| 27624 | 1.24 |
| HIV F11 | 1.24 |
| 236338 | 1.24 |
| 32304 | 1.23 |
| 322452 | 1.23 |
| syn cDNA 10 | 1.23 |
| 115277 | 1.23 |
| 201673 | 1.23 |
| mouse aim1/2.2 | 1.23 |
| 46354 | 1.23 |
| 428404 | 1.23 |
| 471174 | 1.23 |
| 43229 | 1.22 |
| 306170 | 1.22 |
| 39148 | 1.22 |
| 249348 | 1.22 |
| 51686 | 1.22 |
| 253773 | 1.21 |
| 322000 | 1.21 |
| 25485 | 1.21 |
| 361692 | 1.21 |
| 47343 | 1.21 |
| 510130 | 1.21 |
| 133122 | 1.21 |
| 37435 | 1.21 |
| 340947 | 1.21 |
| syn cDNA 31 | 1.21 |
| 209310 | 1.21 |
| 234357 | 1.21 |
| 298314 | 1.21 |
| 302394 | 1.21 |
| 360201 | 1.20 |
| 42927 | 1.20 |
| 47499 | 1.20 |
| 39086 | 1.20 |
| 487097 | 1.20 |
| 219735 | 1.20 |
| 488596 | 1.20 |
| 37962 | 1.20 |
| 49888 | 1.19 |
| 31988 | 1.19 |
| 51687 | 1.19 |
| 34761 | 1.19 |
| 34860 | 1.19 |
| 488989 | 1.19 |
| 377441 | 1.19 |
| 108284 | 1.19 |
| 36844 | 1.19 |
| 510467 | 1.19 |
| 290117 | 1.19 |

TABLE 4-continued

Results from the 1.2K microarray.

| Image ID or clone name | array ratio* |
|---|---|
| 23185 | 1.19 |
| 241412 | 1.19 |
| 290724 | 1.19 |
| 40026 | 1.19 |
| 42363 | 1.19 |
| 356890 | 1.19 |
| 25081 | 1.18 |
| mouse tyrosinase | 1.18 |
| HIV F13 | 1.18 |
| 323162 | 1.18 |
| 363799 | 1.18 |
| 193736 | 1.18 |
| 48077 | 1.18 |
| 323555 | 1.18 |
| 37508 | 1.18 |
| 50666 | 1.18 |
| 44477 | 1.18 |
| 429926 | 1.18 |
| 45794 | 1.17 |
| CoT1 | 1.17 |
| 35110 | 1.17 |
| 509820 | 1.17 |
| 46042 | 1.17 |
| 509682 | 1.17 |
| 512244 | 1.17 |
| 42648 | 1.17 |
| 40304 | 1.17 |
| 359077 | 1.17 |
| 469731 | 1.17 |
| 364975 | 1.16 |
| 82850 | 1.16 |
| 488373 | 1.16 |
| 110589 | 1.16 |
| 37231 | 1.16 |
| 52629 | 1.16 |
| 231497 | 1.16 |
| 286197 | 1.16 |
| 144944 | 1.16 |
| 298314 | 1.16 |
| 48452 | 1.16 |
| 510101 | 1.16 |
| 342256 | 1.16 |
| 358467 | 1.16 |
| 305455 | 1.16 |
| 40831 | 1.15 |
| 47493 | 1.15 |
| 375922 | 1.15 |
| 252185 | 1.15 |
| 39542 | 1.15 |
| 37679 | 1.15 |
| 33176 | 1.15 |
| 36291 | 1.15 |
| 469256 | 1.15 |
| mouse slug | 1.15 |
| 27848 | 1.15 |
| 195889 | 1.15 |
| 80549 | 1.14 |
| 42910 | 1.14 |
| 365647 | 1.14 |
| 32531 | 1.14 |
| 247869 | 1.14 |
| 52019 | 1.14 |
| 324700 | 1.14 |
| 26585 | 1.14 |
| 262691 | 1.14 |
| 32774 | 1.14 |
| 33267 | 1.14 |
| 51318 | 1.14 |
| 36560 | 1.14 |
| 125555 | 1.14 |
| 37904 | 1.14 |
| 32319 | 1.13 |
| 36922 | 1.13 |
| 51666 | 1.13 |
| 260052 | 1.13 |
| 361692 | 1.13 |
| 36975 | 1.13 |
| 180447 | 1.13 |
| 30272 | 1.13 |
| 23692 | 1.13 |
| 44178 | 1.13 |
| 42576 | 1.13 |
| 36007 | 1.13 |
| empty | 1.13 |
| 44266 | 1.13 |
| syn cDNA 10 | 1.13 |
| 49318 | 1.13 |
| 34005 | 1.12 |
| 40670 | 1.12 |
| 324815 | 1.12 |
| 272110 | 1.12 |
| 427750 | 1.12 |
| 125676 | 1.12 |
| 49584 | 1.12 |
| 359171 | 1.12 |
| 470493 | 1.12 |
| 361728 | 1.12 |
| 42532 | 1.12 |
| 44710 | 1.11 |
| 51528 | 1.11 |
| 307471 | 1.11 |
| mouse mart1 | 1.11 |
| 241489 | 1.11 |
| 242134 | 1.11 |
| 487965 | 1.11 |
| 43858 | 1.11 |
| 259241 | 1.11 |
| 471096 | 1.11 |
| 49777 | 1.10 |
| 231292 | 1.10 |
| 43129 | 1.10 |
| 23731 | 1.10 |
| 53084 | 1.10 |
| 53107 | 1.10 |
| 271416 | 1.10 |
| syn cDNA 10 | 1.10 |
| 44218 | 1.10 |
| empty | 1.10 |
| 429368 | 1.10 |
| 364278 | 1.09 |
| 22260 | 1.09 |
| 26052 | 1.09 |
| 84730 | 1.09 |
| 25517 | 1.09 |
| 50032 | 1.09 |
| 52489 | 1.09 |
| 30592 | 1.09 |
| 50117 | 1.09 |
| 135381 | 1.09 |
| 44105 | 1.09 |
| 427686 | 1.09 |
| 346587 | 1.09 |
| 24110 | 1.09 |
| 470185 | 1.09 |
| 49665 | 1.09 |
| 33477 | 1.09 |
| 40765 | 1.08 |
| 29204 | 1.08 |
| 47475 | 1.08 |
| 40493 | 1.08 |
| 79742 | 1.08 |
| 39195 | 1.08 |
| 271416 | 1.08 |
| 30885 | 1.08 |
| 43711 | 1.08 |
| 23073 | 1.08 |
| 52773 | 1.08 |
| syn cDNA 8 | 1.08 |

TABLE 4-continued

Results from the 1.2K microarray.

| Image ID or clone name | array ratio* |
|---|---|
| 39796 | 1.08 |
| 36232 | 1.08 |
| 44367 | 1.08 |
| 231302 | 1.08 |
| 40205 | 1.08 |
| 44414 | 1.08 |
| 27715 | 1.08 |
| 33643 | 1.08 |
| 26599 | 1.08 |
| 347751 | 1.08 |
| 26599 | 1.08 |
| 33525 | 1.08 |
| 29054 | 1.07 |
| 31116 | 1.07 |
| 36950 | 1.07 |
| 320514 | 1.07 |
| 45564 | 1.07 |
| 488658 | 1.07 |
| 26593 | 1.07 |
| 488904 | 1.07 |
| 30730 | 1.07 |
| syn cDNA 30 | 1.07 |
| 418436 | 1.07 |
| 51373 | 1.07 |
| syn cDNA 31 | 1.07 |
| 470470 | 1.06 |
| 36700 | 1.06 |
| 38966 | 1.06 |
| syn cDNA 30 | 1.06 |
| syn cDNA 33 | 1.06 |
| 51961 | 1.06 |
| 34637 | 1.06 |
| 30622 | 1.06 |
| 39380 | 1.06 |
| 282065 | 1.06 |
| 46329 | 1.06 |
| 486410 | 1.06 |
| syn cDNA 38 | 1.06 |
| 40008 | 1.06 |
| 37721 | 1.06 |
| 47110 | 1.06 |
| 37892 | 1.06 |
| 33831 | 1.06 |
| 51940 | 1.05 |
| 41094 | 1.05 |
| 114116 | 1.05 |
| 271478 | 1.05 |
| 232714 | 1.05 |
| 43719 | 1.05 |
| 343871 | 1.05 |
| 26659 | 1.05 |
| 24652 | 1.05 |
| 306013 | 1.05 |
| 42677 | 1.05 |
| 47202 | 1.05 |
| 31852 | 1.04 |
| 362926 | 1.04 |
| 39173 | 1.04 |
| 52222 | 1.04 |
| 22545 | 1.04 |
| 26789 | 1.04 |
| 258747 | 1.04 |
| 53068 | 1.04 |
| 418105 | 1.04 |
| 30852 | 1.04 |
| 35850 | 1.04 |
| 33632 | 1.04 |
| 53238 | 1.04 |
| 364982 | 1.03 |
| 486086 | 1.03 |
| 43338 | 1.03 |
| HIV F6 | 1.03 |
| HIV F10 | 1.03 |
| 45840 | 1.03 |
| 23804 | 1.03 |
| 52896 | 1.03 |
| 417136 | 1.03 |
| empty | 1.03 |
| 40111 | 1.03 |
| 29629 | 1.02 |
| 34647 | 1.02 |
| 41565 | 1.02 |
| 23831 | 1.02 |
| 204681 | 1.02 |
| 44014 | 1.02 |
| 145932 | 1.02 |
| 32875 | 1.02 |
| 26503 | 1.02 |
| 357374 | 1.02 |
| 429057 | 1.02 |
| 32198 | 1.01 |
| 22040 | 1.01 |
| 36681 | 1.01 |
| 47333 | 1.01 |
| 50271 | 1.01 |
| 375843 | 1.01 |
| 376725 | 1.01 |
| 42059 | 1.01 |
| 39861 | 1.01 |
| 45941 | 1.01 |
| 33274 | 1.01 |
| 271198 | 1.01 |
| 24886 | 1.01 |
| 33690 | 1.01 |
| 33438 | 1.01 |
| 24609 | 1.01 |
| 470817 | 1.01 |
| 49691 | 1.01 |
| 110589 | 1.00 |
| 310428 | 1.00 |
| 25400 | 1.00 |
| syn cDNA 8 | 1.00 |
| 52338 | 1.00 |
| 32717 | 1.00 |
| 323500 | 1.00 |
| 27473 | 1.00 |
| 295208 | 1.00 |
| syn cDNA 25 | 1.00 |
| lambda | 1.00 |
| 32822 | 1.00 |
| 46303 | 1.00 |
| 31242 | 1.00 |
| 42352 | 1.00 |
| 194384 | 1.00 |
| 36844 | 0.99 |
| 44537 | 0.99 |
| 347573 | 0.99 |
| 485690 | 0.99 |
| 486335 | 0.99 |
| 40764 | 0.99 |
| 30573 | 0.99 |
| 190711 | 0.99 |
| 50576 | 0.99 |
| 26087 | 0.99 |
| 41773 | 0.99 |
| syn cDNA 31 | 0.99 |
| 43549 | 0.99 |
| 50363 | 0.99 |
| 52489 | 0.99 |
| 39827 | 0.99 |
| 427943 | 0.99 |
| 53128 | 0.99 |
| 42130 | 0.99 |
| 52931 | 0.99 |
| 46302 | 0.99 |
| pUC18 | 0.99 |
| 50609 | 0.99 |
| 27681 | 0.99 |

TABLE 4-continued

Results from the 1.2K microarray.

| Image ID or clone name | array ratio* |
|---|---|
| 35933 | 0.99 |
| empty | 0.99 |
| 53185 | 0.99 |
| 301723 | 0.99 |
| 31155 | 0.99 |
| 33803 | 0.99 |
| empty | 0.99 |
| 38829 | 0.98 |
| 34005 | 0.98 |
| 36916 | 0.98 |
| 44563 | 0.98 |
| 42993 | 0.98 |
| syn cDNA 31 | 0.98 |
| 36790 | 0.98 |
| 366576 | 0.98 |
| 418320 | 0.98 |
| 52342 | 0.98 |
| 487878 | 0.98 |
| 37196 | 0.98 |
| 39781 | 0.98 |
| 341763 | 0.98 |
| 37796 | 0.98 |
| 470635 | 0.98 |
| 31454 | 0.98 |
| 51432 | 0.98 |
| 36109 | 0.98 |
| 46777 | 0.98 |
| syn cDNA 38 | 0.98 |
| 305455 | 0.98 |
| 47384 | 0.97 |
| 300051 | 0.97 |
| 85906 | 0.97 |
| 29640 | 0.97 |
| Bcl-2 | 0.97 |
| 377181 | 0.97 |
| aim2/IFI16 | 0.97 |
| 209310 | 0.97 |
| 380738 | 0.97 |
| 415731 | 0.97 |
| 345600 | 0.97 |
| 40151 | 0.97 |
| 26167 | 0.97 |
| 28309 | 0.97 |
| 33692 | 0.97 |
| 429861 | 0.97 |
| 126519 | 0.97 |
| 357909 | 0.97 |
| 33620 | 0.97 |
| 25154 | 0.96 |
| 51785 | 0.96 |
| 51814 | 0.96 |
| 484993 | 0.96 |
| 25584 | 0.96 |
| 486560 | 0.96 |
| 50322 | 0.96 |
| 415679 | 0.96 |
| 343166 | 0.96 |
| 32898 | 0.96 |
| 471631 | 0.96 |
| 33183 | 0.96 |
| 31116 | 0.96 |
| 25169 | 0.95 |
| 366981 | 0.95 |
| 38567 | 0.95 |
| 44605 | 0.95 |
| 44666 | 0.95 |
| 239287 | 0.95 |
| 37234 | 0.95 |
| 45421 | 0.95 |
| 327396 | 0.95 |
| 35623 | 0.95 |
| 44159 | 0.95 |
| 48713 | 0.95 |
| 427943 | 0.95 |
| 35297 | 0.95 |
| 23332 | 0.95 |
| 37451 | 0.95 |
| 31131 | 0.95 |
| 42058 | 0.95 |
| 259291 | 0.95 |
| 46574 | 0.95 |
| 51241 | 0.95 |
| 486233 | 0.94 |
| 196543 | 0.94 |
| 49898 | 0.94 |
| 43601 | 0.94 |
| 200378 | 0.94 |
| syn cDNA 25 | 0.94 |
| 323648 | 0.94 |
| 48717 | 0.94 |
| 46339 | 0.94 |
| 30691 | 0.94 |
| 328467 | 0.94 |
| 39965 | 0.94 |
| 427857 | 0.94 |
| Gadd153 | 0.94 |
| 51418 | 0.94 |
| syn cDNA 25 | 0.94 |
| 361401 | 0.93 |
| 38876 | 0.93 |
| 49788 | 0.93 |
| 32609 | 0.93 |
| 32626 | 0.93 |
| 33008 | 0.93 |
| 39686 | 0.93 |
| 50555 | 0.93 |
| 23346 | 0.93 |
| 30802 | 0.93 |
| 47038 | 0.93 |
| 44302 | 0.93 |
| syn cDNA 30 | 0.93 |
| 36202 | 0.93 |
| 34327 | 0.92 |
| 267246 | 0.92 |
| 34141 | 0.92 |
| 307741 | 0.92 |
| 301363 | 0.92 |
| 26503 | 0.92 |
| 32649 | 0.92 |
| 37230 | 0.92 |
| 45222 | 0.92 |
| 324698 | 0.92 |
| 37269 | 0.92 |
| 376737 | 0.92 |
| 29799 | 0.92 |
| 488891 | 0.92 |
| 41392 | 0.92 |
| 41813 | 0.92 |
| 23019 | 0.92 |
| 140827 | 0.92 |
| 37433 | 0.92 |
| HIV F7 | 0.92 |
| 46213 | 0.92 |
| 36393 | 0.92 |
| syn cDNA 8 | 0.92 |
| 44311 | 0.92 |
| 42888 | 0.92 |
| 53316 | 0.92 |
| 486375 | 0.91 |
| 49926 | 0.91 |
| 49950 | 0.91 |
| 40959 | 0.91 |
| 357357 | 0.91 |
| syn cDNA 38 | 0.91 |
| 323776 | 0.91 |
| 30588 | 0.91 |
| 35313 | 0.91 |
| 41857 | 0.91 |

TABLE 4-continued

Results from the 1.2K microarray.

| Image ID or clone name | array ratio* |
|---|---|
| 53322 | 0.91 |
| 47125 | 0.91 |
| 357442 | 0.91 |
| 40440 | 0.91 |
| 38805 | 0.90 |
| 49897 | 0.90 |
| 51540 | 0.90 |
| TRP1 | 0.90 |
| syn cDNA 10 | 0.90 |
| 28985 | 0.90 |
| 26599 | 0.90 |
| 22293 | 0.90 |
| 26147 | 0.90 |
| 41199 | 0.90 |
| 415636 | 0.90 |
| 30664 | 0.90 |
| 46419 | 0.90 |
| 485192 | 0.90 |
| 39903 | 0.90 |
| 42615 | 0.90 |
| 512429 | 0.90 |
| 347032 | 0.90 |
| 359465 | 0.90 |
| 302157 | 0.90 |
| empty | 0.90 |
| 43110 | 0.89 |
| 361815 | 0.89 |
| 50576 | 0.89 |
| 40991 | 0.89 |
| 44699 | 0.89 |
| 321246 | 0.89 |
| 34537 | 0.89 |
| 43409 | 0.89 |
| 325182 | 0.89 |
| 36215 | 0.89 |
| syn cDNA 30 | 0.89 |
| 52415 | 0.89 |
| mouse mi/microphthalmia | 0.89 |
| 33045 | 0.89 |
| 37380 | 0.89 |
| 42096 | 0.89 |
| 471889 | 0.89 |
| 322029 | 0.89 |
| 42214 | 0.89 |
| 26922 | 0.89 |
| 35483 | 0.89 |
| 37485 | 0.89 |
| 138998 | 0.89 |
| 31238 | 0.89 |
| 40276 | 0.89 |
| 38471 | 0.89 |
| 27815 | 0.89 |
| 46711 | 0.89 |
| 49322 | 0.89 |
| 51461 | 0.89 |
| 53292 | 0.89 |
| 469272 | 0.89 |
| 33943 | 0.89 |
| 44527 | 0.88 |
| 34357 | 0.88 |
| 43129 | 0.88 |
| 32141 | 0.88 |
| 375724 | 0.88 |
| 30578 | 0.88 |
| 26572 | 0.88 |
| syn cDNA 8 | 0.88 |
| 43504 | 0.88 |
| 323028 | 0.88 |
| 340644 | 0.88 |
| 512458 | 0.88 |
| 39728 | 0.88 |
| 41918 | 0.88 |
| 42284 | 0.88 |
| 37477 | 0.88 |
| empty | 0.88 |
| 24899 | 0.88 |
| EDNRB | 0.88 |
| 121147 | 0.87 |
| 324655 | 0.87 |
| 34945 | 0.87 |
| 39270 | 0.87 |
| 376507 | 0.87 |
| 39159 | 0.87 |
| 222502 | 0.87 |
| 278409 | 0.87 |
| 343465 | 0.87 |
| 293934 | 0.87 |
| 43826 | 0.87 |
| 23132 | 0.87 |
| 49161 | 0.87 |
| 510405 | 0.87 |
| syn cDNA 33 | 0.87 |
| 340878 | 0.87 |
| 152762 | 0.87 |
| 296476 | 0.87 |
| 51854 | 0.86 |
| endothelin1 | 0.86 |
| 32409 | 0.86 |
| syn cDNA 25 | 0.86 |
| 43021 | 0.86 |
| 51685 | 0.86 |
| 489194 | 0.86 |
| 321308 | 0.86 |
| 32644 | 0.86 |
| 487777 | 0.86 |
| 380403 | 0.86 |
| 39169 | 0.86 |
| 35615 | 0.86 |
| tyrosinase | 0.86 |
| 43885 | 0.86 |
| 32790 | 0.86 |
| 27794 | 0.86 |
| 24392 | 0.86 |
| 31154 | 0.86 |
| 37964 | 0.86 |
| 44721 | 0.85 |
| 199381 | 0.85 |
| 38859 | 0.85 |
| 21652 | 0.85 |
| 49751 | 0.85 |
| 38647 | 0.85 |
| 486012 | 0.85 |
| 47631 | 0.85 |
| 34671 | 0.85 |
| 26082 | 0.85 |
| 22611 | 0.85 |
| 114648 | 0.85 |
| 50359 | 0.85 |
| syn cDNA 38 | 0.85 |
| 42088 | 0.85 |
| 343646 | 0.85 |
| 37622 | 0.85 |
| 43960 | 0.85 |
| 31143 | 0.85 |
| 42349 | 0.85 |
| 24145 | 0.85 |
| 293032 | 0.85 |
| 40450 | 0.85 |
| 51454 | 0.85 |
| 49383 | 0.85 |
| 36717 | 0.84 |
| 26483 | 0.84 |
| 213502 | 0.84 |
| 37040 | 0.84 |
| 30012 | 0.84 |
| 30619 | 0.84 |
| 43504 | 0.84 |
| 203184 | 0.84 |

TABLE 4-continued

Results from the 1.2K microarray.

| Image ID or clone name | array ratio* |
|---|---|
| 38500 | 0.84 |
| 27818 | 0.84 |
| 42844 | 0.84 |
| 31863 | 0.84 |
| 81221 | 0.83 |
| 22230 | 0.83 |
| 50234 | 0.83 |
| 376362 | 0.83 |
| 43241 | 0.83 |
| 256323 | 0.83 |
| 323390 | 0.83 |
| 50203 | 0.83 |
| 23014 | 0.83 |
| 293274 | 0.83 |
| 44173 | 0.83 |
| 230976 | 0.83 |
| 50888 | 0.83 |
| 340734 | 0.83 |
| HIV F3 | 0.83 |
| 279727 | 0.83 |
| 42020 | 0.83 |
| 357435 | 0.83 |
| 33794 | 0.83 |
| 470621 | 0.83 |
| 25725 | 0.82 |
| 267682 | 0.82 |
| empty | 0.82 |
| 489217 | 0.82 |
| mouse TRP2 | 0.82 |
| mouse aim2/IFI16 | 0.82 |
| mouse TRP1 | 0.82 |
| 34606 | 0.82 |
| 487386 | 0.82 |
| 30149 | 0.82 |
| pUC18 | 0.82 |
| Gadd34 | 0.82 |
| 48458 | 0.82 |
| 291057 | 0.82 |
| CoT1 | 0.82 |
| 487982 | 0.82 |
| 42380 | 0.82 |
| 51302 | 0.82 |
| Hu placental | 0.82 |
| pUC18 | 0.82 |
| empty | 0.82 |
| empty | 0.82 |
| 51740 | 0.81 |
| 32790 | 0.81 |
| 310390 | 0.81 |
| 21810 | 0.81 |
| 49849 | 0.81 |
| 30781 | 0.81 |
| pUC18 | 0.81 |
| 30543 | 0.81 |
| 279482 | 0.81 |
| 52652 | 0.81 |
| 223176 | 0.81 |
| 345645 | 0.81 |
| 341130 | 0.81 |
| 50999 | 0.81 |
| 48503 | 0.81 |
| 280735 | 0.81 |
| 488092 | 0.81 |
| 38397 | 0.81 |
| 47559 | 0.81 |
| 358848 | 0.81 |
| 37760 | 0.81 |
| 36060 | 0.81 |
| 51219 | 0.81 |
| 470196 | 0.81 |
| 300960 | 0.81 |
| 310406 | 0.80 |
| 25764 | 0.80 |
| 344769 | 0.80 |
| 38840 | 0.80 |
| 47386 | 0.80 |
| 40874 | 0.80 |
| 28573 | 0.80 |
| 309615 | 0.80 |
| 362332 | 0.80 |
| 50232 | 0.80 |
| 39205 | 0.80 |
| 43622 | 0.80 |
| 470792 | 0.80 |
| 47838 | 0.80 |
| 26366 | 0.80 |
| 30970 | 0.80 |
| 510151 | 0.80 |
| 280465 | 0.80 |
| 50576 | 0.80 |
| 509588 | 0.80 |
| 34349 | 0.79 |
| 113941 | 0.79 |
| 471217 | 0.79 |
| 36775 | 0.79 |
| 28776 | 0.79 |
| 36796 | 0.79 |
| 38770 | 0.79 |
| 22445 | 0.79 |
| 45851 | 0.79 |
| 47648 | 0.79 |
| 41796 | 0.79 |
| 26286 | 0.79 |
| 45568 | 0.79 |
| 375724 | 0.79 |
| 49243 | 0.79 |
| 417322 | 0.79 |
| 291736 | 0.79 |
| 31456 | 0.79 |
| 42894 | 0.78 |
| 29438 | 0.78 |
| 32407 | 0.78 |
| 28595 | 0.78 |
| 45376 | 0.78 |
| 271662 | 0.78 |
| 47727 | 0.78 |
| 50171 | 0.78 |
| ME491 | 0.78 |
| 39884 | 0.78 |
| 340922 | 0.78 |
| 24269 | 0.78 |
| 307293 | 0.78 |
| 49608 | 0.78 |
| 40360 | 0.78 |
| 284669 | 0.78 |
| 31164 | 0.78 |
| 43194 | 0.77 |
| 297589 | 0.77 |
| 80239 | 0.77 |
| 45643 | 0.77 |
| 281778 | 0.77 |
| 192694 | 0.77 |
| 43541 | 0.77 |
| 41356 | 0.77 |
| 123953 | 0.77 |
| 48629 | 0.77 |
| 290493 | 0.77 |
| 28245 | 0.77 |
| 46548 | 0.77 |
| 44255 | 0.77 |
| 21477 | 0.76 |
| 299626 | 0.76 |
| 43563 | 0.76 |
| 47833 | 0.76 |
| 112035 | 0.76 |
| 32682 | 0.76 |
| 489327 | 0.76 |
| 221690 | 0.76 |

TABLE 4-continued

Results from the 1.2K microarray.

| Image ID or clone name | array ratio* |
|---|---|
| 257458 | 0.76 |
| 39876 | 0.76 |
| 39993 | 0.76 |
| 42295 | 0.76 |
| 27052 | 0.76 |
| 53071 | 0.76 |
| 248258 | 0.76 |
| 359051 | 0.76 |
| 24638 | 0.76 |
| 36191 | 0.76 |
| 34255 | 0.75 |
| 26128 | 0.75 |
| 26184 | 0.75 |
| 509710 | 0.75 |
| 27549 | 0.75 |
| 116713 | 0.75 |
| 44050 | 0.75 |
| 357239 | 0.75 |
| 31355 | 0.75 |
| 52564 | 0.74 |
| 345527 | 0.74 |
| 26129 | 0.74 |
| 43631 | 0.74 |
| 323181 | 0.74 |
| 32684 | 0.74 |
| 415060 | 0.74 |
| 32615 | 0.74 |
| 39391 | 0.74 |
| 45604 | 0.74 |
| 510245 | 0.74 |
| 27230 | 0.74 |
| 322000 | 0.74 |
| 470610 | 0.74 |
| 27927 | 0.74 |
| 46920 | 0.74 |
| 46936 | 0.74 |
| 44584 | 0.73 |
| 471620 | 0.73 |
| 129268 | 0.73 |
| 49980 | 0.73 |
| 261518 | 0.73 |
| 262575 | 0.73 |
| 375635 | 0.73 |
| 26531 | 0.73 |
| 366904 | 0.73 |
| 50561 | 0.73 |
| 346305 | 0.73 |
| 28410 | 0.73 |
| 24588 | 0.73 |
| 29234 | 0.72 |
| 366942 | 0.72 |
| 50038 | 0.72 |
| 375620 | 0.72 |
| 43092 | 0.72 |
| 45658 | 0.72 |
| 22798 | 0.72 |
| 41559 | 0.72 |
| 231089 | 0.72 |
| 32707 | 0.72 |
| 415102 | 0.72 |
| 32750 | 0.72 |
| 416184 | 0.72 |
| 284459 | 0.72 |
| 49403 | 0.72 |
| 50308 | 0.71 |
| 366647 | 0.71 |
| 376649 | 0.71 |
| 376110 | 0.71 |
| Hu placental | 0.71 |
| 37366 | 0.71 |
| 35320 | 0.71 |
| 417124 | 0.71 |
| 31169 | 0.71 |
| 304947 | 0.71 |
| 24642 | 0.71 |
| 34660 | 0.70 |
| 48406 | 0.70 |
| 192694 | 0.70 |
| 27511 | 0.70 |
| 48762 | 0.70 |
| 357309 | 0.70 |
| 429135 | 0.70 |
| 42700 | 0.70 |
| 53227 | 0.70 |
| 40110 | 0.70 |
| 51504 | 0.70 |
| 34011 | 0.69 |
| 32983 | 0.69 |
| 257766 | 0.69 |
| 34662 | 0.69 |
| 509710 | 0.69 |
| 244355 | 0.69 |
| 193913 | 0.68 |
| 310490 | 0.68 |
| 347685 | 0.68 |
| 471918 | 0.68 |
| 375635 | 0.68 |
| 358538 | 0.68 |
| 322148 | 0.68 |
| 36983 | 0.68 |
| 41511 | 0.68 |
| 39093 | 0.68 |
| 138604 | 0.68 |
| 51018 | 0.68 |
| 28573 | 0.67 |
| 32658 | 0.67 |
| pdgfr | 0.67 |
| 201797 | 0.67 |
| 50106 | 0.67 |
| 29435 | 0.66 |
| 40886 | 0.66 |
| CoT1 | 0.66 |
| 264606 | 0.66 |
| 22285 | 0.66 |
| 45291 | 0.66 |
| 190107 | 0.66 |
| 49255 | 0.66 |
| 38983 | 0.65 |
| 298187 | 0.65 |
| 376294 | 0.65 |
| 48234 | 0.65 |
| 381219 | 0.65 |
| 471218 | 0.65 |
| 417127 | 0.64 |
| 47884 | 0.64 |
| 300071 | 0.64 |
| 356964 | 0.64 |
| 470691 | 0.63 |
| 51621 | 0.63 |
| 45233 | 0.63 |
| 131828 | 0.63 |
| 320538 | 0.63 |
| 46449 | 0.63 |
| HGF | 0.63 |
| 243159 | 0.63 |
| 45188 | 0.62 |
| 37118 | 0.62 |
| 364716 | 0.61 |
| 62186 | 0.61 |
| 40911 | 0.61 |
| 366824 | 0.61 |
| 115336 | 0.61 |
| 138460 | 0.61 |
| 124086 | 0.61 |
| 291943 | 0.61 |
| 62186 | 0.60 |
| 47463 | 0.60 |
| 366509 | 0.60 |

TABLE 4-continued

Results from the 1.2K microarray.

| Image ID or clone name | array ratio* |
|---|---|
| Hu placental | 0.60 |
| 49277 | 0.60 |
| 34555 | 0.59 |
| 37145 | 0.59 |
| 41792 | 0.59 |
| 43550 | 0.59 |
| 510595 | 0.59 |
| 51209 | 0.59 |
| 44689 | 0.58 |
| 358677 | 0.58 |
| 34304 | 0.58 |
| 22493 | 0.58 |
| 115408 | 0.58 |
| 430027 | 0.58 |
| 51555 | 0.57 |
| 34355 | 0.57 |
| 328330 | 0.56 |
| 248613 | 0.56 |
| 469724 | 0.56 |
| lambda | 0.56 |
| 32636 | 0.55 |
| 32438 | 0.54 |
| 376285 | 0.54 |
| 22568 | 0.54 |
| 345722 | 0.54 |
| 309924 | 0.54 |
| 43060 | 0.53 |
| 415206 | 0.53 |
| 42777 | 0.53 |
| HIV F1 | 0.51 |
| 487417 | 0.51 |
| 346534 | 0.47 |
| 233194 | 0.46 |
| 295093 | 0.45 |
| 48085 | 0.44 |
| 26541 | 0.43 |
| empty | 0.41 |
| 28089 | 0.38 |
| 248032 | 0.34 |
| 359119 | 0.27 |
| 28116 | 0.23 |
| empty | 0.19 |
| empty | 0.18 |
| empty | 0.18 |
| empty | 0.15 |
| 417226 | 0.14 |
| 51699 | 0.12 |

*relative expression levels

TABLE 5

Image ID Numbers Present in the 5K microarray.

20115; 21652; 21738; 22012; 22040; 22074; 22260; 22293; 22411; 22493; 22711; 22731; 22918; 23019; 23073; 23132; 23173; 23185; 23282; 23431; 23772; 23776; 23804; 23831; 23878; 23932; 24004; 24032; 24085; 24145; 24415; 24642; 24884; 25499; 25584; 25588; 25679; 25725; 25755; 26021; 26162; 26184; 26314; 26366; 26418; 26566; 26566; 26578; 26616; 26617; 26711; 26811; 26910; 26922; 27104; 27548; 27549; 27624; 27787; 27848; 28012; 28098; 28218; 28309; 28410; 28422; 28469; 28475; 28823; 28985; 29054; 29063; 30093; 30170; 30272; 30502; 30664; 30885; 31072; 31093; 31143; 31169; 31210; 31251; 31842; 31866; 31873; 32231; 32472; 32609; 32684; 32875; 32898; 32996; 33045; 33049; 33051; 33051; 33182; 33299; 33327; 33478; 33525; 33632; 33690; 33826; 33941; 33949; 34106; 34255; 34302; 34315; 34355; 34357; 34396; 34439; 34616; 34671; 34689; 34773; 34778; 34795; 34849; 34852; 34888; 34945; 35077; 35105; 35185; 35191; 35191; 35236; 35271; 35483; 35828; 36374; 36387; 36393; 36493; 36607; 36775; 36950; 37196; 37234; 37366; 37449; 37451; 37491; 37904; 38465; 38471; 38763; 38763; 39093; 39127; 39159; 39173; 39274; 39285; 39593; 39796; 39798; 39808; 39884; 39884; 39993; 40017; 40026; 40042; 40056; 40299; 40304; 40360; 40365; 40562; 40567; 40580; 40643; 40699; 40704; 40721; 40751; 40751; 40781; 40844; 40887; 40946; 41199; 41356; 41452; 41511; 41541; 41565; 41591; 41650; 41658; 41672; 41898; 41929; 42059; 42076; 42076; 42096; 42118; 42214; 42258; 42313; 42313; 42352; 42373; 42558; 42576; 42706; 42739; 42880; 42993; 43021; 43129; 43198; 43207; 43231; 43241; 43338; 43550; 43563; 43622; 43743; 43771; 43826; 43833; 43878; 43884; 43977; 44164; 44180; 44255; 44255; 44307; 44351; 44477; 44505; 44537; 44563; 44692; 44975; 45099; 45138; 45231; 45233; 45272; 45291; 45525; 45525; 45542; 45544; 45556; 45632; 45641; 45921; 45941; 46054; 46154; 46154; 46171; 46182; 46284; 46356; 46518; 46786; 46897; 46916; 46916; 47043; 47110; 47142; 47202; 47475; 47510; 47542; 47559; 47647; 47681; 47833; 47853; 47853; 47900; 47908; 48136; 48182; 48283; 48285; 48398; 48530; 48614; 48631; 48799; 48886; 48906; 49117; 49164; 49260; 49344; 49352; 49404; 49464; 49509; 49518; 49591; 49630; 49665; 49710; 49860; 49873; 49888; 49920; 49970; 50043; 50117; 50182; 50188; 50214; 50359; 50413; 50506; 50614; 50666; 50680; 50754; 50765; 50794; 50941; 50990; 51041; 51263; 51293; 51328; 51362; 51408; 51447; 51448; 51450; 51463; 51532; 51543; 51640; 51666; 51666; 51702; 51737; 51740; 51746;

TABLE 5-continued

Image ID Numbers Present in the 5K microarray.

51814; 51865; 51899; 51916; 51974; 51981; 52079; 52228; 52327; 52419; 52430; 52431; 52629;
52629; 52646; 52933; 53099; 53099; 53316; 53341; 62277; 66316; 66317; 66322; 66327; 66329;
66333; 66335; 66336; 66341; 66352; 66354; 66369; 66377; 66390; 66391; 66400; 66406; 66407;
66420; 66423; 66428; 66430; 66443; 66454; 66467; 66474; 66475; 66497; 66507; 66532; 66533;
66534; 66535; 66540; 66550; 66552; 66555; 66556; 66560; 66562; 66564; 66574; 66582; 66584;
66594; 66596; 66606; 66608; 66609; 66630; 66663; 66685; 66686; 66686; 66694; 66697; 66711;
66714; 66718; 66721; 66728; 66731; 66753; 66774; 66792; 66815; 66829; 66864; 66894; 66895;
66898; 66902; 66903; 66910; 66919; 66931; 66937; 66944; 66946; 66952; 66953; 66972; 66975;
66977; 66982; 67006; 67009; 67016; 67033; 67036; 67037; 67055; 67069; 67070; 67074; 67075;
67654; 68103; 68225; 68977; 69672; 70002; 70349; 70489; 70692; 70827; 71101; 71116; 71432;
71545; 71606; 71622; 71626; 71672; 71727; 72050; 72391; 72778; 72869; 73268; 73381;
73531; 73782; 74119; 74566; 74593; 75009; 75254; 75415; 75923; 76362; 77133; 77391; 77533;
77577; 77577; 77636; 77728; 77805; 77897; 77915; 78217; 78294; 78869; 79022; 79229; 79254;
79353; 79502; 79520; 79520; 79624; 79629; 79688; 79710; 79712; 79828; 79898; 80095; 80109;
80109; 80146; 80374; 80384; 80399; 80410; 80500; 80504; 80549; 80708; 80772; 80910; 80915;
80924; 80946; 80948; 81129; 81289; 81315; 81331; 81336; 81394; 81417; 81427; 81518; 81599;
82710; 82734; 82871; 82879; 82976; 82991; 83083; 83120; 83129; 83210; 83210; 83231; 83363;
83605; 84295; 84750; 84820; 84955; 85093; 85128; 85202; 85259; 85394; 85394; 85497; 85509;
85561; 85624; 85634; 85678; 85682; 85690; 85805; 85840; 85979; 86220; 108177; 108197;
108208; 108208; 108265; 108316; 108330; 108351; 108395; 108422; 108425; 108471; 108651;
108658; 108667; 108716; 108730; 108763; 108783; 108797; 108801; 108815; 108836; 109049;
109089; 109108; 109123; 109153; 109179; 109200; 109221; 109265; 109269; 109271; 109277;
109279; 109304; 109309; 109314; 109316; 109466; 109483; 109488; 109523; 109708; 109811;
109888; 110094; 110198; 110281; 110282; 110307; 110347; 110417; 110436; 110467; 110503;
110503; 110507; 110519; 110578; 110582; 110585; 110653; 110703; 110741; 110746; 110772;
110788; 110791; 110893; 110904; 110912; 110980; 110987; 110996; 111004; 111006; 111054;
111070; 111101; 111122; 111136; 111150; 111200; 111204; 111264; 111266; 111389; 111391;
111413; 111492; 111510; 111516; 111549; 111571; 111634; 111693; 111705; 111714; 111721;
111722; 111750; 111755; 111765; 111825; 111844; 111884; 111981; 112131; 112158; 112371;
112409; 112440; 112494; 112525; 112530; 112541; 112576; 112577; 112629; 112865; 112896;
112906; 113048; 113206; 113281; 113283; 113284; 113298; 113300; 113308; 113394; 113399;
113431; 113488; 113538; 115111; 115143; 115155; 115223; 115230; 115281; 115292; 115307;
115337; 115414; 115447; 119384; 119530; 119882; 119914; 119914; 120015; 120097; 120106;
120113; 120124; 120138; 120153; 120162; 120173; 120189; 120297; 120306; 120309; 120318;
120343; 120362; 120375; 120383; 120413; 120516; 120533; 120544; 120551; 120561; 120572;
120598; 120631; 120634; 120681; 120695; 120701; 120773; 120823; 120863; 120881; 120964;
120973; 121018; 121072; 121133; 121159; 121184; 121206; 121214; 121218; 121220; 121239;
121251; 121252; 121270; 121275; 121316; 121341; 121355; 121365; 121412; 121415; 121420;
121458; 121459; 121462; 121475; 121500; 121501; 121521; 121530; 121533; 121543; 121546;
121558; 121559; 121564; 121577; 121600; 121611; 121615; 121616; 121621; 121625; 121628;
121661; 121662; 121687; 121715; 121722; 121727; 121736; 121756; 121770; 121776; 121792;
121798; 121803; 121808; 121828; 121877; 121880; 121898; 121954; 121977; 121981; 121994;
121997; 122019; 122063; 122077; 122091; 122126; 122150; 122159; 122159; 122161; 122170;
122178; 122194; 122237; 122274; 122295; 122345; 122354; 122359; 122364; 122397; 122428;
122443; 122636; 122684; 122702; 122762; 122787; 122796; 122822; 122875; 122889; 122899;
122906; 122913; 122915; 122946; 122955; 122963; 122982; 123061; 123065; 123067; 123074;
123079; 123087; 123112; 123117; 123196; 123222; 123229; 123255; 123262; 123331; 123354;
123400; 123405; 123408; 123425; 123433; 123436; 123439; 123441; 123448; 123459; 123474;
123506; 123561; 123578; 123579; 123604; 123614; 123627; 123627; 123646; 123649; 123666;
123699; 123700; 123720; 123724; 123729; 123730; 123755; 123788; 123790; 123802; 123805;
123815; 123817; 123858; 123926; 123932; 123952; 123980; 124009; 124014; 124020; 124042;
124043; 124052; 124059; 124070; 124071; 124077; 124079; 124087; 124090; 124091; 124116;
124126; 124127; 124128; 124132; 124137; 124138; 124143; 124155; 124168; 124179; 124203;
124232; 124241; 124261; 124271; 124277; 124286; 124320; 124405; 124502; 124505; 124530;
124578; 124597; 124605; 124629; 124637; 124719; 124730; 124753; 124781; 124788; 124795;
124808; 124822; 124824; 124853; 124891; 124909; 124922; 124965; 125040; 125092; 125134;
125148; 125183; 125308; 125548; 125589; 125608; 125665; 125666; 125685; 125709; 125722;
125737; 125739; 125741; 125767; 125769; 125788; 125799; 125809; 125822; 125828; 126219;
126221; 126225; 126229; 126230; 126234; 126237; 126243; 126320; 126321; 126338; 126341;
126355; 126368; 126371; 126390; 126393; 126401; 126406; 126412; 126413; 126419; 126438;
126450; 126453; 126459; 126465; 126466; 126470; 126497; 126508; 126509; 126519; 126522;
126544; 126568; 126581; 126638; 126650; 126670; 126702; 126722; 126788; 126792; 126795;
126858; 126882; 126883; 126884; 126887; 126988; 127054; 127076; 127096; 127099; 127119;
127120; 127147; 127173; 127182; 127185; 127193; 127194; 127197; 127199; 127216; 127243;
127272; 127354; 127400; 127408; 127409; 127415; 127462; 127473; 127486; 127509; 127514;
127519; 127542; 127610; 127625; 127636; 127646; 127665; 127666; 127677; 127682; 127710;
127729; 127766; 127769; 127821; 127841; 127843; 127881; 127925; 127928; 127943; 127970;
127974; 127983; 128054; 128118; 128126; 128143; 128150; 128159; 128193; 128204; 128208;
128243; 128245; 128248; 128260; 128274; 128290; 128297; 128301; 128302; 128322; 128346;
128351; 128426; 128457; 128460; 128503; 128509; 128518; 128530; 128561; 128602; 128617;
128627; 128632; 128679; 128690; 128695; 128735; 128737; 128738; 128775; 128783; 128785;
128795; 128833; 128875; 128905; 128947; 128954; 128970; 128973; 128985; 128993; 129000;
129071; 129112; 129146; 129177; 129293; 129331; 129332; 129342; 129355; 129392; 129407;
129442; 129446; 129477; 129502; 129506; 129514; 129516; 129541; 129563; 129567; 129569;
129585; 129600; 129610; 129616; 129624; 129644; 129721; 129725; 129748; 129770; 129817;
129840; 129853; 129865; 129922; 129925; 130004; 130005; 130008; 130027; 130028; 130043;
130044; 130053; 130054; 130057; 130100; 130107; 130116; 130120; 130153; 130156; 130233;

TABLE 5-continued

Image ID Numbers Present in the 5K microarray.

130243; 130276; 130280; 130294; 130334; 130342; 130358; 130371; 130421; 130541; 130572;
130582; 130610; 130617; 130656; 130677; 130716; 130747; 130756; 130758; 130773; 130777;
130781; 130788; 130791; 130801; 130820; 130824; 130826; 130835; 130843; 130857; 130868;
130876; 130884; 130892; 130895; 130916; 130972; 130977; 131010; 131016; 131029; 131050;
131104; 131238; 131239; 131307; 131316; 131318; 131362; 131365; 131370; 131388; 131446;
131563; 131595; 131653; 131668; 131764; 131824; 131839; 131867; 131877; 131886; 131887;
132012; 132017; 132019; 132066; 132111; 132122; 132140; 132142; 132159; 132215; 132285;
132304; 132323; 132358; 132373; 132381; 132464; 132524; 132527; 132549; 132569; 132623;
132630; 132631; 132690; 132708; 132748; 132789; 132828; 132835; 132848; 132871; 132899;
132911; 133084; 133096; 133114; 133130; 133158; 133178; 133180; 133197; 133213; 133225;
133236; 133273; 133303; 133331; 133333; 133519; 133534; 133613; 133820; 133964; 133972;
134120; 134172; 134192; 134229; 134235; 134256; 134269; 134270; 134312; 134322; 134368;
134394; 134422; 134439; 134476; 134482; 134495; 134520; 134523; 134525; 134537; 134544;
134643; 134712; 134719; 134748; 134753; 134783; 134829; 134856; 134948; 135010; 135058;
135083; 135083; 135094; 135203; 135212; 135219; 135220; 135221; 135240; 135247; 135273;
135303; 135426; 135431; 135449; 135450; 135454; 135527; 135538; 135561; 135608; 135653;
135654; 135673; 135676; 135688; 135692; 135710; 135713; 135721; 135766; 135773; 135777;
135789; 135791; 135853; 135892; 135901; 135910; 135922; 135941; 135999; 136064; 136073;
136114; 136117; 136180; 136188; 136218; 136223; 136235; 136286; 136301; 136303; 136317;
136382; 136409; 136449; 136536; 136557; 136560; 136571; 136598; 136632; 136706; 136730;
136744; 136772; 136775; 136780; 136801; 136802; 136814; 136821; 136855; 136856; 136874;
136909; 136919; 136933; 136954; 136984; 137016; 137017; 137020; 137063; 137096; 137139;
137158; 137178; 137182; 137208; 137209; 137236; 137254; 137349; 137353; 137387; 137396;
137417; 137456; 137506; 137531; 137535; 137581; 137638; 137647; 137653; 137663; 137736;
137760; 137793; 137794; 137797; 137836; 137853; 137862; 137884; 137885; 137918; 137931;
137940; 137971; 137981; 137989; 138021; 138059; 138104; 138116; 138139; 138141; 138165;
138168; 138189; 138210; 138234; 138239; 138304; 138337; 138374; 138444; 138455; 138477;
138496; 138507; 138533; 138550; 138579; 138589; 138592; 138601; 138672; 138706; 138737;
138745; 138752; 138775; 138837; 138861; 138865; 138917; 138929; 138936; 138974; 138978;
138991; 138999; 139009; 139009; 139051; 139062; 139113; 139138; 139189; 139199; 139217;
139226; 139250; 139268; 139278; 139331; 139354; 139365; 139376; 139462; 139490; 139540;
139558; 139573; 139593; 139641; 139656; 139660; 139680; 139689; 139705; 139708; 139764;
139766; 139818; 139835; 139837; 139872; 139883; 139957; 139962; 140000; 140057; 140100;
140103; 140131; 140171; 140197; 140210; 140252; 140289; 140301; 140304; 140328; 140334;
140337; 140354; 140422; 140455; 140515; 140635; 140655; 140716; 140732; 140759; 140761;
140792; 140806; 140811; 140830; 140852; 140921; 140966; 141106; 141123; 141169; 141171;
141192; 141209; 141230; 141298; 141314; 141316; 141361; 141366; 141453; 141522; 141562;
141589; 141623; 141627; 141675; 141677; 141684; 141723; 141763; 141765; 141768; 141818;
141845; 141854; 141931; 141959; 141966; 142067; 142076; 142087; 142090; 142120; 142122;
142134; 142139; 142259; 142326; 142385; 142395; 142397; 142442; 142499; 142532; 142551;
142556; 142586; 142647; 142689; 142733; 142788; 142851; 142927; 142944; 142984; 143039;
143054; 143115; 143169; 143208; 143209; 143227; 143287; 143306; 143310; 143322; 143443;
143454; 143519; 143523; 143654; 143661; 143748; 143756; 143759; 143846; 143887; 143910;
143919; 143962; 143966; 143995; 144029; 144042; 144675; 144740; 144747; 144762; 144777;
144786; 144791; 144793; 144797; 144802; 144816; 144834; 144852; 144855; 144861; 144867;
144870; 144878; 144880; 144881; 144885; 144893; 144894; 144902; 144905; 144915; 144916;
144924; 144926; 144930; 144932; 144951; 144956; 144977; 145001; 145132; 145284; 145503;
145513; 146081; 146123; 146577; 146605; 146726; 147414; 147630; 148021; 148379; 148421;
148743; 149013; 149373; 149737; 149742; 149910; 150221; 150314; 150466; 150466; 150623;
150702; 151251; 151261; 151418; 151662; 151896; 153006; 153025; 153340; 153411; 153473;
153743; 153779; 154015; 154093; 154138; 154214; 154289; 154312; 154323; 154465; 154477;
154482; 154608; 154616; 154654; 154707; 154749; 154789; 154795; 154999; 155064; 155072;
155128; 155201; 155287; 155434; 155575; 155583; 155716; 156023; 156045; 156211; 156270;
156386; 156473; 156551; 156874; 157856; 159118; 159166; 159455; 159608; 159725; 159935;
160126; 160485; 160488; 160573; 160616; 160628; 160656; 160664; 160723; 160730; 160793;
160838; 161195; 161456; 161484; 161583; 161950; 161992; 161993; 162161; 162208; 162211;
162365; 162722; 162775; 162778; 163174; 163528; 163579; 165818; 165818; 165857; 165878;
165921; 166004; 166195; 166199; 166236; 166934; 167032; 167076; 167280; 171936; 172440;
172440; 172721; 172765; 172783; 173228; 173309; 173674; 173878; 175103; 175123; 175140;
175528; 175727; 176606; 177621; 177737; 178463; 178468; 178779; 178818; 179232; 179256;
179276; 179283; 179334; 179336; 179403; 179426; 179500; 179534; 179804; 179890; 180195;
180244; 180298; 180520; 180803; 180864; 180885; 180902; 181831; 182661; 182977; 183120;
183194; 183200; 183337; 183462; 183476; 184038; 184175; 184240; 184365; 186132; 186918;
187147; 187266; 187616; 188036; 188232; 188388; 188390; 190468; 190491; 190732; 190887;
191497; 191508; 191516; 191569; 191572; 191599; 191603; 191648; 191664; 191882; 191978;
192481; 192694; 193067; 193106; 193122; 193139; 193182; 193200; 193381; 193383; 193394;
193481; 193533; 193546; 193586; 193617; 193690; 193713; 193724; 193742; 193790; 193811;
193892; 193913; 193913; 193923; 193937; 193938; 193987; 193990; 194005; 194006; 194031;
194061; 194131; 194136; 194155; 194161; 194182; 194182; 194214; 194282; 194297; 194307;
194342; 194351; 194364; 194384; 194395; 194399; 194401; 194468; 194587; 194600; 194656;
194670; 194704; 194804; 194872; 194906; 194921; 194949; 194965; 194972; 194985; 194986;
195037; 195051; 195052; 195091; 195117; 195127; 195132; 195138; 195139; 195200; 195232;
195314; 195340; 195346; 195358; 195365; 195381; 195387; 195429; 195458; 195487; 195513;
195524; 195546; 195553; 195555; 195668; 195712; 195720; 195753; 195772; 195784; 195820;
195821; 195852; 195853; 195875; 195903; 195911; 195947; 195974; 195995; 196005; 196038;
196047; 196109; 196115; 196125; 196148; 196185; 196189; 196214; 196222; 196282; 196303;
196345; 196348; 196350; 196387; 196433; 196444; 196501; 196522; 196539; 196612; 196636;

TABLE 5-continued

Image ID Numbers Present in the 5K microarray.

196640; 196650; 196837; 196849; 196860; 196866; 196992; 197051; 197054; 197093; 197128; 197176; 197300; 197323; 197343; 197404; 197413; 197414; 197474; 197500; 197525; 197637; 197676; 197720; 197736; 197765; 197775; 197776; 197791; 197843; 197855; 197856; 197868; 197888; 197907; 197933; 197975; 198011; 198026; 198033; 198104; 198169; 198190; 198312; 198339; 198372; 198451; 198509; 198578; 198580; 198582; 198593; 198605; 198647; 198694; 198807; 198815; 198874; 198904; 198917; 198960; 198961; 199143; 199158; 199180; 199205; 199220; 199228; 199229; 199239; 199243; 199251; 199258; 199272; 199286; 199327; 199403; 199558; 199571; 199602; 199610; 199623; 199624; 199627; 199628; 199641; 199645; 199663; 199709; 199945; 199995; 200015; 200031; 200136; 200174; 200302; 200307; 200395; 200402; 200418; 200545; 200595; 200599; 200604; 200608; 200773; 200780; 200814; 200838; 200840; 200847; 200855; 200863; 200873; 200934; 200937; 200969; 201006; 201030; 201168; 201173; 201192; 201203; 201207; 201229; 201241; 201264; 201274; 201288; 201301; 201309; 201314; 201317; 201322; 201334; 201383; 201393; 201483; 201517; 201519; 201525; 201562; 201586; 201628; 201650; 201651; 201687; 201727; 201757; 201784; 201818; 201819; 201890; 201902; 201961; 201981; 201986; 202034; 202066; 202168; 202209; 202213; 202243; 202315; 202320; 202339; 202348; 202353; 202357; 202414; 202485; 202492; 202514; 202535; 202549; 202553; 202559; 202577; 202607; 202612; 202621; 202682; 202692; 202703; 202704; 202706; 202722; 202740; 202769; 202795; 202802; 202901; 202904; 202919; 202921; 202931; 202990; 203038; 203122; 203132; 203227; 203240; 203275; 203287; 203302; 203347; 203348; 203350; 203351; 203388; 203390; 203400; 203434; 203469; 203514; 203544; 203547; 203551; 203721; 203772; 203791; 203805; 203850; 203905; 203910; 203918; 203931; 203956; 204083; 204098; 204111; 204122; 204148; 204179; 204208; 204211; 204214; 204251; 204299; 204300; 204301; 204312; 204335; 204356; 204360; 204406; 204444; 204489; 204539; 204541; 204545; 204558; 204614; 204614; 204624; 204638; 204684; 204688; 204735; 204737; 204755; 204814; 204897; 205049; 205085; 205090; 205185; 205303; 205417; 205445; 205490; 205633; 205715; 205745; 205913; 205993; 206094; 206217; 206544; 206565; 206651; 206683; 206781; 206786; 206794; 206816; 206831; 206841; 206849; 206867; 206882; 206895; 206907; 206937; 206949; 206986; 206992; 206994; 207006; 207016; 207029; 207082; 207087; 207098; 207107; 207248; 207255; 207288; 207293; 207358; 207370; 207379; 207421; 207448; 207618; 207618; 207649; 207665; 207771; 207778; 207794; 207813; 207850; 207869; 207881; 207920; 207952; 207968; 207989; 207990; 208001; 208001; 208161; 208161; 208210; 208319; 208375; 208383; 208407; 208413; 208434; 208524; 208531; 208570; 208663; 208699; 208718; 208741; 208769; 208790; 208798; 208904; 208940; 208984; 208993; 209014; 209137; 209167; 209224; 209246; 209264; 209277; 209296; 209340; 209381; 209468; 209518; 209583; 209624; 209655; 209683; 209841; 210317; 210343; 210348; 210368; 210405; 210415; 210431; 210494; 210501; 210522; 210523; 210525; 210548; 210565; 210575; 210610; 210622; 210646; 210687; 210688; 210698; 210710; 210717; 210744; 210862; 210873; 210887; 210887; 210919; 210923; 211024; 211202; 211206; 211216; 211319; 211351; 211361; 211548; 211557; 211747; 211758; 211780; 211800; 211813; 211859; 211878; 211940; 211951; 212021; 212078; 212098; 212165; 212180; 212198; 212236; 212252; 212325; 212398; 212406; 212429; 212496; 212542; 212620; 212634; 212640; 212649; 212703; 212704; 212712; 212772; 212787; 212815; 213118; 213136; 213280; 213496; 213509; 213527; 213535; 213577; 213698; 213754; 213871; 213875; 213890; 213969; 214043; 214068; 214077; 214133; 214136; 214162; 214165; 214205; 214331; 214441; 214448; 214537; 214565; 214572; 214577; 214614; 214658; 214731; 214744; 214816; 214823; 214826; 214848; 214858; 214906; 214916; 214981; 214990; 219976; 220096; 221092; 221172; 221808; 221826; 221846; 222181; 223098; 223483; 223661; 229290; 229330; 229365; 229467; 229537; 229579; 229580; 229617; 229651; 229692; 229701; 229702; 229723; 229915; 229997; 230013; 230090; 230100; 230116; 230170; 230180; 230191; 230196; 230202; 230205; 230218; 230224; 230235; 230240; 230247; 230251; 230260; 230261; 230267; 230271; 230274; 230341; 230359; 230360; 230370; 230385; 230509; 230560; 230562; 230613; 230637; 231355; 231574; 231675; 232586; 232612; 232624; 232628; 232658; 232670; 232714; 232723; 232772; 232789; 232826; 232837; 232899; 232908; 232933; 232946; 232950; 232965; 232973; 233071; 233074; 233078; 233179; 233183; 233199; 233214; 233274; 233289; 233299; 233308; 233318; 233347; 233349; 233365; 233399; 233419; 233446; 233457; 233547; 233550; 233579; 233581; 233583; 233645; 233688; 233719; 233721; 233734; 233783; 233802; 233852; 233909; 233927; 233939; 234011; 234036; 234080; 234150; 234170; 234191; 234201; 234237; 234318; 234320; 234331; 234376; 234380; 234398; 234419; 234425; 234468; 234469; 234484; 234527; 234537; 234539; 234559; 234562; 234617; 234647; 234664; 234736; 234856; 234907; 234975; 235008; 235026; 235040; 235055; 235056; 235070; 235102; 235149; 235155; 235164; 235173; 235924; 235934; 236055; 236129; 236305; 236305; 236333; 236355; 239524; 239692; 239708; 239711; 239712; 239835; 239874; 239877; 239958; 240022; 240033; 240050; 240062; 240099; 240138; 240151; 240199; 240208; 240249; 240318; 240353; 240357; 240367; 240406; 240430; 240480; 240500; 240505; 240506; 240518; 240586; 240589; 240634; 240637; 240648; 240674; 240694; 240702; 240748; 240766; 240769; 240843; 240914; 240937; 240938; 240945; 240961; 240977; 240992; 241003; 241038; 241066; 241070; 241097; 241113; 241160; 241171; 241179; 241258; 241274; 241288; 241346; 241348; 241350; 241355; 241365; 241392; 241412; 241474; 241475; 241482; 241497; 241507; 241530; 241539; 241587; 241658; 241677; 241788; 241794; 241824; 241826; 241874; 241880; 241900; 241932; 241982; 241985; 241988; 242010; 242011; 242037; 242062; 242070; 242084; 242087; 242578; 242642; 242644; 242687; 242698; 242700; 242706; 242778; 242779; 242780; 242790; 242797; 242820; 242823; 242955; 242985; 243088; 243100; 243113; 243149; 243151; 243154; 243155; 243186; 243194; 243199; 243202; 243230; 243245; 243260; 243291; 243294; 243312; 243317; 243321; 243343; 243350; 243358; 243360; 243370; 243385; 243399; 243403; 243405; 243414; 243428; 243460; 243524; 243537; 243546; 243549; 243580; 243614; 243638; 243641; 243648; 243652; 243653; 243656; 243659; 243675; 243700; 243741; 243770; 243784; 243808; 243816; 243817; 243878; 243887; 243980; 243989; 244055; 244058; 244062; 244063; 244077; 244079; 244086; 244100; 244147; 244154; 244189; 244201; 244202; 244205; 244227; 244243; 244267; 244277; 244299; 244307; 244310; 244313; 244329; 244343; 244350; 244355; 244386; 244387; 244391;

TABLE 5-continued

Image ID Numbers Present in the 5K microarray.

244618; 244637; 244646; 244652; 244654; 244684; 244686; 244703; 244722; 244764; 244767;
244781; 244784; 244801; 244806; 244815; 244846; 244847; 244879; 244911; 244955; 244974;
245000; 245015; 245062; 245099; 245136; 245147; 245195; 245198; 245217; 245219; 245235;
245242; 245247; 245273; 245296; 245299; 245319; 245330; 245330; 245386; 245388; 245401;
245409; 245413; 245422; 245426; 245442; 245444; 245457; 245479; 245484; 245485; 245489;
245517; 245531; 245534; 245549; 245556; 245570; 245585; 245586; 245624; 245742; 245745;
245764; 245765; 245769; 245774; 245806; 245853; 245860; 245881; 245885; 245894; 245899;
245920; 245936; 245964; 245970; 245986; 246035; 246041; 246073; 246074; 246079; 246116;
246117; 246119; 246120; 246143; 246144; 246194; 246246; 246276; 246292; 246300; 246304;
246377; 246449; 246478; 246522; 246524; 246537; 246541; 246543; 246546; 246549; 246598;
246619; 246620; 246652; 246661; 246680; 246684; 246686; 246703; 246705; 246722; 246749;
246765; 246766; 246786; 246789; 246792; 246808; 246824; 246869; 247081; 247082; 247117;
247125; 247159; 247194; 247216; 247233; 247281; 247367; 247466; 247482; 247546; 247587;
247614; 247616; 247635; 247655; 247660; 247710; 247783; 247803; 247816; 247818; 247833;
247859; 247863; 247901; 247925; 247967; 247986; 248009; 248020; 248039; 248071; 248092;
248095; 248112; 248143; 248256; 248261; 248288; 248306; 248371; 248454; 248478; 248481;
248485; 248504; 248531; 248535; 248545; 248594; 248599; 248601; 248624; 248649; 248688;
248698; 248856; 249688; 249705; 249856; 250519; 250667; 250673; 251019; 251135; 251250;
251461; 251516; 251685; 251875; 252185; 254321; 254625; 256260; 256664; 257011; 258589;
258589; 258790; 260200; 260303; 260325; 260619; 261204; 261494; 261519; 261587; 261828;
261971; 262231; 262920; 262932; 262996; 263040; 263097; 263200; 264117; 265060; 265494;
265680; 265874; 266361; 267431; 267634; 267634; 268412; 269806; 271985; 273435; 274529;
274578; 274638; 274932; 274979; 275173; 275176; 275180; 275612; 275634; 275738; 275802;
275871; 275871; 275950; 276091; 276286; 276449; 276547; 277015; 277274; 277305; 278501;
278808; 278808; 279329; 280122; 280236; 280386; 280666; 280750; 280752; 280837; 280882;
280882; 281114; 281125; 281465; 281467; 281843; 281904; 281978; 282051; 282310; 282378;
282501; 282587; 282980; 283023; 283301; 283398; 283715; 283897; 283954; 284341; 284592;
284620; 284734; 284882; 285226; 287300; 288658; 288896; 289143; 289288; 289337; 289502;
289551; 289615; 289666; 289818; 289923; 289978; 290039; 290054; 290124; 290230; 290308;
290422; 292171; 292201; 292207; 292212; 292213; 292217; 292219; 292222; 292230; 292232;
292236; 292244; 292270; 292272; 292292; 292306; 292308; 292312; 292314; 292332; 292357;
292362; 292364; 292388; 292388; 292391; 292392; 292416; 292424; 292452; 292463; 292471;
292475; 292482; 292496; 292501; 292512; 292515; 292519; 292522; 292528; 292542; 292553;
292559; 292567; 292568; 292612; 292613; 292624; 292628; 292633; 292654; 292679; 292690;
292719; 292726; 292731; 292749; 292770; 292806; 292812; 292833; 292834; 292882; 292908;
292920; 292933; 292938; 292939; 292964; 292966; 292996; 293005; 293045; 293078; 293104;
293128; 293157; 293177; 293178; 293191; 293222; 293257; 293306; 293325; 293328; 293331;
293336; 293356; 293358; 293366; 293380; 293403; 293417; 293421; 293431; 293436; 293437;
293457; 293471; 293500; 293503; 293510; 293539; 293557; 293564; 293569; 293576; 293579;
293599; 293606; 293632; 293637; 293664; 293675; 293676; 293683; 293696; 293715; 293727;
293736; 293755; 293763; 293785; 293820; 293835; 293845; 293847; 293858; 293859; 293901;
293916; 293921; 293932; 293940; 293940; 293977; 293990; 294014; 294018; 294040; 294127;
294133; 294150; 294167; 294221; 294255; 294259; 294304; 294310; 294311; 294444; 294445;
294457; 294483; 294485; 294487; 294496; 294512; 294647; 294682; 294740; 294873; 294881;
294892; 294916; 294942; 294951; 294968; 294973; 294995; 295044; 295106; 295137; 295140;
295206; 295229; 295255; 295283; 295303; 295321; 295324; 295376; 295386; 295389; 295410;
295483; 295492; 295497; 295501; 295514; 295527; 295545; 295577; 295583; 295590; 295594;
295599; 295600; 295604; 295630; 295710; 295723; 295729; 295741; 295781; 295798; 295831;
295866; 295873; 295889; 295916; 295923; 295939; 295973; 295974; 295982; 295985; 295992;
295997; 296010; 296030; 296041; 296072; 296094; 296102; 296132; 296136; 296140; 296141;
296149; 296155; 296162; 296168; 296170; 296177; 296180; 296181; 296184; 296188; 296189;
296190; 296198; 296199; 296330; 296334; 296375; 296393; 296444; 296454; 296472; 296476;
296483; 296498; 296508; 296529; 296549; 296552; 296559; 296562; 296568; 296587; 296597;
296602; 296616; 296623; 296640; 296679; 296683; 296702; 296741; 296749; 296752; 296754;
296757; 296773; 296793; 296795; 296797; 296805; 296838; 296857; 296880; 296883; 296901;
296998; 297050; 297061; 297063; 297084; 297086; 297102; 297107; 297110; 297136; 297148;
297155; 297178; 297212; 297305; 297392; 297403; 297405; 297411; 297421; 297437; 297439;
297442; 297919; 298118; 298155; 298833; 298963; 299085; 299093; 299154; 299388; 299442;
299600; 299630; 299663; 299679; 299737; 299815; 300103; 300237; 300474; 300482; 300590;
300632; 300866; 300972; 301018; 301061; 301082; 301122; 301380; 301504; 301678; 301752;
301849; 301976; 302031; 302190; 302292; 302310; 302369; 302549; 302591; 303035; 303048;
303196; 305227; 305336; 305606; 305606; 306013; 306380; 306412; 306484; 306771; 306806;
306813; 306901; 307231; 307255; 307532; 307553; 307843; 307882; 308041; 308163; 308231;
308281; 308415; 308437; 308478; 308588; 308633; 308682; 308689; 309032; 309039; 309045;
309092; 309161; 309316; 309583; 309685; 309776; 309864; 309894; 309993; 310034; 310105;
310356; 310493; 310519; 320606; 320630; 320763; 320834; 320903; 321189; 321189; 321247;
321354; 321386; 321455; 321529; 321580; 321605; 321661; 321706; 321708; 321723; 322051;
322561; 322617; 322617; 322723; 322759; 322786; 322794; 323404; 323506; 323506; 324210;
324255; 324342; 324745; 324815; 324861; 324901; 325062; 325070; 325102; 325160; 325365;
325365; 325370; 325375; 327094; 327150; 327304; 327350; 327506; 327676; 328591; 328802;
340558; 340630; 340644; 340712; 340722; 340734; 340745; 340840; 341137; 341246; 341269;
341310; 341317; 341328; 341336; 341706; 341805; 341821; 341942; 342069; 342378; 342543;
342593; 342640; 342721; 342994; 343072; 343167; 343320; 343352; 343443; 343646; 343646;
343661; 343737; 344133; 344141; 344251; 344282; 344352; 344672; 344757; 344820; 345047;
345055; 345090; 345128; 345208; 345342; 345348; 345423; 345430; 345559; 345586; 345670;
345751; 345839; 345858; 346117; 346134; 346299; 346484; 346545; 346552; 346995; 347036;
347224; 347373; 347434; 347615; 347687; 347687; 356665; 356707; 356800; 356992; 357031;

TABLE 5-continued

Image ID Numbers Present in the 5K microarray.

357046; 357091; 357120; 357220; 357344; 357970; 358162; 358162; 358333; 358344; 358456;
358457; 358468; 358531; 358531; 358543; 358549; 358609; 358673; 358675; 358736; 358850;
358885; 358984; 359184; 359247; 359395; 359411; 359713; 359747; 359764; 359781; 359835;
359982; 360047; 360079; 360168; 360213; 360245; 360478; 360885; 361048; 361097; 361097;
361171; 361204; 361485; 361565; 361639; 361656; 361943; 361974; 362624; 362694; 362729;
362742; 362853; 363058; 363086; 363103; 363144; 363146; 363377; 363569; 363569; 363575;
363590; 363597; 364329; 364469; 364840; 364873; 364921; 365060; 365098; 365539; 365641;
365755; 365930; 365945; 366085; 366154; 366156; 366341; 366389; 366511; 366526; 366558;
366570; 366580; 366585; 366728; 366834; 366893; 366966; 376290; 376515; 376516; 376875;
377152; 377191; 377320; 380057; 380245; 380263; 380394; 380620; 380737; 380797; 380851;
381067; 381166; 381287; 381812; 381866; 381931; 382195; 382654; 382693; 382773; 382787;
383016; 383089; 413633; 415698; 416280; 416803; 416833; 416833; 416959; 417226; 417385;
417403; 417508; 417509; 418126; 418126; 418422; 427812; 428231; 429182; 429574; 430318;
448190; 469281; 469345; 469412; 469685; 469686; 469704; 469762; 469924; 469952; 469954;
469981; 470061; 470175; 470179; 470216; 470232; 470348; 470368; 470379; 470379; 470393;
470846; 470861; 470930; 471196; 471200; 471266; 471372; 471498; 484535; 484641; 485195;
485744; 485854; 485858; 485989; 486208; 486279; 486544; 487118; 488019; 488019; 488413;
489079; 490306; 490368; 491066; 491232; 501994; 502067; 502369; 502909; 503097; 503617;
504226; 504236; 504544; 504763; 504774; 504877; 505059; 509484; 509495; 509588; 509731;
509760; 509823; 510032; 510396; 510542; 510679; 510702; 510760; 511012; 511066; 511428;
511521; 511521; 511586; 511814; 511816; 511832; 512133; 525518; 525566; 526184; 526282;
526657; 529861; 530662; 530814; 530820; 530875; 531028; 531739; 544639; 544664; 545189;
546600; 547058; 547247; 548693; 548957; 549016; 549073; 549101; 549146; 549728; 550353;
550355; 562867; 562927; 562983; 563201; 563403; 563444; 563444; 563451; 563465; 563574;
563598; 563621; 563673; 563701; 564050; 564621; 564803; 564846; 564962; 565235; 565379;
565493; 566760; 566887; 566887; 567265; 567414; 586698; 587010; 587525; 587847; 588500;
589115; 589362; 589433; 589751; 591266; 591281; 591465; 591653; 591683; 591864; 591907;
592243; 592359; 592498; 592540; 592801; 594540; 594743; 595009; 609332; 609663; 610012;
611956; 612274; 612616; 613126; 625923; 626502; 627114; 627541; 627542; 627939; 628295;
628336; 628357; 628418; 628418; 628529; 628955; 630013; 632074; 632137; 665658; 665774;
666128; 666218; 666377; 666377; 666425; 666639; 666658; 666829; 666879; 667482; 667598;
667883; 668007; 668182; 668442; 668685; 668851; 669419; 669435; 669443; 669471; 681906;
681948; 682522; 682528; 682555; 684634; 684661; 684940; 684940; 685371; 685912; 686164;
686172; 687270; 687397; 687820; 687875; 687990; 700302; 700527; 700699; 700792; 701112;
701231; 701481; 701532; 701751; 703479; 703581; 703739; 703846; 703964; 704020; 704290;
704299; 704459; 704532; 704697; 704760; 704905; 704992; 705110; 705188; 705265; 705265;
705274; 711450; 711552; 711680; 711768; 711826; 711826; 711857; 711918; 711959; 711961;
712023; 712049; 712341; 712378; 712577; 712604; 712641; 712641; 712668; 712683; 712840;
712840; 712848; 713080; 713145; 713382; 713469; 713647; 713653; 713660; 713685; 713782;
713839; 713862; 713886; 713922; 714106; 714210; 714426; 714453; 723972; 723986; 724052;
724112; 724378; 724387; 724588; 724615; 724652; 724892; 725223; 725266; 725274; 725454;
725473; 725503; 725677; 725680; 726086; 726147; 726236; 726637; 726678; 726779; 727026;
727192; 727210; 727229; 727251; 727292; 727390; 727526; 727551; 727792; 729942; 730149;
730410; 730410; 738899; 739126; 739183; 739625; 739625; 739901; 739983; 739990; 739993;
740027; 740122; 740130; 740344; 740457; 740476; 740554; 740554; 740914; 740914; 740925;
741067; 741139; 741379; 741429; 741474; 741497; 741769; 741815; 741841; 741841; 742007;
742082; 742101; 742125; 742143; 745347; 746321; 752557; 752631; 752652; 752732; 753069;
753104; 753184; 753211; 753215; 753234; 753285; 753301; 753313; 753321; 753346; 753381;
753381; 753418; 753420; 753430; 753446; 753447; 753457; 753467; 753587; 753587; 753610;
753620; 753692; 753700; 753770; 753775; 753862; 753897; 753914; 753917; 753923; 753987;
754031; 754046; 754080; 754085; 754093; 754275; 754355; 754358; 754436; 754436; 754479;
754490; 754509; 754538; 754538; 754600; 754601; 754998; 755037; 755054; 755093;
755145; 755239; 755416; 755506; 755663; 755752; 755821; 755891; 755975; 756163; 756211;
756272; 756372; 756373; 756452; 756480; 756488; 756657; 756666; 756666; 756769; 756847;
756898; 756968; 757381; 757961; 758037; 758148; 758222; 758266; 758329; 758365; 758366;
758468; 758662; 759164; 759865; 759873; 759948; 760148; 760224; 760231; 760282; 760298;
760299; 760344; 767034; 767049; 767069; 767183; 767202; 767345; 767638; 767753; 767765;
767769; 767784; 767798; 767817; 767828; 767851; 767994; 768031; 768168; 768205; 768246;
768272; 768296; 768299; 768316; 768324; 768357; 768370; 768443; 768453; 768496; 768497;
768561; 768562; 768638; 768644; 769028; 769513; 769645; 769657; 769676; 769846; 769921;
770012; 770014; 770027; 770066; 770080; 770192; 770212; 770216; 770355; 770377; 770377;
770391; 770452; 770462; 770570; 770593; 770670; 770794; 770858; 770859; 770868; 770868;
770884; 770901; 770910; 770957; 770992; 771000; 771084; 771173; 771196; 771206; 771220;
771236; 771258; 771308; 771323; 772111; 772220; 772261; 772455; 772481; 772878; 772951;
773170; 773188; 773192; 773215; 773217; 773233; 773236; 773246; 773254; 773301; 773305;
773319; 773332; 773344; 773599; 773618; 773724; 773771; 773922; 774036; 774071; 774082;
774082; 774409; 774471; 774502; 774751; 774754; 780937; 781014; 781018; 781019; 781050;
781097; 781222; 781341; 781362; 781510; 781704; 781738; 781766; 782047; 782199; 782315;
782339; 782449; 782488; 782497; 782513; 782513; 782543; 782587; 782594; 782618; 782692;
782760; 782789; 782797; 782800; 782811; 783629; 783645; 783681; 783696; 783697; 783698;
783721; 783729; 783836; 783849; 784104; 784124; 784126; 784224; 784278; 784319; 784337;
784360; 784504; 784593; 784744; 784772; 784777; 784830; 784841; 784876; 784910; 784959;
785148; 785293; 785334; 785371; 785415; 785459; 785574; 785575; 785595; 785605; 785616;
785744; 785745; 785793; 785816; 785816; 785845; 785933; 785963; 785975; 786048; 786048;
786067; 786083; 786084; 786155; 786202; 786213; 786607; 786672; 786674; 786675; 787857;
787861; 787938; 788107; 788136; 788141; 788185; 788190; 788203; 788247; 788285; 788286;
788334; 788421; 788444; 788472; 788486; 788493; 788511; 788518; 788566; 788574; 788645;

TABLE 5-continued

Image ID Numbers Present in the 5K microarray.

788647; 788654; 788695; 788721; 788745; 788832; 789011; 789012; 789014; 789049; 789049;
789069; 789069; 789091; 789147; 789152; 789182; 789204; 789232; 789253; 789318; 789357;
789369; 789376; 789382; 795173; 795178; 795241; 795288; 795296; 795330; 795498; 795543;
795738; 795771; 795805; 795827; 795830; 795840; 795847; 795888; 795936; 795965; 795989;
796000; 796137; 796147; 796181; 796198; 796198; 796253; 796258; 796268; 796341; 796398;
796542; 796646; 796680; 796757; 796904; 796984; 796994; 796996; 797016; 797059; 809353;
809394; 809454; 809464; 809464; 809494; 809523; 809530; 809535; 809541; 809557; 809578;
809588; 809598; 809598; 809627; 809639; 809648; 809696; 809776; 809779; 809784; 809838;
809892; 809901; 809916; 809938; 809939; 809944; 809981; 809992; 810010; 810017; 810019;
810039; 810040; 810053; 810057; 810063; 810092; 810117; 810124; 810131; 810156; 810213;
810242; 810282; 810316; 810321; 810325; 810331; 810358; 810372; 810391; 810408; 810420;
810444; 810445; 810452; 810485; 810504; 810506; 810512; 810521; 810551; 810552; 810600;
810612; 810617; 810625; 810632; 810671; 810703; 810724; 810725; 810729; 810734; 810743;
810761; 810787; 810791; 810802; 810813; 810854; 810859; 810873; 810891; 810899; 810934;
810942; 810974; 810986; 811012; 811029; 811044; 811088; 811096; 811108; 811108; 811162;
811600; 811740; 811771; 811792; 811827; 811842; 811843; 811870; 811890; 811899; 811900;
811911; 811920; 811930; 811942; 811999; 812042; 812048; 812083; 812105; 812126; 812126;
812144; 812155; 812167; 812196; 812227; 812246; 812251; 812266; 812266; 812276; 812965;
812968; 812975; 813149; 813158; 813166; 813171; 813179; 813184; 813254; 813256; 813266;
813279; 813280; 813387; 813402; 813410; 813410; 813419; 813426; 813444; 813459; 813460;
813462; 813520; 813533; 813536; 813552; 813591; 813614; 813630; 813635; 813648; 813651;
813673; 813675; 813678; 813707; 813711; 813712; 813714; 813742; 813751; 813757; 813818;
813823; 813827; 813828; 813830; 813841; 813854; 814014; 814054; 814095; 814101; 814117;
814119; 814119; 814214; 814246; 814260; 814270; 814270; 814306; 814319; 814357; 814378;
814381; 814409; 814460; 814465; 814478; 814508; 814526; 814526; 814546; 814576; 814595;
814615; 814636; 814640; 814696; 814701; 814731; 814765; 814776; 814792; 815235; 815239;
815245; 815285; 815287; 815294; 815501; 815503; 815507; 815526; 815529; 815530; 815534;
815539; 815542; 815555; 815564; 815774; 815781; 815816; 823562; 823590; 823590; 823598;
823614; 823663; 823679; 823691; 823696; 823715; 823756; 823775; 823779; 823794; 823819;
823851; 823851; 823859; 823864; 823871; 823876; 823886; 823900; 823901; 823928; 823930;
823940; 823943; 824024; 824031; 824041; 824044; 824044; 824068; 824070; 824074; 824117;
824340; 824352; 824382; 824393; 824426; 824511; 824527; 824531; 824547; 824568; 824591;
824602; 824704; 824753; 824895; 824906; 824922; 825013; 825060; 825080; 825085; 825214;
825224; 825265; 825271; 825293; 825295; 825296; 825323; 825335; 825369; 825399; 825433;
825442; 825451; 825470; 825470; 825478; 825577; 825583; 825585; 825677; 825842; 826077;
826135; 826137; 826138; 826166; 826173; 826204; 826211; 826217; 826254; 826350; 826405;
826459; 826622; 826668; 827013; 827120; 827132; 827144; 827156; 837870; 837905; 838359;
838373; 838389; 838568; 838676; 838716; 838802; 838856; 839094; 839101; 839516; 839552;
839594; 839623; 839682; 839682; 839736; 839890; 839991; 840158; 840158; 840325; 840333;
840364; 840384; 840404; 840404; 840486; 840493; 840511; 840517; 840524; 840567; 840600;
840606; 840620; 840636; 840654; 840658; 840683; 840687; 840691; 840702; 840768; 840776;
840788; 840818; 840821; 840865; 840878; 840882; 840889; 840894; 840940; 840942; 840944;
840978; 840990; 841008; 841044; 841059; 841093; 841149; 841203; 841261; 841263; 841278;
841282; 841292; 841308; 841331; 841332; 841334; 841340; 841352; 841357; 841370; 841384;
841470; 841478; 841498; 841501; 841507; 841617; 841620; 841641; 841664; 841669; 841679;
841689; 841691; 841691; 841695; 841698; 841703; 842784; 842785; 842802; 842806; 842818;
842820; 842836; 842846; 842849; 842860; 842863; 842894; 842906; 842928; 842939; 842980;
842980; 842989; 843016; 843028; 843049; 843067; 843069; 843070; 843076; 843094; 843110;
843121; 843133; 843134; 843139; 843140; 843159; 843174; 843248; 843249; 843287; 843312;
843319; 843321; 843352; 843426; 843426; 859359; 877613; 877644; 877651; 897497; 897531;
897544; 897563; 897567; 897570; 897594; 897596; 897619; 897626; 897632; 897636; 897642;
897646; 897652; 897655; 897667; 897669; 897670; 897673; 897690; 897751; 897770; 897774;
897781; 897788; 897806; 897814; 897822; 897835; 897840; 897880; 897901; 897901; 897906;
897910; 897952; 897956; 897963; 897971; 897982; 897983; 897987; 897997; 898032; 898035;
898062; 898073; 898092; 898095; 898096; 898108; 898109; 898122; 898123; 898138; 898148;
898198; 898218; 898219; 898221; 898237; 898242; 898253; 898258; 898262; 898265; 898281;
898286; 898305; 898312; 898317; 898328; 949914; 949928; 949932; 949934; 949938; 949940;
950092; 950096; 950356; 950367; 950369; 950430; 950445; 950445; 950482; 950489; 950574;
950578; 950607; 950680; 950682; 950689; 950690; 950710; 951117; 951233; 1035182; 1046522

TABLE 6

Image ID Numbers Present in the 7K microarray.

502055; 809578; 171936; 897646; 810632; 530139; 377252; 731257; 49464; 120881; 755416;
950574; 712341; 783697; 434833; 258606; 743804; 39313; 144924; 209014; 126401; 135450;
243638; 244310; 245489; 126219; 111634; 309515; 340974; 1493527; 362624; 131839; 740554;
214816; 855521; 971372; 195330; 44351; 232772; 134476; 123666; 826459; 214858; 85541;
266318; 878468; 788109; 307255; 341706; 127473; 139217; 195381; 203227; 296754; 200402;
293471; 243603; 809383; 322561; 292463; 725677; 839991; 428412; 796323; 399049; 289978;
550355; 347373; 843067; 700792; 232826; 365973; 490778; 24918; 786677; 121252; 121239;
126465; 135203; 193923; 234469; 247986; 232670; 22074; 782439; 782783; 1455566; 666218;
46182; 108815; 366341; 869375; 300051; 214006; 795498; 810934; 809353; 950092; 787861;
246869; 179753; 430218; 433162; 812955; 36607; 115307; 127542; 137208; 195553; 194307;

TABLE 6-continued

Image ID Numbers Present in the 7K microarray.

295723; 141171; 324861; 770887; 782503; 503841; 810617; 149737; 783696; 323474; 884655;
192569; 432194; 66686; 813166; 207794; 725274; 824068; 52096; 309591; 504791; 79592;
767475; 416833; 121355; 126453; 207098; 548693; 244391; 244806; 281843; 141768; 427692;
21652; 1472150; 713839; 727251; 79520; 877827; 549933; 285780; 240651; 769657; 46518;
525518; 759873; 625923; 137535; 756931; 266106; 767471; 66467; 127185; 127943; 136954;
242011; 292522; 292230; 141675; 343320; 321739; 39993; 280371; 249856; 246619; 703739;
66965; 810999; 811927; 436106; 141818; 365930; 360213; 841689; 897910; 824659; 45284;
345626; 415388; 813513; 293632; 121365; 126508; 199571; 199641; 234419; 245217; 292559;
35236; 1031045; 22260; 1492147; 40643; 208001; 826077; 491403; 310406; 1475659; 243181;
68977; 345586; 243741; 79624; 773724; 1031045; 773637; 278650; 609087; 813738; 246117;
120318; 127666; 136919; 295386; 207665; 295599; 211800; 358531; 269815; 40304; 430614;
147414; 194949; 712683; 809507; 256907; 42906; 436155; 50754; 48136; 127928; 825451;
815534; 415089; 344139; 82225; 767419; 139766; 121415; 241003; 139835; 194587; 195555;
244879; 132871; 149373; 323371; 22493; 1493160; 66982; 813552; 740476; 611532; 757440;
1475797; 154600; 197176; 768496; 547058; 767994; 823871; 269354; 611407; 854645; 345833;
665373; 207813; 126234; 130358; 136933; 195668; 208383; 294167; 212180; 413633; 365841;
41199; 489506; 292475; 823562; 840384; 323603; 489839; 785572; 450152; 181831; 756488;
177737; 773188; 796181; 310138; 194236; 770000; 81475; 768347; 230196; 121159; 292171;
142984; 200031; 246119; 244646; 247466; 42706; 501430; 23132; 1461664; 813841; 148021;
753620; 855749; 153505; 1476181; 156033; 210887; 769921; 84750; 80910; 711918; 109310;
430465; 120600; 625584; 66329; 244063; 127173; 142326; 137663; 295600; 208524; 297437;
247635; 417226; 502506; 41511; 857603; 771323; 214572; 814260; 269878; 486787; 28774;
448514; 811108; 810506; 810724; 825224; 773170; 324494; 289706; 203130; 23514; 138021;
108177; 121206; 151896; 138999; 292966; 213698; 296623; 248545; 160664; 343073; 25584;
859478; 813630; 770858; 427812; 884641; 770880; 1323539; 878564; 755054; 28098; 183337;
49630; 66718; 810059; 811024; 882484; 838434; 66352; 113399; 134525; 130716; 300632;
201519; 208790; 295324; 140422; 429574; 795809; 42096; 969568; 813823; 122159; 898281;
810753; 882548; 42864; 815861; 377320; 810092; 194182; 814409; 83129; 810264; 725335;
757489; 45645; 202901; 212236; 196214; 138374; 138837; 196837; 214823; 296773; 293564;
503737; 416305; 26184; 684626; 204897; 898262; 789369; 489519; 295843; 1456120; 878798;
810452; 293820; 261519; 841308; 85840; 119133; 740672; 882439; 298303; 66369; 297439;
122019; 130756; 140210; 200418; 229290; 239712; 140655; 504794; 487929; 42352; 971199;
292306; 36387; 784224; 884842; 123264; 488964; 824552; 767638; 26021; 41591; 77728; 784772;
429721; 487115; 971212; 855872; 66898; 233349; 123817; 138304; 248535; 196849; 213875;
296857; 197413; 298384; 502818; 815284; 742082; 271985; 843287; 756600; 415817; 1493383;
878681; 41658; 209137; 123926; 68225; 951233; 782578; 429349; 432042; 897865; 66390;
247710; 357970; 130791; 141106; 293128; 240050; 243460; 241113; 325155; 810083; 1409509;
359747; 307231; 840889; 502690; 428103; 1473304; 825418; 810600; 46897; 77897; 48631;
504774; 488645; 323500; 773568; 511909; 123255; 137182; 123858; 134192; 144956; 243652;
295140; 296141; 297919; 324225; 771197; 815110; 85509; 841149; 842894; 289447; 344997;
461516; 1055753; 144816; 196115; 211548; 785793; 781050; 590544; 377275; 773511; 66540;
111884; 122126; 130747; 141169; 201586; 292308; 293356; 144878; 296095; 112565; 213607;
214068; 166199; 788647; 247103; 455121; 1486082; 825606; 48614; 41356; 112629; 564803;
814526; 263836; 854668; 868332; 280740; 159166; 129177; 124730; 131877; 262920; 196636;
121727; 296170; 142927; 359933; 488707; 712460; 23831; 841703; 898092; 452374; 757873;
487297; 45636; 23772; 247281; 201628; 839516; 758365; 856354; 141852; 1031747; 270136;
66533; 121072; 123065; 134829; 140759; 206781; 240318; 144885; 825842; 795735; 810923;
725746; 221092; 124127; 297392; 858204; 854760; 123916; 825740; 172765; 293104; 827144;
841093; 814119; 878744; 757222; 255333; 324715; 151261; 123112; 244062; 132285; 244299;
201006; 300972; 296188; 130773; 809517; 299274; 815535; 809598; 843159; 85497; 769890;
855624; 471725; 1358393; 70002; 308588; 86220; 839094; 788421; 174627; 856174; 511459;
293191; 123788; 122237; 134368; 140966; 204098; 240586; 310034; 110347; 566474; 810096;
292996; 469412; 812083; 758222; 502832; 179603; 110226; 826352; 80146; 347434; 85678;
144777; 137638; 755751; 897107; 866882; 593183; 66475; 120309; 124788; 132358; 151418;
201030; 243808; 132464; 108330; 376767; 365177; 40704; 150702; 842846; 898122; 731648;
588829; 489553; 511814; 823851; 155583; 897670; 815235; 428231; 770444; 251936; 148225;
416643; 111492; 121133; 126221; 134856; 141230; 203791; 240674; 292633; 111054; 324313;
810229; 341328; 308437; 81417; 275180; 590727; 82131; 193087; 45556; 190468; 124781;
897952; 826350; 293403; 489664; 430928; 745214; 784109; 240977; 111136; 127462; 133130;
292496; 201902; 308231; 136855; 132066; 430153; 795277; 66731; 812246; 430318; 85634;
878835; 241489; 1404841; 753430; 229723; 43207; 897982; 795543; 448190; 205239; 471598;
586895; 784253; 277274; 121462; 126371; 138550; 194704; 203805; 241350; 195911; 111264;
487819; 795439; 24085; 681948; 809394; 66534; 460487; 949939; 162533; 207082; 213890;
27548; 258790; 796147; 356707; 382564; 745007; 755228; 788420; 142076; 110507; 127881;
137653; 195387; 202066; 243385; 292812; 135220; 488386; 429799; 49553; 159118; 44563;
701481; 83605; 166245; 49318; 1391682; 357031; 136744; 813714; 839552; 71101; 809694;
433567; 853809; 971382; 726791; 34302; 198647; 126650; 136301; 234380; 205490; 245484;
308163; 194155; 269354; 366848; 1412398; 810512; 34849; 897788; 360885; 145112; 287125;
183602; 813444; 823876; 137794; 51974; 897971; 143306; 244951; 239446; 49560; 796475;
66902; 161195; 128193; 132748; 211319; 202485; 309685; 299442; 230116; 810762; 324699;
32493; 30093; 36374; 840865; 773301; 33643; 825170; 450949; 768370; 160793; 139573; 824041;
786155; 488303; 431908; 383175; 271045; 233308; 121214; 126702; 135853; 206949; 205085;
245556; 139558; 80384; 291974; 811028; 1412412; 795178; 241474; 774502; 160664; 754406;
796287; 220851; 770452; 345858; 194214; 713469; 824393; 470061; 344243; 781047; 252663;
785707; 293177; 111006; 194136; 140337; 194972; 202348; 293005; 246546; 485195; 810741;
268152; 246748; 127841; 28475; 628336; 307138; 855586; 266312; 451098; 724588; 741067;
243580; 813266; 75254; 811168; 744917; 264646; 796759; 767236; 197676; 120297; 214744;

TABLE 6-continued

Image ID Numbers Present in the 7K microarray.

139051; 242010; 292628; 245765; 130892; 172440; 376802; 26922; 1412503; 770014; 668851;
772455; 853368; 755402; 85514; 221828; 299388; 130153; 365060; 949928; 897626; 66714;
263229; 198982; 869538; 767312; 232658; 234398; 128460; 193381; 195127; 210494; 292690;
232628; 586698; 249949; 42993; 430297; 756452; 240518; 260200; 302286; 469306; 25988;
450777; 754085; 293325; 130820; 613126; 78217; 809456; 161998; 855684; 796134; 244847;
247216; 126883; 137981; 195720; 232965; 245936; 135910; 180902; 66437; 27624; 1416782;
768296; 194384; 609663; 345553; 68049; 1325605; 362278; 725473; 119384; 234237; 504877;
897901; 810272; 415086; 51064; 869187; 768464; 248624; 233347; 128973; 470232; 195117;
210501; 293500; 130777; 755093; 811097; 43129; 884743; 160723; 202682; 685371; 301735;
878406; 503717; 451907; 305336; 261828; 340558; 842820; 783629; 344091; 447365; 1031552;
67759; 110893; 130276; 301752; 138507; 193200; 235026; 245986; 296041; 187616; 66373;
28309; 1473289; 47142; 132373; 382195; 884766; 435953; 1455976; 395708; 809776; 753069;
812251; 713782; 810942; 298231; 121551; 773381; 755581; 681917; 127970; 203469; 130826;
154312; 212815; 210525; 293664; 132549; 782594; 502496; 43338; 773367; 179500; 809639;
704290; 324437; 724932; 488956; 452780; 341942; 726637; 810986; 726236; 788107; 782853;
781139; 41345; 129516; 121501; 128617; 138579; 245413; 244784; 246537; 296162; 196282;
323623; 28985; 1474337; 140806; 153473; 758037; 280735; 68950; 811088; 110467; 204539;
781510; 784744; 417855; 739511; 1056200; 611075; 66582; 144902; 206544; 130857; 138141;
206849; 210343; 293675; 274578; 136780; 795442; 43550; 755474; 469345; 809901; 71672;
488276; 193736; 247483; 453107; 240367; 567265; 50506; 810703; 70489; 809526; 491565;
739109; 70245; 295376; 110094; 121803; 322786; 138672; 197093; 293990; 296199; 796198;
219976; 504300; 30272; 592592; 128143; 682528; 487118; 80186; 436062; 1472336; 757500;
771236; 549073; 125092; 897563; 842939; 795730; 490763; 882488; 302632; 66596; 128204;
296883; 130972; 138189; 359411; 210565; 120701; 753381; 155072; 809596; 43622; 267420;
810325; 810358; 843140; 782193; 740801; 82297; 897720; 234736; 240062; 144834; 786084;
826173; 320509; 262251; 67769; 280837; 110198; 123805; 128690; 138752; 197776; 214848;
296334; 121420; 259587; 810992; 31143; 263716; 754600; 842802; 897690; 525926; 868652;
1472698; 1472753; 146123; 754538; 810444; 789204; 785744; 810502; 343871; 773137; 838149;
66608; 247660; 122354; 130572; 140252; 201173; 234170; 132789; 293510; 327221; 343343;
44255; 322079; 823696; 298155; 725503; 745343; 797048; 432050; 897978; 725680; 131653;
323506; 52629; 760224; 770614; 510002; 306444; 842861; 292232; 125828; 124132; 207649;
139189; 197736; 230180; 295501; 172721; 810395; 470144; 183556; 72869; 758266; 236305;
868484; 756556; 1456937; 1474684; 362853; 727210; 701112; 713886; 594743; 490556; 756596;
1142132; 840766; 66630; 210923; 122359; 130582; 471372; 207016; 241475; 193937; 143756;
341588; 279399; 346009; 811044; 51448; 815555; 971276; 25517; 395711; 279378; 124138;
770192; 245920; 79022; 66564; 488157; 969854; 505491; 842918; 211813; 128503; 124143;
294483; 288658; 292568; 243405; 295206; 244055; 365665; 809488; 878652; 129506; 796000;
782811; 769716; 878280; 1048985; 34184; 841357; 782800; 825433; 146577; 756709; 252515;
129387; 843098; 66910; 111549; 122684; 130977; 138337; 201334; 241587; 230274; 120306;
366009; 291623; 379920; 811162; 628357; 784777; 461804; 756533; 769552; 756708; 471200;
123730; 134748; 739126; 40017; 471859; 49963; 135085; 810801; 234036; 110578; 123932;
132848; 293755; 198026; 243887; 295321; 123229; 810664; 810389; 741880; 327350; 148421;
796984; 83444; 491692; 1309620; 1032405; 345348; 813675; 784124; 788745; 632137; 257523;
770394; 362910; 299559; 66903; 295985; 122796; 135058; 137760; 206882; 240992; 366526;
128795; 280286; 66965; 448619; 809464; 127821; 244147; 431296; 869466; 263894; 814080;
26314; 299679; 80549; 815285; 898258; 435551; 23012; 625683; 66977; 200863; 233688; 132524;
470348; 194297; 485858; 297411; 811890; 810510; 491157; 502518; 296587; 71727; 795830;
756502; 896962; 1343468; 700721; 119530; 754355; 81599; 73381; 207358; 291448; 77539;
51826; 610097; 546600; 111714; 122397; 135777; 137862; 204638; 241258; 345342; 130610;
795499; 810989; 366893; 767851; 43826; 307532; 284001; 484874; 280252; 265102; 178463;
123980; 81518; 814465; 121776; 857661; 50519; 345957; 839888; 274529; 110912; 124126;
132623; 160616; 197500; 296180; 129600; 129514; 488359; 795529; 810802; 124824; 504763;
774754; 462953; 70332; 1343971; 144867; 811920; 135692; 843248; 47908; 429466; 155768;
740604; 855890; 753794; 209624; 111722; 126581; 136117; 137885; 204814; 241070; 296030;
149742; 810038; 282907; 823864; 236355; 773215; 51640; 781233; 235135; 271744; 151662;
246304; 37491; 788472; 712848; 130100; 290091; 562811; 745503; 505225; 208798; 140171;
127729; 133197; 162161; 295527; 197843; 244637; 213754; 810864; 505062; 204299; 753215;
839623; 795840; 433553; 823982; 1375309; 210687; 45542; 198917; 785933; 841679; 491121;
884438; 1031799; 450307; 627039; 294133; 111755; 126544; 135922; 194656; 204444; 241932;
128457; 208699; 323474; 795803; 240766; 665774; 703581; 548693; 260035; 269381; 257135;
345430; 246522; 752732; 810859; 740914; 299630; 854696; 725721; 530185; 812967; 309092;
203918; 128118; 133303; 209583; 202243; 243878; 109049; 130120; 195813; 343562; 853570;
126470; 361639; 48886; 713145; 279790; 67221; 868838; 143443; 360168; 309316; 815774;
628418; 782824; 293925; 784257; 192271; 295410; 248288; 125608; 136730; 193533; 204312;
247159; 297063; 233579; 109310; 66676; 1486260; 810873; 35828; 837870; 504452; 415145;
366945; 132144; 240634; 292933; 754046; 842836; 77533; 309092; 358643; 268188; 815303;
811848; 121521; 120153; 128954; 134120; 210622; 202612; 296181; 299093; 120516; 357626;
505289; 843398; 132911; 143523; 840942; 193913; 365515; 309288; 454333; 742143; 145001;
153411; 75415; 563574; 344039; 742798; 590615; 361239; 204545; 214165; 297442; 136632;
233289; 207248; 247859; 136560; 232714; 259462; 132248; 127709; 115143; 204541; 826211;
291255; 281145; 72663; 810959; 768316; 130280; 154749; 85202; 74566; 233547; 277906;
268736; 51950; 43733; 66552; 120631; 129442; 233547; 195513; 202769; 296752; 142134;
175528; 429555; 504783; 665674; 811012; 244387; 80109; 427750; 868380; 461327; 49591;
46356; 66317; 786083; 626502; 488435; 377692; 857652; 79782; 236129; 206565; 125822;
140057; 295866; 207293; 248092; 112371; 258589; 809490; 31210; 248631; 123579; 179890;
789253; 840708; 756490; 33294; 267725; 44255; 753587; 813158; 784126; 840606; 563621;
121406; 769901; 884822; 53039; 38465; 120162; 129407; 197054; 195524; 293178; 296901;

TABLE 6-continued

Image ID Numbers Present in the 7K microarray.

139278; 202921; 491559; 44537; 754649; 71622; 245853; 789069; 795309; 68557; 505881;
471742; 45544; 44505; 669443; 824527; 796253; 284701; 78353; 852829; 246430; 247803;
295492; 126988; 141298; 193713; 230560; 246824; 115414; 267431; 249895; 32898; 392622;
813279; 246765; 361974; 295093; 343867; 1472743; 259579; 223483; 188036; 770216; 810729;
591281; 306921; 306575; 755612; 82903; 786673; 115155; 120533; 129567; 154789; 195232;
229702; 297136; 294127; 234664; 344648; 45941; 812033; 340644; 124605; 82734; 308746;
845419; 857681; 486076; 180864; 293859; 898218; 75009; 782385; 854284; 69184; 742576;
124891; 121687; 129840; 141366; 193790; 233734; 248688; 344352; 268412; 284479; 33632;
280507; 36493; 242062; 841352; 856796; 279970; 1492104; 289677; 809784; 52933; 471266;
52079; 773192; 782688; 588598; 450386; 1032004; 767277; 109108; 120823; 131316; 140852;
195820; 211361; 294485; 203302; 295873; 811150; 47110; 796388; 343072; 283023; 825060;
324383; 884867; 248295; 487761; 361171; 23173; 203721; 774036; 212165; 502333; 51817;
295857; 627273; 109279; 121543; 358543; 139656; 198578; 240406; 248601; 358673; 273435;
795151; 34357; 1342650; 365755; 769513; 41650; 364510; 432651; 1492304; 306358; 484641;
33049; 612274; 784830; 814460; 267390; 33096; 179163; 769942; 66944; 128150; 120173;
131388; 202514; 206937; 292424; 294942; 204208; 233927; 810411; 47833; 450745; 811740;
127974; 666425; 377731; 298268; 858293; 489535; 346552; 292388; 753467; 684661; 687875;
257422; 433481; 151449; 845363; 136223; 108730; 121898; 296177; 139689; 198582; 233719;
130916; 134422; 278501; 782306; 34396; 307873; 738899; 666879; 504544; 139840; 264640;
1326920; 814961; 682522; 24642; 841334; 758662; 62277; 283751; 586685; 148968; 366132;
67016; 109277; 122443; 131370; 160628; 200855; 229915; 356800; 241179; 136814; 503335;
50117; 453641; 811096; 222181; 51666; 297731; 724831; 293924; 855391; 28469; 138917;
214990; 784910; 838568; 223274; 241481; 30175; 629896; 292528; 294973; 293380; 144791;
139705; 198169; 294150; 122963; 563701; 260707; 795677; 35483; 42070; 154707; 950489;
781341; 53092; 322148; 1461138; 825411; 293696; 548957; 726086; 841617; 841282; 377166;
525799; 297895; 950709; 67006; 109309; 240199; 131050; 138455; 233852; 230013; 275950;
211859; 782161; 795647; 50666; 486110; 813179; 23804; 842849; 138788; 360778; 741988;
277537; 547247; 809494; 813757; 293940; 51814; 430471; 502161; 724893; 950568; 246598;
126882; 124241; 341805; 188390; 199205; 230090; 123448; 130835; 366238; 811035; 782406;
809557; 784337; 786213; 586839; 854338; 1468310; 502141; 198372; 46284; 724652; 825085;
502369; 428338; 51320; 212115; 758343; 67009; 239692; 123405; 132159; 141453; 200840;
242084; 292624; 235149; 782462; 144801; 487704; 180803; 289923; 838373; 725285; 183440;
288796; 704690; 207920; 754479; 143519; 772261; 505059; 460114; 745138; 203003; 780977;
132527; 110703; 127354; 198190; 162722; 199229; 123755; 128290; 125685; 290893; 809397;
838366; 308041; 359781; 840600; 759163; 223350; 1393018; 685801; 770080; 813184; 80915;
321386; 859359; 154720; 773617; 869233; 795254; 67069; 111844; 122906; 132019; 141765;
200937; 230251; 251516; 144870; 220077; 503083; 506369; 156473; 788141; 753862; 415828;
432210; 290378; 713129; 767049; 165878; 809939; 741841; 310519; 856135; 857640; 882483;
796946; 203350; 110741; 124530; 134520; 209167; 199220; 293858; 132111; 133972; 415948;
795256; 129988; 296757; 785574; 785975; 45600; 809720; 244146; 704254; 768562; 810974;
840691; 687397; 589751; 145383; 726658; 1049330; 244194; 154999; 129293; 214577; 135901;
142385; 201393; 242780; 486279; 194872; 179419; 771133; 878578; 124597; 841203; 278501;
454822; 121454; 1405689; 825287; 210405; 47475; 949914; 814478; 271899; 773478; 884355;
842973; 66474; 110996; 124277; 325375; 309039; 210710; 280386; 139818; 134712; 325150;
770838; 71626; 248261; 74119; 897531; 784589; 856650; 896949; 713047; 261204; 35077;
843076; 711959; 214162; 435434; 133637; 283436; 531862; 201981; 246143; 123222; 136286;
142532; 294018; 242797; 200302; 160573; 259169; 809552; 126858; 49665; 49164; 324861;
780947; 897485; 379771; 284799; 33949; 243358; 786067; 897814; 42258; 358433; 757404;
768292; 594322; 138592; 110791; 124014; 143208; 191508; 202553; 243641; 126229; 139680;
265350; 505199; 137531; 811792; 898242; 704459; 770454; 814353; 1393834; 771220; 155716;
813707; 310105; 814378; 782462; 788256; 417424; 884539; 265645; 121577; 109811; 125548;
136571; 155128; 248481; 243088; 360885; 205417; 811126; 810133; 128875; 26418; 843134;
809603; 781506; 431397; 741497; 130884; 839594; 380737; 321723; 877782; 586725; 841179;
509943; 293078; 112525; 128301; 134753; 191569; 202704; 243656; 206986; 141684; 415700;
810483; 240099; 713922; 898219; 490368; 447509; 85643; 1161775; 592243; 810063; 293916;
51746; 788190; 417251; 878413; 287749; 470261; 73609; 138059; 129563; 129721; 234150;
193586; 204251; 243154; 133236; 233074; 67002; 809719; 320763; 22411; 363569; 251351;
155717; 786194; 417783; 41565; 301504; 21738; 897567; 416833; 66711; 590640; 744047;
487373; 788196; 53099; 111510; 200608; 133964; 195995; 202802; 243659; 203547; 243546;
126284; 283375; 681997; 713685; 35185; 839594; 950710; 725321; 431803; 120108; 214133;
363597; 108667; 897956; 814508; 344825; 344134; 770579; 454908; 143227; 242070; 127199;
137096; 197343; 208319; 292244; 124578; 296797; 269930; 359539; 378565; 82871; 741769;
773771; 272183; 162491; 884480; 1240116; 233583; 756373; 363144; 80708; 381067; 108330;
270626; 202897; 773479; 796513; 247818; 120681; 130054; 134394; 244781; 203390; 294951;
206992; 295916; 121731; 504575; 1411726; 31072; 771196; 774471; 773305; 781017; 730124;
489631; 810521; 301122; 45272; 781362; 795936; 810762; 472095; 366105; 868400; 120561;
121977; 143759; 136856; 207990; 213118; 292364; 125739; 279329; 263846; 809513; 1389018;
186132; 755506; 843174; 323577; 795526; 627306; 344272; 120106; 470179; 809992; 897570;
825577; 840683; 855864; 344432; 731308; 786078; 112577; 120695; 129332; 121546; 243360;
203434; 295106; 202549; 135791; 359119; 418299; 1475595; 812048; 243202; 592540; 884790;
796197; 295551; 502582; 280752; 307553; 179283; 785415; 704299; 491559; 221076; 857319;
25922; 139138; 121558; 127766; 140000; 241171; 211351; 292654; 839682; 285226; 810403;
36950; 1358229; 753184; 810625; 383089; 460398; 745116; 813654; 345787; 346117; 50413;
184365; 841620; 811870; 273435; 772425; 739090; 897823; 1046484; 283897; 126355; 299737;
193139; 196350; 212398; 296094; 233550; 138444; 244044; 51293; 1323328; 143287; 122091;
714453; 755373; 742115; 611027; 506032; 230261; 128783; 234011; 782797; 785459; 309515;
429448; 341978; 841070; 123408; 127625; 230224; 139883; 194965; 235040; 292964; 233071;

TABLE 6-continued

Image ID Numbers Present in the 7K microarray.

293715; 810861; 37366; 1292073; 754509; 201650; 842784; 282956; 502622; 1466844; 378955;
126413; 204755; 302591; 796757; 788334; 491418; 882515; 178792; 52076; 785847; 109271;
294881; 293683; 154138; 293431; 212252; 297050; 232789; 159725; 290753; 51740; 1323157;
240151; 51865; 488019; 486623; 343987; 767495; 506658; 250667; 159455; 589433; 825323;
530814; 855843; 450854; 856585; 80338; 108836; 121736; 296155; 139365; 195037; 239874;
293257; 774082; 305606; 810059; 37904; 1344137; 200814; 753346; 788654; 878836; 40773;
1412245; 379309; 753917; 183462; 241880; 712023; 813520; 487773; 725533; 34102; 509800;
42123; 122889; 120863; 131668; 198451; 290054; 295497; 296568; 214981; 131239; 810878;
1456160; 740925; 549728; 813830; 503338; 123971; 823574; 1292432; 324210; 752557; 811999;
842806; 753700; 296032; 461759; 840474; 837904; 108425; 121770; 130116; 246292; 199272;
240637; 293331; 115337; 309864; 282404; 39093; 1160732; 470393; 70827; 840990; 250654;
415102; 1412344; 379708; 754093; 40946; 491066; 824117; 898253; 489805; 502682; 22883;
884272; 66443; 121270; 120973; 131446; 366966; 200545; 245764; 296597; 233419; 154323;
809850; 878689; 292219; 545189; 83231; 1020315; 714213; 35318; 1033708; 813419; 142395;
138936; 843139; 843049; 855786; 487988; 270505; 950507; 246703; 108763; 139113; 364873;
139268; 197868; 295992; 208904; 470846; 322617; 32444; 39173; 324901; 196612; 195903;
700527; 377441; 377461; 1412502; 713236; 221808; 66946; 79502; 788832; 609332; 782725;
433573; 796689; 770675; 31251; 109488; 244686; 136772; 140328; 241658; 244077; 129569;
245534; 232826; 418394; 1161155; 810331; 77133; 782760; 769600; 786680; 1469234; 810550;
280666; 292272; 33826; 814214; 795827; 153355; 80633; 471664; 276237; 203544; 275802;
124071; 130294; 140103; 213969; 241507; 244343; 129071; 366933; 327250; 39796; 755145;
178468; 610012; 51702; 853151; 845355; 1434948; 746232; 50614; 727792; 784593; 842863;
42076; 346947; 770424; 755526; 843234; 154654; 243770; 128297; 143322; 142689; 201229;
244267; 233802; 245774; 782203; 504516; 1384851; 665658; 815526; 795296; 586803; 853687;
1470333; 815575; 289666; 770910; 809916; 827013; 840486; 884425; 502486; 51406; 897575;
233183; 246116; 123646; 292939; 191648; 245299; 230509; 292471; 130421; 306216; 266531;
34778; 82879; 711961; 72395; 377314; 1435003; 814086; 31873; 361048; 773599; 824426;
782339; 809453; 140574; 249603; 60605; 173878; 120097; 122875; 136317; 241482; 201314;
243230; 233274; 247616; 203474; 795572; 1460110; 756666; 897642; 950690; 454475; 82195;
434768; 511850; 187147; 144932; 810039; 814306; 730410; 971399; 857874; 203732; 610113;
324255; 240353; 245549; 131764; 242700; 199623; 244243; 201651; 247081; 758332; 770866;
812965; 276449; 897667; 81289; 853906; 745402; 625011; 814240; 33327; 202535; 785148;
950578; 38763; 853988; 135630; 293792; 277339; 196038; 229701; 122946; 233318; 157856;
202353; 245401; 275173; 241794; 809489; 782719; 1474174; 23776; 714106; 839736; 502499;
491727; 1390584; 774446; 47647; 248371; 179403; 897594; 242578; 809946; 769571; 731273;
509570; 201483; 297107; 240357; 135273; 470368; 199624; 284341; 202414; 126225; 271378;
809685; 810420; 768246; 773246; 258589; 345232; 80221; 969914; 814410; 753285; 33941;
840940; 897806; 838359; 298417; 755385; 773290; 897641; 242706; 112494; 122955; 234617;
160730; 246792; 243312; 200307; 243414; 771023; 33616; 1486109; 196992; 841292; 281476;
897177; 814798; 450574; 37553; 812196; 246524; 488413; 897636; 897880; 460673; 854581;
588822; 951022; 111721; 113281; 124795; 234376; 243294; 297084; 244722; 243428; 136180;
272063; 810519; 78294; 741474; 32684; 267634; 868169; 286378; 1155071; 814773; 193067;
811899; 712049; 119882; 289496; 235938; 725176; 782275; 29063; 112541; 123441; 142090;
144905; 296132; 230260; 122787; 113300; 810609; 504207; 813614; 125722; 898138; 243603;
361840; 595175; 452588; 768644; 810612; 770462; 71434; 809648; 194600; 250069; 295412;
769911; 593251; 297102; 127272; 124909; 135654; 295229; 203038; 245062; 246686; 142067;
126277; 503214; 753923; 127509; 840493; 785845; 855910; 108377; 1408710; 292613; 194364;
49860; 796268; 627939; 249687; 287687; 432581; 364934; 774420; 120413; 245742; 127096;
137016; 143995; 207968; 234320; 301082; 143661; 308497; 810402; 205633; 510679; 85979;
415700; 289857; 838611; 454896; 811900; 823940; 470930; 898221; 785334; 310034; 146868;
214985; 80659; 271670; 201264; 243614; 130044; 135676; 208570; 203122; 243700; 295389;
144880; 415406; 322695; 134544; 681906; 814095; 109179; 471642; 490947; 810806; 39798;
823663; 295729; 510396; 840517; 771089; 755578; 433307; 490805; 727147; 138929; 123724;
127147; 143654; 242687; 198807; 362694; 121798; 240208; 297043; 66576; 49970; 753447;
898123; 357626; 252259; 626206; 1390860; 42558; 343443; 341246; 843094; 814640; 301082;
238821; 742767; 148469; 785886; 135561; 244618; 130004; 135094; 195852; 244086; 246766;
197855; 135688; 366971; 306726; 503724; 51981; 363103; 192694; 284882; 122394; 772304;
757165; 212021; 361565; 281978; 824531; 897632; 240961; 280970; 854576; 288695; 811813;
132569; 121475; 126459; 135454; 197300; 203956; 247967; 485854; 201517; 771272; 770785;
1325751; 209655; 197525; 509484; 788285; 429557; 628602; 195751; 34773; 122915; 40056;
897646; 788286; 300474; 755299; 293950; 469369; 665356; 246041; 245000; 127514; 132708;
195772; 194061; 294014; 223661; 229580; 344825; 293094; 504682; 365945; 196189; 796646;
714426; 487071; 363055; 399456; 51328; 325062; 42118; 366728; 781019; 768344; 365973;
897271; 49351; 53384; 295982; 294892; 126450; 135426; 295973; 204558; 248009; 309583;
110503; 321163; 795832; 1471829; 212429; 810899; 704905; 566760; 502355; 757375; 239611;
770027; 755975; 212078; 80399; 772951; 209224; 153694; 131988; 345063; 813611; 142944;
207869; 293736; 234425; 195546; 109123; 296010; 299815; 342069; 195723; 320712; 23353;
549101; 195712; 789357; 263846; 743077; 81604; 435219; 25499; 509588; 377152; 898109;
782692; 810104; 855390; 365326; 624634; 768406; 296483; 121341; 126497; 358549; 242778;
204624; 244815; 244277; 33051; 206632; 22012; 1472689; 756272; 771258; 824024; 852520;
840460; 223176; 202958; 509495; 249705; 138116; 700302; 843319; 261494; 296123; 269292;
266146; 34837; 66711; 293336; 127983; 340745; 195784; 292357; 292332; 814270; 343646;
487087; 40026; 283034; 223098; 85561; 784278; 782835; 263014; 36491; 399532; 241530;
241985; 78869; 838676; 773220; 471641; 739155; 52996; 813168; 209277; 121412; 126509;
139764; 194600; 358984; 245219; 212620; 38763; 323577; 22293; 1492412; 121218; 125134;
80374; 298062; 289606; 1475746; 247241; 142556; 24032; 810791; 416959; 814765; 323371;
487429; 844725; 726768; 111516; 295583; 127710; 137349; 196047; 208375; 292501; 247783;

TABLE 6-continued

Image ID Numbers Present in the 7K microarray.

380620; 262053; 40360; 435597; 591864; 810321; 33045; 415084; 41195; 785930; 447167; 23282;
723972; 813591; 842818; 814731; 272327; 744052; 530545; 50491; 754582; 127769; 207379;
156023; 139490; 245517; 229997; 244350; 246194; 42076; 429323; 23019; 1493175; 810017;
66322; 773332; 740620; 491763; 1476065; 179617; 810331; 229579; 199663; 138139; 842928;
810558; 811046; 47665; 627251; 796448; 234318; 124853; 135766; 137647; 293637; 208407;
293222; 139376; 416280; 782841; 41452; 878815; 687270; 126795; 773236; 502977; 878838;
768377; 448386; 183194; 26910; 742101; 796680; 49260; 272690; 436135; 588559; 80162;
785760; 125666; 121184; 179426; 138978; 294444; 213509; 245457; 248698; 48283; 280527;
24145; 1467195; 244307; 243816; 79712; 868212; 759200; 1323448; 161172; 345559; 767798;
73782; 713660; 877613; 284479; 436029; 268946; 151595; 66333; 113394; 246074; 130656;
137506; 200773; 293847; 293358; 138865; 428231; 810868; 42059; 844816; 289615; 249688;
376875; 258120; 730002; 786537; 449058; 51543; 50680; 511066; 81394; 796341; 323989;
243159; 49311; 47037; 290308; 108197; 125769; 127486; 139062; 248020; 213535; 296741;
292770; 77577; 490755; 25725; 1468820; 809981; 241365; 703964; 293032; 128493; 1456424;
878545; 47681; 309032; 768357; 47510; 843121; 811150; 50888; 85313; 416316; 66341; 113431;
121994; 130677; 293599; 200395; 208663; 233214; 141192; 448190; 809645; 42214; 970271;
770012; 771308; 789012; 782545; 325182; 501939; 725340; 188232; 360047; 470175; 815539;
703479; 346360; 503579; 153541; 796806; 66420; 193122; 123506; 196860; 138974; 245235;
214136; 296838; 293835; 782718; 811066; 26366; 1032431; 51916; 208161; 214441; 454083;
128753; 1435300; 878676; 141562; 563598; 265874; 490306; 951117; 503083; 49548; 435561;
131626; 66377; 113538; 240937; 130758; 140792; 245386; 233783; 230341; 138234; 299197;
279407; 42576; 1408407; 153025; 813711; 80410; 970590; 431655; 490244; 824728; 45138;
243321; 770868; 814014; 795173; 505538; 853938; 530282; 122150; 108471; 211024; 321580;
563621; 196222; 232624; 296136; 294740; 1030929; 810852; 83011; 550353; 24415; 712840;
230882; 46166; 1493390; 896921; 242037; 823614; 770212; 774071; 797059; 282907; 884783;
595604; 66555; 290230; 296444; 130801; 141123; 201525; 280750; 244386; 143910; 127860;
795798; 120468; 126390; 247117; 80500; 624627; 789314; 1474149; 825604; 288896; 48182;
755037; 781018; 789318; 358752; 450661; 1031076; 324122; 261587; 245745; 123578; 292236;
143887; 296508; 260619; 296168; 840404; 321271; 309803; 686081; 245422; 486208; 949940;
39920; 130242; 462113; 50887; 380797; 45231; 262231; 40299; 83363; 742064; 161373; 502753;
838744; 66550; 128561; 122170; 130824; 140732; 243194; 469981; 297405; 244202; 504979;
364555; 399318; 126368; 813280; 789147; 360854; 949971; 1474955; 825726; 810743; 26578;
33690; 898317; 841698; 361899; 470279; 248463; 855620; 740554; 109523; 198874; 137918;
154477; 159935; 282980; 296184; 143169; 810154; 310894; 713193; 293859; 81427; 418422;
51373; 455128; 487348; 49389; 810551; 300482; 274638; 40562; 233581; 214982; 455115;
435036; 278101; 66562; 198605; 123067; 134229; 140811; 206831; 240843; 126393; 129541;
771215; 795382; 769542; 260325; 128243; 115281; 755689; 789383; 110168; 826256; 292212;
124753; 773254; 704532; 796542; 590692; 230971; 251591; 951142; 67037; 121880; 244058;
133331; 322759; 296498; 309045; 296189; 344133; 809995; 356835; 826984; 289337; 526657;
83210; 884301; 854879; 1404396; 1470060; 302549; 813827; 758366; 840404; 239877; 856489;
432072; 725501; 950473; 383016; 110436; 294255; 134439; 140921; 203910; 240648; 292222;
112896; 771255; 810843; 190491; 133213; 243100; 66560; 487777; 594120; 211275; 788269;
203240; 27787; 897619; 814117; 165921; 502669; 280356; 743041; 626531; 132215; 111101;
124808; 138737; 197975; 296149; 292270; 132690; 131887; 810575; 771233; 149013; 897497;
795330; 85624; 845415; 346604; 1350468; 51408; 813460; 361097; 814696; 789232; 429574;
214884; 470122; 200018; 626716; 195051; 111200; 126237; 143919; 140304; 211557; 292834;
230360; 109483; 271357; 282320; 723986; 669419; 841384; 208413; 361323; 564492; 248583;
510032; 134269; 244703; 814246; 785745; 812144; 491486; 857002; 26568; 593023; 66406;
111413; 142087; 133158; 274979; 247194; 366085; 128260; 121251; 809422; 277003; 283954;
212649; 322051; 85128; 755750; 562813; 1367900; 810445; 40887; 209841; 843249; 839890;
755093; 755301; 376785; 852913; 108801; 111705; 128322; 135212; 194395; 203850; 241355;
130334; 126438; 357681; 191743; 530875; 146605; 827132; 280882; 1035889; 233479; 395440;
770670; 298963; 234562; 79629; 841332; 283715; 346696; 856434; 769579; 26884; 51450;
245885; 132835; 132323; 195358; 207778; 295997; 248143; 769846; 191826; 502405; 588911;
770391; 195340; 815542; 841059; 49987; 897950; 1376827; 668007; 44975; 127193; 898265;
429182; 344274; 1031203; 745433; 460106; 768329; 142139; 111825; 126670; 136382; 293328;
234647; 245479; 357120; 156874; 502421; 811095; 1412238; 205185; 49509; 51041; 137158;
469969; 745496; 190666; 162775; 823598; 49518; 842989; 796996; 246722; 769948; 278242;
486113; 38642; 154616; 130243; 128346; 134482; 194921; 202315; 293436; 126341; 194031;
323117; 811607; 148231; 245296; 220096; 824070; 950096; 362409; 384078; 450983; 136821;
358457; 811842; 39593; 949932; 810395; 491544; 769712; 845663; 726846; 50214; 137793;
126722; 136909; 294647; 204489; 245570; 325365; 163579; 810558; 810846; 1412481; 246300;
756163; 759164; 269806; 377671; 626358; 172751; 308281; 292806; 823930; 704760; 824922;
838856; 882506; 324891; 856535; 785967; 83210; 293569; 128737; 154214; 195052; 202357;
293045; 121997; 491232; 795604; 795750; 309970; 340630; 42373; 68103; 811585; 586888;
52741; 450711; 376290; 160838; 262996; 825013; 713080; 127860; 139681; 731339; 51083;
306806; 121220; 126884; 137931; 297061; 207370; 245894; 212406; 175727; 1048810; 27549;
1412504; 812276; 753301; 950445; 754034; 22895; 586990; 360392; 809627; 756769; 469686;
814701; 843070; 194161; 472186; 303109; 811000; 842968; 40751; 121877; 142647; 154289;
195091; 210431; 292908; 125308; 730410; 343744; 43021; 488873; 813742; 247816; 740457;
327635; 288663; 25807; 451855; 813459; 296529; 203351; 824602; 739993; 321734; 178825;
264895; 84713; 108265; 123439; 126887; 137989; 193481; 232723; 245964; 109200; 1035182;
66491; 27848; 1435862; 810372; 768168; 897669; 1030769; 296448; 1325816; 141221; 627114;
221846; 511428; 289818; 826135; 504207; 261580; 243882; 838612; 813499; 200969; 841691;
128993; 138104; 195139; 210523; 293503; 292542; 770593; 256515; 43231; 725076; 32609;
246246; 840687; 281003; 842825; 489485; 453005; 35105; 356665; 202904; 814546; 789011;
809621; 470128; 199833; 108316; 121500; 138589; 143454; 193546; 235102; 246144; 297178;

TABLE 6-continued

Image ID Numbers Present in the 7K microarray.

193913; 66950; 28410; 1435029; 133273; 201727; 711826; 784179; 756405; 1455641; 236263;
810242; 265680; 727292; 843321; 782488; 810567; 220655; 285544; 856961; 767188; 293417;
296393; 137456; 138168; 195974; 210348; 293676; 193938; 783697; 322537; 43241; 897158;
213280; 301061; 774409; 428756; 433253; 197657; 452963; 127677; 25588; 509760; 789091;
711768; 782679; 859807; 884719; 86160; 108351; 121808; 128627; 141209; 197051; 293845;
246684; 295514; 207618; 365423; 29054; 1486083; 594540; 753897; 826204; 844680; 624754;
1456900; 725672; 166934; 510702; 767753; 877651; 825214; 279146; 152453; 770588; 884500;
66584; 251461; 123720; 130876; 138165; 200780; 209340; 293727; 343737; 148743; 123546;
43563; 269606; 50182; 134783; 840944; 365826; 770835; 783998; 453183; 43771; 562983;
768299; 949934; 328802; 284160; 502151; 586854; 40608; 66919; 274932; 121828; 128679;
138706; 230637; 214826; 296330; 301678; 230370; 345177; 30664; 108378; 134322; 295137;
687397; 435330; 83549; 1472643; 1456118; 342378; 813426; 811942; 824511; 358531; 809390;
486678; 1032796; 526945; 66606; 246680; 122295; 133180; 138210; 230191; 233939; 234468;
199258; 144930; 257823; 44180; 284220; 244355; 140131; 950367; 342008; 344430; 282977;
897767; 727192; 179804; 296998; 71545; 810787; 268876; 455025; 770337; 85320; 144894;
110282; 124128; 128695; 138745; 197720; 232950; 296454; 323404; 810509; 277044; 31169;
430314; 509823; 485744; 727390; 433474; 460470; 1472719; 1473788; 42739; 327150; 563673;
814636; 627542; 491460; 342647; 755302; 509887; 66609; 234975; 122364; 130617; 140301;
234484; 234201; 345751; 201383; 809456; 782766; 44307; 324492; 727551; 309993; 815564;
383188; 41208; 436121; 771303; 198815; 752652; 71606; 825677; 767817; 795522; 252953;
433666; 731051; 363146; 294221; 124137; 129624; 139250; 198593; 296795; 295545; 235008;
201641; 810571; 813997; 813387; 712641; 416803; 773330; 713974; 1472735; 1049030; 197128;
771206; 783729; 796258; 203132; 490995; 45578; 884692; 742977; 66685; 124020; 122702;
144893; 138239; 201309; 241497; 209381; 193811; 135752; 809961; 378461; 754080; 26617;
705274; 162199; 788764; 392390; 347560; 46786; 129865; 197888; 795738; 753862; 810697;
177772; 757248; 123262; 296549; 124179; 129817; 295577; 198339; 243524; 295303; 344141;
795229; 795399; 859858; 23185; 789376; 840158; 154790; 769959; 1321598; 684655; 754031;
564962; 841340; 773344; 235155; 362718; 141815; 384081; 266085; 66895; 111571; 212634;
144802; 137736; 296640; 240506; 343661; 124271; 249618; 133735; 436094; 752631; 366511;
950680; 773567; 154472; 725649; 814251; 50188; 306771; 768443; 685912; 142788; 868368;
487338; 869450; 510856; 240033; 110582; 123952; 132899; 175140; 198033; 243980; 297212;
840683; 809603; 258454; 814780; 767828; 52327; 724615; 436554; 433155; 1320746; 687054;
592359; 51737; 840567; 815245; 841695; 263727; 855745; 131091; 784065; 66931; 111693;
123331; 135721; 137797; 206895; 240769; 359247; 129770; 195129; 39874; 450060; 360478;
48799; 141314; 362926; 741977; 266720; 814123; 753914; 236333; 82991; 814101; 825335;
236059; 345525; 724888; 773383; 245485; 110904; 123699; 132631; 160485; 242644; 130027;
300866; 132304; 811168; 809969; 809421; 811827; 787857; 898286; 611255; 868304; 1343768;
814989; 234559; 204214; 757961; 841261; 787938; 731029; 745019; 259842; 773579; 66400;
144852; 124087; 136114; 137884; 292292; 241274; 197414; 131238; 321734; 770935; 755821;
66728; 687820; 80095; 845477; 290234; 271102; 814316; 730149; 179534; 784876; 591907;
144881; 432564; 769603; 854401; 545403; 66574; 139354; 124168; 133096; 248306; 235924;
347036; 247614; 128632; 325380; 809815; 26616; 563444; 841669; 839101; 359661; 322914;
1343980; 526282; 204148; 145503; 231355; 756968; 811006; 811015; 32565; 41648; 772938;
247655; 111750; 126522; 136409; 137853; 204688; 241677; 230240; 136874; 810809; 67067;
130788; 135449; 22731; 682555; 855800; 141972; 291756; 49920; 246120; 129146; 774751;
843312; 308682; 51022; 725395; 307471; 837923; 126466; 110987; 198961; 133225; 197775;
202990; 243350; 128985; 129748; 415215; 809504; 214537; 178779; 784959; 711552; 784296;
756549; 1391644; 509731; 810282; 771084; 417508; 79688; 300137; 743188; 249606; 277186;
771295; 52419; 247125; 126568; 135999; 214658; 209468; 246276; 248599; 140761; 782635;
782335; 179334; 209296; 612616; 292222; 130201; 855523; 1435638; 194804; 810725; 132012;
814615; 788247; 302310; 770837; 743038; 586706; 785778; 201301; 123079; 297403; 133333;
194670; 202320; 243989; 111122; 131307; 415022; 201056; 882522; 321661; 381812; 824704;
783836; 502367; 49410; 844768; 36393; 234191; 724112; 825080; 824591; 782217; 138369;
248412; 179776; 244079; 124286; 125665; 136598; 211758; 206683; 247833; 130895; 229330;
289638; 416042; 121659; 812227; 770957; 789182; 284619; 259591; 66315; 756401; 243549;
813673; 810040; 898237; 39274; 126221; 141731; 382457; 66599; 768515; 51640; 120634;
345670; 135240; 196522; 245247; 296683; 213496; 347224; 291097; 502062; 897768; 359184;
229692; 71432; 343646; 855755; 41607; 460806; 823886; 143846; 256664; 712577; 811771;
415264; 222025; 83279; 291478; 113048; 121459; 125799; 247082; 193617; 242790; 248071;
111070; 244652; 281901; 244896; 245979; 190732; 813635; 838802; 416567; 448032; 27516;
811161; 813256; 210522; 813751; 754436; 758329; 144905; 811145; 430968; 111460; 42313;
120113; 294259; 207850; 203772; 202795; 296805; 143310; 196640; 279195; 758301; 753157;
342543; 813254; 824547; 782427; 307660; 86160; 415978; 47542; 39127; 767183; 826217;
786607; 356783; 590759; 742862; 49303; 196650; 121616; 125809; 139331; 193690; 204356;
248112; 115223; 1046522; 809858; 32875; 1435339; 153006; 740130; 855395; 755881; 502706;
291216; 544664; 233909; 299154; 381287; 773217; 262920; 884718; 461727; 135338; 767422;
123604; 124320; 129477; 205715; 294968; 229651; 295483; 202559; 240480; 322961; 45233;
768064; 167032; 564050; 842785; 809619; 530359; 744940; 486607; 161456; 810316; 212640;
815239; 897987; 416099; 204257; 141495; 743230; 129000; 121662; 127054; 141316; 193742;
233179; 292201; 143115; 267634; 795877; 33525; 278570; 300103; 809523; 67654; 729964;
45464; 1472775; 259973; 340734; 179276; 251019; 843110; 782449; 502891; 770059; 418138;
592802; 811956; 109089; 120773; 129922; 154795; 195314; 296140; 294445; 209683; 295604;
323917; 46171; 823718; 342721; 363058; 725266; 321470; 39722; 868308; 486186; 756372;
769028; 823901; 796137; 781014; 198093; 366100; 745360; 68605; 108651; 295594; 129853;
141361; 193724; 233446; 248594; 235055; 269806; 488155; 34255; 1387760; 810671; 178818;
511586; 362483; 156437; 1492230; 298612; 199403; 204335; 755239; 772220; 587525; 810167;
32664; 1020212; 743278; 813698; 124965; 120598; 131318; 240938; 195821; 211940; 294512;

TABLE 6-continued

Image ID Numbers Present in the 7K microarray.

204360; 161583; 119133; 47202; 796613; 154015; 296198; 591683; 811166; 884894; 627533;
487296; 110281; 131595; 52228; 713647; 40580; 429494; 742792; 278483; 624360; 108716;
121564; 321706; 139660; 198580; 240500; 194282; 257011; 277305; 487444; 34355; 1388395;
50043; 810117; 85690; 433350; 344759; 1473274; 324885; 41898; 376516; 788695; 843352;
714210; 271662; 743229; 590500; 840803; 66937; 293606; 125767; 131010; 210919; 293932;
229617; 294873; 322723; 240961; 809587; 49888; 454048; 770859; 727526; 630013; 810711;
755923; 971367; 491001; 811843; 282310; 173228; 811600; 841470; 811023; 531957; 854899;
770704; 321723; 200595; 121954; 125040; 139708; 275634; 294457; 112409; 131016; 278808;
376058; 34945; 41074; 136188; 49352; 85259; 177967; 366541; 1461104; 824025; 52431; 667598;
71116; 843028; 294487; 795191; 866694; 796297; 1049033; 66975; 109304; 130028; 131029;
248504; 200873; 247863; 121615; 210744; 143054; 809788; 50359; 454339; 233721; 813712;
365641; 745003; 342181; 809910; 586650; 120015; 245330; 230218; 785595; 840894; 725968;
1031940; 26249; 725188; 200599; 127610; 124502; 346484; 139957; 234527; 296749; 125737;
140635; 342522; 811582; 36775; 549139; 131362; 797016; 486175; 46367; 1468263; 826142;
230385; 213136; 840788; 840524; 788185; 810496; 845453; 223128; 593114; 67036; 206651;
124042; 143209; 138477; 200838; 211747; 204406; 128426; 811609; 810939; 50941; 489489;
66428; 704992; 841478; 741960; 206795; 511303; 684879; 31866; 768497; 306901; 841691;
789049; 215000; 246872; 295986; 377048; 203931; 124077; 245442; 137971; 162365; 199228;
230170; 123729; 247367; 505344; 795216; 85171; 261971; 897822; 841008; 731054; 472008;
1461737; 685808; 511832; 175123; 841507; 897652; 745347; 366859; 299360; 856427; 564756;
67070; 109269; 200174; 132017; 141723; 200847; 242087; 135219; 235173; 811059; 343079;
502177; 276091; 824074; 257162; 841221; 289645; 280934; 729942; 357344; 741429; 824382;
77805; 257445; 302933; 741958; 626555; 241066; 110746; 124505; 294496; 162778; 199239;
239708; 128248; 144029; 247582; 809729; 626967; 812126; 76362; 221826; 291880; 366067;
878129; 701625; 328591; 37234; 282501; 81315; 48285; 611443; 884462; 131268; 488207; 66423;
296472; 122913; 137178; 142397; 247482; 244100; 193182; 281467; 795371; 810613; 878178;
823943; 815816; 842860; 325641; 50480; 1359579; 824081; 246549; 207288; 813678; 669435;
897655; 21899; 471799; 611586; 595109; 357091; 111004; 124203; 133613; 202740; 199243;
213871; 142120; 144855; 268960; 376652; 753234; 45632; 950482; 357046; 969748; 859586;
1160723; 712401; 813149; 193990; 950607; 810854; 785293; 273546; 82738; 429368; 769926;
66430; 111765; 123196; 140830; 142442; 203551; 242779; 591653; 172783; 251028; 809413;
878259; 366834; 840511; 309864; 897233; 279172; 378502; 825648; 810124; 810391; 485989;
162208; 42880; 435858; 109863; 40692; 252382; 282378; 128602; 124637; 134643; 201562;
202492; 275176; 155201; 135247; 270997; 811010; 50794; 136235; 785616; 725454; 590264;
825312; 1160558; 713230; 566887; 510542; 840702; 760299; 83083; 447568; 510381; 490819;
345103; 144797; 121661; 195346; 136064; 155064; 207421; 242698; 110307; 198104; 490751;
809569; 809535; 66532; 840768; 666169; 435470; 773392; 431376; 809998; 754601; 359395;
49710; 810552; 122150; 744800; 277229; 28510; 897595; 345047; 245860; 124009; 134719;
191497; 204122; 243648; 125709; 127400; 377587; 325090; 229365; 823928; 950430; 739183;
854444; 740907; 1161013; 163174; 769645; 531028; 838389; 795771; 324618; 266094; 756687;
328745; 206816; 111391; 341821; 136557; 240748; 207771; 243113; 469952; 232586; 129530;
795582; 359835; 66507; 824568; 341588; 361122; 417920; 399604; 753457; 357220; 129644;
897544; 897774; 244955; 725308; 531319; 809876; 594633; 144042; 206841; 128518; 133534;
191599; 202703; 243653; 324342; 137158; 505573; 341654; 770901; 137940; 796994; 504226;
810142; 236034; 868575; 382787; 248531; 138991; 47853; 788566; 268727; 857264; 855385;
741885; 47481; 241988; 244154; 125589; 136706; 200015; 204300; 243199; 111150; 234539;
67031; 66457; 205303; 753104; 382654; 323777; 362795; 300012; 433544; 196348; 176606;
72050; 825295; 827120; 66574; 41406; 770074; 845519; 813384; 47853; 341336; 128905; 133519;
199327; 202931; 195487; 295889; 308415; 345523; 428773; 1410444; 753211; 815501; 128302;
47359; 840753; 878112; 263097; 241160; 668442; 898328; 898073; 415022; 51582; 770388;
759173; 281114; 235070; 127216; 136801; 197323; 210548; 292312; 126230; 305227; 271952;
341901; 384851; 149910; 276547; 897673; 357681; 725877; 75644; 148444; 810213; 184240;
70349; 77391; 825478; 769846; 769537; 755952; 81203; 1046542; 243817; 196109; 130053;
134495; 196125; 203400; 295044; 296562; 284592; 213660; 502762; 1475633; 235934; 109708;
897781; 809828; 884546; 489677; 755663; 211216; 813854; 484535; 841331; 343744; 486591;
773286; 856447; 244955; 121981; 243403; 138496; 197637; 208940; 292391; 128245; 280882;
809758; 810463; 461425; 666829; 208718; 950682; 429323; 970591; 73527; 345077; 40781;
123802; 166236; 825585; 898312; 135247; 50930; 345935; 840466; 42627; 292749; 120375;
243291; 296552; 196303; 207448; 295590; 214331; 138533; 417694; 140267; 1476053; 245242;
264117; 772878; 453147; 384015; 882510; 431501; 813402; 345208; 564621; 898062; 565235;
417694; 878833; 745188; 859422; 204735; 121600; 210688; 139593; 194906; 208434; 293421;
129616; 292726; 360075; 37196; 1358266; 770794; 240249; 788136; 343736; 264556; 788205;
377468; 47900; 196501; 210317; 760298; 825296; 293715; 855438; 124575; 725630; 27544;
245195; 207006; 129342; 292392; 196345; 211951; 296102; 214043; 144861; 343990; 51666;
1323432; 130541; 241348; 489079; 562115; 361688; 738900; 506548; 47559; 811911; 813536;
686164; 815287; 782439; 884673; 725877; 594517; 108783; 121715; 127409; 144793; 194985;
240138; 294311; 134312; 302369; 809824; 37451; 1404995; 296880; 44164; 788518; 196543;
290724; 1468461; 378488; 668685; 183476; 549146; 782315; 503617; 490232; 415870; 884993;
839374; 30850; 132630; 120383; 203514; 138601; 243784; 212098; 296559; 214614; 246377;
115443; 53316; 1323203; 275738; 84295; 236282; 271006; 813637; 745249; 292213; 768205;
210862; 705110; 840821; 490772; 45376; 841287; 877835; 201241; 121756; 130057; 139962;
195365; 137396; 293306; 136984; 309776; 771172; 38471; 1376853; 809938; 813651; 587847;
236155; 361807; 1412300; 385003; 296476; 767034; 810813; 824352; 488888; 148028; 502565;
813815; 109466; 120964; 131104; 167076; 280122; 234080; 296602; 230613; 135713; 365536;
1456419; 39884; 511521; 40017; 486221; 291985; 823665; 878130; 823590; 741815; 241412;
34439; 840776; 151501; 415554; 1031185; 511091; 200934; 121792; 130107; 140334; 197856;
241097; 293785; 210610; 321189; 795453; 39159; 1161797; 22040; 823775; 82710; 562729;

TABLE 6-continued

Image ID Numbers Present in the 7K microarray.

858292; 1416502; 385017; 246786; 320606; 713382; 724387; 814381; 810960; 340657; 175536;
328207; 66497; 112530; 121018; 134235; 195429; 200604; 233399; 297110; 239711; 203348;
771016; 32257; 141966; 810408; 739901; 855061; 856454; 1469230; 878182; 809892; 31093;
184175; 785575; 840978; 454440; 435611; 460403; 741831; 66407; 129331; 343352; 139837;
139462; 197907; 239835; 191572; 293457; 324815; 44310; 39285; 210575; 589115; 154608;
841370; 756595; 345538; 1473131; 713263; 22918; 144675; 759948; 45099; 196387; 884436;
624429; 342349; 40721; 206794; 123074; 131563; 214205; 201192; 212712; 137139; 134537;
233645; 782578; 1374571; 810019; 417403; 949938; 250883; 454672; 1469292; 811013; 813533;
767765; 810053; 705188; 306013; 769686; 868630; 60565; 77244; 193987; 241539; 124091;
130342; 140455; 198011; 230359; 195132; 233299; 415178; 782537; 39884; 753418; 212496;
897906; 382693; 857243; 897164; 1434905; 813983; 206217; 127519; 773319; 897751; 127925;
428223; 32304; 743701; 530035; 214906; 111389; 209264; 131886; 142733; 201961; 212787;
240914; 127646; 307314; 428582; 1471841; 361943; 795847; 841641; 725284; 74537; 1470048;
214965; 34888; 380394; 810057; 785371; 305606; 377560; 287745; 435855; 30473; 294040;
292482; 124079; 135892; 191516; 232837; 244201; 246652; 281125; 205152; 144862; 782789;
667482; 773618; 28218; 855547; 854138; 1388373; 814124; 173674; 768272; 898148; 73531;
38763; 505005; 435076; 489823; 267865; 293901; 230247; 122899; 196185; 156270; 201317;
243186; 126321; 132140; 161988; 321330; 1473300; 77636; 81336; 701751; 272529; 795321;
448432; 774078; 321529; 823691; 301976; 711450; 85805; 969877; 241736; 487425; 877664;
136073; 111266; 128785; 130233; 204179; 199602; 245806; 201203; 161993; 214583; 771058;
260303; 753775; 840364; 783849; 293925; 744417; 858469; 814287; 190887; 812105; 712378;
72778; 33051; 586796; 291057; 39843; 626822; 111981; 112440; 127120; 131824; 141522;
201784; 243245; 109314; 241038; 417305; 782283; 1475730; 813648; 760344; 795965; 283315;
307069; 450375; 207274; 28823; 823679; 44692; 767345; 156386; 46938; 624617; 796278;
773203; 345090; 113284; 127415; 135303; 135789; 199709; 245899; 248478; 206867; 209182;
66656; 809454; 122636; 788511; 322617; 344589; 26295; 1422723; 814444; 769676; 756847;
898198; 781097; 77577; 755599; 795729; 882511; 321389; 340840; 123433; 123436; 682555;
183120; 201818; 243317; 194131; 234537; 269680; 810272; 151104; 810156; 826254; 491113;
489626; 856519; 451706; 154651; 726779; 243343; 726147; 668182; 154093; 855487; 80649;
378813; 611150; 139199; 113283; 124822; 134256; 188388; 245586; 244846; 294995; 141931;
268951; 241847; 124261; 471498; 166195; 760148; 854701; 277660; 1155191; 815794; 809588;
156045; 825442; 796904; 246035; 742132; 866874; 858153; 1031748; 66391; 199627; 123459;
136775; 143748; 207881; 242642; 124232; 208210; 195370; 810448; 486544; 45291; 950356;
269815; 322160; 610362; 453689; 302190; 31842; 137836; 80948; 781704; 297061; 866702;
741891; 51363; 839882; 234331; 113308; 160488; 135653; 194401; 204684; 244313; 139226;
142851; 195034; 810299; 469954; 51362; 80946; 191664; 362059; 611581; 187614; 182661;
341310; 810761; 814595; 109888; 307933; 588915; 415529; 877832; 82556; 125741; 202209;
127099; 137020; 143962; 207952; 244227; 121611; 813410; 132217; 810754; 768561; 128126;
70692; 505573; 882459; 814266; 462595; 51447; 230100; 128530; 75923; 824906; 139278;
285460; 416390; 781075; 839980; 133820; 110417; 130043; 135710; 295741; 203287; 246478;
194399; 212542; 115408; 501674; 529861; 823859; 767202; 897596; 884644; 856167; 271748;
135221; 289551; 740027; 759865; 789014; 487172; 415899; 755630; 34140; 768260; 366156;
115230; 127182; 144762; 202621; 208984; 245409; 296616; 142586; 415741; 346447; 754998;
26811; 503097; 429555; 309893; 298965; 462645; 810504; 810010; 254321; 795288; 840818;
233071; 204686; 32299; 841396; 754378; 144747; 128054; 130005; 135010; 195853; 203388;
245273; 206786; 240430; 272183; 503033

The disclosed microarrays can be constructed using the Image ID number provided in these tables, and other available information. In particular, the Image ID number can be searched on the ATCC website, with hypertext links available to ATCC deposit numbers for deposited clones corresponding to the Image ID numbers. Hypertext links are also available to Genbank entries, which disclose sequence information about the nucleic acid at each array site corresponding to Image ID numbers.

Tables 7 and 8 summarize the results for exposure of cells to ionizing radiation using the 1.2K, 5K and 7K microarrays. Table 7 shows the results of different radiation doses (2 and 20 Gy), and hypoxia (which triggers p53 induction) using the 1.2K and 5K microarrays. As shown in Table 7, a very large fraction of the genes tested showed altered expression. As shown in the last two rows of Table 7, a substantial number of genes responded both acutely (3 hours) and at a later time (24 hours) after irradiation. The genes which showed expression at 24 hours were considered particularly suitable for a clinical biodetector that would detect the effects of radiation exposure during a time period when laboratory investigations of potential radiation exposure are likely to occur. However the genes which respond acutely (at three hours) could also be placed in an array to measure even more immediate exposures. Other arrays that include both acute (e.g. three hours) and later (e.g. 24 hours) response can be included in a single array. Differences between response of these two subsets can be used to help determine a probable time of radiation exposure. For example, if the three hour responders are positive but the 24 hours responders are not, then the time of exposure would have been at least three but less than 24 hours before the test. The results shown in Table 8 focus on lower doses and longer timepoints than the studies shown in Table 7.

TABLE 7

Summary of results for microarray analysis of stress responses[1]

| Array[2] | Targets | Treatment | Induced[3] | Reduced[4] | 99% Conf.[5] |
|---|---|---|---|---|---|
| 1.2K Chip | 1238 | 20 Gy + 4 hr | 38 | 11 | 0.63–2.37 |
| | 1238 | 6 hr hypoxia | 135 | 19 | 0.51–2.47 |
| | 1238 | 24 hr hypoxia | 202 | 8 | 0.55–2.38 |

TABLE 7-continued

Summary of results for microarray analysis of stress responses[1]

| Array[2] | Targets | Treatment | Induced[3] | Reduced[4] | 99% Conf.[5] |
|---|---|---|---|---|---|
| 5K Chip | 5408 | 2 Gy + 3 hr | 67 | 21 | 0.68–2.31 |
|  | 5408 | 2 Gy + 24 hr | 161 | 26 | 0.69–1.89 |

[1]Results are summarized for microarray hybridizations conducted in ML-1 cells. Many of the results for row 1 and 3 have been verified by quantitative single-probe hybridization.
[2]Two different microarrays (chips) used contained only limited overlap in the genes represented.
[3]The number induced refers to cDNA clones showing significant induction (≧99% confidence).
[4]For cDNA clones showing a significant reduction, values are shown for those having at least a 2-fold reduction in expression compared to untreated cells; all these values exceeded 99% confidence.
[5]Values represent range of relative expression of irradiated sample compared to untreated control; e.g. only targets showing an increase in the relative mRNA level of 2.37-fold or more were scored as induced in the first row.

TABLE 8

Summary of γ-ray Experiments with 7K Microarrays

| Cell Line | Dose | Time | # Up[a] | # Down[b] | 99% Conf. | C.V. |
|---|---|---|---|---|---|---|
| ML-1 | 10 Gy | 4 hr | 86 | 23 | .38–3.00 | .16 |
| ML-1 | 2 Gy | 4 hr | 32 | 3 | .51–4.38 | .27 |
| ML-1 | 2.5 Gy | 24 hr | 62 | 8 | .93–7.08 | .23 |
| ML-1 | 2.5 Gy | 48 hr | 60 | 17 | .60–4.85 | .24 |
| ML-1 | 0.2 Gy | 3 hr | 86 | 29 | .74–2.43 | .15 |
| ML-1 | 0.2 Gy | 24 hr | 114 | 11 | .83–3.42 | .18 |
| ML-1 | 0.02 Gy | 3 hr | 68 | 40 | 1.16–9.18 | .24 |
| ML-1 | 0.02 Gy | 24 hr | 55 | 6 | .78–5.92 | .23 |
| HL60 | 0.25 Gy | 3 hr | 77 | 2 | .63–4.95 | .24 |

[a]Number of Image ID clones that were upregulated in response the irradition.
[b]Number of Image ID clones that were downregulated in response the irradition.

Tables 9–12 lists the clones (by Image ID number) for which there was 99.9% confidence that the genes were differentially expressed in ML-1 cells with the 7K array at: 24 hours after 200 cGy of irradiation (Table 9); 24 hours after 20 cGy of irradiation (Table 10); 24 hours after 2 cGy of irradiation (Table 11) and; 48 hours after 200 cGy of irradiation (Table 12). Late responding genes were found by using RNA harvested at the timepoint of interest, for example 24 or 48 hours after exposure to ionizing radiation. A more detailed timecourse of expression (such as that disclosed in EXAMPLE 3) can be used to determine if expression peaks at the time of identification (24 or 48 hours), or if there is a sustained elevation of expression. To identify genes for other timepoints post-exposure, or for different exposures, the cells would be treated with the agent/dose of interest, and the RNA would be harvested at the appropriate time.

TABLE 9

Image ID numbers of genes differentially expressed after 200 cGy and 24 hours.

280386; 753418; 308588; 241412; 109123; 47475; 549146; 841278; 221846; 159455; 251516; 345839; 240249; 136114; 703846; 66972; 153025; 713145; 366558; 209340; 242780; 293325; 843312; 240843; 35828; 810391; 264117; 293940; 244227; 262231; 180520; 294487; 562927; 160793; 72391; 120362; 346995; 232837; 297442; 295939; 810372; 120572; 666658; 550355; 48398; 469954; 110653; 211548; 260619; 128290; 210522; 241788; 122091; 140921; 120881; 755416; 504226; 738899; 346552; 248256; 66728; 122159; 232612; 753447; 813591; 245585; 325375; 289551; 366341; 36950; 236355; 125092; 204814; 196387; 843287; 34773; 120695; 287300; 234376; 813179; 293557; 712840; 244703; 24415; 138579; 229723; 206816; 108658; 157856; 308041; 727026; 292217; 231675; 135240; 194965; 246661; 812196; 135538; 41452; 123474; 49710; 823928; 141818; 823940; 327094; 141854; 282051; 195720; 813675; 795543; 128530; 124071; 810156; 293727; 768638; 773332; 121159; 724892; 295710; 809588; 121251; 139835; 781341; 815534; 770355; 841703; 293306; 202549; 39993; 195365

TABLE 10

Image ID numbers of genes differentially expressed after 20 cGy and 24 hours.

854401; 854701; 131887; 112896; 296149; 725501; 41648; 66400; 132690; 415022; 770866; 292222; 323917; 83210; 772220; 288896; 110436; 248306; 743278; 826984; 760148; 322160; 234527; 969748; 291985; 795877; 430968; 487172; 198815; 343646; 204814; 562115; 491692; 274638; 244227; 111571; 242780; 279195; 509887; 343744; 769603; 264117; 771295; 322961; 825295; 141768; 753418; 686164; 383016; 109123; 80649; 841282; 450375; 66898; 111693; 210317; 627251; 24415; 740027; 685801; 448619; 773567; 768272; 854576; 510381; 66457; 298963; 611443; 243100; 771023; 884500; 221846; 200031; 843312; 839516; 120695; 195129; 266094; 234562; 127709; 704690; 768443; 796278; 242087; 47475; 195346; 123441; 140921; 214165; 34255; 549146; 626555; 713193; 142087; 811015; 815816; 126453; 123408; 46786; 359395; 269381; 122443; 1408710; 825442; 111765; 241412; 490763; 739183; 30272; 152453; 108801; 82556; 204148

TABLE 11

Image ID numbers of genes differentially expressed after 2 cGy and 24 hours.

703846; 84820; 745347; 274638; 24415; 841278; 66975; 221846; 712840; 308041; 562927;
359184; 135538; 308588; 282051; 738899; 109123; Bcl-x; 359793; 246661; 204814; 755416;
897781; 773332; 813591; 52681; 810142

TABLE 12

Image ID numbers of genes differentially expressed after 200 cGy and 48 hours.

264117; 240430; 811015; 262231; 308588; 159455; 549933; 323474; 840944; 432194; 109123;
321739; 366945; 843287; 240249; 111765; 48182; 130541; 771295; 624627; 294487; 812126;
345559; 382654; 755037; 203130; 739183; 193087; 843312; 214133; 811000; 308437; 431655;
448619; 823940; 41356; 612616; 725746; 47475; 549146; 162775; 35828; 46284; 120881; 770935;
208161; 745188; 843139; 377671; 838373; 809639; 686164; 206816; 770394; 179617; 809394;
591281; 294496; 124795; 782760; 767828; 308041; 731308

Genes with sustained elevated expression (for example 24–48 hours following the exposure) may be suitable for inclusion in probe sets for clinical tests which would not be performed for several days after potential exposure to ionizing radiation. Using dose response information, different probe sets can be designed for different clinical situations, tailored to detection of exposure a certain number of hours following potential exposure.

Probe sets can also be designed that detect certain subsets of genes that are differentially expressed at a particular post-exposure time and level of expression. The levels of differential expression can be correlated to the dose of ionizing radiation to which the subject was exposed, such that the probe set can also be informative about the dose of exposure. This information can provide helpful prognositc information, such as the likelihood of carcinogenesis brought about by the exposure. Alternatively, levels of differential expression can be used to determine a subjects' response to radiation therapy for a tumor, as described in EXAMPLE 10.

EXAMPLE 7

Nucleic Acid Probe Sets

Nucleic acid hybridization technologies may be used to survey gene expression patterns in organisms or cells that have been exposed to ionizing radiation. Such technologies are not necessarily limited to nucleic acid arrays. By way of example, northern blot and/or dot blot techniques (see EXAMPLE 3) may also be used to determine the quantitative and qualitative expression patterns of some or all of the disclosed radiation responsive sequences.

While more conventional nucleic acid hybridization techniques (such as northern and dot blots) have been used for many years, nucleic acid array technology is now widely used for monitoring and analyzing gene expression patterns. This array technology may be used in a number of forms, including microarrays. Microarrays typically comprise a large number of nucleic acid probes spotted at high density onto a surface. Descriptions of nucleic acid array and microarray technology may be found in the scientific literature, including, for example, in Chee et al., Science 274: 610–4 (1996); Lockhart et al., Nature Biotechnol. 14:1675–80 (1996); Lipshutz et al. Biotechniques 19:4427 (1995); Southern et al., Trends Genetics 12:110–5 (1996); Soares et al., Curr. Op. in Biotech. 8:542–6 (1997); Ramsay et al., Nature Biotech. 16:40-4 (1997); Schena et al., Science 270:467–70 (1995); Schena et al., BioEssays 18:427–31 (1996); DeRisi et al., Science 278:680 (1998), and Iyer et al., Science 283:83–7 (1999). Detailed technical descriptions of various forms of this technology can also be found in the patent literature, including in the following patent documents:

U.S. Pat. No. 5,744,305 ("Arrays of materials attached to a substrate");
U.S. Pat. No. 5,807,522 ("Methods for fabricating microarrays of biological samples");
U.S. Pat. No. 5,545,531 ("Methods for making a device for concurrently processing multiple biological chip assays");
U.S. Pat. No. 5,593,839 ("Computer-aided engineering system for design of sequence arrays and lithographic masks");
U.S. Pat. No. 5,837,832 ("Arrays of nucleic acid probes on biological chips");
WIPO publication number WO 9710365 ("Expression monitoring by hybridization to high density oligonucleotide arrays").

cDNA arrays can be formed on non-porous surfaces (such as glass) by in situ synthesis of oligodeoxynucleotides on a chemically sensitized glass surface (as in WO 92/10588 and WO 95/11995), or by robotic micropipetting of nanoliter quantities of DNA to predetermined positions on a non-porous glass surface (as in Schema et al., Science 270: 467–470, 1995, and WO 95/35505). DNA may be coupled to the solid support by electrostatic interactions with a coating film of a polycationic polymer such as poly-L-lysine (WO 95/35505), or covalently bound to the solid support.

Nucleic acid arrays employ conventional nucleic acid hybridization methods that have been used for decades to identify and quantify nucleic acids in biological samples (such conventional methods include southern and northern blots, colony hybridizations and dot blots). However, whereas such conventional techniques typically employ one or two hybridization probes to obtain information on the expression patterns of one or a few genes, array techniques typically employ very large probe sets (for example at least 100, 1000 or even 5000 or 10,000 probes) to obtain data on the expression of a vast number of genes simultaneously.

The basic principle underlying the array technology is the hybridization of a sample nucleic acid composition with a defined set of nucleic acid probes, followed by detection of specific hybridization of the sample to one of more of these probes. The hybridization pattern obtained is then analyzed and compared to hybridization patterns obtained with control nucleic acid samples.

Most arrays comprise a defined set of nucleic acid probes immobilized on a fixed surface in an ordered and known sequence, forming an array of discrete spots of nucleic acid material. A number of substrates may be used to form the fixed surface, including silica-based chips, nylon membranes, microtiter plates and glass slides. Each probe within the set is typically produced by polymerase chain reaction amplification (alternative methods include purification from cloning vectors and, for oligonucleotide probes, chemical synthesis). Each amplification product (probe) is then typically spotted onto the fixed surface using a mechanized means (such as a robotic arm) to form the array. The sample nucleic acid composition (for example, labeled cDNA produced by RT-PCR from mRNA extracted from a tissue sample) is labeled with a detectable marker (e.g., a fluorescent label) prior to hybridization to the array to permit detection of specific hybridization of the sample to a particular probe. Following hybridization, the hybridization pattern is detected and an image of the array is produced for analysis of gene expression. The use of multiple different fluorescent labels to label the samples permits multiple different samples to be hybridized to a single array. Typically however, no more than two samples are hybridized to a single array.

Alternatively, the arrangement may be reversed. The fixed array may include a number of nucleic acid test samples and the probes may be hybridized to a number of duplicates of the array. In this situation, a large number of test sample nucleic acid compositions are attached to the surface to form the array. Subsets of the nucleic acid probe set are subsequently hybridized to duplicates of the array, and hybridization of the probes to individual spots of the array is detected. The use of multiple different fluorophores to label the probes permits multiple different probes from the probe set to be hybridized to a single array.

By way of illustration, a microarray may be produced and employed using the following techniques:

Each probe in the microarray probe set is produced by PCR amplification. This may be achieved by using primers that are specific for the sequence of the differentially expressed gene (as disclosed herein) in conjunction with genomic DNA or cDNA as a template. The amplified PCR products are purified to remove excess primer and template, for example by column chromatography, or by simple sodium acetate or ammonium acetate precipitation, followed by either isopropanol or ethanol washing, and drying. In certain instances, the probe may be used without purification. Following purification, the PCR-amplified probes are resuspended in 10 μl of a salt solution (3×SSC) and transferred into 96-well or 384-well microtiter plates (if they were not already in a microtiter plate from previous steps). The samples are mechanically spotted onto coated glass slides, using a robotic arm containing pins that transfer an amount of each probe from the microtiter plate onto the coated glass slide. Several hundred or several thousand probe spots are spotted onto the array such that each probe is represented by a discrete spot with a center to center distance between spots of about 250 μm to about 500 μm. The glass slides are then processed to cross-link the probe set onto the glass surface.

The nucleic acid sample to be hybridized to the array is typically cDNA obtained by RT-PCR of mRNA extracted from a biological sample (e.g., plant or animal cells) (see EXAMPLE 2). The detectable label (e.g., the fluorophore) may be incorporated during the RT-PCR amplification step. Typical experiments involve either single-color fluorescence hybridization to measure the absolute levels of gene expression in a single sample, or two-color fluorescence hybridization to examine the relative expression of genes in two different samples.

For single-color fluorescence hybridization experiments, mRNA is isolated from a sample of interest and used as a template to produce cDNA. The cDNA is labeled, for example using a fluorescent dye such as Cy-3 or Cy-5 (Amersham Pharmacia Biotech, Piscataway, N.J.), or any other fluorophore or label. The label can be incorporated directly during the reverse transcription step. The sample is then hybridized to the array. Following washing to remove non-specifically bound sample, the array is scanned for fluorescent emission following laser excitation, and the intensity of each fluorescing spot is measured. The intensity of each spot is approximately proportional to the expression of the gene (corresponding to the probe) in the sample examined. This data provides an indication of the expression of a particular gene in the tissues from which the sample nucleic acid was prepared.

For two-color fluorescence hybridization experiments, RNA is isolated from two samples of interest and labeled as described above, except that each sample is labeled with a different fluorescent label, each of which fluoresces at a different wavelength (for example, one sample may be labeled with Cy-3 and the other with Cy-5). After the two sample preparations are labeled, they are mixed together and hybridized to a single microarray. After washing, the microarray slide is scanned in two fluorescence channels. Because the two fluorescent labels are selected such that their emission spectra do not overlap, the signal of each of the two fluors can measured for each of the probes of the array. The absolute levels of intensity for each probe in an array is approximately proportional to the expression of the gene in the sample examined, and the ratio of the two fluor intensities indicates the relative expression of a gene in the two different samples.

Each probe includes at least one copy (and more typically many copies) of an isolated nucleic acid molecule. Typically, the nucleic acid molecule is in substantially pure form, i.e., while there may be small amounts of other nucleic acid molecules in the probe preparation (such as degradation products), the selected nucleic acid molecule will be the predominant nucleic acid molecule present. In addition, a probe is generally of known sequence. A "probe set" comprises a collection of two or more such probes (the individual probes within the probe set not being co-mingled). A probe set will include probes selected for a particular purpose (such as detection of acute or semi-acute exposure to ionizing radiation), but may also include controls or other probes for different purposes. In some examples, at least 10% of the probes in the probe set are selected for the particular purpose of determining an actual or potential biological response to an actual or potential radiation exposure. In other examples, at least 5, 10 25, or 50 of the probes of an array are selected for this purpose.

A hybridization probe for use in an array produced according to the present invention may be referred to as a sequence "representing" a particular gene product. A sequence "representing" a particular gene product is one that will specifically hybridize to a nucleic acid molecule encoding that gene product, thereby permitting identification of that gene product. A sequence representing a particular gene product may comprise an entire cDNA sequence (or the corresponding genomic gene sequence) or less than an entire cDNA sequence. For example, the probe may comprise an oligonucleotide comprising a minimum specified number of consecutive bases of a selected gene that is differentially expressed following irradiation. Oligonucleotides as short as 8–10 consecutive bases of a cDNA will be effective to produce meaningful gene expression data using microarray technology. For example, a nine base oligonucleotide can distinguish 262,144 transcripts ($4^9$). However, for enhanced specificity of hybridization, longer oligonucleotides may be employed, such as at least 10, 15, 20, 25, 30, 50, 50 or more consecutive bases of a cDNA. Furthermore, a probe "representing" a particular gene product need not be a complete match. While probes that share 100% sequence identity over their entire length to the corresponding cDNA sequence will typically provide enhanced specificity of hybridization, probes that share less than 100% sequence identity may also be useful in such microarray applications. Typically, such probes will share at least 70% sequence identity with the corresponding cDNA, but probes sharing at least 75%, 80%, 85%, 90%, 95%, 97%, 98%, and 99% sequence identity may be utilized to achieve enhanced specificity.

EXAMPLE 8

EXAMPLES OF ARRAYS FOR DETECTING GENOTOXIC STRESS

An examples of a probe sets that has been used to make a cDNA array that detects differential expression of genes following irradiation is shown in Tables 13. The clones on this chips include all the positive hits from studies with larger arrays (5K and 7K), in addition to probes for other genes that have been reported in the literature as being stress-induced.

TABLE 13

Image ID Numbers of Genes Differentially Expressed in Response to Irradiation.

21652; 23132; 753430; 78294; 127193; 155287; 825080; 703846; 121877; 128785; 549933;
781139; 811927; 884500; 381287; 700792; 196185; 133225; 739183; 502832; 40692; 626531;
840511; 39993; 41511; 812196; 346995; 123926; 240249; 504226; 510760; 160573; 324861;
81203; 85195; Bcl-x; 784179; 66428; 125741; 134537; 795877; 46284; 134476; 377587; 141763;
22260; 25584; 753418; 141818; 129506; 547058; 814701; 686172; 121159; 297442; 289606;
78353; 34184; 785847; 760299; 788185; 134235; 143208; 323474; 433253; 950507; 754378;
126858; 40304; 42096; 727026; 229723; 262231; 51448; 191664; 203132; 769846; 240961; 49410;
80162; GADD153; 322160; 77636; 241539; 136984; 856961; 41356; 511066; 323577; 25588;
22493; 26184; 345839; 130788; 120572; 549146; 772220; 77728; 247216; 143209; 756405;
624617; 878676; 12637; 41074; 33051; 131886; 138496; 811166; 757873; 509887; 108801;
810372; 41199; 42352; 140716; 550355; 125092; 788141; 297392; 294487; 160664; 795893;
147050; 22428; GADD34; 293925; 80946; 201241; 770887; 22293; 740027; 840691; 770935;
26922; 28985; 36393; 214537; 50506; 562927; 72391; 843312; 135240; 138579; 45578; 243882;
504745; CR6; 297061; 257445; 137020; 234527; 431655; 366945; 120383; 138477; 772878;
42993; 43550; 160793; 221846; 714106; 841703; 859359; 841278; 272183; 504372; 28985;
291985; 279172; 206651; 111004; 31169; 50794; 773319; 686164; 245774; 27624; 30272; 813614;
359184; 308041; 66728; 774036; 826166; 136114; 140921; 266094; 882484; BAX; GADD45;
300137; 151501; 139462; 198011; 856519; 247483; 131010; 204179; 824352; 43129; 43622;
289551; 135538; 950356; 842802; 214162; 122822; 487819; 502977; 36950; 53164; 384015;
454672; 230247; 113284; 489506; 550353; 843249; 815245; 120306; 28309; 31143; 204299;
813841; 823928; 306901; 293940; 781019; 154214; 157856; 235938; 745116; c-Myc; MDM2;
490232; 769686; 197720; 230191; 756549; 487348; 133331; 296189; 66975; 43338; 44255;
666658; 261828; 24415; 841334; 292217; 245444; 119133; 41452; 110589; 223350; 1388373;
112530; 111693; 489489; 727551; 231355; 796904; 590544; 31210; 34357; 128143; 589115;
156473; 753104; 739625; 587847; 194965; 240843; 884719; 781017; RelB; 417694; 204686;
744047; 204122; 229617; 179617; 814123; 244386; 132304; 855521; 44537; 47833; 159455;
145503; 785574; 192694; 205049; 282051; 323185; 491403; 35516; 193901; 878182; Hskg21F11;
296393; 123436; 767828; 49509; 74566; 856489; 85195; 32898; 34396; 34773; 153025; 809939;
770957; 781341; 23073; 232837; 242780; 810999; 128493; V(D)J (RAG2); 270626; 340657;
1031185; 208940; 295497; 432194; 214133; 193182; 135713; 253009; 45941; 50117; 308588;
175123; 789182; 768638; 295939; 50765; 282978; 884425; 234357; 280507; 1049030; 754601;
207006; 124168; 45632; 810408; 235155; 21899; 85906; 33632; 35483; 738899; 327676; 232612;
753447; 48398; 231675; 204814; 260619; 251591; 436062; HbclW8; 44495; 148028; 435855;
233939; 230359; 713236; 240634; 132140; 321271; 949971; 47110; 50666; 813675; 202535;
70692; 786067; 245585; 66972; 280893; 590544; 773367; 774078; 234559; 121715; 124091;
308437; 49352; 429574; 50888; 44495; 36950; 39093; 813179; 725680; 741769; 42373; 760224;
841641; 280386; 139226; 724888; 360778; 510130; H36; 840466; 784065; 241097; 299815;
810331; 592359; 377587; CIP1/WAF1; 51293; 26578; 810391; 725266; 789369; 34689; 66430;
487777; 586839; 626358; 31093; 759948; 130053; 139837; 712641; 51041; 280356; 852829;
37366; 39173; 810485; 729942; 195712; 264117; 630013; 204301; 293727; 296030; 193736;
740907; 433551; 52753; 839374; 82556; 295303; 112371; 190887; 361097; 323577; GADD45;
51740; 244703; 128530; 592540; 287300; 246722; 546600; 780947; 145383; 269606; 35318;
812105; 825295; 128695; 137456; 166195; 796994; 866874; 85313; 37904; 39796; 810600; 42739;
249688; 122091; 842849; 841470; 345751; 172721; 755923; 378813; 52681; 51699; 252382;
27544; 246652; 121798; 28823; 51737; 770935; 145503; 129865; 207794; 772878; 712840;
295710; 108351; 462953; 855521; 73527; 489485; 40056; 484535; 130057; 130617; 809394;
842860; 857002; 854899; 22012; 24145; 755145; 124261; 293916; 823901; 898062; 84820;
120695; 125589; 310406; 377692; 220851; 951142; 795771; 305606; 131824; 134643; 307532;
845415; 743230; 785778; 36393; 40026; 42059; 823940; 244767; 211548; 122159; 713145;
358531; 121251; 417226; 125187; 85195; CIP1/WAF1; 236155; 233721; 66574; 295514; 428582;
35077; 241880; 161988; 325062; 22293; 25725; 812965; 666218; 124824; 752732; 843321;
815539; 123439; 130043; 491763; 345525; 825740; 124143; 814117; 196387; 131563; 134256;
810711; 271006; 416316; 242706; 214537; 40360; 42214; 141763; 120881; 274638; 701112;

TABLE 13-continued

Image ID Numbers of Genes Differentially Expressed in Response to Irradiation.

172440; 199180; 123229; 268727; 309288; 26997; GADD45; 755750; 141966; 292482; 262053;
121611; 129146; 770212; 310894; 159455; 23019; 26366; 180520; 205185; 669443; 177737;
824352; 613126; 124071; 325375; 487820; 845363; 488596; 549139; 194600; 132708; 137016;
361323; 858292; 811000; 125767; 223483; 41452; 42576; 110653; 325062; 811942; 840511;
85840; 745347; 232714; 269815; 83999; 50615; 429555; 854701; 28218; 200934; 427692; 30664;
234562; 898198; 810448; 70692; 27549; 29054; 126858; 245296; 323506; 197525; 71545; 416833;
234376; 139957; 133637; 745433; 814476; GADD153; 233071; 377560; 195429; 197907; 841221;
197657; 123067; 262920; 712840; 43021; 43563; 809588; 210522; 898138; 825470; 48285;
133114; 782712; 34005; 47359; 714213; 109271; 128602; 40360; 340630; 773254; 843139;
172721; 27848; 30664; 26616; 469954; 136235; 236355; 724892; 897690; 144762; 137853;
770424; 384081; Bcl-x; Killer/DR5; 487172; 454440; 195853; 200780; 322914; 1472735; 137918;
212712; 613126; 43231; 44180; 769921; 293325; 208161; 612274; 196387; 141627; 810059;
782545; 39993; 85906; 361688; 1473274; 109466; 113283; 450745; 810017; 757961; 73531;
769846; 28410; 31169; 203275; 810372; 137940; 241788; 795543; 815534; 139835; 195720;
266106; 253009; CIP1/WAF1; MyD118; 215000; 755599; 198593; 234484; 856167; 1320746;
139490; 300866; 345751; 43241; 44307; 292806; 25588; 841149; 726086; 366341; 108658;
809585; 489805; 26474; 26295; 1416502; 110582; 296472; 814780; 178779; 684661; 787861;
845477; 32875; 34355; 770670; 223483; 137017; 35828; 85259; 376875; 195365; 240648; 796278;
26568; V(D)J (RAG-1); 347586; 46938; 755630; 245586; 212098; 385003; 163174; 359247;
141931; 491763; 45233; 49888; 823614; 212198; 74119; 82991; 120362; 293557; 324494; 289428;
49950; 288650; 687054; 173674; 196109; 123459; 812126; 665774; 591281; 447568; 80162;
33525; 34945; 162775; 770355; 241412; 810156; 135083; 840944; 109123; 244227; 263014;
415817; Bak; 43021; 415870; 460403; 208984; 214826; 1472753; 753457; 194131; 809995;
251591; 46171; 50359; 727210; 248454; 361974; 796646; 141854; 248256; 342008; 364510;
486074; 768064; 824081; 230100; 121600; 124822; 35185; 51865; 122150; 435858; 878676;
34255; 36775; 22040; 122428; 22411; 26811; 39274; 950680; 209340; 293858; 39722; 491692;
GADD34; 45794; 32304; 192271; 230013; 244201; 825726; 380797; 109483; 810154; 85195;
47202; 50941; 135692; 135527; 77915; 49710; 246661; 129585; 204569; 624627; 359793;
1467195; 1493160; 341310; 244686; 126568; 49509; 43826; 429494; 773637; Bcl-x; 37196;
39159; 240151; 346552; 292463; 771196; 666425; 839736; 293306; 202549; 949971; 66599;
503724; 133637; 297061; 773579; 239835; 194399; 511832; 767765; 161988; GADD153; 51666;
123474; 823691; 897781; 843287; 205993; 111981; 845477; 810142; 120468; 882510; 213136;
485989; 129332; 130342; 950430; 503097; 770394; 268946; 37451; 39285; 126243; 210887;
85561; 245388; 51666; 898286; 128290; 245774; 788764; 245990; 592485; 264937; 594633;
626822; 123729; 50188; 204214; 310894; GADD34; 53316; 131653; 755416; 810131; 897570;
327094; 206816; 756502; 1035889; 454339; 82297; 236333; 80948; 135892; 130876; 841384;
705274; 415529; 505491; 38471; 39884; 127677; 232772; 28475; 179403; 838373; 725454;
251516; 120306; 342181; 757350; B1; 280386; 771295; 136188; 297405; 296616; 31842; 51737;
810448; 47475; 813591; 773332; 366728; 66975; 110746; 359661; 586796; 75644; 858293;
810813; 759865; 130107; 131668; 612616; 724615; 376785; 856535

A microarray was assembled which contained each clone in Table 13 printed only once on the array. However the arrays can routinely include duplicates of each position as the stress-array, to provide an additional degree of certainty for positive "hits." In addition, internal controls of the type known in the art can be used on each array.

The probe set for a cDNA array can be made using a probe set comprising nucleic acid molecules representing a portion of the cDNAs disclosed in Tables 9–13. Alternatively, such probe sets may be used to analyze gene expression patterns using other hybridization techniques, such as northern and dot blots (see EXAMPLE 3). However, useful information may also be obtained using arrays or other techniques that employ probe sets representing less than all of the disclosed cDNAs in the array of Tables 9–13. For example, arrays that employ probe sets representing between 10% and 99% of the disclosed cDNA sequences may be employed. Thus, arrays employing probe sets representing at least 25%, 50%, 80% or 90% of the disclosed cDNAs depicted in any of Tables 9–13 may be employed. Alternatively the probe set may represent at least 5, 10, 25, or 50 of the disclosed cDNAs depicted in any of Tables 9–13. Each probe can "represent" the cDNA by having sufficient contiguous nucleotide (or variant thereof) that hybridizes to a target nucleic acid of interest. Alternatively, an array can be made using probes that detect differential expression of genes within a certain time period. An example would be an array consisting of the probes of any of Tables 9–12 or combinations thereof.

The sets of disclosed probes may also be used in nucleic acid hybridization techniques. Such probe sets are particularly useful for assessing differential gene expression in cells that have been exposed to radiation. The probe sets comprise nucleic acid probes representing specified percentages of the differentially expressed cDNAs disclosed herein. These probe sets may be used with any nucleic acid hybridization technique that can be used to analyze patterns of gene expression, including but not limited to: northern blotting, dot blotting, arrays and microarrays.

In addition, the invention also provides methods for analyzing expression of multiple genes in a biological sample. A biological sample is provided which includes nucleic acids, and the biological sample is hybridized to a nucleic acid probe set arrayed on a surface. Typically, the nucleic acids of the biological sample are labeled with a detectable label such as a fluorescent label, to permit easy detection of hybridization between the sample and a probe. The nucleic acid probe set arrayed on the surface includes nucleic acid probes representing, for example at least 2%, 5%, 10%, 25%, 50% or more of the radiation induced cDNA sequences disclosed in any of Tables 9–13, such as subsets of probes for genes that have sustained expression at 24 or 48 hours, or expression at a level that corresponds to clinical exposure to a certain dose of ionizing radiation.

The present invention also includes providing a plurality of duplicate arrays of test sample nucleic acid compositions (such as samples taken from one or more subjects) immobilized on a fixed surface. These arrays are then hybridized with a nucleic acid probe set (typically labeled with a detectable label). Hybridization using the complete set of probes is typically achieved by hybridizing a small subset of the probes (typically 2–5 probes) to one of the array duplicates, and then repeating the procedure by hybridizing additional subsets of the probe set to additional duplicates of the array. To facilitate detection of hybridization, each of the probes within a particular subset is typically conjugated to a different detectable label. The probe set used in this method comprises nucleic acid probes representing at least 2%, 5%, 10%, 25%, 50% or more of the cDNA sequences disclosed in any of Tables 9–13, or the complete probe sets disclosed in those Tables, other subsets thereof (such as at least 5, 10, 25, or 50 of the disclosed sequences), or probe sets that are larger than any of these sets and include additional informative markers that have been or are discovered.

Arrays of polynucleotide DNA probes immobilized on solid supports have been used to study the composition of complex mixtures of DNA by hybridization techniques. For example, a complex mixture of labeled cDNA is hybridized to the DNA array under conditions of appropriate stringency, and unbound material is washed away. The array is then scanned using a detector, such as a scanning fluorescent microscope, capable of sensing the remaining bound labeled cDNA. The intensity of the detected signal at any given element is a measure of the concentration of the corresponding cDNA in the original complex mixture. See Schema et al., *Science* 270:467–470, 1995 and WO 96/17958.

EXAMPLE 9

Analysis of Biological Specimens

This example demonstrates that cDNA microarrays can be used to assess the effects on gene expression of irradiating isolated human peripheral blood lymphocytes or alternatively can detect altered gene expression to assess potential radiation exposure. Peripheral blood lymphocytes provide an easily accessible source of radiation sensitive tissue from a subject who has potentially been exposed to ionizing radiation. To determine whether the subject has experienced a biologically significant radiation exposure, approximately 30 ml may be obtained by conventional phlebotomy. This amount of blood provides sufficient mRNA for hybridization to a large array (such as a 5K array or 7K array), or several smaller arrays (such as 1.2K arrays), during efforts to determine which genes are differentially expressed. However, much smaller probe sets can be used diagnostically, with corresponding smaller amounts of blood required.

Although this example describes methods which were used to analyze peripheral blood lymphocytes, one skilled in the art will recognize that similar methods can be used to analyze any biological specimen. Biological specimens can be obtained from subjects who have potentially been, or are known to have been, exposed to ionizing radiation. A variety of biological specimens can be used in the present invention. Examples include, but are not limited to: peripheral blood, urine, saliva, tissue biopsy, surgical specimen, amniocentesis samples and autopsy material.

Blood may be drawn from potentially exposed individuals, RNA extracted immediately, and tested against an established baseline to determine relative levels of a number of genes, then compared to profiles for various qualities or quantities of radiation, or other environmental agents, to determine likelihood of exposure. Approximate dose and time since exposure can also be determined.

Human blood from normal healthy donors were obtained from the NIH blood bank (Department of Transfusion Medicine) and within 30–60 minutes of drawing, the components were separated by centrifugation on a Lymphoprep (Nycomed, Oslo, Norway) density gradient according to the manufacturer's instructions. The buffy coat layers were recovered, washed in phosphate buffered saline and resuspended at a density of $0.5-1\times10^6$ cells per ml in RPMI 1640 medium supplemented with 10% heat-inactivated (56° C. for 45 minutes) fetal calf serum and 100 U/ml penicillin and 100 $\mu$g/ml streptomycin at 37° C. in a humidified, 5% $CO_2$ atmosphere. Peripheral blood lymphocytes (PBLs) were allowed to equilibrate to culture conditions for 45–60 minutes, then irradiated at approximately 60 cGy/min. to total doses of 20–200 cGy using a Mark 1-68 $^{137}$Cs source (J.L. Shepherd and Associates, Inc., San Fernando, Calif.) with lead attenuators in place.

RNA was harvested at 0, (unirradiated) 4, 24, 48 or 72 hours after irradiation using an acid guanidinium thiocyanate-phenol-chloroform mixture, as described by Chomczynski et al. (*Anal. Biochem.* 162:156–9, 1987). RNA harvested 24 hours after irradiation was hybridized to the 7K microarray (Table 6) and to the array shown in Table 13 and analyzed as described in EXAMPLE 2.

The results shown in Table 14 show the Image ID of PBL genes which were differentially expressed 24 hours following 2 Gy of irradiation. These results indicate that cDNA microarrays, such as the 7K microarray shown in Table 6, can be used to identify genes which are differentially expressed in response to irradiation. Such information can be used to identify genes to include in a probe set (such as those shown in Table 14) which will be useful for assessing potential radiation exposure in a cell from an animal or plant subject.

TABLE 14

Image ID Numbers of Differentially Expressed PBL Genes by 2 Gy.

244386; 1486083; 194395; 191826; 230100; 310406; 377314; 487172; 491763; 241097; 269815; 49389; 511091; 626716; 154472; 753104; 205633; 810711; 77577; 130826; 769603; 884425; 811015; 1475730; 826254; 80649; 82556; 825080; 213136; 898221; 273546; 701112; 843312; 128126; 415899; 146605; 823665; 745019; 1391644; 461759; 810017; 591653; 713193; 687054; 70692; 126466; 242790

Figure 10:
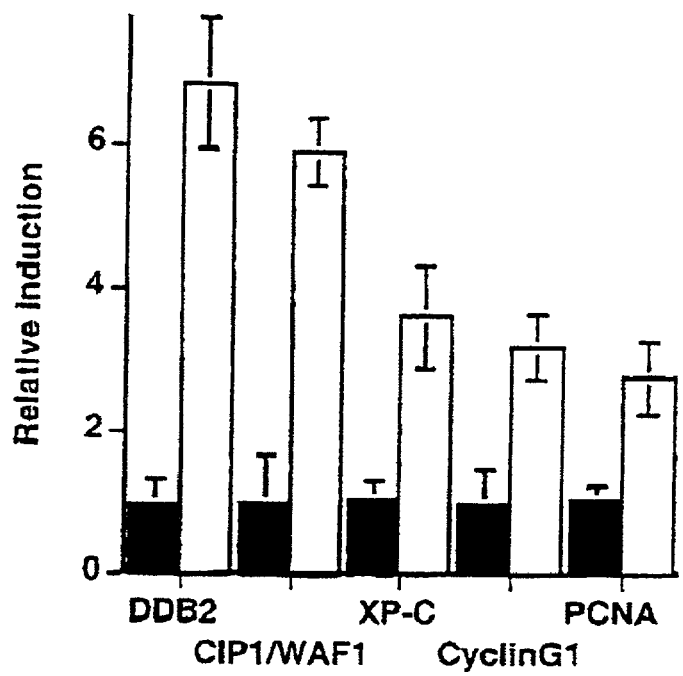
FIG. 10 is a bar graphic representation of a section of a microarray hybridized to RNA from unirradiated (filled bars, normalized to the levels in the first donor) and 2 Gy gamma-irradiated (open bars) human peripheral blood lymphocytes harvested 24 hours after irradiation. Results are from 4–8 independent donors. Error bars are standard deviations.

The alteration in gene expression following $\gamma$-irradiation was examined in PBLs for five genes identified as being differentially expressed in response to irradiation (Table 14). As shown in FIG. 10, the expression of DDB2, CIP/WAF1, XPC, cyclin G1 and PCNA genes in response to irradiation was induced 3–6 fold over non-irradiated PBLs. These results demonstrate that the present invention can be used to determine if a subject has been exposed to ionizing radiation by testing PBLs, which are sensitive to the effects of irradiation. Genes which are identified as being differentially expressed in response to irradiation (for example Table 14) are incorporated into a probe set, which is exposed to the labeled nucleic acid of a test cell (such as PBLs) using a microarray.

Figure 11:
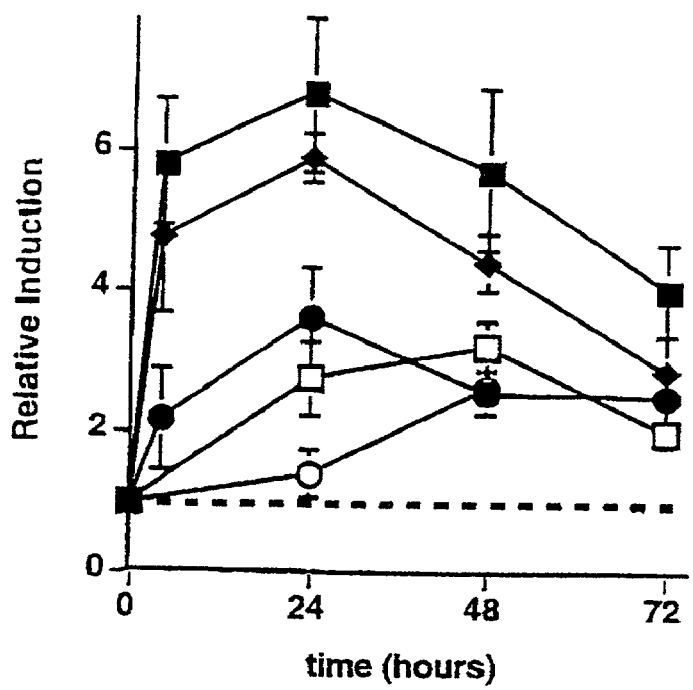
FIG. 11 is a graphical representation showing a time-course of marker levels following 2 Gy gamma-rays delivered ex vivo. Each point is the mean of relative induction above background in 3–4 independent donors for DDB2 (■), CIP1/WAF1 (♦), XP-C (●), PCNA (□) and IFNγp10 (○). RNA was harvested from lymphocytes following one, two, or three days of incubation. Error bars are standard errors of the mean. The dashed line shows the basal level of expression in untreated PBLs.
Figure 12A:
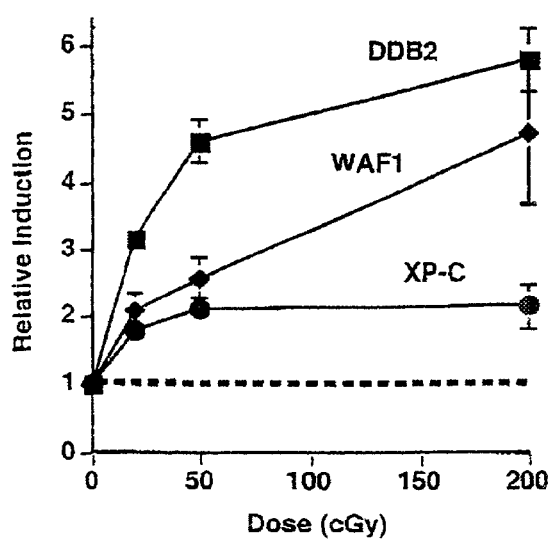
FIGS. 12A–D are graphical representations showing the dose-response relationship for the induction of DDB2 (■), CIP1/WAF1 (♦), and XP-C (●) in human PBL. PBL were irradiated ex vivo with graded doses of γ-rays and RNA was harvested after (A) 4 hours, (B) 24 hours or (C) 48 hours (D) 72 hours of incubation. Points are the mean of relative expression in three or more independent donors, and error bars are standard errors of the mean. The dashed lines indicate the level of expression in un-irradiated control cultures.
Figure 12B:
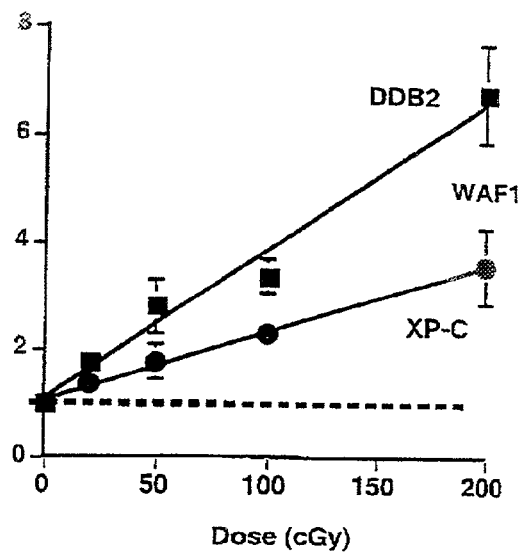
Figure 12C:
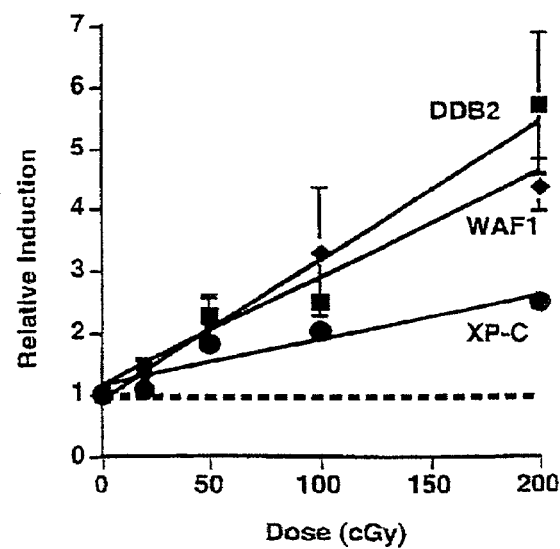
Figure 12D:
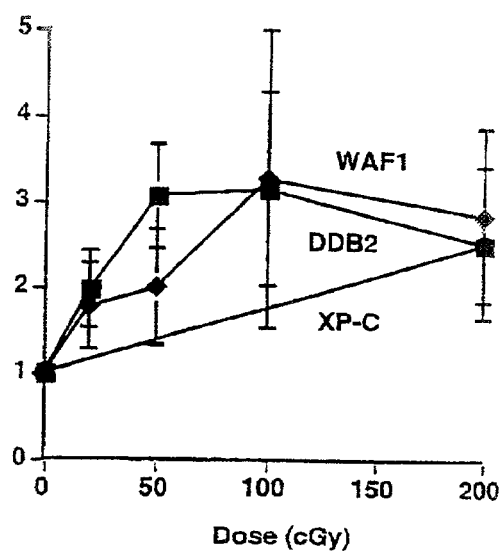

A timecourse of induction following 2 Gy γ-rays delivered ex vivo to PBLs was also examined as described in EXAMPLE 3. RNA was harvested from lymphocytes following one, two, or three days of incubation. Following irradiation, the DDB2, CIP1/WAF1, and XP-C genes reached maximal induction 24 hours after irradiation, then declined (FIG. 11). The induction of PCNA and IFNγp10 reached maximal levels 48 hours after induction (FIG. 11). These results demonstrate that the identification of which genes are differentially expressed in in a biological specimen, can be correlated with the approximate time of irradiation. For example, a probe set which contains the DDB2, CIP1/WAF1, and XP-C genes would be useful for determining if a subject has been exposed within the past 24 hours, and a probe set which contains the PCNA and IFNγp10 gene would be useful for determining if a subject has been exposed within the past 48 hours.

The relative induction of expression was correlated to dosage, as shown in FIGS. 12A–12D for several genes. PBL were irradiated ex vivo with graded doses of γ-rays and RNA was harvested after four hours (FIG. 12A), 24 hours (FIG. 12B), 48 hours (FIG. 12C), or 72 hours (FIG. 12D) of incubation. These results demonstrate that the measured relative induction of expression of genes that are differentially expressed in response to irradiation, can be used to interpret the results. For example, by determining the relative induction of the radiosensitive genes DDB2 or WAF-1 in a particular cell type, that relative induction is correlated to the dosage of irradiation received by a subject, such as a plant, animal, or microbial subject.

In conclusion, this example demonstrates that biological specimens can be used to determine if a cell has been exposed to a biologically significant amount of ionizing radiation, and approximately how much time has elapsed since the cell was exposed. In addition, the relative induction of radiosensitive genes can be correlated to the dosage of irradiation received by the cell.

EXAMPLE 10

Analysis of In Vivo Irradiated Organisms

This example describes methods which can be used to analyze organisms which have been, or may have been, exposed to ionizing radiation.

Analysis of Irradiated Animals

The analysis of animals which have potentially been exposed to, or are known to have been exposed to, ionizing irradiation can be performed. As test subjects, rodents such as mice or rats are whole body irradiated, for example using a Mark 1-68 $^{137}$Cs source (JL Shepherd and Associates, San Fernando, Calif.) to deliver total doses between 2 and 500 cGy as described in the above examples. Following irradiation, biological samples are harvested from the animals. Examples of biological samples include, but are not limited to, those listed above in EXAMPLE 9. Tissues are flash frozen in GTC (guanidine thiocyanate solution, used above), and the RNA is isolated and reverse transcribed incorporating a label, as described above. The labeled nucleic acids are then exposed to an array, for example using mouse equivalents of the genes shown in any of Tables 9–13. A test array can be generated, by selecting for probe sets as described herein, for example probe sets designed to detect radiation exposure in a specimen that is to be tested, such as peripheral blood cells for example leukocytes. Patterns or hybridization to the array can then be observed to determine the likelihood of exposure, and/or a dose of exposure in subsequent test subjects.

Analysis of Subjects Undergoing Radiation Therapy

The disclosed arrays can also be used to evaluate and/or select patients who are undergoing (or are candidates for) radiation therapy, for the treatment of cancer or a tumor. For example, subjects can be monitored during radiotherapy to detect gene expression induced by irradiation. Differential gene expression provides diagnostic or prognostic information, for example, it may indicate whether sufficient doses of radiation are being administered to cause regression of the cancer. An indication that a sufficient dose of radiation has been used may be a pattern of differential gene expression associated with a successful outcome of treatment of tumors of a particular type. In addition, subjects can be monitored to determine if the dose of radiation is causing harmful effects, for example iatrogenic carcinogenesis or suppression of the immune system by determining whether a pattern of differential expression has occurred that is associated with either of these outcomes.

The RNA from subjects is isolated, reverse-transcribed, and labeled as described above in EXAMPLE 2. The labeled nucleic acids are then exposed to an array, for example an array which contains a probe set which has been selected for genes which are differentially expressed at the radiation dose which the subject is being treated with. For example, the array may include genes which have been shown using the methods described in the above examples to be differentially expressed at 2 Gy, a typical daily dose which a subject might receive in radiotherapy. In addition, an array can be selected based on the tumor which is being treated. For example, the array can include or consist of genes which have been shown (using the methods described in the above examples) to be differentially expressed at the dose which the subject is receiving, in the type of tumor the subject suffers from. Such specific probe sets provide useful diagnostic information regarding the subject's progress in the radiotherapy.

Analysis of Irradiated Plants or Microbes

In addition to humans and other animals, plants or microbes which have been, or may have been, exposed to radiation can be analyzed using the present invention. In one example, following a nuclear accident, if there are no animals present to examine to determine the amount of exposure, the plant or microbial flora present in the area can be analyzed. Nucleic acids, for example RNA is isolated using standard methods. Nucleic acids are isolated from any part of the plant, for example roots, stems, leaves or flowers. The RNA is isolated, reverse-transcribed, and labeled as described above. The labeled plant nucleic acids can then be exposed to an array, for example using plant equivalents of the genes shown in Tables 9–13, or other plant genes that are found to be differentially expressed following radiation exposure.

Having illustrated and described the principles of assessing whether an organism has been exposed to biologically significant levels of ionizing radiation by detecting differential cellular expression of genes that are differentially expressed following such exposure, it should be apparent to one skilled in the art that the invention can be modified in arrangement and detail without departing from such principles. In view of the many possible embodiments to which the principles of our invention may be applied, it should be recognized that the illustrated embodiments are only examples of the invention and should not be taken as a limitation on the scope of the invention. Rather, the scope of the invention is in accord with the following claims. We therefore claim as our invention all that comes within the scope and spirit of these claims.

We claim:

1. A method of identifying cells that have been exposed to radiation induced biological stress, comprising:

exposing a probe set comprising nucleic acid molecules representing genes that are differentially expressed in cells that have been exposed to an amount of ionizing radiation sufficient to cause differential expression of genes in the cell to a labeled nucleic acid composition from a test cell which specifically hybridizes to members of the probe set when the cell has been exposed to an amount of ionizing radiation sufficient to cause differential expression of genes in the cell, wherein at least one nucleic acid molecule of the probe set comprises SEQ ID NO: 1; and determining whether the probe set hybridizes to the nucleic acid composition.

2. The method of claim 1, wherein the probe set is bound in an array to a surface.

3. The method of claim 2, wherein the probe set comprises oligonucleotides that specifically hybridize to sequences in the nucleic acid composition.

4. The method of claim 3, wherein the nucleic acid composition comprises cDNA reverse transcribed from mRNA in the test cell.

5. The method of claim 1, wherein the labeled nucleic acid is labeled with a fluorophore.

6. The method of claim 1, further comprising exposing the probe set to a labeled nucleic acid composition from a control cell, such that the labeled nucleic acid composition from the control cell specifically hybridizes to members of the probe set.

7. The method of claim 1, further comprising determining a probable time of radiation exposure, wherein the probe set comprises probes that specifically hybridize to the labeled nucleic acid composition, when the nucleic acid composition has been obtained more than four hours after exposure to an amount of ionizing radiation sufficient to cause differential expression of genes in the cell, and wherein hybridization to the probe set indicates that the cells have been exposed to the amount of ionizing radiation sufficient to cause differential expression of genes in the cell at least four hours previously.

8. The method of claim 1, further comprising determining a probable time of radiation exposure, wherein the probe set comprises probes that specifically hybridize to the labeled nucleic acid composition, when the nucleic acid composition has been obtained more than 24 hours after exposure to an amount of ionizing radiation sufficient to cause differential expression of genes in the cell, and wherein hybridization to the probe set indicates that the cells have been exposed to the amount of ionizing radiation sufficient to cause differential expression of genes in the cell at least 24 hours previously.

9. The method of claim 1, further comprising determining a probable time of radiation exposure, wherein the probe set comprises probes that specifically hybridize to the labeled nucleic acid composition, when the nucleic acid composition has been obtained more than 48 hours after exposure to an amount of ionizing radiation sufficient to cause differential expression of genes in the cell, and wherein hybridization to the probe set indicates that the cells have been exposed to the amount of ionizing radiation sufficient to cause differential expression of genes in the cell at least 48 hours previously.

10. The method of claim 1, wherein the probe set comprises probes that specifically hybridize to the labeled nucleic acid composition, when the nucleic acid composition has been exposed to less than about 25 cGy of ionizing radiation.

11. The method of claim 1, wherein the probe set comprises genes that are differentially expressed by at least 1.5 fold following exposure to the amount of ionizing radiation sufficient to cause differential expression of genes in the cell.

12. The method of claim 11, wherein the genes are differentially expressed by at least 2-fold following exposure to the amount of ionizing radiation sufficient to cause differential expression of genes in the cell.

13. The method of claim 1, wherein the probe nucleic acids are DNA.

14. The method of claim 13, wherein the probe nucleic acids are cDNA.

15. The method of claim 14, wherein the test nucleic acids are cDNA obtained from mRNA expressed by the test cell.

16. The method of claim 1, wherein the probe nucleic acids are about 10 to about 1,000,000 nucleotides in length.

17. The method of claim 1, further comprising contacting the probe set with a plurality of control nucleic acids obtained from mRNA of a control cell that has not been exposed to an amount of ionizing radiation sufficient to cause differential expression of genes in the cell; and
    determining whether the nucleic acids from mRNA of the control cells hybridize differentially to the probe set than the nucleic acid composition from the test cell.

18. The method of claim 1, wherein the probe set comprises the probes identified in Table 9.

19. The method of claim 1, wherein the probe set comprises the probes identified in Table 13.

20. The method of claim 1, wherein the probe set comprises at least 10% of the probes identified in Table 9, wherein the at least 10% of the probes includes SEQ ID NO: 1.

21. The method of claim 1, wherein the probe set comprises at least 10% of the probes identified in Table 13, wherein the at least 10% of the probes includes SEQ ID NO: 1.

22. The method of claim 1, wherein the probe set comprises at least 10 of the probes identified in Table 9, wherein at least one of the 10 probes comprises SEQ ID NO: 1.

23. The method of claim 1, wherein the probe set comprises at least 10 of the probes identified in Table 13, wherein at least one of the 10 probes comprises SEQ ID NO: 1.

24. The method of claim 1, wherein the probe set comprises at least 50% of the probes identified in Table 9, wherein at least one of the probes comprises SEQ ID NO: 1.

25. A method of identifying cells that have been exposed to radiation induced biological stress, the method comprising:
    providing a plurality of probe elements bound to a surface, each probe element comprising a nucleic acid that is differentially expressed by a cell following ionizing radiation induced biological stress, wherein at least one probe element comprises SEQ ID NO: 1;
    contacting the plurality of probe elements with a plurality of test nucleic acid sequences obtained from a test cell, under conditions that allow the test nucleic acid sequences to specifically hybridize to one or more of the probe elements, and provide a signal which indicates differential expression of one or more genes if the cell has been exposed to an amount of ionizing radiation sufficient to cause differential expression of genes in the cell; and
    detecting the presence or absence of the signal.

26. The method of claim 25, wherein the plurality of probe elements is a selected set of nucleic acids from a set of nucleic acids that hybridize to nucleic acids obtained from cells exposed to ionizing radiation.

27. The method of claim 25, wherein the probe elements are nucleic acid sequences that are differentially expressed by a cell more than four hours after exposure to the ionizing radiation.

28. The method of claim 27, wherein the probe elements are nucleic acid sequences that are differentially expressed at a time at least 24 hours after exposure to the ionizing radiation.

29. The method of claim 27, wherein the probe elements are nucleic acid sequences that are differentially expressed more than 48 hours after exposure to the ionizing radiation.

30. The method of claim 27, wherein the probe elements comprise nucleic acid sequences that are differentially expressed by at least 1.5-fold following exposure to an amount of ionizing radiation sufficient to cause differential expression of genes in the cell.

31. The method of claim 30, wherein the nucleic acid sequences are differentially expressed by at least 2-fold following exposure to an amount of ionizing radiation sufficient to cause differential expression of genes in the cell.

32. The method of claim 25, wherein the test nucleic acid sequences are labeled with a fluorophore that detects hybridization of the test nucleic acid sequences to the one or more of the probe elements.

33. The method of claim 32, wherein the test nucleic acid sequences are labeled with a first label that detects hybridization of the test nucleic acids to the probe elements, and a plurality of control nucleic acids are labeled with a second label that detects hybridization of the plurality of control nucleic acids to the probe sequences, and the first and second labels interact to indicate whether expression of a nucleic acid in the test cell has increased or decreased, relative to expression of the plurality of control nucleic acids.

34. The method of claim 33, wherein the first and second labels are fluorophores of different colors.

35. The method of claim 24, wherein the different colors are red and green.

36. The method of claim 25, wherein the cells are animal cells.

37. The method of claim 36 wherein the animal cells are human cells.

38. The method of claim 36, wherein the animal cells are peripheral blood cells.

39. The method of claim 38, wherein the peripheral blood cells are peripheral blood mononuclear cells.

40. The method of claim 39, wherein the peripheral blood mononuclear cells are lymphocytes.

41. The method of claim 25, wherein the cells are microbial or plant cells.

42. A method of making a microarray for identifying cells that have actually or potentially been exposed to an amount of ionizing radiation sufficient to cause differential expression of genes in the cell, comprising:
   identifying genes that are differentially expressed by a cell following exposure to the amount of ionizing radiation sufficient to cause differential expression of genes in the cell; and
   providing a plurality of probe elements bound to a substrate surface, the probe elements comprising probe nucleic acids from genes that are identified as differentially expressed by a cell following ionizing radiation induced biological stress, wherein at least one probe element comprises SEQ ID NO: 1, and wherein the probe nucleic acid is capable of hybridizing to a nucleic acid differentially expressed by the cell following exposure of the cell to the ionizing radiation.

43. The method of claim 42, wherein identifying genes that are differentially expressed by a cell following exposure to the amount of ionizing radiation sufficient to cause differential expression of genes in the cell comprises exposing the cell to a biologically significant amount of ionizing radiation, obtaining mRNA expressed by the cell, reverse transcribing the mRNA into cDNA, labeling the cDNA, and hybridizing the labeled cDNA to a probe set and identifying members of the probe set that hybridize with the labeled cDNA.

44. The method of claim 43, where in the genes comprise p53 regulated genes.

45. The method of claim 42, further comprising determining a dose response relationship between radiation exposure and differential expression of one or more genes.

46. The method of claim 42, wherein identifying genes that are differentially expressed comprises identifying genes that are differentially expressed in a cell type that is to be obtained from a subject for testing.

47. The method of claim 46, wherein the cell type is peripheral blood cells.

48. The method of claim 47, wherein the peripheral blood cells are peripheral blood mononuclear cells.

49. The method of claim 48, wherein the peripheral blood mononuclear cells are lymphocytes.

50. A method of diagnosing ionizing radiation exposure in a subject, comprising:
   obtaining a biological sample from the subject;
   synthesizing cDNA from mRNA expressed in one or more cells of the biological sample, and labeling the cDNA with a detectable label;
   exposing the labeled cDNA to a probe set which represents genes that are differentially expressed in the biological sample following exposure to ionizing radiation, and determining if the labeled cDNA selectively hybridizes to one or more probes of the probe set that are associated with the radiation exposure, wherein the probe set comprises SEQ ID NO: 1.

51. The method of claim 50, further comprising detecting patterns of differential expression associated with an amount of ionizing radiation sufficient to cause differential expression of genes in the cell.

52. A method for measuring a biological response in a subject comprising:
   obtaining a biological sample from the subject;
   synthesizing cDNA from mRNA expressed in one or more cells of the biological sample;
   labeling the cDNA with a detectable label;
   exposing the labeled cDNA to a probe set comprising nucleic acid molecules representing genes that are differentially expressed in cells that have been exposed to an amount of ionizing radiation sufficient to cause differential expression of genes in the cell, wherein at least one nucleic acid molecule of the probe set comprises SEQ ID NO: 1; and
   determining if the labeled cDNA selectively hybridizes to one or more probes of the probe set differentially expressed following exposure to ionizing radiation.

53. The method of claim 52 wherein the subject is undergoing radiotherapy for the treatment of cancer and the probe set is used to monitor the subject's biological response to the radiotherapy.

54. The method of claim 52 wherein the biological response is a biological response to potential radiation exposure in the subject.

55. The method of claim 54, wherein the biological response is measured in a cell type.

56. The method of claim 55, wherein the cell type is a peripheral blood cell obtained from the subject.

57. The method of claim 52, further comprising determining a relationship between radiation exposure and differential expression of one or more genes to determine a probable radiation dose in cells that have actually or potentially been exposed to the ionizing radiation.

58. A method of identifying cells that have been exposed to radiation induced biological stress, the method comprising:
   contacting a plurality of probe elements with a plurality of test nucleic acid sequences obtained from a test cell, under conditions that allow the test nucleic acid sequences to specifically hybridize to one or more of said plurality of probe elements, and provide a signal which indicates differential expression of one or more genes if the cell has been exposed to an amount of ionizing radiation sufficient to cause differential expression of genes in the cell, wherein the plurality of probe elements comprise nucleic acid sequences that are differentially expressed by a cell following ionization radiation induced biological stress, wherein at least one probe element of said plurality of probe elements comprises SEQ ID NO: 1; and
   detecting the presence or absence of the signal.

* * * * *

UNITED STATES PATENT AND TRADEMARK OFFICE
CERTIFICATE OF CORRECTION

PATENT NO. : 7,008,768 B1
APPLICATION NO. : 09/913171
DATED : March 7, 2006
INVENTOR(S) : Fornace, Jr. et al.

It is certified that error appears in the above-identified patent and that said Letters Patent is hereby corrected as shown below:

On the Cover Page:

In the first column on the cover page, item (86), the § 371(c)(1), (2), (4) Date "Aug. 8, 2001" should be --Aug. 9, 2001--.

In the second column on the cover page under the heading "Other Publications," the fourth-listed publication should read --Carulli et al., "High Throughput Analysis of Differential Gene Expression," *J. Cell. Biochem. Suppl. 30/31*:286-296 (1998).--

In the Specification:

Column 1, line 40, "Woloschakand" should be --Woloschak and--.

Column 4, lines 50-51, "microar-rays" should be --micro-arrays--.

Column 6, line 31, "C1P1/WAF1" should be --CIP1/WAF1--.

Column 7, lines 19-20, "or (C) 48 hours (D) 72 hours" should be --, (C) 48 hours or (D) 72 hours--.

Column 9, lines 43-44, "2,2′dis-ulfonic" should be --2,2′-disulfonic--.

Column 9, lines 46-47, "4-amino-N-[3-vinylsulfonyl)phenyl]naphthalimide-3,5 disulfonate (Lucifer Yellow VS)" should be --4-amino-N-[3-(vinylsulfonyl)phenyl]naphthalimide-3,6 disulfonate (Lucifer Yellow VS)--.

Column 14, line 54, "1989)." should be --1989))--.

Column 15, line 58, "neoplasm" should be --neoplasm.--.

Column 16, line 12, "37°" should be --37°C--.

Column 17, line 42, "northen" should be --Northern--.

Column 22, line 41, "See also http://rex.nci.nih.gov/RESEARCH/basic/lbc/fornace.htm" should be deleted.

UNITED STATES PATENT AND TRADEMARK OFFICE
CERTIFICATE OF CORRECTION

| | | |
|---|---|---|
| PATENT NO. | : 7,008,768 B1 | |
| APPLICATION NO. | : 09/913171 | |
| DATED | : March 7, 2006 | |
| INVENTOR(S) | : Fornace, Jr. et al. | |

It is certified that error appears in the above-identified patent and that said Letters Patent is hereby corrected as shown below:

Column 22, line 45, "Nature" should be --*Nature*--.

Column 22, line 46, "Cell" should be --*Cell*--.

Column 22, lines 48-60, the lettered list beginning with item "a." and ending with item "e." is duplicative and should be deleted.

Column 26, line 21, "by the more" should be --by more--.

Column 28, line 63, "northern" should be --Northern--.

Column 29, line 50, "o" should be --of--.

Column 80, line 18, "of" should be --of--.

Column 81, line 35, "prognositc" should be --prognostic--.

Column 81, line 50, "northern" should be --Northern--.

Column 81, line 55, "northern" should be --Northern--.

Column 82, line 40, "WO 9710365" should be --WO 97/10365--.

Column 82, line 56, "southern and northern" should be --Southern and Northern--.

Column 85, line 11, "50, 50 or more" should be --50, or 50 or more--.

Column 86, line 15, "this" should be --these--.

Column 87, line 51, "northern" should be --Northern--.

Column 88, line 51, "northern" should be --Northern--.

Column 90, line 30, "Mark 1-68" should be --Mark I-68--.

UNITED STATES PATENT AND TRADEMARK OFFICE
CERTIFICATE OF CORRECTION

PATENT NO. : 7,008,768 B1
APPLICATION NO. : 09/913171
DATED : March 7, 2006
INVENTOR(S) : Fornace, Jr. et al.

It is certified that error appears in the above-identified patent and that said Letters Patent is hereby corrected as shown below:

Column 90, line 64, "CIP/WAF1" should be --CIP1/WAF1--.

Column 91, line 60, "Mark 1-68" should be --Mark I-68--.

Signed and Sealed this

Thirtieth Day of January, 2007

JON W. DUDAS
*Director of the United States Patent and Trademark Office*